(12) United States Patent
Dalkilic-Liddle et al.

(10) Patent No.: US 11,827,702 B2
(45) Date of Patent: Nov. 28, 2023

(54) ANTI-TRANSFERRIN RECEPTOR ANTIBODIES AND USES THEREOF

(71) Applicant: Biogen MA Inc., Cambridge, MA (US)

(72) Inventors: Isin Dalkilic-Liddle, Watertown, MA (US); Benjamin A. Smith, Belmont, MA (US); Karl J. M. Hanf, Billerica, MA (US); Fang Qian, Southborough, MA (US); R. Blake Pepinsky, Arlington, MA (US); Thomas O. Cameron, Cambridge, MA (US)

(73) Assignee: Biogen MA Inc., Cambridge, MA (US)

( * ) Notice: Subject to any disclaimer, the term of this patent is extended or adjusted under 35 U.S.C. 154(b) by 0 days.

(21) Appl. No.: 17/900,161

(22) Filed: Aug. 31, 2022

(65) Prior Publication Data

US 2023/0131379 A1    Apr. 27, 2023

Related U.S. Application Data

(60) Provisional application No. 63/388,088, filed on Jul. 11, 2022, provisional application No. 63/239,630, filed on Sep. 1, 2021.

(51) Int. Cl.
*C07K 16/28*       (2006.01)
*C12N 15/113*      (2010.01)

(52) U.S. Cl.
CPC ............ *C07K 16/28* (2013.01); *C12N 15/113* (2013.01); *C07K 2317/565* (2013.01)

(58) Field of Classification Search
CPC .................... C07K 16/28; C07K 2317/565
See application file for complete search history.

(56) References Cited

U.S. PATENT DOCUMENTS

| | | | |
|---|---|---|---|
| 5,648,469 | A  | 7/1997  | Trowbridge et al. |
| 9,708,406 | B2 | 7/2017  | Zhang et al. |
| 10,106,796 | B2 | 10/2018 | Kole et al. |
| 10,457,717 | B2 | 10/2019 | Chen et al. |
| 10,550,188 | B2 | 2/2020  | Geall et al. |
| 2013/0171061 | A1 | 7/2013 | Yang et al. |
| 2014/0370004 | A1 | 12/2014 | Way |
| 2019/0240346 | A1 | 8/2019 | Sugo et al. |

FOREIGN PATENT DOCUMENTS

| | | |
|---|---|---|
| WO | WO 1991004753 | 4/1991 |
| WO | WO 1991014452 | 10/1991 |
| WO | WO 2005094364 | 10/2005 |
| WO | WO 2005100401 | 10/2005 |
| WO | WO 2005111082 | 11/2005 |
| WO | WO 2005121179 | 12/2005 |
| WO | WO 2007000671 | 1/2007 |
| WO | WO 2011073943 | 6/2011 |
| WO | WO 2011138557 | 11/2011 |
| WO | WO 2012075037 | 6/2012 |
| WO | WO 2012153707 | 11/2012 |
| WO | WO 2013103800 | 7/2013 |
| WO | WO 2014033074 | 3/2014 |
| WO | WO 2014073641 | 5/2014 |
| WO | WO 2014144060 | 9/2014 |
| WO | WO 2014189973 | 11/2014 |
| WO | WO 2015098989 | 7/2015 |
| WO | WO 2015101588 | 7/2015 |
| WO | WO 2016081643 | 5/2016 |
| WO | WO 2016179257 | 11/2016 |
| WO | WO 2016207240 | 12/2016 |
| WO | WO 2016208695 | 12/2016 |
| WO | WO 2017013230 | 1/2017 |
| WO | WO 2017055542 | 4/2017 |
| WO | WO 2017173408 | 10/2017 |
| WO | WO 2017221883 | 12/2017 |
| WO | WO 2018081720 | 5/2018 |
| WO | WO 2018124121 | 7/2018 |
| WO | WO 2018152375 | 8/2018 |
| WO | WO 2019032955 | 2/2019 |
| WO | WO 2019033046 | 2/2019 |
| WO | WO 2019113393 | 6/2019 |
| WO | WO 2019151539 | 8/2019 |
| WO | WO 2020028831 | 2/2020 |
| WO | WO 2020028832 | 2/2020 |
| WO | WO 2020028836 | 2/2020 |
| WO | WO 2020028840 | 2/2020 |
| WO | WO 2020028841 | 2/2020 |
| WO | WO 2020028842 | 2/2020 |
| WO | WO 2020028844 | 2/2020 |
| WO | WO 2020028857 | 2/2020 |
| WO | WO 2020028861 | 2/2020 |
| WO | WO 2020028864 | 2/2020 |
| WO | WO 2020104479 | 5/2020 |
| WO | WO 2021076856 | 4/2021 |

(Continued)

OTHER PUBLICATIONS

Daniels et al., "The transferrin receptor part I: Biology and targeting with cytotoxic antibodies for the treatment of cancer," Clin Immunol., Nov. 2006, 121(2):144-158.

(Continued)

*Primary Examiner* — Ruixiang Li

(74) *Attorney, Agent, or Firm* — Fish & Richardson P.C.

(57) ABSTRACT

The present disclosure provides anti-transferrin receptor antibodies, compositions comprising the same and methods of their use. This disclosure also provides polynucleotides and vectors encoding the anti-transferrin receptor antibodies and cells comprising the same, methods of making the antibodies, and molecules comprising the antibodies.

11 Claims, 12 Drawing Sheets

Specification includes a Sequence Listing.

(56) References Cited

FOREIGN PATENT DOCUMENTS

| | | |
|---|---|---|
| WO | WO 2021142234 | 7/2021 |
| WO | WO 2021142313 | 7/2021 |
| WO | WO 2021154477 | 8/2021 |
| WO | WO 2022020105 | 1/2022 |
| WO | WO 2022147209 | 7/2022 |

OTHER PUBLICATIONS

Ebner et al., "Strategies for skeletal muscle targeting in drug discovery," Curr Pharm Des., 2015, 21(10):1327-1336.

Helguera et al., "An Antibody Recognizing the Apical Domain of Human Transferrin Receptor 1 Efficiently Inhibits the Entry of All New World Hemorrhagic Fever Arenaviruses," J. Virol., Apr. 2012, 86(7):4024-4028.

Lawrence et al., "Crystal Structure of the Ectodomain of Human Transferrin Receptor," Science, Oct. 1999, 286(5440):779-82.

Li et al., "Transferrin receptor 1 plays an important role in muscle development and denervation-induced muscular atrophy," Neural Regen Res., Jul. 2021, 16(7):1308-1316.

Schnyder et al., "Targeting of skeletal muscle in vitro using biotinylated immunoliposomes," Biochem J., Jan. 2004, 377(Pt 1):61-67.

Candelaria et al., "Antibodies Targeting the Transferrin Receptor 1 (TfR1) as Direct Anti-Cancer Agents," Frontiers in Immunology, Mar. 2021, 12, 21 pages.

International Search Report and Written Opinion in International Application No. PCT/US2022/042196, dated Dec. 19, 2022, 17 pages.

Luria-Perez et al., "Antibody-mediated targeting of the transferrin receptor in cancer cells," Bol. Med. Hosp. Infant Mex., Nov. 2016, 372-379.

Shen et al., "An anti-transferrin receptor antibody enhanced the growth inhibitory effects of chemotherapeutic drugs on human non-hematopoietic tumor cells," International Immunopharmacology, Sep. 2008, 8(13):1813-1820.

Takahashi et al., "An epitope on the transferrin receptor preferentially exposed during tumor progression in human lymphoma is close to the ligand binding site," Blood, Feb. 1991, 77(4):826-832.

```
ANTIBODY-A Family VL
       1       5       10      15      20      25      30      35      40      45      50      55      60      65      70      75      80      85      90      100           107   Kabat pos #
       1       5       10      15      20      25      29 39   45      50      55      67 70   75      80      87 90   95      100     105     110 133       140           148   AHo pos #
       1       5       10      15      20      25      30      35      40      45      50      55      60      65      70      75      80      85      90      abcd    100   105   111   sequential pos #, rabAB-A_VL
ELDMTQTPASVEAVGGTVTIKCQASQNINSYLAWYQQKPGQPPKLLIYRASTLASGVPSRFKGSGSGTEFTLTISDLECADAATYYCQSYYYSGSSNYNAFGGGTELEIL      rabAB-A_VL (SEQ ID NO:34)
DIQMTQSPSTLSASVGDRVTITCQASQNINSYLAWYQQKPGKAPKLLIYRASSLESGVPSRFSGSGSGTEFTLTISSLQPDDFATYYCQSYYYSGSSNYNAFGGGTKVEIK     ANTIBODY-A_L0 (SEQ ID NO:35)
DIQMTQSPSTLSASVGDRVTITCQASQNINSYLAWYQQKPGKAPKLLIYRASTLASGVPSRFSGSGSGTEFTLTISSLQPDDFATYYCQSYYYSGSSNYNAFGGGTKVEIK     ANTIBODY-A_L1 (SEQ ID NO:36)
ELDMTQSPSTLSASVGDRVTITCQASQNINSYLAWYQQKPGKAPKLLIYRASTLASGVPSRFSGSGSGTEFTLTISSLQPDDFATYYCQSYYYSGSSNYNAFGGGTKVEIK     ANTIBODY-A_L2 (SEQ ID NO:37)
    MTQ P   A  VG   VTI C QASQNINSYLAWYQQKPG   PKLLIYRAS L SGVPSRF GSGSGTEFTLTIS L  D ATYYCQSYYYSGSSNYNAFGGGT   EI       conserved
```

Fig. 1C

```
ANTIBODY-B Family VL
       1       5       10      15      20      25      30      35      40      45      50      55      60      65      70      75      80      85      90      100           107   Kabat pos #
       1       5       10      15      20      25      29 39   45      50      55      67 70   75      80      87 90   95      100     105     110 134       140           148   AHo pos #
       1       5       10      15      20      25      30      35      40      45      50      55      60      65      70      75      80      85      90      abc     100   105   110   sequential pos #, rabAB-B_VL
ELVLTQTPASVSEAVGGTVTIKCQASQNIGSNLAWYQQKPGQPPKLLIYDASKLASGVPSRFSGSGSGTEFTLTISDLECADAATYYCQCTVRGGAYGNAFGGGTEVVVK        rabAB-B_VL (SEQ ID NO:38)
ELVLTQSPSTLSASVGDRVTITCRASQNIGSNLAWYQQKPGKAPKLLIYDASKLESGVPSRFSGSGSGTEFTLTISSLQPDDFATYYCQQTVRGGAYGLAFGGGTKVEIK       ANTIBODY-B_L0 (SEQ ID NO:39)
ELVLTQSPSTLSASVGDRVTITCRASQNIGSNLAWYQQKPGKAPKLLIYDASKLESGVPSRFSGSGSGTEFTLTISSLQPDDFATYYCQATVRGGAYGLAFGGGTKVEIK       ANTIBODY-B_L1 (SEQ ID NO:40)
ELVLTQSPSTLSASVGDRVTITCRASQNIGSNLAWYQQKPGKAPKLLIYDASKLESGVPSRFSGSGSGTEFTLTISSLQPDDFATYYCQCTVRGGAYGNAFGGGTKVEIK       ANTIBODY-B_L2 (SEQ ID NO:41)
ELVLTQSPSTLSASVGDRVTITCRASQNIGSNLAWYQQKPGKAPKLLIYDASKLESGVPSRFSGSGSGTEFTLTISSLQPDDFATYYCQSTVRGGAYGNAFGGGTKVEIK       ANTIBODY-B_L2(C90S) (SEQ ID NO:42)
ELVLTQSPSTLSASVGDRVTITCRASQNIGSNLAWYQQKPGKAPKLLIYDASKLESGVPSRFSGSGSGTEFTLTISSLQPDDFATYYCQTTVRGGAYGNAFGGGTKVEIK       ANTIBODY-B_L2(C90T) (SEQ ID NO:43)
ELVLTQSPSTLSASVGDRVTITCRASQNIGSNLAWYQQKPGKAPKLLIYDASKLESGVPSRFSGSGSGTEFTLTISSLQPDDFATYYCQVTVRGGAYGNAFGGGTKVEIK       ANTIBODY-B_L2(C90V) (SEQ ID NO:44)
    TQ P   S  VG   VTI C ASQNIGSNLAWYQQKPG   PKLLIYDASKL SGVPSRFSGSGSGTEFTLTIS L  D ATYYCQ  TVRGGAYG AFGGGT V K         conserved
```

```
ANTIBODY-A Family VL
1       5        10        15        20      25    30       35       40       45    50    55       60       65       70   75       80       85       90        100         107    Kabat pos #
1       5        10        15        20      29 39 30       35    45 50       40       45 50 67 55 50       55       60       65       70 87 90 75       80       85       90 110 133 100    140         148    AHo pos #
1       5        10        15        20      25    30                35       40       45    50    55       60       65       70    75       80       85       90    95    100    105         111    sequential pos #, rabAB-A_VL
ELDMTQTPASVEAVGGTVTIKCQASQNINSYLAWYQQKPGQPPKLLIYRASTLASGVPSRFKGSGSGTEFTLTISDLECADAATYYCQSYYYSGSSNYNAFGGGTELEIL                            rabAB-A_VL (SEQ ID NO:34)
DIQMTQSPSTLSASVGDRVTITCQASQNINSYLAWYQQKPGKAPKLLIYRASSLESGVPSRFSGSGSGTEFTLTISSLQPDDFATYYCQSYYYSGSSNYNAFGGGTKVEIK                         ANTIBODY-A_L0 (SEQ ID NO:35)
DIQMTQSPSTLSASVGDRVTITCQASQNINSYLAWYQQKPGKAPKLLIYRASTLASGVPSRFSGSGSGTEFTLTISSLQPDDFATYYCQSYYYSGSSNYNAFGGGTKVEIK                         ANTIBODY-A_L1 (SEQ ID NO:36)
ELDMTQSPSTLSASVGDRVTITCQASQNINSYLAWYQQKPGKAPKLLIYRASTLASGVPSRFSGSGSGTEFTLTISSLQPDDFATYYCQSYYYSGSSNYNAFGGGTKVEIK                         ANTIBODY-A_L2 (SEQ ID NO:37)
 MTQ P      A VG   VTI CQASQNINSYLAWYQQKPG  PKLLIYRAS L SGVPSRF GSGSGTEFTLTIS L   D ATYYCQSYYYSGSSNYNAFGGGT  EI                          conserved
```

Fig. 2C

```
ANTIBODY-B Family VL
1       5        10        15        20      25    30       35       40       45    50    55       60       65       70   75       80       85       90        100         107    Kabat pos #
1       5        10        15        20      29 39 30       35    45 50       40       45 50 67 55 50       55       60       65       70 87 90 75       80       85       90 110 134 100    140         148    AHo pos #
1       5        10        15        20      25    30                35       40       45    50    55       60       65       70    75       80       85       90    96    100    105         110    sequential pos #, rabAB-B_VL
ELVLTQTPASVSEAVGGTVTIKCQASQNIGSNLAWYQQKPGQPPKLLIYDASKLASGVPSRFSGSGSGTEFTLTISDLECADAATYYCQCTVRGGAYGNAFGGGTEVVVK                           rabAB-B_VL (SEQ ID NO:38)
ELVLTQSPSTLSASVGDRVTITCRASQNIGSNLAWYQQKPGKAPKLLIYDASKLESGVPSRFSGSGSGTEFTLTISSLQPDDFATYYCQCTVRGGAYGNAFGGGTKVEIK                          ANTIBODY-B_L0 (SEQ ID NO:39)
ELVLTQSPSTLSASVGDRVTITCRASQNIGSNLAWYQQKPGKAPKLLIYDASKLESGVPSRFSGSGSGTEFTLTISSLQPDDFATYYCQATVRGGAYGLAFGGGTKVEIK                          ANTIBODY-B_L1 (SEQ ID NO:40)
ELVLTQSPSTLSASVGDRVTITCRASQNIGSNLAWYQQKPGKAPKLLIYDASKLESGVPSRFSGSGSGTEFTLTISSLQPDDFATYYCQCTVRGGAYGNAFGGGTKVEIK                          ANTIBODY-B_L2 (SEQ ID NO:41)
ELVLTQSPSTLSASVGDRVTITCRASQNIGSNLAWYQQKPGKAPKLLIYDASKLESGVPSRFSGSGSGTEFTLTISSLQPDDFATYYCQSTVRGGAYGNAFGGGTKVEIK                          ANTIBODY-B_L2(C90S) (SEQ ID NO:42)
ELVLTQSPSTLSASVGDRVTITCRASQNIGSNLAWYQQKPGKAPKLLIYDASKLESGVPSRFSGSGSGTEFTLTISSLQPDDFATYYCQTTVRGGAYGNAFGGGTKVEIK                          ANTIBODY-B_L2(C90T) (SEQ ID NO:43)
ELVLTQSPSTLSASVGDRVTITCRASQNIGSNLAWYQQKPGKAPKLLIYDASKLESGVPSRFSGSGSGTEFTLTISSLQPDDFATYYCQVTVRGGAYGNAFGGGTKVEIK                          ANTIBODY-B_L2(C90V) (SEQ ID NO:44)
 TQ P   S  VG   VTI C ASQNIGSNLAWYQQKPG  PKLLIYDASKL SGVPSRFSGSGSGTEFTLTIS L   D ATYYCQ   TVRGGAYG AFGGGT V K                            conserved
```

Fig. 2D

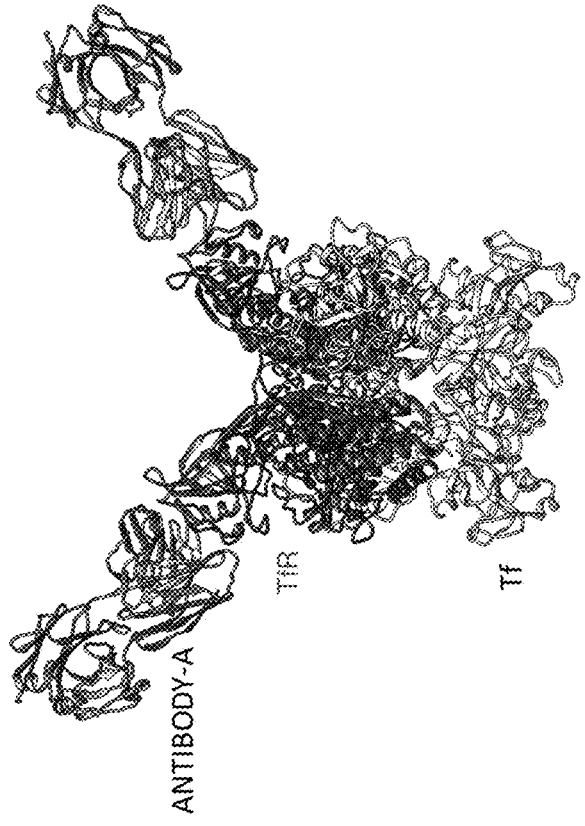

Fig. 3

| | | |
|---|---|---|
| Human | SKVWRDQHFVKIQVKDSAQNSVIIVDKNGRLVLVLVENPGGYVAYSKAATVTGKLVHANFG | 238 |
| Cyno | SKVWRDQHFVKIQVKDSAQNSVIIVDKNGGLVLVLVENPGGYVAYSKAAFVTGKLVHANFG | 238 |
| Mouse | SKVWRDEHYVKIQVKSSIGQNMVTIVQSNGNLDFVEASPEGYVAFSKFTEVSGKLVHANFG | 240 |
| | ******:*** :::: : :. : *. ::***** | |
| Human | TKKDFEFVNGSIVIVRAGKITFAEKVANAESLNAIGVLIYMDQTKFPIVNAELSFF | 298 |
| Cyno | TKKDFEDLDSFVNGSIVIVRAGKITFAEKVANAESLNAIGVLIYMDQTKFPIVKADLSFF | 298 |
| Mouse | TKKDFEELSYSVNGSLVIVRAGEITFAEKVANAQSFNAIGVLIYMDKNKFPVVEADLALF | 300 |
| | ****   :*.:****:*****:* *****::.::.  **: | |
| Human | GHAHLGTGDPYTPGFPSFNHTQFPPSRSSGLPNIPVQTISRAAAEKLFGNMWK | 358 |
| Cyno | GHAHLGTGDPYTPGFPSFNHTQFPPSQSSGLPNIPVQTISRAAAEKLFGNMEGDCPSDWK | 358 |
| Mouse | GHAHLGTGDPYTFGFPSFNHTQFPPSQSSGLPNIPVQTISRAAAEKLFGKMEGSCFARWN | 360 |
| | ********** ********:*****************:*  .: *. | |
| Human | TCKNVTSKNVLKEIKILNIFGVIKGFVEPDHYVVGAQRDAWGPGA-A | 417 (SEQ ID NO: 165) |
| Cyno | TDSTCKNVTSENKSVKLTVSNVLKETKLLNIFGVIKGFVEPDHYVVGAQRDAWGPGA-A | 417 (SEQ ID NO: 166) |
| Mouse | IDSSCKLELSQNQNVLLIVKNVLKERRILNIFGVIKGYEEPDRYVVGYALGAGVAA | 420 (SEQ ID NO: 167) |
| | **:*::  *:.:.*** *,:***** ******:: ** ****.:.*  * | |

Fig. 4

ANTI-TRANSFERRIN RECEPTOR ANTIBODIES AND USES THEREOF

CROSS-REFERENCE TO RELATED APPLICATIONS

This application claims priority to U.S. Provisional Application No. 63/239,630, filed Sep. 1, 2021, and U.S. Provisional Application No. 63/388,088, filed Jul. 11, 2022. The content of the foregoing applications are incorporated by reference herein in its entirety.

SEQUENCE LISTING

The instant application contains a Sequence Listing which has been submitted electronically in XML file format and is hereby incorporated by reference in its entirety. Said XML copy, created on Sep. 26, 2022, is named 13751-0357001_SL.xml and is 222,365 bytes in size.

TECHNICAL FIELD

This disclosure relates to anti-transferrin receptor antibodies, compositions comprising the same and uses thereof. This disclosure also provides related polynucleotides and vectors encoding the anti-transferrin receptor antibodies and cells comprising the same.

BACKGROUND

The transferrin receptor (TfR) is a cell membrane-associated glycoprotein involved in the cellular uptake of iron and in the regulation of cell growth. Iron uptake occurs via the internalization of iron-loaded transferrin (Tf) mediated by the interaction with the TfR. Transferrin receptor 1 (TfR1; also known as CD71 or p90) is a high affinity ubiquitously expressed receptor that plays an important role in muscle development and denervation-induced muscular atrophy (Li Y, et al. Neural Regen Res 2021; 16:1308-16). Given the prevalence of TfRs in muscle tissue, delivering drugs in vivo to muscle may be achieved by targeting of the TfRs (Schnyder A, et al. Biochem J. 2004 Jan. 1; 377(Pt 1):61-7). TfRs can be targeted by monoclonal antibodies specific for the extracellular domain of the receptor. (Daniels T R et al., Clin Immunol. 2006 November; 121(2):144-58).

Muscle targeting presents some specific challenges to both uptake in muscle and limiting uptake in other tissues. Muscular tissue is thought to be a difficult tissue for drug delivery due to the vascular endothelium in muscle that acts like a barrier to drug intake (Ebner D C et al., Current pharmaceutical design. 21. 10.2174/13816128206661 40929095755 and US20190240346).

Thus, there is a need to develop more efficient methods for drug delivery into muscles, such as novel and improved anti-TfR antibodies, which can be used for the treatment of a range of muscle-associated diseases, including muscular dystrophies and lysosomal storage diseases. In addition, such antibodies can also be used in gene therapy for non-muscle disorders. Given the prevalence of TfR1 expression in non-muscle tissue such as hepatocytes, tumor cells, immune cells, and endothelial cells of the blood brain barrier, there is also a need to develop antibodies to target these tissues, for drug delivery and/or therapeutic purposes.

SUMMARY

This disclosure relates to anti-transferrin receptor antibodies, and methods of their use, for the treatment of muscle disorders, arteriosclerotic diseases, cardiac-related diseases, and lysosomal storage disorders. The antibodies of the disclosure may also be used to target brain tissue, liver tissue, tumor cells and immune cells.

In a first aspect, this disclosure features an antibody that binds to human transferrin receptor, comprising a heavy chain variable region (VH) comprising VH complementarity determining region (CDR)1, VH CDR2, and VH CDR3, wherein: the VH CDR1 comprises the amino acid sequence GIDFSSSGYMX (SEQ ID NO:149), wherein X is any amino acid; the VH CDR2 comprises the amino acid sequence XIYTYSSNTYYAXXXKG (SEQ ID NO:151), wherein X is any amino acid; and the VH CDR3 comprises the amino acid sequence GTYGYTGYTYTMGYFSL (SEQ ID NO:106); and wherein the antibody comprises a light chain variable region (VL) comprising VL CDR1, VL CDR2, and VL CDR3, wherein: the VL CDR1 comprises the amino acid sequence QASQNINSYLA (SEQ ID NO:107); the VL CDR2 comprises the amino acid sequence RASXLXS (SEQ ID NO:153), wherein X is any amino acid; and the VL CDR3 comprises the amino acid sequence QSYYYSGSSNYNA (SEQ ID NO:110).

In some embodiments, the VH CDR1 comprises the amino acid sequence GIDFSSSGYMX$_1$ (SEQ ID NO:150), wherein X$_1$ is C, A, or H; the VH CDR2 comprises the amino acid sequence X$_2$IYTYSSNTYYAX$_3$X$_4$X$_5$KG (SEQ ID NO:152), wherein X$_2$ is C or A, wherein X$_3$ is S or A, wherein X$_4$ is W or S, and wherein X$_5$ is A or V; the VH CDR3 comprises the amino acid sequence GTYGYTGYTYTMGYFSL (SEQ ID NO:106); the VL CDR1 comprises the amino acid sequence QASQNINSYLA (SEQ ID NO:107); the VL CDR2 comprises the amino acid sequence RASX$_6$LX$_7$S (SEQ ID NO:154), wherein X$_6$ is T or S, and wherein X$_7$ is A or E; and the VL CDR3 comprises the amino acid sequence QSYYYSGSSNYNA (SEQ ID NO:110). In some embodiments, the VH-CDR1, the VH-CDR2, and the VH-CDR3 each correspond to the VH CDRs set forth in FIG. 1A for a single VH clone, and wherein the VL-CDR1, the VL-CDR2, and the VL-CDR3 each correspond to the VL CDRs set forth in FIG. 1C for a single VL clone. In some embodiments, the VH-CDR1, the VH-CDR2, the VH-CDR3, the VL-CDR1, the VL-CDR2, and the VL-CDR3 each correspond to the VH and VL CDRs set forth in Table 1A for a single clone.

In some embodiments, (a) the VH CDR1 comprises the amino acid sequence GIDFSSSGYMC (SEQ ID NO:101); the VH CDR2 comprises the amino acid sequence CIYTYSSNTYYASWAKG (SEQ ID NO:104); the VH CDR3 comprises the amino acid sequence GTYGYTGYTYTMGYFSL (SEQ ID NO:106); the VL CDR1 comprises the amino acid sequence QASQNINSYLA (SEQ ID NO:107); the VL CDR2 comprises the amino acid sequence RASTLAS (SEQ ID NO:109); and the VL CDR3 comprises the amino acid sequence QSYYYSGSSNYNA (SEQ ID NO:110); (b) the VH CDR1 comprises the amino acid sequence GIDFSSSGYMH (SEQ ID NO:102); the VH CDR2 comprises the amino acid sequence AIYTYSSNTYYASWAKG (SEQ ID NO:105); the VH CDR3 comprises the amino acid sequence GTYGYTGYTYTMGYFSL (SEQ ID NO:106); the VL CDR1 comprises the amino acid sequence QASQNINSYLA (SEQ ID NO:107); the VL CDR2 comprises the amino acid sequence RASSLES (SEQ ID NO:108); and the VL CDR3 comprises the amino acid sequence QSYYYSGSSNYNA (SEQ ID NO:110); (c) the VH CDR1 comprises the amino acid sequence GIDFSSSGYMC (SEQ ID NO:101); the VH CDR2 comprises the amino acid sequence CIYTYSSNTYYAASVKG (SEQ ID NO:103); the VH CDR3 comprises the amino acid sequence GTYGYTGYTYTMGYFSL (SEQ ID NO:106); the VL CDR1 comprises the amino acid sequence QASQNINSYLA (SEQ ID NO:107); the VL CDR2 comprises the amino acid sequence RASSLES (SEQ ID NO:108); and the VL CDR3 comprises the amino acid sequence QSYYYSGSSNYNA (SEQ ID NO:110); or (d) the VH CDR1 comprises the amino acid sequence GIDFSSSGYMC (SEQ ID NO:101); the VH CDR2 comprises the amino acid sequence CIYTYSSNTYYASWAKG (SEQ ID NO:104); the VH CDR3 comprises the amino acid sequence GTYGYTGYTYTMGYFSL (SEQ ID NO:106); the VL CDR1 comprises the amino acid sequence QASQNINSYLA (SEQ ID NO:107); the VL CDR2 comprises the amino acid sequence RASSLES (SEQ ID NO:108); and the VL CDR3 comprises the amino acid sequence QSYYYSGSSNYNA (SEQ ID NO:110).

In some embodiments, (i) the VH is at least 80%, 85%, 90%, 95%, 99%, or 100% identical to any one of SEQ ID NOs:12, or 15-18; and (ii) the VL is at least 80%, 85%, 90%, 95%, 99%, or 100% identical to any one of SEQ ID NOs:35-37. In some embodiments, the VH comprises the amino acid sequence of any one of SEQ ID NOs:4, 12, or 15-18 and the VL comprises the amino acid sequence of SEQ ID NOs:34-37.

In some embodiments, (a) the VH comprises the amino acid sequence of SEQ ID NO:4 and the VL comprises the amino acid sequence of SEQ ID NO:34; (b) the VH comprises the amino acid sequence of SEQ ID NO:12 and the VL comprises the amino acid sequence of SEQ ID NO:35; (c) the VH comprises the amino acid sequence of SEQ ID NO:15 and the VL comprises the amino acid sequence of SEQ ID NO:35; (d) the VH comprises the amino acid sequence of SEQ ID NO:16 and the VL comprises the amino acid sequence of SEQ ID NO:35; (e) the VH comprises the amino acid sequence of SEQ ID NO:17 and the VL comprises the amino acid sequence of SEQ ID NO:35; or (f) the VH comprises the amino acid sequence of SEQ ID NO:18 and the VL comprises the amino acid sequence of SEQ ID NO:35.

In a second aspect, the disclosure features an antibody that binds to human transferrin receptor and competes for binding to human transferrin receptor with an antibody comprising: (a) a VH comprising the amino acid sequence of SEQ ID NO:4 and a VL comprising the amino acid sequence of SEQ ID NO:34; (b) a VH comprising the amino acid sequence of SEQ ID NO:12 and a VL comprising the amino acid sequence of SEQ ID NO:35; (c) a VH comprising the amino acid sequence of SEQ ID NO:15 and a VL comprising the amino acid sequence of SEQ ID NO:35; (d) a VH comprising the amino acid sequence of SEQ ID NO:16 and a VL comprising the amino acid sequence of SEQ ID NO:35; (e) a VH comprising the amino acid sequence of SEQ ID NO:17 and a VL comprising the amino acid sequence of SEQ ID NO:35; or (f) a VH comprising the amino acid sequence of SEQ ID NO:18 and a VL comprising the amino acid sequence of SEQ ID NO:35.

In a third aspect, the disclosure features an antibody that binds to human transferrin receptor, comprising a heavy chain variable region (VH) comprising VH complementarity determining region (CDR)1, VH CDR2, and VH CDR3, wherein: the VH CDR1 comprises the amino acid sequence GFSFSNSYWIX (SEQ ID NO:155), wherein X is any amino acid; the VH CDR2 comprises the amino acid sequence XINTDADSTNYAXXXXG (SEQ ID NO:157), wherein X is any amino acid; and the VH CDR3 comprises the amino acid sequence QNNVFDPGYNL (SEQ ID NO:119); and wherein the antibody comprises a light chain variable region (VL) comprising VL CDR1, VL CDR2, and VL CDR3, wherein: the VL CDR1 comprises the amino acid sequence XASQNIGSNLA (SEQ ID NO:159); the VL CDR2 comprises the amino acid sequence DASKLXS (SEQ ID NO:161), wherein X is any amino acid; and the VL CDR3 comprises the amino acid sequence QXTVRGGAYGXA (SEQ ID NO:163), wherein X is any amino acid.

In some embodiments of the third aspect, the VH CDR1 comprises the amino acid sequence GFSFSNSYWIX$_1$ (SEQ ID NO:156), wherein X$_1$ is C, A, or H; the VH CDR2 comprises the amino acid sequence X$_2$INTDADSTNYAX$_3$X$_4$X$_5$X$_6$G (SEQ ID NO:158), wherein X$_2$ is C or A, wherein X$_3$ is S or D, wherein X$_4$ is W or S, wherein X$_5$ is A or V, and wherein X$_6$ is R or K; the VH CDR3 comprises the amino acid sequence QNNVFDPGYNL (SEQ ID NO:119); the VL CDR1 comprises the amino acid sequence X$_7$ASQNIGSNLA (SEQ ID NO:160), wherein X$_7$ is Q or R; the VL CDR2 comprises the amino acid sequence DASKLX$_8$S (SEQ ID NO:162), wherein X$_8$ is A or E; and the VL CDR3 comprises the amino acid sequence QX$_9$TVRGGAYGX$_{10}$A (SEQ ID NO:164), wherein X$_9$ is C, Q, A, S, T, or V, and wherein X$_{10}$ is N or L.

In some embodiments of the third aspect, the VH-CDR1, the VH-CDR2, and the VH-CDR3 each correspond to the VH CDRs set forth in FIG. 1B for a single VH clone, and wherein the VL-CDR1, the VL-CDR2, and the VL-CDR3 each correspond to the VL CDRs set forth in FIG. 1D for a single VL clone. In some embodiments of the third aspect, the VH-CDR1, the VH-CDR2, the VH-CDR3, the VL-CDR1, the VL-CDR2, and the VL-CDR3 each correspond to the VH and VL CDRs set forth in Table 2A for a single clone.

In some embodiments of the third aspect, (a) the VH CDR1 comprises the amino acid sequence GFSFSNSYWIC (SEQ ID NO:116); the VH CDR2 comprises the amino acid sequence CINTDADSTNYASWARG (SEQ ID NO:117); the VH CDR3 comprises the amino acid sequence QNNVFDPGYNL (SEQ ID NO:119); the VL CDR1 comprises the amino acid sequence QASQNIGSNLA (SEQ ID NO:121); the VL CDR2 comprises the amino acid sequence DASKLAS (SEQ ID NO:123); and the VL CDR3 comprises the amino acid sequence QCTVRGGAYGNA (SEQ ID NO:124); (b) the VH CDR1 comprises the amino acid sequence GFSFSNSYWIC (SEQ ID NO:116); the VH CDR2 comprises the amino acid sequence CINTDADSTNYADSVKG (SEQ ID NO:118); the VH CDR3 comprises the amino acid sequence QNNVFDPGYNL (SEQ ID NO:119); the VL CDR1 comprises the amino acid sequence RASQNIGSNLA (SEQ ID NO:120); the VL CDR2 comprises the amino acid sequence DASKLES (SEQ ID NO:122); and the VL CDR3 comprises the amino acid sequence QCTVRGGAYGNA (SEQ ID NO:124); (c) the VH CDR1 comprises the amino acid sequence GFSFSNSYWIC (SEQ ID NO:116); the VH CDR2 comprises the amino acid sequence CINTDADSTNYASWARG (SEQ ID NO:117); the VH CDR3 comprises the amino acid sequence QNNVFDPGYNL (SEQ ID NO:119); the VL CDR1 comprises the amino acid sequence RASQNIGSNLA (SEQ ID NO:120); the VL CDR2 comprises the amino acid sequence DASKLES (SEQ ID NO:122); and the VL CDR3 comprises the amino acid sequence QCTVRGGAYGNA (SEQ ID NO:124); (d) the VH CDR1 comprises the amino acid sequence GFSFSNSYWIC (SEQ ID NO:116); the VH CDR2 comprises the amino acid sequence CINTDADSTNYASWARG (SEQ ID NO:117); the VH CDR3 comprises the amino acid sequence QNNVFDPGYNL (SEQ ID NO:119); the VL CDR1 comprises the amino acid sequence RASQNIGSNLA (SEQ ID NO:120); the VL CDR2 comprises the amino acid sequence DASKLES (SEQ ID NO:122); and the VL CDR3 comprises the amino acid sequence QSTVRGGAYGNA (SEQ ID NO:125); (e) the VH CDR1 comprises the amino acid sequence GFSFSN-SYWIC (SEQ ID NO:116); the VH CDR2 comprises the amino acid sequence CINTDADSTNYASWARG (SEQ ID NO:117); the VH CDR3 comprises the amino acid sequence QNNVFDPGYNL (SEQ ID NO:119); the VL CDR1 comprises the amino acid sequence RASQNIGSNLA (SEQ ID NO:120); the VL CDR2 comprises the amino acid sequence DASKLES (SEQ ID NO:122); and the VL CDR3 comprises the amino acid sequence QTTVRGGAYGNA (SEQ ID NO:126); or (f) the VH CDR1 comprises the amino acid sequence GFSFSNSYWIC (SEQ ID NO:116); the VH CDR2 comprises the amino acid sequence CINTDAD-STNYASWARG (SEQ ID NO:117); the VH CDR3 comprises the amino acid sequence QNNVFDPGYNL (SEQ ID NO:119); the VL CDR1 comprises the amino acid sequence RASQNIGSNLA (SEQ ID NO:120); the VL CDR2 comprises the amino acid sequence DASKLES (SEQ ID NO:122); and the VL CDR3 comprises the amino acid sequence QVTVRGGAYGNA (SEQ ID NO:127).

In some embodiments of the third aspect, (i) the VH is at least 80%, 85%, 90%, 95%, 99%, or 100% identical to any one of SEQ ID NOs:30-33; and (ii) the VL is at least 80%, 85%, 90%, 95%, 99%, or 100% identical to any one of SEQ ID NOs:41-44. In some embodiments, the VH comprises the amino acid sequence of any one of SEQ ID NOs:30-33 and the VL comprises the amino acid sequence of any one of SEQ ID NOs: 41-44.

In some embodiments of the third aspect, (a) the VH comprises the amino acid sequence of SEQ ID NO:19 and the VL comprises the amino acid sequence of SEQ ID NO:38; (b) the VH comprises the amino acid sequence of SEQ ID NO:30 and the VL comprises the amino acid sequence of SEQ ID NO:41; (c) the VH comprises the amino acid sequence of SEQ ID NO:31 and the VL comprises the amino acid sequence of SEQ ID NO:41; (d) the VH comprises the amino acid sequence of SEQ ID NO:32 and the VL comprises the amino acid sequence of SEQ ID NO:41; (e) the VH comprises the amino acid sequence of SEQ ID NO:33 and the VL comprises the amino acid sequence of SEQ ID NO:41; (f) the VH comprises the amino acid sequence of SEQ ID NO:33 and the VL comprises the amino acid sequence of SEQ ID NO:42; (g) the VH comprises the amino acid sequence of SEQ ID NO:33 and the VL comprises the amino acid sequence of SEQ ID NO:43; or (h) the VH comprises the amino acid sequence of SEQ ID NO:33 and the VL comprises the amino acid sequence of SEQ ID NO:44.

In a fourth aspect, the disclosure features an antibody that binds to human transferrin receptor and competes for binding to human transferrin receptor with an antibody comprising: (a) a VH comprising the amino acid sequence of SEQ ID NO:19 and a VL comprising the amino acid sequence of SEQ ID NO:38; (b) a VH comprising the amino acid sequence of SEQ ID NO:30 and a VL comprising the amino acid sequence of SEQ ID NO:41; (c) a VH comprising the amino acid sequence of SEQ ID NO:31 and a VL comprising the amino acid sequence of SEQ ID NO:41; (d) a VH comprising the amino acid sequence of SEQ ID NO:32 and a VL comprising the amino acid sequence of SEQ ID NO:41; (e) a VH comprising the amino acid sequence of SEQ ID NO:33 and a VL comprising the amino acid sequence of SEQ ID NO:41; (f) a VH comprising the amino acid sequence of SEQ ID NO:33 and a VL comprising the amino acid sequence of SEQ ID NO:42; (g) a VH comprising the amino acid sequence of SEQ ID NO:33 and a VL comprising the amino acid sequence of SEQ ID NO:43; or (h) a VH comprising the amino acid sequence of SEQ ID NO:33 and a VL comprising the amino acid sequence of SEQ ID NO:44.

In some embodiments of any of the above aspects, the antibody is an Fab fragment or an Fab' fragment. In some embodiments, the antibody is a bispecific antibody, single chain antibody, an Fab fragment, an F(ab')$_2$ fragment, an Fab' fragment, an Fsc fragment, an Fv fragment, an scFv, an sc(Fv)$_2$, or a diabody.

In some embodiments, the antibody comprises a constant heavy chain (CH) domain and a constant light chain (CL) domain. In some embodiments, the CH domain comprises a CH1 domain comprising the amino acid sequence set forth in any one of SEQ ID NOs:45-52. In some embodiments, the CH1 domain comprises the amino acid sequence set forth in any one of SEQ ID NOs:45, 47, and 49. In some embodiments, the CH1 domain is fused to a hinge comprising the amino acid sequence set forth in any one of SEQ ID NOs:53-55 and 57. In some embodiments, the CH1 domain comprises the amino acid sequence set forth in SEQ ID NO:51. In some embodiments, the CH1 domain is fused to a hinge comprising the amino acid sequence ES or the amino acid sequence set forth in SEQ ID NO:56. In some embodiments, the antibody the CH1 domain is fused to a hinge comprising the amino acid sequence ES, ESK, or the amino acid sequence set forth in any one of SEQ ID NOs: 53-90. In some embodiments, the CL domain comprises the amino acid sequence set forth in SEQ ID NO:91 or 92.

In some embodiments, the antibody comprises: (i) a heavy chain comprising the amino acid sequence set forth in SEQ ID NO:93, and a light chain comprising the amino acid sequence set forth in SEQ ID NO:94; (ii) a heavy chain comprising the amino acid sequence set forth in SEQ ID NO:95, and a light chain comprising the amino acid sequence set forth in SEQ ID NO:96; (iii) a heavy chain comprising the amino acid sequence set forth in SEQ ID NO:97, and a light chain comprising the amino acid sequence set forth in SEQ ID NO:96; (iv) a heavy chain comprising the amino acid sequence set forth in SEQ ID NO:98, and a light chain comprising the amino acid sequence set forth in SEQ ID NO:96; or (v) a heavy chain comprising the amino acid sequence set forth in SEQ ID NO:99, and a light chain comprising the amino acid sequence set forth in SEQ ID NO:100.

In another aspect, the disclosure features an antibody that binds to human transferrin receptor at an epitope located wholly or partially within amino acids K231-E369 of SEQ ID NO:1. In some embodiments, the antibody binds to one or more residues selected from the group consisting of residues K231, D245, L246, Y247, T248, P249, E350, G351, D352, C353, P354, 5355, D356, K358, T359, D360, S361, R364, M365, V366, T367, and E369 of SEQ ID NO:1. In some embodiments, the antibody binds to one or more amino acids within SEQ ID NO:1 selected from the group consisting of K231, D245 to P249, E244 to V250, E350 to S361, M349 to T362, R364 to E369, and C363 to 5370.

In another aspect, the disclosure features an antibody that binds to human transferrin receptor at an epitope located wholly or partially within amino acids D139-K145 and G490-E582 of SEQ ID NO:1. In some embodiments, the antibody binds to one or more residues selected from the group consisting of residues D139, T141, K145, G490, T491, V517, T518, Y573, K574, I577, E578, R579, I580, P581, and E582 of SEQ ID NO:1. In some embodiments, the antibody binds to one or more amino acids within any of the following sequences: D139 to E369, D139 to E582, T141 to E369, T141 to E582, K145 to E369, K145 to E582, K231 to E369, K231 to E582, D245 to E369, D245 to E582, E350 to E369, E350 to E582, K358 to E369, K358 to E582, R364 to E369, R364 to E582, G490 to E582, V517 to E582, K573 to E582, I577 to E582, or Y573 to E582 of SEQ ID NO:1. In some embodiments, the antibody binds to one or more amino acids within any of the following sequences: D139 to T141, D139 to K145, T141 to K145, T138 to K145, T138 to L146, G490 to T491, L489 to T491, L489 to 5492, V517 to T518, P516 to T518, P516 to G519, Y573 to E582, Y573 to L583, T572 to E582, or T572 to L583 of SEQ ID NO:1.

In another aspect, the disclosure features a nucleic acid or nucleic acids encoding the antibody of any one of the above aspects. In yet another aspect, the disclosure features an expression vector or expression vectors comprising the nucleic acid or nucleic acids operably linked to a promoter. In another aspect, the disclosure features an isolated cell comprising the nucleic acid or nucleic acids, or the expression vector or expression vectors.

In another aspect, the disclosure features an isolated cell comprising a first expression vector comprising a first nucleic acid encoding a first polypeptide comprising the VH of the antibody of the disclosure operably linked to a promoter, and a second expression vector comprising a second nucleic acid encoding a second polypeptide comprising the VL of the antibody of the disclosure operably linked to a promoter.

In yet another aspect, the disclosure features method of making the antibody of the disclosure, comprising culturing the cell of the disclosure and isolating the antibody. In another aspect, the disclosure features a pharmaceutical composition comprising the antibody of the disclosure and a pharmaceutically acceptable carrier. In another aspect, the disclosure features a conjugate comprising the antibody of the disclosure and an agent.

In some embodiments, the agent is a nucleic acid. In some embodiments, the nucleic acid is an mRNA, a siRNA, an antisense oligonucleotide, microRNA (miRNA), guide RNA (gRNA), or a phosphoroamidate morpholino oligomer (PMO). In some embodiments, the nucleic acid is an antisense oligonucleotide. In some embodiments, the agent is linked to the antibody via a linker.

In another aspect, the disclosure features a method of delivering an agent in vivo, the method comprising administering to a human subject the conjugate of the disclosure. In some embodiments (a) the human subject has a muscular disease, a muscular atrophy disease, an arteriosclerotic disease, a cardiac-related disease, or a lysosomal storage disease, and the method delivers the agent to muscle tissue; (b) the human subject has a neurological disorder (e.g., a brain disease) and the method delivers the agent to brain tissue; (c) the human subject has a hepatic disease and the method delivers the agent to hepatocytes; (d) the human subject has cancer and the method delivers the agent to tumor cells; or (e) the human subject has an immune condition and the method delivers the agent to immune cells.

BRIEF DESCRIPTION OF THE DRAWINGS

Figures 1A, 1B:
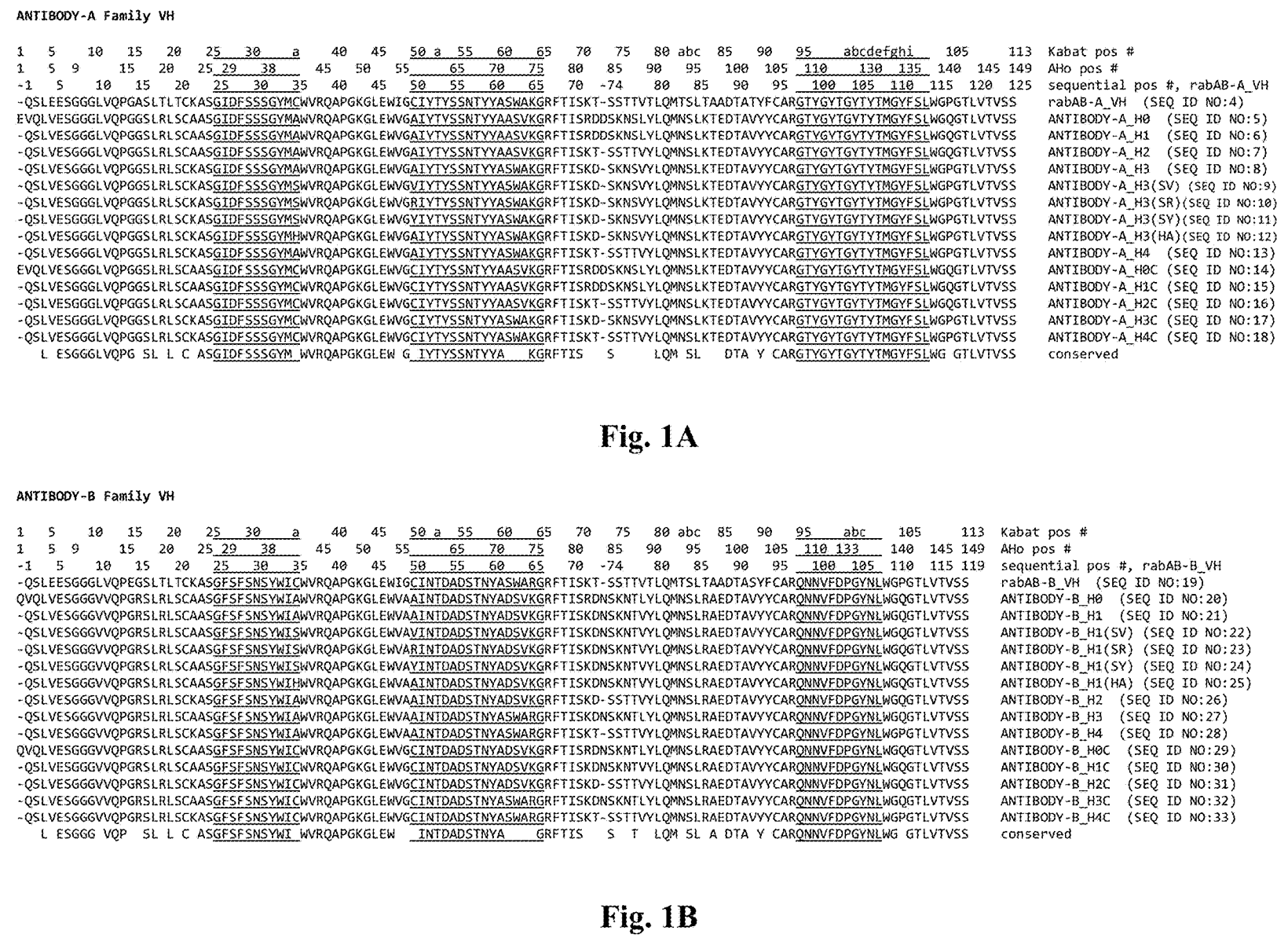

FIGS. 1A-1D are alignments of VH and VL sequences of the ANTIBODY-A and ANTIBODY-B anti-TfR1 antibody families with Union CDRs (underlined).

Figures 2A, 2B:
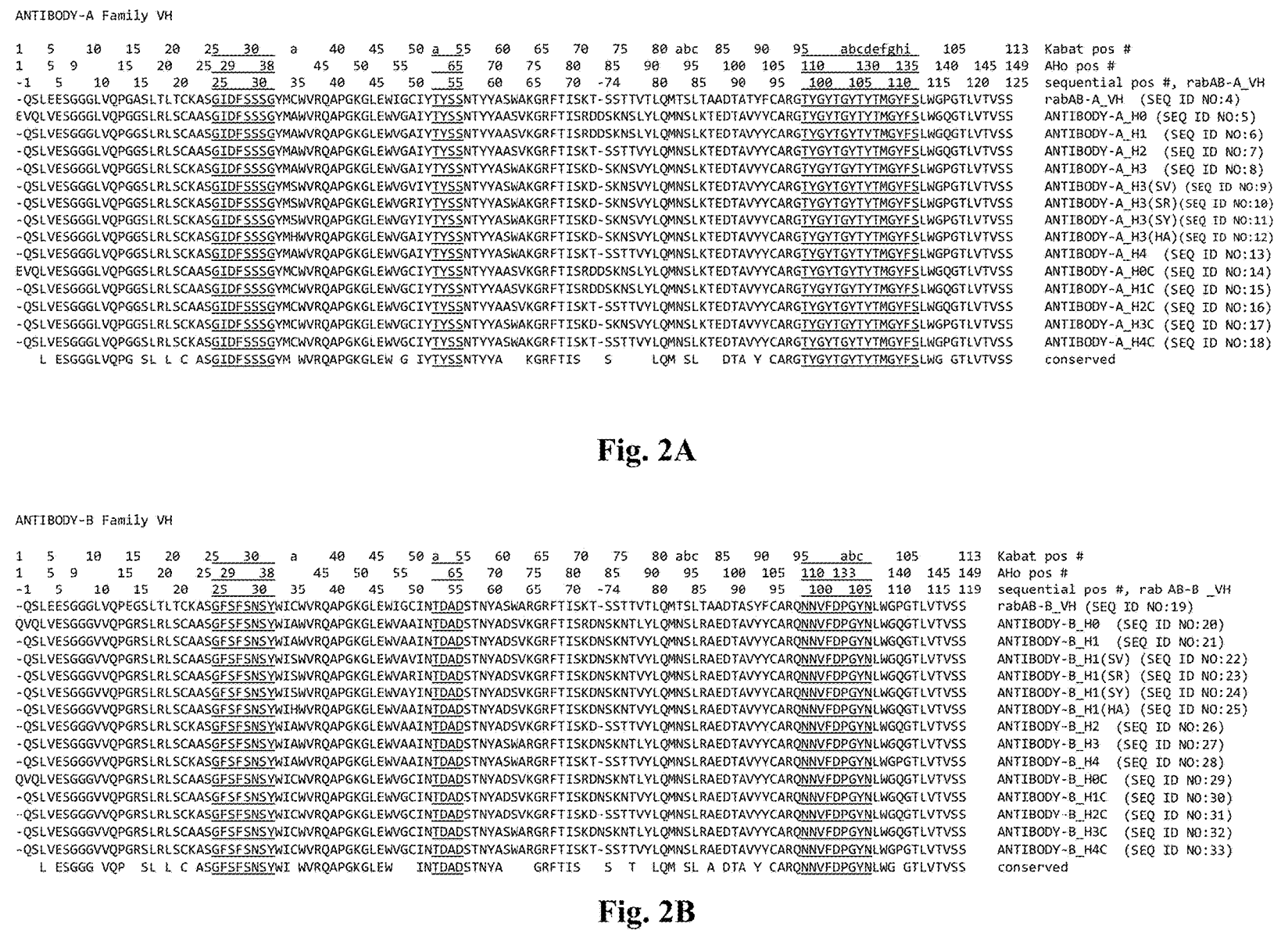

FIGS. 2A-2D are alignments of VH and VL sequences of the ANTIBODY-A and ANTIBODY-B anti-TfR1 antibody families with Chothia CDRs (underlined).

FIG. 3 is an atomic model of humanized ANTIBODY-A Fab bound to the human transferrin receptor in the presence of the endogenous ligand transferrin built into the cryo-EM density at 3.4 Å resolution.

FIG. 4 is a partial alignment of transferrin receptor apical domain sequences with ANTIBODY-A epitope. The residues within 5 Å of ANTIBODY-A Fab, as observed in the cryo-EM structure of ANTIBODY-A bound to the human transferrin receptor ectodomain, are highlighted in grey. Epitope residues that differ from human transferrin receptor are in bold. Strictly conserved residues are denoted by asterisk, strongly conserved residues by colon, and moderately conserved residues by period. Sources of sequences: Human (*Homo sapiens*, Uniprot P02786.2); Cynomolgus (*Macaca fascicularis*, Uniprot G8F602); Mouse (*Mus musculus*, GenBank NP_035768.1).

DETAILED DESCRIPTION

Figure 5:
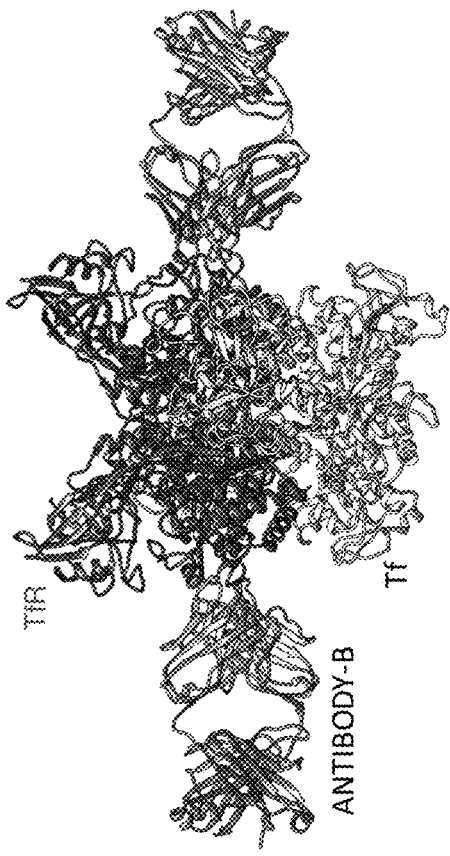
FIG. 5 is an atomic model of humanized ANTIBODY-B Fab bound to the human transferrin receptor in the presence of the endogenous ligand transferrin built into the cryo-EM density at 3.96 Å resolution.

The present disclosure provides antibodies that specifically bind transferrin receptor 1 (TfR1). Related polypeptides, polynucleotides, vectors, cells, compositions and conjugates comprising the antibodies, methods of making the antibodies, and methods of delivering the compositions and conjugates are also provided. The disclosure also provides methods of using the novel anti-TfR antibodies.

Definitions

Unless otherwise defined herein, technical and scientific terms used in the present description have the meanings that are commonly understood by those of ordinary skill in the art. For purposes of interpreting this specification, the following description of terms will apply and whenever appropriate, terms used in the singular will also include the plural and vice versa. In the event that any description of a term set forth conflicts with any document incorporated herein by reference, the description of the term set forth below shall control.

The term "antibody" as used herein refers to an immunoglobulin molecule that recognizes and binds a target through at least one antigen-binding site. "Antibody" is used herein in the broadest sense and encompasses various antibody structures, including "antibody fragments" and "antigen-binding fragments." Thus, the term "antibody" includes, but is not limited to, recombinant antibodies, monoclonal antibodies, chimeric antibodies, humanized antibodies, human antibodies, bispecific antibodies, multispecific antibodies, diabodies, tribodies, tetrabodies, single chain Fv (scFv) antibodies, and antibody fragments as long as they exhibit the desired antigen-binding activity.

The term "intact antibody" or "full-length antibody" refers to an antibody having a structure substantially similar to a native antibody structure. This includes, for example, an antibody comprising two light chains each comprising a variable region and a light chain constant region (CL) and two heavy chains each comprising a variable region and at least heavy chain constant regions CH1, CH2, and CH3 and a hinge region between CH1 and CH2 regions.

The term "antigen-binding fragment", as used herein refers to a molecule other than an intact antibody that comprises a portion of an antibody and an antigen-binding site. Examples of antibody fragments include, but are not limited to, Fab, Fab', F(ab')$_2$, Fv, single chain antibody molecules (e.g., scFv, sc(Fv)$_2$), disulfide-linked scFv (dss-cFv), diabodies, tribodies, tetrabodies, minibodies, dual variable domain antibodies (DVD), single variable domain antibodies (e.g., camelid antibodies), and multispecific antibodies formed from antibody fragments.

The term "monoclonal antibody" as used herein refers to a substantially homogenous antibody population involved in the highly specific recognition and binding of a single antigenic determinant or epitope. The term "monoclonal antibody" encompasses intact and full-length monoclonal antibodies as well as antibody fragments (e.g., Fab, Fab', F(ab')$_2$, Fv), single chain antibodies (e.g., scFv), fusion proteins comprising an antibody fragment, and any other modified immunoglobulin molecule comprising at least one antigen-binding site. Furthermore, "monoclonal antibody" refers to such antibodies made by any number of techniques, including but not limited to, hybridoma production, phage library display, recombinant expression, and transgenic animals.

The term "chimeric antibody" refers to an antibody in which a portion of the heavy and/or light chain is derived from a first source or species, while the remainder of the heavy and/or light chain is derived from a different source or species.

The term "humanized antibody" as used herein refers to an antibody that comprises a human heavy chain variable region and a light chain variable region wherein the native CDR amino acid residues are replaced by residues from corresponding CDRs from a nonhuman antibody (e.g., mouse, rat, rabbit, or nonhuman primate), wherein the nonhuman antibody has the desired specificity, affinity, and/or activity. In some embodiments, one or more framework region amino acid residues of the human heavy chain or light chain variable regions are replaced by corresponding residues from nonhuman antibody. Furthermore, humanized antibodies can comprise amino acid residues that are not found in the human antibody or in the nonhuman antibody. In some embodiments, these modifications are made to further refine and/or optimize antibody characteristics. In some embodiments, the humanized antibody comprises at least a portion of an immunoglobulin constant region (e.g., CH1, hinge, CH2, CH3, Fc), typically that of a human immunoglobulin.

The term "human antibody" as used herein refers to an antibody that possesses an amino acid sequence that corresponds to an antibody produced by a human and/or an antibody that has been made using any of the techniques that are known to those of skill in the art for making human antibodies. These techniques include, but are not limited to, phage display libraries, yeast display libraries, transgenic animals, recombinant protein production, and B-cell hybridoma technology.

The terms "epitope" and "antigenic determinant" are used interchangeably herein and refer to that portion of an antigen or target capable of being recognized and bound by a particular antibody. When the antigen or target is a polypeptide, epitopes can be formed both from contiguous amino acids and noncontiguous amino acids juxtaposed by tertiary folding of the protein. Epitopes formed from contiguous amino acids (also referred to as linear epitopes) are typically retained upon protein denaturing, whereas epitopes formed by tertiary folding (also referred to as conformational epitopes) are typically lost upon protein denaturing. An epitope typically includes at least 3, and more usually, at least 5, 6, 7, or 8-10 amino acids in a unique spatial conformation. Epitopes can be predicted using any one of a large number of software bioinformatic tools available on the internet. X-ray crystallography or electron microscopy (e.g., cryo-electron microscopy) may be used to characterize an epitope on a target protein by analyzing the amino acid residue interactions of an antigen/antibody complex.

The term "specifically binds" or "binds" as used herein refers to an antibody that interacts more frequently, more rapidly, with greater duration, with greater affinity, or with some combination of the above to a particular antigen, epitope, protein, or target molecule than with alternative substances. An antibody that specifically binds an antigen can be identified, for example, by immunoassays, ELISAs, surface plasmon resonance (SPR), or other techniques known to those of skill in the art. In some embodiments, an antibody that specifically binds an antigen (e.g., human TfR1) can bind related antigens (e.g., cyno TfR1). An antibody that specifically binds an antigen can bind the target antigen at a higher affinity than its affinity for a different antigen. The different antigen can be a related antigen. In some embodiments, an antibody that specifically binds an antigen can bind the target antigen with an affinity that is at least 20 times greater, at least 30 times greater, at least 40 times greater, at least 50 times greater, at least 60 times greater, at least 70 times greater, at least 80 times greater, at least 90 times greater, or at least 100 times greater, than its affinity for a different antigen. In some embodiments, an antibody that specifically binds a particular antigen binds a different antigen at such a low affinity that binding cannot be detected using an assay described herein or otherwise known in the art. In some embodiments, affinity is measured using SPR technology in a Biacore system as described herein or as known to those of skill in the art.

The terms "polypeptide" and "peptide" and "protein" are used interchangeably herein and refer to polymers of amino acids of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification. Also included within the definition are, for example, polypeptides containing one or more analogs of an amino acid, including but not limited to, unnatural amino acids, as well as other modifications known in the art. It is understood that, because the polypeptides of this disclosure may be based upon antibodies, the term "polypeptide" encompasses polypeptides as a single chain and polypeptides of two or more associated chains.

The terms "polynucleotide" and "nucleic acid" and "nucleic acid molecule" are used interchangeably herein and refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase.

The terms "identical" or percent "identity" in the context of two or more nucleic acids or polypeptides, refer to two or more sequences or subsequences that are the same or have a specified percentage of nucleotides or amino acid residues that are the same, when compared and aligned (introducing gaps, if necessary) for maximum correspondence, not considering any conservative amino acid substitutions as part of the sequence identity. The percent identity may be measured using sequence comparison software or algorithms or by visual inspection. Various algorithms and software that may be used to obtain alignments of amino acid or nucleotide sequences are well-known in the art. These include, but are not limited to, BLAST, ALIGN, Megalign, BestFit, GCG Wisconsin Package, and variants thereof. In some embodiments, two nucleic acids or polypeptides of the disclosure are substantially identical, meaning they have at least 70%, at least 75%, at least 80%, at least 85%, at least 90%, and in some embodiments at least 95%, 96%, 97%, 98%, 99% nucleotide or amino acid residue identity, when compared and aligned for maximum correspondence, as measured using a sequence comparison algorithm or by visual inspection. In some embodiments, identity exists over a region of the sequences that is at least about 10, at least about 20, at least about 20-40, at least about 40-60 nucleotides or amino acid residues, at least about 60-80 nucleotides or amino acid residues in length or any integral value there between. In some embodiments, identity exists over a longer region than 60-80 nucleotides or amino acid residues, such as at least about 80-100 nucleotides or amino acid residues, and in some embodiments the sequences are substantially identical over the full length of the sequences being compared, for example, (i) the coding region of a nucleotide sequence or (ii) an amino acid sequence.

The phrase "conservative amino acid substitution" as used herein refers to a substitution in which one amino acid residue is replaced with another amino acid residue having a similar side chain. Families of amino acid residues having similar side chains have been generally defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). For example, substitution of a phenylalanine for a tyrosine is considered to be a conservative substitution. Generally, conservative substitutions in the sequences of polypeptides and/or antibodies do not abrogate the binding of the polypeptide or antibody to the target binding site. Methods of identifying nucleotide and amino acid conservative substitutions that do not eliminate binding are well-known in the art.

The term "vector" as used herein means a construct that is capable of delivering, and usually expressing, one or more gene(s) or sequence(s) of interest in a host cell. Examples of vectors include, but are not limited to, viral vectors, naked DNA or RNA expression vectors, wplasmid, cosmid, or phage vectors, DNA or RNA expression vectors associated with cationic condensing agents, and DNA or RNA expression vectors encapsulated in liposomes.

The term "isolated" as used herein refers to a polypeptide, soluble protein, antibody, polynucleotide, vector, cell, or composition that is in a form not found in nature. An "isolated" antibody is substantially free of material from the cellular source from which it is derived. In some embodiments, isolated polypeptides, soluble proteins, antibodies, polynucleotides, vectors, cells, or compositions are those that have been purified to a degree that they are no longer in a form in which they are found in nature. In some embodiments, a polypeptide, soluble protein, antibody, polynucleotide, vector, cell, or composition that is isolated is substantially pure. A polypeptide, soluble protein, antibody, polynucleotide, vector, cell, or composition can be isolated from a natural source (e.g., tissue) or from a source such as an engineered cell line. The term "substantially pure" as used herein refers to material that is at least 50% pure (i.e., free from contaminants), at least 90% pure, at least 95% pure, at least 98% pure, or at least 99% pure.

The term "pharmaceutically acceptable" as used herein refers to a substance approved or approvable by a regulatory agency or listed in the U.S. Pharmacopeia, European Pharmacopeia, or other generally recognized pharmacopeia for use in animals, including humans.

The terms "pharmaceutically acceptable excipient, carrier, or adjuvant" as used herein refer to an excipient, carrier, or adjuvant that can be administered to a subject, together with at least one antibody of the disclosure, and that is generally safe, non-toxic, and has no effect on the pharmacological activity of the therapeutic agent. In general, those of skill in the art and the U.S. FDA consider a pharmaceutically acceptable excipient, carrier, or adjuvant to be an inactive ingredient of any formulation.

The term "pharmaceutical composition" as used herein refers to a preparation that is in such form as to permit the biological activity of the antibody to be effective. A pharmaceutical formulation or composition generally comprises additional components, such as a pharmaceutically acceptable excipient, carrier, adjuvant, buffers, etc.

The term "conjugate" as used herein refers to a combination in which two substances are linked by a covalent bond (e.g., an antibody of the disclosure joined to a therapeutic agent). In the conjugate, the two substances may be directly connected or may be connected via a linker. In the present disclosure, one of the two substances is an antibody of the disclosure, and the other is a drug (for example, a physiologically active substance). The linker may be a cleavable linker or a non-cleavable linker.

The term "effective amount" or "therapeutically effective amount" as used herein refers to an amount of an antibody of the disclosure that is required to reach the tissue of interest, or to an amount of a conjugate, a fusion protein or polypeptide, or a complex comprising an antibody of the disclosure and a therapeutic agent that is sufficient to reduce and/or ameliorate the severity and/or duration of (i) a disease, disorder or condition in a subject, and/or (ii) a symptom in a subject. The term also encompasses an amount of a conjugate necessary for the (i) reduction or amelioration of the advancement or progression of a given disease, disorder, or condition, (ii) reduction or amelioration of the recurrence, development, or onset of a given disease, disorder, or condition, and/or (iii) the improvement or enhancement of the prophylactic or therapeutic effect(s) of another agent or therapy (e.g., an agent other than the conjugates provided herein).

The term "therapeutic effect" as used herein refers to the effect and/or ability of an agent, e.g., an antibody, a conjugate, a fusion protein or polypeptide, or a complex comprising the antibody of the disclosure to reduce and/or ameliorate the severity and/or duration of (i) a disease, disorder, or condition in a subject, and/or (ii) a symptom in a subject. The term also encompasses the ability of an agent, e.g., a conjugate, to (i) reduce or ameliorate the advancement or progression of a given disease, disorder, or condition, (ii) reduce or ameliorate the recurrence, development, or onset of a given disease, disorder, or condition, and/or (iii) to improve or enhance the prophylactic or therapeutic effect(s) of another agent or therapy (e.g., an agent other than the conjugates provided herein).

As used herein, reference to "about" or "approximately" a value or parameter includes (and describes) embodiments that are directed to that value or parameter. For example, a description referring to "about X" includes description of "X". "About X" means +/−10% of X. So, "about 10" means a value between 9 to 11.

TfR1 and Anti-TfR1 Antibodies

Transferrin receptor, also known as CD71, is a transmembrane glycoprotein expressed in various sites of the human body at differing levels, whose function is to mediate cellular uptake of iron from a plasma glycoprotein, transferrin. Iron uptake from transferrin involves the binding of transferrin to the transferrin receptor, internalization of transferrin within an endocytic vesicle by receptor-mediated endocytosis and the release of iron from the protein by a decrease in endosomal pH. Ponka P, Lok C N. Int J Biochem Cell Biol. 1999 October; 31(10):1111-37 and Xiaopeng Mo, in Brain Targeted Drug Delivery System, 2019. TfR is highly expressed in muscle (e.g., myocardium and gastrocnemius). Apotransferrin (ie, non-iron conjugate) binds to TfR when bound to two $Fe^{3+}$ ions to form holotransferrin (ie, iron conjugate). The complex of TfR and holotransferrin is translocated into the cell by receptor-mediated endocytosis. CD71 and transferrin dissociate in an endosomal environment, and transferrin moves into the cell while CD71 is recycled to the cell membrane. Thus, transferrin is thought to translocate into cells by proper binding to TfR and proper dissociation. The transferrin receptor system has been exploited for delivery of anticancer drugs and proteins, therapeutic genes into malignant cells, and to deliver other therapeutic agents across the blood brain barrier to the brain.

In humans and cynomolgus monkeys, two transferrin receptors, TfR1 and TfR2 have been characterized. TfR1 is a high affinity ubiquitously expressed receptor while expression of TfR2 is restricted to certain cell types and is unaffected by intracellular iron concentrations. TfR2 binds to transferrin with a 25-30 fold lower affinity than TfR1. The antibodies of the present disclosure bind to TfR1.

Representative amino acid (aa) sequences for human TfR1 (UniProt No. P02786.2); cynomolgus monkey TfR1 ("cyno" TfR1 (Genbank No. XP 005545315.1); and mouse TfR1 (Genbank No. NP_035768.1) are provided herein as SEQ ID NO: 1, SEQ ID NO: 2, and SEQ ID NO: 3 respectively. As used herein, reference to amino acid positions of TfR1 refer to the numbering of amino acid sequences including the signal sequence. The sequences for human TfR1, cyno TfR1, and mouse TfR1 are as follows:

```
Human TfR1 (UniProtNo. P02786.2; SEQ ID NO: 1)
MMDQARSAFSNLFGGEPLSYTRFSLARQVDGDNSHVEMKLAVDEEENADNNTKANVTKPKRC

SGSICYGTIAVIVFFLIGFMIGYLGYCKGVEPKTECERLAGTESPVREEPGEDFPAARRLYWDDLK

RKLSEKLDSTDFTGTIKLLNENSYVPREAGSQKDENLALYVENQFREFKLSKVWRDQHFVKIQV

KDSAQNSVIIVDKNGRLVYLVENPGGYVAYSKAATVTGKLVHANFGTKKDFEDLYTPVNGSIVI

VRAGKITFAEKVANAESLNAIGVLIYMDQTKFPIVNAELSFFGHAHLGTGDPYTPGFPSFNHTQFP

PSRSSGLPNIPVQTISRAAAEKLFGNMEGDCPSDWKTDSTCRMVTSESKNVKLTVSNVLKEIKILN

IFGVIKGFVEPDHYVVVGAQRDAWGPGAAKSGVGTALLLKLAQMFSDMVLKDGFQPSRSIIFAS

WSAGDFGSVGATEWLEGYLSSLHLKAFTYINLDKAVLGTSNFKVSASPLLYTLIEKTMQNVKHP

VTGQFLYQDSNWASKVEKLTLDNAAFPFLAYSGIPAVSFCFCEDTDYPYLGTTMDTYKELIERIP

ELNKVARAAAEVAGQFVIKLTHDVELNLDYERYNSQLLSFVRDLNQYRADIKEMGLSLQWLYS

ARGDFFRATSRLTTDFGNAEKTDRFVMKKLNDRVMRVEYHFLSPYVSPKESPFRHVFWGSGSHT

LPALLENLKLRKQNNGAFNETLFRNQLALATWTIQGAANALSGDVWDIDNEF
```

Cyno TfR1 (UniProtNo. G8F602; SEQ ID NO: 2)
MMDQARSAFSNLFGGEPLSYTRFSLARQVDGDNSHVEMKLAVDDEENADNNTKANGTKPKRC

GGNICYGTIAVIIFFLIGFMIGYLGYCKGVEPKTECERLAGTESPAREEPEEDFPAAPRLYWDDLK

RKLSEKLDTTDFTSTIKLLNENLYVPREAGSQKDENLALYIENQFREFKLSKVWRDQHFVKIQVK

DSAQNSVIIVDKNGGLVYLVENPGGYVAYSKAATVTGKLVHANFGTKKDFEDLDSPVNGSIVIV

RAGKITFAEKVANAESLNAIGVLIYMDQTKFPIVKADLSFFGHAHLGTGDPYTPGFPSFNHTQFPP

SQSSGLPNIPVQTISRAAAEKLFGNMEGDCPSDWKTDSTCKMVTSENKSVKLTVSNVLKETKILN

IFGVIKGFVEPDHYVVVGAQRDAWGPGAAKSSVGTALLLKLAQMFSDMVLKDGFQPSRSIIFAS

WSAGDFGSVGATEWLEGYLSSLHLKAFTYINLDKAVLGTSNFKVSASPLLYTLIEKTMQDVKHP

VTGRSLYQDSNWASKVEKLTLDNAAFPFLAYSGIPAVSFCFCEDTDYPYLGTTMDTYKELVERIP

ELNKVARAAAEVAGQFVIKLTHDTELNLDYERYNSQLLLFLRDLNQYRADVKEMGLSLQWLYS

ARGDFFRATSRLTTDFRNAEKRDKFVMKKLNDRVMRVEYYFLSPYVSPKESPFRHVFWGSGSH

TLSALLESLKLRRQNNSAFNETLFRNQLALATWTIQGAANALSGDVWDIDNEF

Mouse TfR1 (Genbank No. NP_035768.1; SEQ ID NO: 3)
MMDQARSAFSNLFGGEPLSYTRFSLARQVDGDNSHVEMKLAADEEENADNNMKASVRKPKRF

NGRLCFAAIALVIFFLIGFMSGYLGYCKRVEQKEECVKLAETEETDKSETMETEDVPTSSRLYWA

DLKTLLSEKLNSIEFADTIKQLSQNTYTPREAGSQKDESLAYYIENQFHEFKFSKVWRDEHYVKIQ

VKSSIGQNMVTIVQSNGNLDPVESPEGYVAFSKPTEVSGKLVHANFGTKKDFEELSYSVNGSLVI

VRAGEITFAEKVANAQSFNAIGVLIYMDKNKFPVVEADLALFGHAHLGTGDPYTPGFPSFNHTQF

PPSQSSGLPNIPVQTISRAAAEKLFGKMEGSCPARWNIDSSCKLELSQNQNVKLIVKNVLKERRIL

NIFGVIKGYEEPDRYVVVGAQRDALGAGVAAKSSVGTGLLLKLAQVFSDMISKDGFRPSRSIIFA

SWTAGDFGAVGATEWLEGYLSSLHLKAFTYINLDKVVLGTSNFKVSASPLLYTLMGKIMQDVK

HPVDGKSLYRDSNWISKVEKLSFDNAAYPFLAYSGIPAVSFCFCEDADYPYLGTRLDTYEALTQK

VPQLNQMVRTAAEVAGQLIIKLTHDVELNLDYEMYNSKLLSFMKDLNQFKTDIRDMGLSLQWL

YSARGDYFRATSRLTTDFHNAEKTNRFVMREINDRIMKVEYHFLSPYVSPRESPFRHIFWGSGSH

TLSALVENLKLRQKNITAFNETLFRNQLALATWTIQGVANALSGDIWNIDNEF

The present disclosure provides antibodies that bind TfR1. In some embodiments, an anti-TfR1 antibody binds a fragment of TfR1. In some embodiments, an anti-TfR1 antibody binds the extracellular domain of TfR1. In some embodiments, an anti-TfR1 antibody binds the protease-like domain, the helical domain, and/or the apical domain(s) of TfR1. In some embodiments, an anti-TfR1 antibody binds a conformational epitope on TfR1. In some embodiments, an anti-TfR1 antibody binds to a conformational epitope located at the apical domain of TfR1. In some embodiments, an anti-TfR1 antibody binds to a conformational epitope located at the protease-like domain of TfR1. In some embodiments, an anti-TfR1 antibody binds to a conformational epitope located at the helical domain of TfR1. In some embodiments, an anti-TfR1 antibody binds human TfR1. In some embodiments, an anti-TfR1 antibody binds cyno TfR1. In some embodiments, an anti-TfR1 antibody binds human TfR1 and cyno TfR1.

In some embodiments, the anti-TfR1 antibody binds to human TfR1 wholly or partially within amino acids K231-E369 of SEQ ID NO:1. In some embodiments, the anti-TfR1 antibody binds human TfR1 at an epitope comprising amino acids within K231-E369 of SEQ ID NO:1. In some embodiments, the anti-TfR1 antibody binds at least one amino acid within amino acids within K231-E369 of SEQ ID NO:1.

In some embodiments, the anti-TfR1 antibody binds to human TfR1 wholly or partially within amino acids D139-K145 and G490-E582 of SEQ ID NO:1. In some embodiments, the anti-TfR1 antibody binds human TfR1 an epitope comprising amino acids within D139-K145 and G490-E582 of SEQ ID NO:1. In some embodiments, the anti-TfR1 antibody binds at least one amino acid within D139-K145 and G490-E582 of SEQ ID NO:1.

In some embodiments, the anti-TfR1 antibody specifically binds a discontinuous epitope of human or cynomolgus TfR1. In one instance, the anti-TfR1 antibody specifically binds human TfR1, wherein the antibody binds to one or more residues selected from the group consisting of residues K231, D245, L246, Y247, T248, P249, E350, G351, D352, C353, P354, S355, D356, K358, T359, D360, S361, R364, M365, V366, T367, and E369. In another instance, the anti-TfR1 antibody specifically binds cynomolgus TfR1, wherein the antibody binds to one or more residues selected from the group consisting of residues K231, D245, L246, D247, S248, P249, E350, G351, D352, C353, P354, S355, D356, K358, T359, D360, S361, K364, M365, V366, T367, and E369. In one instance, the anti-TfR1 antibody specifically binds human TfR1, wherein the antibody binds to one or more residues selected from the group consisting of residues D139, T141, K145, G490, T491, V517, T518, Y573, K574, I577, E578, R579, I580, P581, and E582. In another instance, the anti-TfR1 antibody specifically binds cynomolgus TfR1, wherein the antibody binds to one or more residues selected from the group consisting of residues D139, T141, K145, G490, T491, V517, T518, Y573, K574, V577, E578, R579, I580, P581, and E582.

In some embodiments, the anti-TfR1 antibody binds to binds human TfR1 at one or more amino acids within amino acids D139 to E582 of SEQ ID NO:1, where the one or more amino acids are within any of the following sequences: D139 to E369, D139 to E582, T141 to E369, T141 to E582, K145 to E369, K145 to E582, K231 to E369, K231 to E582, D245 to E369, D245 to E582, E350 to E369, E350 to E582, K358 to E369, K358 to E582, R364 to E369, R364 to E582, G490 to E582, V517 to E582, K573 to E582, I577 to E582, and/or Y573 to E582.

In some embodiments, the anti-TfR1 antibody binds to binds human TfR1 at one or more of the following amino acids of SEQ ID NO:1: K231, D245 to P249, E244 to V250, E350 to S361, M349 to T362, R364 to E369, and/or C363 to 5370.

In some embodiments, the anti-TfR1 antibody binds to one or more amino acids within amino acids K231 to 5370 of SEQ ID NO:1.

In some embodiments, the anti-TfR1 antibody binds to human TfR1 at one or more amino acids within amino acids D139 to L583 of SEQ ID NO:1, where the one or more amino acids are within any of the following sequences: D139 to T141, D139 to K145, T141 to K145, T138 to K145, T138 to L146, G490 to T491, L489 to T491, L489 to 5492, V517 to T518, P516 to T518, P516 to G519, Y573 to E582, Y573 to L583, T572 to E582, and/or T572 to L583.

In some embodiments, an anti-TfR1 antibody binds to one or more residues within the region spanning amino acids 607-760 of human TfR1 (SEQ ID NO:1), e.g., the antibody binds to one or more residues within the region spanning amino acids 607-730, 607-700, 607-670, 640-760, 640-730, 640-700, 670-760, 670-730, 700-760, or 730-760 of human TfR1.

In some embodiments, an anti-TfR1 antibody binds to one or more residues within the region spanning amino acids 189-383 of human TfR1 (SEQ ID NO:1), e.g., the antibody binds to one or more residues within the region spanning amino acids 189-350, 189-320, 189-290, 189-260, 189-230, 220-383, 220-350, 220-320, 220-290, 220-260, 230-383, 230-350, 230-320, 230-290, 230-260, 240-383, 240-350, 240-320, 240-290, 240-260, 250-383, 250-350, 250-320, 250-290, 280-383, 280-350, 280-320, 310-383, 310-350, 330-383, 330-370, 340-370, 340-383, 350-370, or 350-383 of human TfR1. In some embodiments, an anti-TfR1 antibody binds to one or more residues within the region spanning amino acids 208-348 of human TfR1. In some embodiments, an anti-TfR1 antibody binds to one or more residues within the region spanning amino acids 340-370 of human TfR1. In some embodiments, an anti-TfR1 antibody binds to one or more residues within the region spanning amino acids 190-230 of human TfR1.

In some embodiments, an anti-TfR1 antibody binds to one or more residues within the region spanning amino acids 122-188 of human TfR1 (SEQ ID NO:1), e.g., the antibody binds to one or more residues within the region spanning amino acids 122-170, 122-150, 130-188, 130-170, 130-150, 140-188, 140-170, 150-188, or 150-170 of human TfR1.

In some embodiments, an anti-TfR1 antibody binds to one or more residues within the region spanning amino acids 384-606 of human TfR1 (SEQ ID NO:1), e.g., the antibody binds to one or more residues within the region spanning amino acids 384-570, 384-540, 384-510, 384-480, 384-450, 384-420, 410-606, 410-570, 410-540, 410-510, 410-480, 410-450, 440-606, 440-570, 440-540, 440-510, 440-480, 470-606, 470-590, 470-570, 470-540, 470-510, 490-606, 490-590, 490-570, 490-540, 490-510, 510-606, 510-590, 510-570, 510-540, 540-606, 540-590, 540-570, 570-590, or 570-606 of human TfR1.

In some embodiments, the anti-TfR1 Ab (e.g., an ANTIBODY A or ANTIBODY B described herein) binds to the extracellular domain of TfR1. In some embodiments, the anti-TfR1 Ab (e.g., an ANTIBODY A or ANTIBODY B described herein) binds the protease-like domain, the helical domain, and/or the apical domain(s) of TfR1. In some embodiments, the anti-TfR1 Ab (e.g., an ANTIBODY A or ANTIBODY B described herein) binds a conformational epitope on TfR1. In some embodiments, the anti-TfR1 Ab (e.g., an ANTIBODY A or ANTIBODY B described herein) binds to a conformational epitope located at the apical domain of TfR1. In some embodiments, the anti-TfR1 Ab (e.g., an ANTIBODY A or ANTIBODY B described herein) binds to a conformational epitope located at the protease-like domain of TfR1. In some embodiments, the anti-TfR1 Ab (e.g., an ANTIBODY A or ANTIBODY B described herein) binds to a conformational epitope located at the helical domain of TfR1. In some embodiments, the anti-TfR1 Ab (e.g., an ANTIBODY A or ANTIBODY B described herein) binds human TfR1. In some embodiments, the anti-TfR1 Ab (e.g., an ANTIBODY A or ANTIBODY B described herein) binds cyno TfR1. In some embodiments, the anti-TfR1 Ab (e.g., an ANTIBODY A or ANTIBODY B described herein) binds human TfR1 and cyno TfR1.

In some embodiments, the anti-TfR1 antibody is a recombinant antibody. In some embodiments, the antibody is a monoclonal antibody. In some embodiments, the antibody is a chimeric antibody. In some embodiments, the antibody is a humanized antibody. In some embodiments, the antibody is a human antibody. In some embodiments, the antibody is an IgA, IgD, IgE, IgG, or IgM antibody. In some embodiments, the antibody is an IgG antibody. In some embodiments, the antibody is an IgG1 antibody. In some embodiments, the antibody is an IgG2 antibody. In some embodiments, the antibody is an IgG3 antibody. In some embodiments, the antibody is an IgG4 antibody. In some instances, the antibody comprises the human kappa light chain constant region. In other embodiments, the antibody comprises a human lambda light chain constant region. In some embodiments, the antibody is an antibody fragment comprising an antigen-binding site. In some embodiments, the antibody is a scFv. In some embodiments, the antibody is a disulfide-linked scFv. In some embodiments, the antibody is a bispecific antibody or a multispecific antibody. In some embodiments, the antibody is a monovalent antibody. In some embodiments, the antibody is a monospecific antibody. In some embodiments, the antibody is a bivalent antibody.

In some instances, the antibody is an Fab, Fab', F(ab)$_2$, scFv, sc(Fv)$_2$, diabody, or nanobody. In some embodiments, the interchain disulfide in the antibody or antigen binding fragment (e.g., Fab) is removed. The Fab or Fab' contains a variable heavy (VH) and a variable light domain (VL).

In some embodiments, the antibody is isolated. In some embodiments, the antibody is substantially pure.

In some embodiments, the anti-TfR1 antibody is a monoclonal antibody. Monoclonal antibodies can be prepared by any method known to those of skill in the art. In some embodiments, monoclonal antibodies are prepared using hybridoma methods known to one of skill in the art. For example, using a hybridoma method, a mouse, rat, rabbit, hamster, or other appropriate host animal, is immunized as described above. In some embodiments, lymphocytes are immunized in vitro. In some embodiments, the immunizing antigen is a human protein or a fragment thereof. In some embodiments, the immunizing antigen is a cyno protein or a fragment thereof.

Following immunization, lymphocytes are isolated and fused with a suitable myeloma cell line using, for example, polyethylene glycol. The hybridoma cells are selected using specialized media as known in the art and unfused lymphocytes and myeloma cells do not survive the selection process. Hybridomas that produce monoclonal antibodies directed to a chosen antigen can be identified by a variety of methods including, but not limited to, immunoprecipitation, immunoblotting, and in vitro binding assays (e.g., flow cytometry, FACS, ELISA, SPR (e.g., Biacore), and radioimmunoassay). Once hybridoma cells that produce antibodies of the desired specificity, affinity, and/or activity are identified, the clones may be subcloned by limiting dilution or other techniques. The hybridomas can be propagated either in in vitro culture using standard methods or in vivo as ascites tumors in an animal. The monoclonal antibodies can be purified from the culture medium or ascites fluid according to standard methods in the art including, but not limited to, affinity chromatography, ion-exchange chromatography, gel electrophoresis, and dialysis.

In some embodiments, monoclonal antibodies are made using recombinant DNA techniques as known to one skilled in the art. For example, the polynucleotides encoding an antibody are isolated from mature B-cells or hybridoma cells, such as by RT-PCR using oligonucleotide primers that specifically amplify the genes encoding the heavy and light chains of the antibody and their sequence is determined using standard techniques. The isolated polynucleotides encoding the heavy and light chains are then cloned into suitable expression vectors that produce the monoclonal antibodies when transfected into host cells such as *E. coli*, simian COS cells, Chinese hamster ovary (CHO) cells, or myeloma cells that do not otherwise produce immunoglobulin proteins.

In some embodiments, recombinant monoclonal antibodies are isolated from phage display libraries expressing variable domains or CDRs of a desired species. Screening of phage libraries can be accomplished by various techniques known in the art.

In some embodiments, a monoclonal antibody is modified by using recombinant DNA technology to generate alternative antibodies. In some embodiments, the constant domains of the light chain and heavy chain of a mouse monoclonal antibody are replaced with the constant regions of a human antibody to generate a chimeric antibody. In some embodiments, the constant regions are truncated or removed to generate a desired antibody fragment of a monoclonal antibody. In some embodiments, site-directed or high-density mutagenesis of the variable region(s) is used to optimize specificity and/or affinity of a monoclonal antibody.

In some embodiments, the anti-TfR1 antibody is a humanized antibody. Various methods for generating humanized antibodies are known in the art. In some embodiments, a humanized antibody comprises one or more amino acid residues that have been introduced into its sequence from a source that is non-human. In some embodiments, humanization is performed by substituting one or more non-human CDR sequences for the corresponding CDR sequences of a human antibody. In some embodiments, the humanized antibodies are constructed by substituting all six CDRs of a non-human antibody (e.g., a mouse antibody) for the corresponding CDRs of a human antibody.

The choice of which human heavy chain variable region and/or light chain variable region are used for generating humanized antibodies can be made based on a variety of factors and by a variety of methods known in the art. In some embodiments, the "best-fit" method is used where the sequence of the variable region of a non-human (e.g., rodent) antibody is screened against the entire library of known human variable region sequences. The human sequence that is most similar to that of the non-human (e.g., rodent) sequence is selected as the human variable region framework for the humanized antibody. In some embodiments, a particular variable region framework derived from a consensus sequence of all human antibodies of a particular subgroup of light or heavy chains is selected as the variable region framework. In some embodiments, the variable region framework sequence is derived from the consensus sequences of the most abundant human subclasses. In some embodiments, human germline genes are used as the source of the variable region framework sequences.

Other methods for humanization include, but are not limited to, (i) a method called "superhumanization" that is described as the direct transfer of CDRs to a human germline framework, (ii) a method termed Human String Content (HSC) that is based on a metric of "antibody humanness", (iii) methods based on generation of large libraries of humanized variants (including phage, ribosomal, and yeast display libraries), and (iv) methods based on framework region shuffling.

In some embodiments, the anti-TfR1 antibody is a "human antibody". Human antibodies can be prepared using various techniques known in the art. In some embodiments, human antibodies are generated from immortalized human B lymphocytes immunized in vitro. In some embodiments, human antibodies are generated from lymphocytes isolated from an immunized individual. In any case, cells that produce an antibody directed against a target antigen can be generated and isolated. In some embodiments, a human antibody is selected from a phage library, where that phage library expresses human antibodies. Alternatively, phage display technology may be used to produce human antibodies and antibody fragments in vitro, from immunoglobulin variable region gene repertoires from unimmunized donors. Techniques for the generation and use of antibody phage libraries are well-known in the art. Once antibodies are identified, affinity maturation strategies known in the art, including but not limited to, chain shuffling and site-directed mutagenesis, may be employed to generate higher affinity human antibodies. In some embodiments, human antibodies are produced in transgenic mice that contain human immunoglobulin loci. Upon immunization these mice are capable of producing the full repertoire of human antibodies in the absence of endogenous immunoglobulin production.

In some embodiments, the anti-TfR1 antibody is a bispecific antibody. Bispecific antibodies are capable of recognizing and binding at least two different antigens or epitopes. The different epitopes can either be within the same molecule (e.g., two epitopes on TfR1) or on different molecules (e.g., one epitope on TfR1 and one epitope on a different target). In some embodiments, a bispecific antibody has enhanced potency as compared to an individual antibody or to a combination of more than one antibody. In some embodiments, a bispecific antibody has reduced toxicity as compared to an individual antibody or to a combination of more than one antibody. It is known to those of skill in the art that any therapeutic agent may have unique pharmacokinetics (PK) (e.g., circulating half-life). In some embodiments, a bispecific antibody has the ability to synchronize the PK of two active binding agents wherein the two individual binding agents have different PK profiles. In some embodiments, a bispecific antibody has the ability to concentrate the actions of two agents in a common area (e.g., tissue) in a subject. In some embodiments, a bispecific antibody has the ability to concentrate the actions of two agents to a common target (e.g., a specific cell type). In some embodiments, a bispecific antibody has the ability to target the actions of two agents to more than one biological pathway or function. In some embodiments, a bispecific antibody has the ability to target two different cells and bring them closer together.

In some embodiments, a bispecific antibody has decreased toxicity and/or side effects. In some embodiments, a bispecific antibody has decreased toxicity and/or side effects as compared to a mixture of the two individual antibodies or the antibodies as single agents. In some embodiments, a bispecific antibody has an increased therapeutic index. In some embodiments, a bispecific antibody has an increased therapeutic index as compared to a mixture of the two individual antibodies or the antibodies as single agents.

Several techniques for making bispecific antibodies are known by those skilled in the art. In some embodiments, the bispecific antibodies comprise heavy chain constant regions with modifications in the amino acids that are part of the interface between the two heavy chains. These modifications are made to enhance heterodimer formation and generally reduce or eliminate homodimer formation. In some embodiments, the bispecific antibodies are generated using a knobs-into-holes (KIH) strategy. See, e.g., Ridgway et al. Protein Eng. 1996; 9(7):617-21 and Klein et al. MAbs. 2012; 4(6):653-663.

In some embodiments, the bispecific antibodies comprise light chain constant regions with modifications in the amino acids that are part of the interface between the two light chains. These modifications are made to reduce or eliminate light chain mispairing. See, e.g., Lewis et al. Nat Biotech 2014; 32(2):191-98. In some embodiments, the bispecific antibodies comprise an scFv that covalently links the VH and VL and removes CH1 and CL. In some embodiments, the bispecific antibodies comprise an scFab or Fcab (see, e.g., Wozniak-Knopp et al. PEDS 2010; 23(4):289-97), single-domain antibodies (e.g., with VHHs from camelid species or sharks), or Duet Mabs (see, e.g., Mazor et al. Mabs 2015; 7(2):377-89).

Bispecific antibodies can be intact antibodies or antibody fragments comprising antigen-binding sites.

Anti-TfR1 antibodies with more than two specificities are contemplated in this disclosure. In some embodiments, trispecific or tetraspecific antibodies are generated. Anti-TfR1 antibodies with more than two valencies are contemplated. In some embodiments, trivalent or tetravalent antibodies are generated.

CDRs of an antibody are defined by those skilled in the art using a variety of methods/systems. These systems and/or definitions have been developed and refined over a number of years and include Kabat, Chothia, IMGT, AbM, and Contact. The Kabat definition is based on sequence variability and is commonly used. The Chothia definition is based on the location of the structural loop regions. The IMGT system is based on sequence variability and location within the structure of the variable domain. The AbM definition is a compromise between Kabat and Chothia. The Contact definition is based on analyses of the available antibody crystal structures. An Exemplary system is a combination of Kabat and Chothia. Software programs (e.g., abYsis) are available and known to those of skill in the art for analysis of antibody sequence and determination of CDRs.

The CDR sequences described in FIGS. 1A-1D include the union of all positions in the Kabat CDR definitions (Kabat, E. A., Wu, T. T., Perry, H. M., Gottesman, K. S. & Foeller, C. (1991). Sequences of Proteins of Immunological Interest, 5th edit. National Institutes of Health, Bethesda, MD) and the Chothia CDR definitions (Chothia, C. & Lesk, A. M. J. Mol. Biol (1987) 196, 901-917) (Chothia, C. et al. Nature (1989) 342, 877-883) (Al-Lazikani, B., Lesk, A. M. & Chothia, C. J. Mol. Biol (1997) 273, 927-948). This "union" definition of the CDRs is also known as the "Wolfguy" definition by Bujotzek et al. (Bujotzek A I, Dunbar J, Lipsmeier F, Schafer W, Antes I, Deane C M, Georges G. (2015) "Prediction of VH-VL domain orientation for antibody variable domain modeling." Proteins April; 83(4):681-95. doi: 10.1002/prot.24756)). In some embodiments, the CDR definition is based on a combination of Kabat and Chothia definitions (Exemplary system). However, it will be understood that reference to a heavy chain CDR or CDRs and/or a light chain CDR or CDRs of a specific antibody will encompass all CDR definitions as known to those of skill in the art. In one instance, the anti-TfR1 antibody used in the methods described herein comprises the six CDRs of any ANTIBODY-A clone disclosed herein or any ANTIBODY-B clone disclosed herein based on the Wolfguy or Union definition.

In one instance, the anti-TfR1 antibody used in any of the methods described herein comprises the six CDRs of any ANTIBODY-A clone disclosed herein or any ANTIBODY-B clone disclosed herein based on the Chothia definition. In one instance, the anti-TfR1 antibody used in the methods described herein comprises the six CDRs of any ANTIBODY-A clone disclosed herein or any ANTIBODY-B clone disclosed herein based on the Kabat definition. In one instance, the anti-TfR1 antibody used in the methods described herein comprises the six CDRs of any ANTIBODY-A clone disclosed herein or any ANTIBODY-B clone disclosed herein based on the AbM definition. In one instance, the anti-TfR1 antibody used in the methods described herein comprises the six CDRs of any ANTIBODY-A clone disclosed herein or any ANTIBODY-B clone disclosed herein based on the IMGT definition. In one instance, the anti-TfR1 antibody used in the methods described herein comprises the six CDRs of any ANTIBODY-A clone disclosed herein or any ANTIBODY-B clone disclosed herein based on the Contact definition.

In some embodiments, the anti-TfR1 antibody is an anti-TfR1 antibody that comprises one, two, three, four, five, and/or six CDRs of any one of the antibodies described herein. In some embodiments, an anti-TfR1 antibody comprises (i) one, two, and/or three heavy chain CDRs of any one of the clones presented in Table 1A, and/or (ii) one, two, and/or three light chain CDRs from any one of the clones presented in Table 1A. In some embodiments, an anti-TfR1 antibody comprises (i) one, two, and/or three heavy chain CDRs from any one of the clones presented in Table 2A, and/or (ii) one, two, and/or three light chain CDRs from any one of the clones presented in Table 2A.

In some embodiments, the anti-TfR1 antibody is an anti-TfR1 antibody that comprises one, two, three, four, five, and/or six CDRs of any one of the antibodies described herein. In some embodiments, an anti-TfR1 antibody comprises (i) one, two, and/or three heavy chain CDRs of any one of the clones presented in Table 1B, and/or (ii) one, two, and/or three light chain CDRs from any one of the clones presented in Table 1B. In some embodiments, an anti-TfR1 antibody comprises (i) one, two, and/or three heavy chain CDRs from any one of the clones presented in Table 2B, and/or (ii) one, two, and/or three light chain CDRs from any one of the clones presented in Table 2B.

In some embodiments, an anti-TfR1 antibody comprises three heavy chain CDRs and three light chain CDRs from any one of the clones presented in Table 1A. In some embodiments, an anti-TfR1 antibody comprises three heavy chain CDRs and three light chain CDRs from any one of the clones presented in Table 2A.

In some embodiments, an anti-TfR1 antibody comprises three heavy chain CDRs and three light chain CDRs from any one of the clones presented in Table 1B. In some embodiments, an anti-TfR1 antibody comprises three heavy chain CDRs and three light chain CDRs from any one of the clones presented in Table 2B.

In some embodiments, an anti-TfR1 antibody comprises (i) one, two, and/or three heavy chain CDRs of any one of the clones presented in Table 3A, and/or (ii) one, two, and/or three light chain CDRs from any one of the clones presented in Table 3B. In some embodiments, an anti-TfR1 antibody comprises (i) one, two, and/or three heavy chain CDRs from any one of the clones presented in Table 4A, and/or (ii) one, two, and/or three light chain CDRs from any one of the clones presented in Table 4B.

In some embodiments, an anti-TfR1 antibody comprises (i) one, two, and/or three heavy chain CDRs of any one of the clones presented in Table 3C, and/or (ii) one, two, and/or three light chain CDRs from any one of the clones presented in Table 3D. In some embodiments, an anti-TfR1 antibody comprises (i) one, two, and/or three heavy chain CDRs from any one of the clones presented in Table 4C, and/or (ii) one, two, and/or three light chain CDRs from any one of the clones presented in Table 4D.

In some embodiments, an anti-TfR1 antibody comprises (i) three heavy chain CDRs from any one of the clones presented in Table 3A, and (ii) three light chain CDRs from any one of the clones presented in Table 3B. In some embodiments, an anti-TfR1 antibody comprises (i) three heavy chain CDRs from any one of the clones presented in Table 4A, and (ii) three light chain CDRs from any one of the clones presented in Table 4B.

In some embodiments, an anti-TfR1 antibody comprises (i) three heavy chain CDRs from any one of the clones presented in Table 3C, and (ii) three light chain CDRs from any one of the clones presented in Table 3D. In some embodiments, an anti-TfR1 antibody comprises (i) three heavy chain CDRs from any one of the clones presented in Table 4C, and (ii) three light chain CDRs from any one of the clones presented in Table 4D.

TABLE 1A

Union CDRs for ANTIBODY-A clones

| Clone | H2C/L0 | H3C/L0 | H4C/L0 | H1C/L0 | H3C(HA)/L0 | RabAB-A |
|---|---|---|---|---|---|---|
| Heavy Chain CDR1 | GIDFSSSGYMC (SEQ ID NO: 101) | GIDFSSSGYMC (SEQ ID NO: 101) | GIDFSSSGYMC (SEQ ID NO: 101) | GIDFSSSGYMC (SEQ ID NO: 101) | GIDFSSSGYMH (SEQ ID NO: 102) | GIDFSSSGYMC (SEQ ID NO: 101) |
| Heavy Chain CDR2 | CIYTYSSNTYY AASVKG (SEQ ID NO: 103) | CIYTYSSNTYY ASWAKG (SEQ ID NO: 104) | CIYTYSSNTYY ASWAKG (SEQ ID NO: 104) | CIYTYSSNTYY AASVKG (SEQ ID NO: 103) | AIYTYSSNTYY ASWAKG (SEQ ID NO: 105) | CIYTYSSNTYY ASWAKG (SEQ ID NO: 104) |
| Heavy Chain CDR3 | GTYGYTGYTY TMGYFSL (SEQ ID NO: 106) | GTYGYTGYTY TMGYFSL (SEQ ID NO: 106) | GTYGYTGYTY TMGYFSL (SEQ ID NO: 106) | GTYGYTGYTY TMGYFSL (SEQ ID NO: 106) | GTYGYTGYTY TMGYFSL (SEQ ID NO: 106) | GTYGYTGYTY TMGYFSL (SEQ ID NO: 106) |
| Light Chain CDR1 | QASQNINSYLA (SEQ ID NO: 107) | QASQNINSYLA (SEQ ID NO: 107) | QASQNINSYLA (SEQ ID NO: 107) | QASQNINSYLA (SEQ ID NO: 107) | QASQNINSYLA (SEQ ID NO: 107) | QASQNINSYLA (SEQ ID NO: 107) |
| Light Chain CDR2 | RASSLES (SEQ ID NO: 108) | RASSLES (SEQ ID NO: 108) | RASSLES (SEQ ID NO: 108) | RASSLES (SEQ ID NO: 108) | RASSLES (SEQ ID NO: 108) | RASTLAS (SEQ ID NO: 109) |
| Light Chain CDR3 | QSYYYSGSSNY NA (SEQ ID NO: 110) | QSYYYSGSSNY NA (SEQ ID NO: 110) | QSYYYSGSSNY NA (SEQ ID NO: 110) | QSYYYSGSSNY NA (SEQ ID NO: 110) | QSYYYSGSSNY NA (SEQ ID NO: 110) | QSYYYSGSSNY NA (SEQ ID NO: 110) |

TABLE 1B

Chothia CDRs for ANTIBODY-A clones

| Clone | H2C/L0 | H3C/L0 | H4C/L0 | H1C/L0 | H3C(HA)/L0 | RabAB-A |
|---|---|---|---|---|---|---|
| Heavy Chain CDR1 | GIDFSSSG (SEQ ID NO: 111) | GIDFSSSG (SEQ ID NO: 111) | GIDFSSSG (SEQ ID NO: 111) | GIDFSSSG (SEQ ID NO: 111) | GIDFSSSG (SEQ ID NO: 111) | GIDFSSSG (SEQ ID NO: 111) |

TABLE IB-continued

Chothia CDRs for ANTIBODY-A clones

| Clone | H2C/L0 | H3C/L0 | H4C/L0 | H1C/L0 | H3C(HA)/L0 | RabAB-A |
|---|---|---|---|---|---|---|
| Heavy Chain CDR2 | TYSS (SEQ ID NO: 112) | TYSS (SEQ ID NO: 112) | TYSS (SEQ ID NO: 112) | TYSS (SEQ ID NO: 112) | TYSS (SEQ ID NO: 112) | TYSS (SEQ ID NO: 112) |
| Heavy Chain CDR3 | TYGYTGYTYTMGYFS (SEQ ID NO: 113) | TYGYTGYTYTMGYFS (SEQ ID NO: 113) | TYGYTGYTYTGYFS (SEQ ID NO: 113) | TYGYTGYTYTMGYFS (SEQ ID NO: 113) | TYGYTGYTYTMGYFS (SEQ ID NO: 113) | TYGYTGYTYTMGYFS (SEQ ID NO: 113) |
| Light Chain CDR1 | SQNINSY (SEQ ID NO: 114) | SQNINSY (SEQ ID NO: 114) | SQNINSY (SEQ ID NO: 114) | SQNINSY (SEQ ID NO: 114) | SQNINSY (SEQ ID NO: 114) | SQNINSY (SEQ ID NO: 114) |
| Light Chain CDR2 | RAS | RAS | RAS | RAS | RAS | RAS |
| Light Chain CDR3 | YYYSGSSNYN (SEQ ID NO: 115) | YYYSGSSNYN (SEQ ID NO: 115) | YYYSGSSNYN (SEQ ID NO: 115) | YYYSGSSNYN (SEQ ID NO: 115) | YYYSGSSNYN (SEQ ID NO: 115) | YYYSGSSNYN (SEQ ID NO: 115) |

TABLE 2A

Union CDRs for ANTIBODY-B clones

| Clone | H4C/L2 | H1C/L2 | H3C/L2 | H4C (C90S)/L2 | H4C (C90T)/L2 | H4C (C90V)/L2 | H2C/L2 | RabANTIBODY-B |
|---|---|---|---|---|---|---|---|---|
| Heavy Chain CDR1 | GFSFSNSYWIC (SEQ ID NO: 116) | GFSFSNSYWIC (SEQ ID NO: 116) | GFSFSNSYWIC (SEQ ID NO: 116) | GFSFSNSYWIC (SEQ ID NO: 116) | GFSFSNSYWIC (SEQ ID NO: 116) | GFSFSNSYWIC (SEQ ID NO: 116) | GFSFSNSYWIC (SEQ ID NO: 116) | GFSFSNSYWIC (SEQ ID NO: 116) |
| Heavy Chain CDR2 | CINTDADSTNYASWARG (SEQ ID NO: 117) | CINTDADSTNYADSVKG (SEQ ID NO: 118) | CINTDADSTNYASWARG (SEQ ID NO: 117) | CINTDADSTNYASWARG (SEQ ID NO: 117) | CINTDADSTNYASWARG (SEQ ID NO: 117) | CINTDADSTNYASWARG (SEQ ID NO: 117) | CINTDADSTNYADSVKG (SEQ ID NO: 118) | CINTDADSTNYASWARG (SEQ ID NO: 117) |
| Heavy Chain CDR3 | QNNVFDPGYNL (SEQ ID NO: 119) | QNNVFDPGYNL (SEQ ID NO: 119) | QNNVFDPGYNL (SEQ ID NO: 119) | QNNVFDPGYNL (SEQ ID NO: 119) | QNNVFDPGYNL (SEQ ID NO: 119) | QNNVFDPGYNL (SEQ ID NO: 119) | QNNVFDPGYNL (SEQ ID NO: 119) | QNNVFDPGYNL (SEQ ID NO: 119) |
| Light Chain CDR1 | RASQNIGSNLA (SEQ ID NO: 120) | RASQNIGSNLA (SEQ ID NO: 120) | RASQNIGSNLA (SEQ ID NO: 120) | RASQNIGSNLA (SEQ ID NO: 120) | RASQNIGSNLA (SEQ ID NO: 120) | RASQNIGSNLA (SEQ ID NO: 120) | RASQNIGSNLA (SEQ ID NO: 120) | QASQNIGSNLA (SEQ ID NO: 121) |
| Light Chain CDR2 | DASKLES (SEQ ID NO: 122) | DASKLES (SEQ ID NO: 122) | DASKLES (SEQ ID NO: 122) | DASKLES (SEQ ID NO: 122) | DASKLES (SEQ ID NO: 122) | DASKLES (SEQ ID NO: 122) | DASKLES (SEQ ID NO: 122) | DASKLAS (SEQ ID NO: 123) |
| Light Chain CDR3 | QCTVRGGAYGNA (SEQ ID NO: 124) | QCTVRGGAYGNA (SEQ ID NO: 124) | QCTVRGGAYGNA (SEQ ID NO: 124) | QSTVRGGAYGNA (SEQ ID NO: 125) | QTTVRGGAYGNA (SEQ ID NO: 126) | QVTVRGGAYGNA (SEQ ID NO: 127) | QCTVRGGAYGNA (SEQ ID NO: 124) | QCTVRGGAYGNA (SEQ ID NO: 124) |

TABLE 2B

Chothia CDRs for ANTIBODY-B clones

| Clone | H4C/L2 | H1C/L2 | H3C/L2 | H4C (C90S)/L2 | H4C (C90T)/L2 | H4C (C90V)/L2 | H2C/L2 | RabANTIBODY-B |
|---|---|---|---|---|---|---|---|---|
| Heavy Chain CDR1 | GFSFSNSY (SEQ ID NO: 128) | GFSFSNSY (SEQ ID NO: 128) | GFSFSNSY (SEQ ID NO: 128) | GFSFSNSY (SEQ ID NO: 128) | GFSFSNSY (SEQ ID NO: 128) | GFSFSNSY (SEQ ID NO: 128) | GFSFSNSY (SEQ ID NO: 128) | GFSFSNSY (SEQ ID NO: 128) |
| Heavy Chain CDR2 | TDAD (SEQ ID NO: 129) | TDAD (SEQ ID NO: 129) | TDAD (SEQ ID NO: 129) | TDAD (SEQ ID NO: 129) | TDAD (SEQ ID NO: 129) | TDAD (SEQ ID NO: 129) | TDAD (SEQ ID NO: 129) | TDAD (SEQ ID NO: 129) |
| Heavy Chain CDR3 | NNVFDPGYN (SEQ ID NO: 130) | NNVFDPGYN (SEQ ID NO: 130) | NNVFDPGYN (SEQ ID NO: 130) | NNVFDPGYN (SEQ ID NO: 130) | NNVFDPGYN (SEQ ID NO: 130) | NNVFDPGYN (SEQ ID NO: 130) | NNVFDPGYN (SEQ ID NO: 130) | NNVFDPGYN (SEQ ID NO: 130) |
| Light Chain CDR1 | SQNIGSN (SEQ ID NO: 131) | SQNIGSN (SEQ ID NO: 131) | SQNIGSN (SEQ ID NO: 131) | SQNIGSN (SEQ ID NO: 131) | SQNIGSN (SEQ ID NO: 131) | SQNIGSN (SEQ ID NO: 131) | SQNIGSN (SEQ ID NO: 131) | SQNIGSN (SEQ ID NO: 131) |
| Light Chain CDR2 | DAS | DAS | DAS | DAS | DAS | DAS | DAS | DAS |
| Light Chain CDR3 | TVRGGAYGN (SEQ ID NO: 132) | TVRGGAYGN (SEQ ID NO: 132) | TVRGGAYGN (SEQ ID NO: 132) | TVRGGAYGN (SEQ ID NO: 132) | TVRGGAYGN (SEQ ID NO: 132) | TVRGGAYGN (SEQ ID NO: 132) | TVRGGAYGN (SEQ ID NO: 132) | TVRGGAYGN (SEQ ID NO: 132) |

TABLE 3A

Union Heavy Chain CDRs for ANTIBODY-A clones

| Clone | Heavy Chain CDR1 | Heavy Chain CDR2 | Heavy Chain CDR3 |
|---|---|---|---|
| H0 | GIDFSSSGYMA (SEQ ID NO: 133) | AIYTYSSNTYYAASVKG (SEQ ID NO: 135) | GTYGYTGYTYTMGYFSL (SEQ ID NO: 106) |
| H1 | GIDFSSSGYMA (SEQ ID NO: 133) | AIYTYSSNTYYAASVKG (SEQ ID NO: 135) | GTYGYTGYTYTMGYFSL (SEQ ID NO: 106) |
| H2 | GIDFSSSGYMA (SEQ ID NO: 133) | AIYTYSSNTYYAASVKG (SEQ ID NO: 135) | GTYGYTGYTYTMGYFSL (SEQ ID NO: 106) |
| H3 | GIDFSSSGYMA (SEQ ID NO: 133) | AIYTYSSNTYYASWAKG (SEQ ID NO: 105) | GTYGYTGYTYTMGYFSL (SEQ ID NO: 106) |
| H3(SV) | GIDFSSSGYMS (SEQ ID NO: 134) | VIYTYSSNTYYASWAKG (SEQ ID NO: 136) | GTYGYTGYTYTMGYFSL (SEQ ID NO: 106) |
| H3(SR) | GIDFSSSGYMS (SEQ ID NO: 134) | RIYTYSSNTYYASWAKG (SEQ ID NO: 137) | GTYGYTGYTYTMGYFSL (SEQ ID NO: 106) |
| H3(SY) | GIDFSSSGYMS (SEQ ID NO: 134) | YIYTYSSNTYYASWAKG (SEQ ID NO: 138) | GTYGYTGYTYTMGYFSL (SEQ ID NO: 106) |
| H3(HA) | GIDFSSSGYMH (SEQ ID NO: 102) | AIYTYSSNTYYASWAKG (SEQ ID NO: 105) | GTYGYTGYTYTMGYFSL (SEQ ID NO: 106) |
| H4 | GIDFSSSGYMA (SEQ ID NO: 133) | AIYTYSSNTYYASWAKG (SEQ ID NO: 105) | GTYGYTGYTYTMGYFSL (SEQ ID NO: 106) |
| H0C | GIDFSSSGYMC (SEQ ID NO: 101) | CIYTYSSNTYYAASVKG (SEQ ID NO: 103) | GTYGYTGYTYTMGYFSL (SEQ ID NO: 106) |
| H1C | GIDFSSSGYMC (SEQ ID NO: 101) | CIYTYSSNTYYAASVKG (SEQ ID NO: 103) | GTYGYTGYTYTMGYFSL (SEQ ID NO: 106) |
| H2C | GIDFSSSGYMC (SEQ ID NO: 101) | CIYTYSSNTYYAASVKG (SEQ ID NO: 103) | GTYGYTGYTYTMGYFSL (SEQ ID NO: 106) |

TABLE 3A-continued

Union Heavy Chain CDRs for ANTIBODY-A clones

| Clone | Heavy Chain CDR1 | Heavy Chain CDR2 | Heavy Chain CDR3 |
|---|---|---|---|
| H3C | GIDFSSSGYMC (SEQ ID NO: 101) | CIYTYSSNTYYASWAKG (SEQ ID NO: 104) | GTYGYTGYTYTMGYFSL (SEQ ID NO: 106) |
| H4C | GIDFSSSGYMC (SEQ ID NO: 101) | CIYTYSSNTYYASWAKG (SEQ ID NO: 104) | GTYGYTGYTYTMGYFSL (SEQ ID NO: 106) |
| RabAb | GIDFSSSGYMC (SEQ ID NO: 101) | CIYTYSSNTYYASWAKG (SEQ ID NO: 104) | GTYGYTGYTYTMGYFSL (SEQ ID NO: 106) |

TABLE 3B

Union Light Chain CDRs for ANTIBODY-A clones

| Clone | L0 | L1 | L2 | RabAb-A |
|---|---|---|---|---|
| Light Chain CDR1 | QASQNINSYLA (SEQ ID NO: 107) | QASQNINSYLA (SEQ ID NO: 107) | QASQNINSYLA (SEQ ID NO: 107) | QASQNINSYLA (SEQ ID NO: 107) |
| Light Chain CDR2 | RASSLES (SEQ ID NO: 108) | RASTLAS (SEQ ID NO: 109) | RASTLAS (SEQ ID NO: 109) | RASTLAS (SEQ ID NO: 109) |
| Light Chain CDR3 | QSYYYSGSSNYNA (SEQ ID NO: 110) | QSYYYSGSSNYNA (SEQ ID NO: 110) | QSYYYSGSSNYNA (SEQ ID NO: 110) | QSYYYSGSSNYNA (SEQ ID NO: 110) |

TABLE 3C

Chothia Heavy Chain CDRs for ANTIBODY-A clones

| Clone | Heavy Chain CDR1 | Heavy Chain CDR2 | Heavy Chain CDR3 |
|---|---|---|---|
| H0 | GIDFSSSG (SEQ ID NO: 111) | TYSS (SEQ ID NO: 112) | TYGYTGYTYTMGYFS (SEQ ID NO: 113) |
| H1 | GIDFSSSG (SEQ ID NO: 111) | TYSS (SEQ ID NO: 112) | TYGYTGYTYTMGYFS (SEQ ID NO: 113) |
| H2 | GIDFSSSG (SEQ ID NO: 111) | TYSS (SEQ ID NO: 112) | TYGYTGYTYTMGYFS (SEQ ID NO: 113) |
| H3 | GIDFSSSG (SEQ ID NO: 111) | TYSS (SEQ ID NO: 112) | TYGYTGYTYTMGYFS (SEQ ID NO: 113) |
| H3(SV) | GIDFSSSG (SEQ ID NO: 111) | TYSS (SEQ ID NO: 112) | TYGYTGYTYTMGYFS (SEQ ID NO: 113) |
| H3(SR) | GIDFSSSG (SEQ ID NO: 111) | TYSS (SEQ ID NO: 112) | TYGYTGYTYTMGYFS (SEQ ID NO: 113) |
| H3(SY) | GIDFSSSG (SEQ ID NO: 111) | TYSS (SEQ ID NO: 112) | TYGYTGYTYTMGYFS (SEQ ID NO: 113) |
| H3(HA) | GIDFSSSG (SEQ ID NO: 111) | TYSS (SEQ ID NO: 112) | TYGYTGYTYTMGYFS (SEQ ID NO: 113) |

TABLE 3C-continued

Chothia Heavy Chain CDRs for ANTIBODY-A clones

| Clone | Heavy Chain CDR1 | Heavy Chain CDR2 | Heavy Chain CDR3 |
|---|---|---|---|
| H4 | GIDFSSSG (SEQ ID NO: 111) | TYSS (SEQ ID NO: 112) | TYGYTGYTYTMGYFS (SEQ ID NO: 113) |
| H0C | GIDFSSSG (SEQ ID NO: 111) | TYSS (SEQ ID NO: 112) | TYGYTGYTYTMGYFS (SEQ ID NO: 113) |
| H1C | GIDFSSSG (SEQ ID NO: 111) | TYSS (SEQ ID NO: 112) | TYGYTGYTYTMGYFS (SEQ ID NO: 113) |
| H2C | GIDFSSSG (SEQ ID NO: 111) | TYSS (SEQ ID NO: 112) | TYGYTGYTYTMGYFS (SEQ ID NO: 113) |
| H3C | GIDFSSSG (SEQ ID NO: 111) | TYSS (SEQ ID NO: 112) | TYGYTGYTYTMGYFS (SEQ ID NO: 113) |
| H4C | GIDFSSSG (SEQ ID NO: 111) | TYSS (SEQ ID NO: 112) | TYGYTGYTYTMGYFS (SEQ ID NO: 113) |
| RabAb | GIDFSSSG (SEQ ID NO: 111) | TYSS (SEQ ID NO: 112) | TYGYTGYTYTMGYFS (SEQ ID NO: 113) |

TABLE 3D

Chothia Light Chain CDRs for ANTIBODY-A clones

| Clone | L0 | L1 | L2 | RabAb-A |
|---|---|---|---|---|
| Light Chain CDR1 | SQNINSY (SEQ ID NO: 114) | SQNINSY (SEQ ID NO: 114) | SQNINSY (SEQ ID NO: 114) | SQNINSY (SEQ ID NO: 114) |
| Light Chain CDR2 | RAS | RAS | RAS | RAS |
| Light Chain CDR3 | YYYSGSSNYN (SEQ ID NO: 115) | YYYSGSSNYN (SEQ ID NO: 115) | YYYSGSSNYN (SEQ ID NO: 115) | YYYSGSSNYN (SEQ ID NO: 115) |

TABLE 4A

Union Heavy Chain CDRs for ANTIBODY-B clones

| Clone | Heavy Chain CDR1 | Heavy Chain CDR2 | Heavy Chain CDR3 |
|---|---|---|---|
| H0 | GFSFSNSYWIA (SEQ ID NO: 139) | AINTDADSTNYADSVKG (SEQ ID NO: 142) | QNNVFDPGYNL (SEQ ID NO: 119) |
| H1 | GFSFSNSYWIA (SEQ ID NO: 139) | AINTDADSTNYADSVKG (SEQ ID NO: 142) | QNNVFDPGYNL (SEQ ID NO: 119) |
| H1(SV) | GFSFSNSYWIS (SEQ ID NO: 140) | VINTDADSTNYADSVKG (SEQ ID NO: 143) | QNNVFDPGYNL (SEQ ID NO: 119) |
| H1(SR) | GFSFSNSYWIS (SEQ ID NO: 140) | RINTDADSTNYADSVKG (SEQ ID NO: 144) | QNNVFDPGYNL (SEQ ID NO: 119) |
| H1(SY) | GFSFSNSYWIS (SEQ ID NO: 140) | YINTDADSTNYADSVKG (SEQ ID NO: 145) | QNNVFDPGYNL (SEQ ID NO: 119) |
| H1(HA) | GFSFSNSYWIH (SEQ ID NO: 141) | AINTDADSTNYADSVKG (SEQ ID NO: 142) | QNNVFDPGYNL (SEQ ID NO: 119) |
| H2 | GFSFSNSYWIA (SEQ ID NO: 139) | AINTDADSTNYADSVKG (SEQ ID NO: 142) | QNNVFDPGYNL (SEQ ID NO: 119) |
| H3 | GFSFSNSYWIA (SEQ ID NO: 139) | AINTDADSTNYASWARG (SEQ ID NO: 146) | QNNVFDPGYNL (SEQ ID NO: 119) |
| H4 | GFSFSNSYWIA (SEQ ID NO: 139) | AINTDADSTNYASWARG (SEQ ID NO: 146) | QNNVFDPGYNL (SEQ ID NO: 119) |
| H0C | GFSFSNSYWIC (SEQ ID NO: 116) | CINTDADSTNYADSVKG (SEQ ID NO: 118) | QNNVFDPGYNL (SEQ ID NO: 119) |
| H1C | GFSFSNSYWIC (SEQ ID NO: 116) | CINTDADSTNYADSVKG (SEQ ID NO: 118) | QNNVFDPGYNL (SEQ ID NO: 119) |
| H2C | GFSFSNSYWIC (SEQ ID NO: 116) | CINTDADSTNYADSVKG (SEQ ID NO: 118) | QNNVFDPGYNL (SEQ ID NO: 119) |
| H3C | GFSFSNSYWIC (SEQ ID NO: 116) | CINTDADSTNYASWARG (SEQ ID NO: 117) | QNNVFDPGYNL (SEQ ID NO: 119) |
| H4C | GFSFSNSYWIC (SEQ ID NO: 116) | CINTDADSTNYASWARG (SEQ ID NO: 117) | QNNVFDPGYNL (SEQ ID NO: 119) |
| RabAb | GFSFSNSYWIC (SEQ ID NO: 116) | CINTDADSTNYASWARG (SEQ ID NO: 117) | QNNVFDPGYNL (SEQ ID NO: 119) |

TABLE 4B

Union Light Chain CDRs for ANTIBODY-B clones

| Clone | Light Chain CDR1 | Light Chain CDR2 | Light Chain CDR3 |
|---|---|---|---|
| L0 | RASQNIGSNLA (SEQ ID NO: 120) | DASKLES (SEQ ID NO: 122) | QQTVRGGAYGLA (SEQ ID NO: 147) |
| L1 | RASQNIGSNLA (SEQ ID NO: 120) | DASKLES (SEQ ID NO: 122) | QATVRGGAYGLA (SEQ ID NO: 148) |
| L2 | RASQNIGSNLA (SEQ ID NO: 120) | DASKLES (SEQ ID NO: 122) | QCTVRGGAYGNA (SEQ ID NO: 124) |
| L2(C90S) | RASQNIGSNLA (SEQ ID NO: 120) | DASKLES (SEQ ID NO: 122) | QSTVRGGAYGNA (SEQ ID NO: 125) |
| L2(C90T) | RASQNIGSNLA (SEQ ID NO: 120) | DASKLES (SEQ ID NO: 122) | QTTVRGGAYGNA (SEQ ID NO: 126) |
| L2(C90V) | RASQNIGSNLA (SEQ ID NO: 120) | DASKLES (SEQ ID NO: 122) | QVTVRGGAYGNA (SEQ ID NO: 127) |
| rabAB-B | QASQNIGSNLA (SEQ ID NO: 121) | DASKLAS (SEQ ID NO: 123) | QCTVRGGAYGNA (SEQ ID NO: 124) |

TABLE 4C

Chothia Heavy Chain CDRs for ANTIBODY-B clones

| Clone | Heavy Chain CDR1 | Heavy Chain CDR2 | Heavy Chain CDR3 |
|---|---|---|---|
| H0 | GFSFSNSY (SEQ ID NO: 128) | TDAD (SEQ ID NO: 129) | NNVFDPGYN (SEQ ID NO: 130) |
| H1 | GFSFSNSY (SEQ ID NO: 128) | TDAD (SEQ ID NO: 129) | NNVFDPGYN (SEQ ID NO: 130) |
| H1(SV) | GFSFSNSY (SEQ ID NO: 128) | TDAD (SEQ ID NO: 129) | NNVFDPGYN (SEQ ID NO: 130) |
| H1(SR) | GFSFSNSY (SEQ ID NO: 128) | TDAD (SEQ ID NO: 129) | NNVFDPGYN (SEQ ID NO: 130) |
| H1(SY) | GFSFSNSY (SEQ ID NO: 128) | TDAD (SEQ ID NO: 129) | NNVFDPGYN (SEQ ID NO: 130) |
| H1(HA) | GFSFSNSY (SEQ ID NO: 128) | TDAD (SEQ ID NO: 129) | NNVFDPGYN (SEQ ID NO: 130) |
| H2 | GFSFSNSY (SEQ ID NO: 128) | TDAD (SEQ ID NO: 129) | NNVFDPGYN (SEQ ID NO: 130) |
| H3 | GFSFSNSY (SEQ ID NO: 128) | TDAD (SEQ ID NO: 129) | NNVFDPGYN (SEQ ID NO: 130) |
| H4 | GFSFSNSY (SEQ ID NO: 128) | TDAD (SEQ ID NO: 129) | NNVFDPGYN (SEQ ID NO: 130) |
| H0C | GFSFSNSY (SEQ ID NO: 128) | TDAD (SEQ ID NO: 129) | NNVFDPGYN (SEQ ID NO: 130) |
| H1C | GFSFSNSY (SEQ ID NO: 128) | TDAD (SEQ ID NO: 129) | NNVFDPGYN (SEQ ID NO: 130) |
| H2C | GFSFSNSY (SEQ ID NO: 128) | TDAD (SEQ ID NO: 129) | NNVFDPGYN (SEQ ID NO: 130) |
| H3C | GFSFSNSY (SEQ ID NO: 128) | TDAD (SEQ ID NO: 129) | NNVFDPGYN (SEQ ID NO: 130) |
| H4C | GFSFSNSY (SEQ ID NO: 128) | TDAD (SEQ ID NO: 129) | NNVFDPGYN (SEQ ID NO: 130) |
| RabAb | GFSFSNSY (SEQ ID NO: 128) | TDAD (SEQ ID NO: 129) | NNVFDPGYN (SEQ ID NO: 130) |

TABLE 4D

Chothia Light Chain CDRs for ANTIBODY-B clones

| Clone | Light Chain CDR1 | Light Chain CDR2 | Light Chain CDR2 |
|---|---|---|---|
| L0 | SQNIGSN (SEQ ID NO: 131) | DAS | TVRGGAYGN (SEQ ID NO: 132) |
| L1 | SQNIGSN (SEQ ID NO: 131) | DAS | TVRGGAYGN (SEQ ID NO: 132) |
| L2 | SQNIGSN (SEQ ID NO: 131) | DAS | TVRGGAYGN (SEQ ID NO: 132) |
| L2(C90S) | SQNIGSN (SEQ ID NO: 131) | DAS | TVRGGAYGN (SEQ ID NO: 132) |
| L2(C90T) | SQNIGSN (SEQ ID NO: 131) | DAS | TVRGGAYGN (SEQ ID NO: 132) |
| L2(C90V) | SQNIGSN (SEQ ID NO: 131) | DAS | TVRGGAYGN (SEQ ID NO: 132) |
| rabAB-B | SQNIGSN (SEQ ID NO: 131) | DAS | TVRGGAYGN (SEQ ID NO: 132) |

In some embodiments, an anti-TfR1 antibody comprises a heavy chain CDR1, CDR2, and CDR3 and/or a light chain variable region CDR1, CDR2, and CDR3 from an antibody described herein. In some embodiments, an anti-TfR1 antibody comprises a heavy chain CDR1, CDR2, and CDR3 and a light chain CDR1, CDR2, and CDR3 from an antibody described herein. In some embodiments, an anti-TfR1 antibody comprises a humanized version or humanized variant of an antibody described herein.

In some embodiments, an anti-TfR1 antibody comprises a heavy chain CDR1, CDR2, and CDR3 and/or a light chain variable region CDR1, CDR2, and CDR3 from any ANTIBODY-A clone disclosed herein, a humanized version thereof, or variants thereof. In some embodiments, an anti-TfR1 antibody comprises a heavy chain CDR1, a heavy chain variable region CDR2, and a heavy chain variable region CDR3 from any ANTIBODY-A clone disclosed herein. In other embodiments, an anti-TfR1 antibody comprises a light chain variable region CDR1, a light chain variable region CDR2, and a light chain variable region CDR3 from any ANTIBODY-A clone disclosed herein. In certain embodiments, an anti-TfR1 antibody comprises a heavy chain CDR1, a heavy chain variable region CDR2, a heavy chain variable region CDR3, a light chain variable region CDR1, a light chain variable region CDR2, and a light chain variable region CDR3 from antibody any ANTIBODY-A clone disclosed herein. In some embodiments, an anti-TfR1 antibody is a humanized version of any ANTIBODY-A clone disclosed herein. In some embodiments, an anti-TfR1 antibody is a variant of any ANTIBODY-A clone disclosed herein.

In some embodiments, an anti-TfR1 antibody comprises a heavy chain CDR1, CDR2, and CDR3 and/or a light chain variable region CDR1, CDR2, and CDR3 from any ANTIBODY-B clone disclosed herein, a humanized version thereof, or variants thereof. In some embodiments, an anti-TfR1 antibody comprises a heavy chain CDR1, a heavy chain variable region CDR2, and a heavy chain variable region CDR3 from any ANTIBODY-B clone disclosed herein. In other embodiments, an anti-TfR1 antibody comprises a light chain variable region CDR1, a light chain variable region CDR2, and a light chain variable region CDR3 from any ANTIBODY-B clone disclosed herein. In certain embodiments, an anti-TfR1 antibody comprises a heavy chain CDR1, a heavy chain variable region CDR2, a heavy chain variable region CDR3, a light chain variable region CDR1, a light chain variable region CDR2, and a light chain variable region CDR3 from antibody any ANTIBODY-B clone disclosed herein. In some embodiments, an anti-TfR1 antibody is a humanized version of ANTIBODY-B. In some embodiments, an anti-TfR1 antibody is a variant of ANTIBODY-B.

In some embodiments, the anti-TfR1 antibody is a variant of an anti-TfR1 antibody described herein which comprises one to thirty conservative amino acid substitutions. In some embodiments, a variant of the anti-TfR1 antibody comprises one to twenty-five conservative amino acid substitutions. In some embodiments, a variant of the anti-TfR1 antibody comprises one to twenty conservative amino acid substitutions. In some embodiments, a variant of the anti-TfR1 antibody comprises one to fifteen conservative amino acid substitutions. In some embodiments, a variant of the anti-TfR1 antibody comprises one to ten conservative amino acid substitution(s). In some embodiments, a variant of the anti-TfR1 antibody comprises one to five conservative amino acid substitution(s). In some embodiments, a variant of the anti-TfR1 antibody comprises one to three conservative amino acid substitution(s). In some embodiments, the conservative amino acid substitution(s) is in a CDR of the antibody. In some embodiments, the conservative amino acid substitution(s) is not in a CDR of the antibody. In some embodiments, the conservative amino acid substitution(s) is in a framework region of the antibody.

In some embodiments, the anti-TfR1 antibody comprises: (a) a heavy chain variable region CDR1 comprising GIDFSSSGYMC (SEQ ID NO:101), a heavy chain variable region CDR2 comprising CIYTYSSNTYYAASVKG (SEQ ID NO:103), and a heavy chain variable region CDR3 comprising GTYGYTGYTYTMGYFSL (SEQ ID NO:106); and/or (b) a light chain variable region CDR1 comprising QASQNINSYLA (SEQ ID NO:107); a light chain variable region CDR2 comprising RASSLES (SEQ ID NO:108), and a light chain variable region CDR3 comprising QSYYYSGSSNYNA (SEQ ID NO:110). In some embodiments, an anti-TfR1 antibody comprises a heavy chain variable region CDR1 comprising GIDFSSSGYMC (SEQ ID NO:101), a heavy chain variable region CDR2 comprising CIYTYSSNTYYAASVKG (SEQ ID NO:103, and a heavy chain variable region CDR3 comprising GTYGYTGYTYTMGYFSL (SEQ ID NO:106). In some embodiments, an anti-TfR1 antibody comprises a light chain variable region CDR1 comprising QASQNINSYLA (SEQ ID NO:107), a light chain variable region CDR2 comprising RASSLES (SEQ ID NO:108), and a light chain variable region CDR3 comprising QSYYYSGSSNYNA (SEQ ID NO:110). In some embodiments, an anti-TfR1 antibody comprises (a) a heavy chain variable region CDR1 comprising GIDFSSSGYMC (SEQ ID NO:101), a heavy chain variable region CDR2 comprising CIYTYSSNTYYAASVKG (SEQ ID NO:103), and a heavy chain variable region CDR3 comprising GTYGYTGYTYTMGYFSL (SEQ ID NO:106), and (b) a light chain variable region CDR1 comprising QASQNINSYLA (SEQ ID NO:107), a light chain variable region CDR2 comprising RASSLES (SEQ ID NO:108), and a light chain variable region CDR3 comprising QSYYYSGSSNYNA (SEQ ID NO:110). In some embodiments, an anti-TfR1 antibody comprises (a) a heavy chain variable region comprising a heavy chain CDR1 comprising GIDFSSSGYMC (SEQ ID NO:101), a heavy chain CDR2 comprising CIYTYSSNTYYAASVKG (SEQ ID NO:103), and a heavy chain CDR3 comprising GTYGYTGYTYTMGYFSL (SEQ ID NO:106), or (b) a light chain variable region comprising light chain CDR1 comprising QASQNINSYLA (SEQ ID NO:107), a light chain CDR2 comprising RASSLES (SEQ ID NO:108), and a light chain CDR3 comprising QSYYYSGSSNYNA (SEQ ID NO:110).

In some embodiments, an anti-TfR1 antibody comprises: a heavy chain variable region CDR1 comprising GIDFSSSGYMC (SEQ ID NO:101), or a variant thereof comprising 1, 2, 3, or 4 amino acid substitutions; a heavy chain variable region CDR2 comprising CIYTYSSNTYYAASVKG (SEQ ID NO:103), or a variant thereof comprising 1, 2, 3, or 4 amino acid substitutions; a heavy chain variable region CDR3 comprising GTYGYTGYTYTMGYFSL (SEQ ID NO:106), or a variant thereof comprising 1, 2, 3, or 4 amino acid substitutions; a light chain variable region CDR1 comprising QASQNINSYLA (SEQ ID NO:107), or a variant thereof comprising 1, 2, 3, or 4 amino acid substitutions; a light chain variable region CDR2 comprising RASSLES (SEQ ID NO:108), or a variant thereof comprising 1, 2, 3, or 4 amino acid substitutions; and a light chain variable region CDR3 comprising QSYYYSGSSNYNA (SEQ ID NO:110) or a variant thereof comprising 1, 2, 3, or 4 amino acid substitutions. In some embodiments, a CDR comprises one amino acid substitution. In some embodiments, a CDR comprises two amino acid substitutions. In some embodiments, a CDR comprises three amino acid substitutions. In some embodiments, a CDR comprises four amino acid substitutions. In some embodiments, the one or more amino acid substitutions are conservative substitutions. In some embodiments, the CDR is a heavy chain CDR1. In some embodiments, the CDR is a heavy chain variable region CDR2. In some embodiments, the CDR is a heavy chain variable region CDR3. In some embodiments, the CDR is a light chain variable region CDR1. In some embodiments, the CDR is a light chain variable region CDR2. In some embodiments, the CDR is a light chain variable region CDR3. In some embodiments, the one or more substitutions are made as part of a humanization process. In some embodiments, the one or more substitutions are made as part of a germline humanization process. In some embodiments, the one or more substitutions are made as part of an affinity maturation process. In some embodiments, the one or more substitutions are made as part of an optimization process.

In some embodiments, the anti-TfR1 antibody of the disclosure comprising a heavy chain variable region (VH) comprising VH CDR1, VH CDR2, and VH CDR3, wherein the VH CDR1 comprises the amino acid sequence GIDFSSSGYMX (SEQ ID NO:149), wherein X is any amino acid; the VH CDR2 comprises the amino acid sequence XIYTYSSNTYYAXXXKG (SEQ ID NO:151), wherein X is any amino acid; and the VH CDR3 comprises the amino acid sequence GTYGYTGYTYTMGYFSL (SEQ ID NO:106); and wherein the antibody comprises a light chain variable region (VL) comprising VL CDR1, VL CDR2, and VL CDR3, wherein: the VL CDR1 comprises the amino acid sequence QASQNINSYLA (SEQ ID NO:107); the VL CDR2 comprises the amino acid sequence RASXLXS (SEQ ID NO:153), wherein X is any amino acid; and the VL CDR3 comprises the amino acid sequence QSYYYSGSSNYNA (SEQ ID NO:110). In some embodiments, the VH CDR1 comprises the amino acid sequence GIDFSSSGYMX$_1$ (SEQ ID NO:150), wherein X$_1$ is C, A, or H; the VH CDR2 comprises the amino acid sequence X$_2$IYTYSSNTYYAX$_3$X$_4$X$_5$KG (SEQ ID NO:152), wherein X$_2$ is C or A, wherein X$_3$ is S or A, wherein X$_4$ is W or S, and wherein X$_5$ is A or V; the VH CDR3 comprises the amino acid sequence GTYGYTGYTYTMGYFSL (SEQ ID NO:106); the VL CDR1 comprises the amino acid sequence QASQNINSYLA (SEQ ID NO:107); the VL CDR2 comprises the amino acid sequence RASX$_6$LX$_7$S (SEQ ID NO:154), wherein X$_6$ is T or S, and wherein X$_7$ is A or E; and the VL CDR3 comprises the amino acid sequence QSYYYSGSSNYNA (SEQ ID NO:110).

In some embodiments of the methods described herein, an anti-TfR1 antibody comprises a heavy chain variable region comprising an amino acid sequence that has the three VH CDRs of any ANTIBODY-A clone disclosed herein and which has at least 75%, 80%, 85%, 90%, 95%, 96%, 97%, 98%, 99%, or 100% identity to the sequence set forth in SEQ ID NO:16 and a light chain variable region comprising an amino acid sequence that has the three VL CDRs of any ANTIBODY-A clone disclosed herein and which has at least 75%, 80%, 85%, 90%, 95%, 96%, 97%, 98%, 99%, or 100% identity to the sequence set forth in SEQ ID NO:35.

In some embodiments of the methods described herein, an anti-TfR1 antibody comprises a heavy chain variable region comprising at least 75%, 80%, 85%, 90%, 95%, 96%, 97%, 98%, 99%, or 100% identity to the sequence set forth in SEQ ID NO:16 and a light chain variable region comprising at least 75%, 80%, 85%, 90%, 95%, 96%, 97%, 98%, 99%, or 100% identity to the sequence set forth in SEQ ID NO:35. In some embodiments of the methods described herein, an anti-TfR1 antibody comprises a heavy chain variable region with one or more (e.g., 1, 2, or 3) substitutions, deletions, or insertions in the sequence set forth in SEQ ID NO:16 and a light chain variable region with one or more substitutions, deletions, or insertions in the sequence set forth in SEQ ID NO:35. In some embodiments of the methods described herein, an anti-TfR1 antibody comprises a heavy chain variable region comprising an amino acid sequence that has the three VH CDRs of any ANTIBODY-A clone disclosed herein and which has at least 75%, 80%, 85%, 90%, 95%, 96%, 97%, 98%, 99%, or 100% identity to any one of the VH sequences set forth in FIG. 1A and a light chain variable region comprising an amino acid sequence that has the three VL CDRs of any ANTIBODY-B clone disclosed herein and which has at least 75%, 80%, 85%, 90%, 95%, 96%, 97%, 98%, 99%, or 100% identity to any one of the sequences set forth in FIG. 1C.

In some embodiments, an anti-TfR1 antibody comprises a heavy chain variable region having at least about 80% sequence identity to SEQ ID NO:16, and/or a light chain variable region having at least about 80% sequence identity to SEQ ID NO:35. In some embodiments, an anti-TfR1 antibody comprises a heavy chain variable region having at least about 85%, at least about 90%, at least about 95%, at least about 97%, or at least about 99% sequence identity to SEQ ID NO:16. In some embodiments, an anti-TfR1 antibody comprises a light chain variable region having at least about 85%, at least about 90%, at least about 95%, at least about 97%, or at least about 99% sequence identity to SEQ ID NO:35.

In some embodiments, an anti-TfR1 antibody comprises a heavy chain variable region having at least about 80% sequence identity to SEQ ID NO:16 and/or a light chain variable region having at least about 80% sequence identity to SEQ ID NO:35. In some embodiments, an anti-TfR1 antibody comprises a heavy chain variable region having at least about 80% sequence identity to SEQ ID NO:16 and a light chain variable region having at least about 80% sequence identity to SEQ ID NO:35. In some embodiments, an anti-TfR1 antibody comprises a heavy chain variable region having at least about 90% sequence identity to SEQ ID NO:16 and/or a light chain variable region having at least about 90% sequence identity to SEQ ID NO:35. In some embodiments, an anti-TfR1 antibody comprises a heavy chain variable region having at least about 90% sequence identity to SEQ ID NO:16 and a light chain variable region having at least about 90% sequence identity to SEQ ID NO:35. In some embodiments, an anti-TfR1 antibody comprises a heavy chain variable region having at least about 95% sequence identity to SEQ ID NO:16 and/or a light chain variable region having at least about 95% sequence identity to SEQ ID NO:35. In some embodiments, an anti-TfR1 antibody comprises a heavy chain variable region having at least about 95% sequence identity to SEQ ID NO:16 and a light chain variable region having at least about 95% sequence identity to SEQ ID NO:35.

In some embodiments, an anti-TfR1 antibody comprises a heavy chain variable region comprising SEQ ID NO:16. In some embodiments, an anti-TfR1 antibody comprises a light chain variable region comprising SEQ ID NO:35. In some embodiments, an anti-TfR1 antibody comprises a heavy chain variable region comprising SEQ ID NO:16 and a light chain variable region comprising SEQ ID NO:35.

In some embodiments, an anti-TfR1 antibody comprises a CDR1, CDR2, and CDR3 from a heavy chain variable region having the amino acid sequence of SEQ ID NO:16 and a CDR1, CDR2, and CDR3 from a light chain variable region having the amino acid sequence of SEQ ID NO:35. In some embodiments, an anti-TfR1 antibody comprises: (i) a heavy chain variable region comprising a CDR1, CDR2, and CDR3 from a heavy chain variable region having the amino acid sequence of SEQ ID NO:16, and (ii) a light chain variable region comprising a CDR1, CDR2, and CDR3 from a light chain variable region having the amino acid sequence of SEQ ID NO:35.

In some embodiments, the anti-TfR1 antibody comprises: (a) a heavy chain variable region CDR1 comprising GFSFSNSYWIC (SEQ ID NO:116), a heavy chain variable region CDR2 comprising CINTDADSTNYASWARG (SEQ ID NO:117), and a heavy chain variable region CDR3 comprising QNNVFDPGYNL (SEQ ID NO:119); and/or (b) a light chain variable region CDR1 comprising RASQNIGSNLA (SEQ ID NO:120); a light chain variable region CDR2 comprising DASKLES (SEQ ID NO:122), and a light chain variable region CDR3 comprising QCTVRGGAYGNA (SEQ ID NO:124). In some embodiments, an anti-TfR1 antibody comprises a heavy chain variable region CDR1 comprising GFSFSNSYWIC (SEQ ID NO:116), a heavy chain variable region CDR2 comprising CINTDADSTNYASWARG (SEQ ID NO:117), and a heavy chain variable region CDR3 comprising QNNVFDPGYNL (SEQ ID NO:119). In some embodiments, an anti-TfR1 antibody comprises a light chain variable region CDR1 comprising RASQNIGSNLA (SEQ ID NO:120), a light chain variable region CDR2 comprising DASKLES (SEQ ID NO:122), and a light chain variable region CDR3 comprising QCTVRGGAYGNA (SEQ ID NO:124). In some embodiments, an anti-TfR1 antibody comprises (a) a heavy chain variable region CDR1 comprising GFSFSNSYWIC (SEQ ID NO:116), a heavy chain variable region CDR2 comprising CINTDADSTNYASWARG (SEQ ID NO:117), and a heavy chain variable region CDR3 comprising QNNVFDPGYNL (SEQ ID NO:119), and (b) a light chain variable region CDR1 comprising RASQNIGSNLA (SEQ ID NO:120); a light chain variable region CDR2 comprising DASKLES (SEQ ID NO:122), and a light chain variable region CDR3 comprising QCTVRGGAYGNA (SEQ ID NO:124). In some embodiments, an anti-TfR1 antibody comprises (a) a heavy chain variable region comprising a heavy chain CDR1 comprising GFSFSNSYWIC (SEQ ID NO:116), a heavy chain CDR2 comprising CINTDADSTNYASWARG (SEQ ID NO:117), and a heavy chain CDR3 comprising QNNVFDPGYNL (SEQ ID NO:119), or (b) a light chain variable region comprising light chain CDR1 comprising RASQNIGSNLA (SEQ ID NO:120), a light chain CDR2 comprising DASKLES (SEQ ID NO:122), and a light chain CDR3 comprising QCTVRGGAYGNA (SEQ ID NO:124).

In some embodiments, an anti-TfR1 antibody comprises: (a) a heavy chain variable region CDR1 comprising GFSFSNSYWIC (SEQ ID NO:116), or a variant thereof comprising 1, 2, 3, or 4 amino acid substitutions; a heavy chain variable region CDR2 comprising CINTDADSTNYASWARG (SEQ ID NO:117) or a variant thereof comprising 1, 2, 3, or 4 amino acid substitutions; a heavy chain variable region CDR3 comprising QNNVFDPGYNL (SEQ ID NO:119), or a variant thereof comprising 1, 2, 3, or 4 amino acid substitutions; a light chain variable region CDR1 comprising RASQNIGSNLA (SEQ ID NO:120), or a variant thereof comprising 1, 2, 3, or 4 amino acid substitutions; a light chain variable region CDR2 comprising DASKLES (SEQ ID NO:122), or a variant thereof comprising 1, 2, 3, or 4 amino acid substitutions; and a light chain variable region CDR3 comprising QCTVRGGAYGNA (SEQ ID NO:124) or a variant thereof comprising 1, 2, 3, or 4 amino acid substitutions. In some embodiments, a CDR comprises one amino acid substitution. In some embodiments, a CDR comprises two amino acid substitutions. In some embodiments, a CDR comprises three amino acid substitutions. In some embodiments, a CDR comprises four amino acid substitutions. In some embodiments, the one or more amino acid substitutions are conservative substitutions. In some embodiments, the CDR is a heavy chain CDR1. In some embodiments, the CDR is a heavy chain variable region CDR2. In some embodiments, the CDR is a heavy chain variable region CDR3. In some embodiments, the CDR is a light chain variable region CDR1. In some embodiments, the CDR is a light chain variable region CDR2. In some embodiments, the CDR is a light chain variable region CDR3. In some embodiments, the one or more substitutions are made as part of a humanization process. In some embodiments, the one or more substitutions are made as part of a germline humanization process. In some embodiments, the one or more substitutions are made as part of an affinity maturation process. In some embodiments, the one or more substitutions are made as part of an optimization process.

In some embodiments, the anti-TfR1 antibody comprising a heavy chain variable region (VH) comprising VH CDR1, VH CDR2, and VH CDR3, wherein the VH CDR1 comprises the amino acid sequence GFSFSNSYWIX (SEQ ID NO:155), wherein X is any amino acid; the VH CDR2 comprises the amino acid sequence XINTDADSTNYAXXXXG (SEQ ID NO:157), wherein X is any amino acid; and the VH CDR3 comprises the amino acid sequence QNNVFDPGYNL (SEQ ID NO:119); and wherein the antibody comprises a light chain variable region (VL) comprising VL CDR1, VL CDR2, and VL CDR3, wherein: the VL CDR1 comprises the amino acid sequence XASQNIGSNLA (SEQ ID NO:159); the VL CDR2 comprises the amino acid sequence DASKLXS (SEQ ID NO:161), wherein X is any amino acid; and the VL CDR3 comprises the amino acid sequence QXTVRGGAYGXA (SEQ ID NO:163), wherein X is any amino acid. In some embodiments, the VH CDR1 comprises the amino acid sequence GFSFSNSYWIX$_1$ (SEQ ID NO:156), wherein X$_1$ is C, A, or H; the VH CDR2 comprises the amino acid sequence X$_2$INTDADSTNYAX$_3$X$_4$X$_5$X$_6$G (SEQ ID NO:158), wherein X$_2$ is C or A, wherein X$_3$ is S or D, wherein X$_4$ is W or S, wherein X$_5$ is A or V, and wherein X$_6$ is R or K; the VH CDR3 comprises the amino acid sequence QNNVFDPGYNL (SEQ ID NO:119); the VL CDR1 comprises the amino acid sequence X$_7$ASQNIGSNLA (SEQ ID NO:160), wherein X$_7$ is Q or R; the VL CDR2 comprises the amino acid sequence DASKLX$_8$S (SEQ ID NO:162), wherein X$_8$ is A or E; and the VL CDR3 comprises the amino acid sequence QX$_9$TVRGGAYGX$_{10}$A (SEQ ID NO:164), wherein X$_9$ is C, Q, A, S, T, or V, and wherein X$_{10}$ is N or L.

In some embodiments of the methods described herein, an anti-TfR1 antibody comprises a heavy chain variable region comprising an amino acid sequence that has the three VH CDRs of any ANTIBODY-B clone disclosed herein and which has at least 75%, 80%, 85%, 90%, 95%, 96%, 97%, 98%, 99%, or 100% identity to the sequence set forth in SEQ ID NO:33 and a light chain variable region comprising an amino acid sequence that has the three VL CDRs of any ANTIBODY-B clone disclosed herein and which has at least 75%, 80%, 85%, 90%, 95%, 96%, 97%, 98%, 99%, or 100% identity to the sequence set forth in SEQ ID NO:41.

In some embodiments of the methods described herein, an anti-TfR1 antibody comprises a heavy chain variable region comprising at least 75%, 80%, 85%, 90%, 95%, 96%, 97%, 98%, 99%, or 100% identity to the sequence set forth in SEQ ID NO:33 and a light chain variable region comprising at least 75%, 80%, 85%, 90%, 95%, 96%, 97%, 98%, 99%, or 100% identity to the sequence set forth in SEQ ID NO:41.

In some embodiments of the methods described herein, an anti-TfR1 antibody comprises a heavy chain variable region with one or more substitutions, deletions, or insertions in the sequence set forth in SEQ ID NO:33 and a light chain variable region with one or more substitutions, deletions, or insertions in the sequence set forth in SEQ ID NO:41.

In some embodiments of the methods described herein, an anti-TfR1 antibody comprises a heavy chain variable region comprising an amino acid sequence that has the three VH CDRs of any ANTIBODY-B clone disclosed herein and which has at least 75%, 80%, 85%, 90%, 95%, 96%, 97%, 98%, 99%, or 100% identity to any one of the VH sequences set forth in FIG. 1B and a light chain variable region comprising an amino acid sequence that has the three VL CDRs of any ANTIBODY-B clone disclosed herein and which has at least 75%, 80%, 85%, 90%, 95%, 96%, 97%, 98%, 99%, or 100% identity to any one of the sequences set forth in FIG. 1D.

In some embodiments, an anti-TfR1 antibody comprises a heavy chain variable region having at least about 80% sequence identity to SEQ ID NO:33, and/or a light chain variable region having at least 80% sequence identity to SEQ ID NO:41. In some embodiments, an anti-TfR1 antibody comprises a heavy chain variable region having at least about 85%, at least about 90%, at least about 95%, at least about 97%, or at least about 99% sequence identity to SEQ ID NO:33. In some embodiments, an anti-TfR1 antibody comprises a light chain variable region having at least about 85%, at least about 90%, at least about 95%, at least about 97%, or at least about 99% sequence identity to SEQ ID NO:41.

In some embodiments, an anti-TfR1 antibody comprises a heavy chain variable region having at least about 80% sequence identity to SEQ ID NO:33 and/or a light chain variable region having at least about 80% sequence identity to SEQ ID NO:41. In some embodiments, an anti-TfR1 antibody comprises a heavy chain variable region having at least about 80% sequence identity to SEQ ID NO:33 and a light chain variable region having at least about 80% sequence identity to SEQ ID NO:41. In some embodiments, an anti-TfR1 antibody comprises a heavy chain variable region having at least about 90% sequence identity to SEQ ID NO:33 and/or a light chain variable region having at least about 90% sequence identity to SEQ ID NO:41. In some embodiments, an anti-TfR1 antibody comprises a heavy chain variable region having at least about 90% sequence identity to SEQ ID NO:33 and a light chain variable region having at least about 90% sequence identity to SEQ ID NO:41. In some embodiments, an anti-TfR1 antibody comprises a heavy chain variable region having at least about 95% sequence identity to SEQ ID NO:33 and/or a light chain variable region having at least about 95% sequence identity to SEQ ID NO:41. In some embodiments, an anti-TfR1 antibody comprises a heavy chain variable region having at least about 95% sequence identity to SEQ ID NO:33 and a light chain variable region having at least about 95% sequence identity to SEQ ID NO:41.

In some embodiments, an anti-TfR1 antibody comprises a heavy chain variable region comprising SEQ ID NO:33. In some embodiments, an anti-TfR1 antibody comprises a light chain variable region comprising SEQ ID NO:41. In some embodiments, an anti-TfR1 antibody comprises a heavy chain variable region comprising SEQ ID NO:33 and a light chain variable region comprising SEQ ID NO:41.

In some embodiments, an anti-TfR1 antibody comprises a CDR1, CDR2, and CDR3 from a heavy chain variable region having the amino acid sequence of SEQ ID NO:33 and a CDR1, CDR2, and CDR3 from a light chain variable region having the amino acid sequence of SEQ ID NO:41. In some embodiments, an anti-TfR1 antibody comprises: (i) a heavy chain variable region comprising a CDR1, CDR2, and CDR3 from a heavy chain variable region having the amino acid sequence of SEQ ID NO:33, and (ii) a light chain variable region comprising a CDR1, CDR2, and CDR3 from a light chain variable region having the amino acid sequence of SEQ ID NO:41.

The humanized VH/VL constructs of this disclosure include, but are not limited to the SEQ ID NOs depicted in FIGS. 1A-1D.

Constant Regions of Anti-TfR1 Antibodies

In some embodiments, the variable region of an anti-TfR1 antibody described herein is fused to a constant region. A constant region has a constant heavy chain (CH) domain (e.g., CH1, hinge, CH2, and/or CH3 domain(s) or any combination thereof) and a constant light chain (CL) domain. In some embodiments, the CH domain is from an IgG1 molecule or an IgG4 molecule. In some embodiments, the CH domain is from an IgG2 molecule, an IgG3 molecule, or an IgG molecule. The VH of an anti-TfR1 antibody described herein can be fused to any one of the following constant heavy chain (CH) constructs as shown in Table 5 below. The VL of the anti-TfR1 antibody described herein can be fused to any one of the following constant light chain (CL) constructs as shown in Table 5 below. In some embodiments, the VH/CH1 (CH1 from IgG1) construct is further fused to a hinge region shown in Table 5 below (e.g., ES). In some embodiments, the VH/CH1 (CH1 from IgG1) construct is further fused to a hinge region that comprises the amino acid sequence E, EP, EPK, or any one of SEQ ID NOs:58-74. In some embodiments, the VH/CH1 (CH1 from IgG4) construct is further fused to a hinge region shown in Table 5 below (e.g., ES). In some embodiments, the VH/CH1 (CH1 from IgG4) construct is further fused to a hinge region that comprises the amino acid sequence E, ES, ESK, or any one of SEQ ID NOs:75-90. In some embodiments, the VH/VL-CH1/CL construct does not contain a hinge. In some embodiments, the hinge region is any hinge region known in the art. In some embodiments, the hinge region is naturally occurring, e.g., from a naturally occurring IgG1, IgG2, IgG3, or IgG4 molecule. In other embodiments, the hinge region contains modification(s) relative to a naturally occurring hinge.

In some embodiments, an anti-TfR1 antibody of the disclosure is one in which at least one or more of the constant regions has been modified or deleted. In some embodiments, an antibody may comprise one or more modifications to the heavy chain constant domain (CH1, CH2 or CH3) and/or to the light chain constant region (CL). In some embodiments, the heavy chain constant region of the modified antibody comprises at least one human constant region. In some embodiments, the heavy chain constant region of the modified antibody comprises more than one human constant region. In some embodiments, the VH is fused to any CH1 construct known in the art, and the VL is fused to any CL known in the art. In some embodiments, the constant light chain (CL) of the constructs is a naturally occurring human Kappa constant region. In some embodiments, modifications to the constant region comprise additions, deletions, or substitutions of one or more amino acids in one or more regions. In some embodiments, one or more regions are partially or entirely deleted from the constant regions of a modified antibody. In some embodiments, the entire CH2 and CH3 domains have been removed from an antibody. In some embodiments, a deleted constant region is replaced by a short amino acid spacer that provides some of the molecular flexibility typically imparted by the absent constant region. In some embodiments, a modified antibody comprises a CH1 domain directly fused to the hinge region of the antibody. In some embodiments, a modified antibody comprises an Fab fused to the bottom of an Fc.

In some embodiments, an anti-TfR1 antibody of the disclosure contains a linker (e.g., a linker as shown in Table 5 below). In some embodiments, a linker is positioned between the Fc region and the Fab region of an anti-TfR1 antibody of the disclosure.

TABLE 5

Constant Region and Hinge Sequences

| Domain | Sequence |
|---|---|
| IgG1 or IgG4 CH1 | |
| IgG1 CH1 (no hinge) (SEQ ID NO: 45) | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKKV |

TABLE 5-continued

Constant Region and Hinge Sequences

| Domain | Sequence |
|---|---|
| IgG1 CH1 (with hinge underlined) (SEQ ID NO: 46) | ASTKGPSVFPLAPSSKSTSGGTAALGCLVKDYFPEPVTVSWNSGAL<br>TSGVHTFPAVLQSSGLYSLSSVVTVPSSSLGTQTYICNVNHKPSNT<br>KVDKKV<u>EPKSCDKTHTCPP</u> |
| IgG1 CH1 (no hinge) (SEQ ID NO: 47) | ASTKGPSVFPLAPSSKSTSGGTAALGCLVKDYFPEPVTVSWNSGAL<br>TSGVHTFPAVLQSSGLYSLSSVVTVPSSSLGTQTYICNVNHKPSNT<br>KVDKRV |
| IgG1 CH1 (with hinge underlined) (SEQ ID NO: 48) | ASTKGPSVFPLAPSSKSTSGGTAALGCLVKDYFPEPVTVSWNSGAL<br>TSGVHTFPAVLQSSGLYSLSSVVTVPSSSLGTQTYICNVNHKPSNT<br>KVDKRV<u>ESKYGPPCP</u> |
| IgG1 CH1 (no hinge) (SEQ ID NO: 49) | ASTKGPSVFPLAPSSKSTSGGTAALGCLVKDYFPEPVTVSWNSGAL<br>TSGVHTFPAVLQSSGLYSLSSVVTVPSSSLGTQTYICNVNHKPSNT<br>KVDKKV |
| IgG1 CH1 (with hinge underlined) (SEQ ID NO: 50) | ASTKGPSVFPLAPSSKSTSGGTAALGCLVKDYFPEPVTVSWNSGAL<br>TSGVHTFPAVLQSSGLYSLSSVVTVPSSSLGTQTYICNVNHKPSNT<br>KVDKKV<u>EPKSC</u> |
| IgG4 CH1 (no hinge) (SEQ ID NO: 51) | ASTKGPSVFPLAPCSRSTSESTAALGCLVKDYFPEPVTVSWNSGAL<br>TSGVHTFPAVLQSSGLYSLSSVVTVPSSSLGTKTYTCNVDHKPSNT<br>KVDKRV |
| IgG4 CH1 (with hinge underlined) (SEQ ID NO: 52) | ASTKGPSVFPLAPCSRSTSESTAALGCLVKDYFPEPVTVSWNSGAL<br>TSGVHTFPAVLQSSGLYSLSSVVTVPSSSLGTKTYTCNVDHKPSNT<br>KVDKRV<u>ES</u> |
| Fc hIgG1.agly DelPG (SEQ ID NO: 198) | KTHTCPPCPAPELLGGPSVFLFPPKPKDTLMISRTPEVTCVVVDVS<br>HEDPEVKFNWYVDGVEVHNAKTKPREEQYQSTYRVVSVLTVLHQDW<br>LNGKEYKCKVSNKALPAPIEKTISKAKGQPREPQVYTLPPSRDELT<br>KNQVSLTCLVKGFYPSDIAVEWESNGQPENNYKTTPPVLDSDGSFF<br>LYSKLTVDKSRWQQGNVFSCSVMHEALHNHYTQKSLSLS |
| Fc hIgG1.agly DelG (SEQ ID NO: 199) | KTHTCPPCPAPELLGGPSVFLFPPKPKDTLMISRTPEVTCVVVDVS<br>HEDPEVKFNWYVDGVEVHNAKTKPREEQYQSTYRVVSVLTVLHQDW<br>LNGKEYKCKVSNKALPAPIEKTISKAKGQPREPQVYTLPPSRDELT<br>KNQVSLTCLVKGFYPSDIAVEWESNGQPENNYKTTPPVLDSDGSFF<br>LYSKLTVDKSRWQQGNVFSCSVMHEALHNHYTQKSLSLSP |
| Fc hIgG1.agly (SEQ ID NO: 200) | KTHTCPPCPAPELLGGPSVFLFPPKPKDTLMISRTPEVTCVVVDVS<br>HEDPEVKFNWYVDGVEVHNAKTKPREEQYQSTYRVVSVLTVLHQDW<br>LNGKEYKCKVSNKALPAPIEKTISKAKGQPREPQVYTLPPSRDELT<br>KNQVSLTCLVKGFYPSDIAVEWESNGQPENNYKTTPPVLDSDGSFF<br>LYSKLTVDKSRWQQGNVFSCSVMHEALHNHYTQKSLSLSPG |
| HingeFc hIgG1.agly (SEQ ID NO: 201) | DKTHTCPPCPAPELLGGPSVFLFPPKPKDTLMISRTPEVTCVVVDV<br>SHEDPEVKFNWYVDGVEVHNAKTKPREEQYQSTYRVVSVLTVLHQD<br>WLNGKEYKCKVSNKALPAPIEKTISKAKGQPREPQVYTLPPSRDEL<br>TKNQVSLTCLVKGFYPSDIAVEWESNGQPENNYKTTPPVLDSDGSF<br>FLYSKLTVDKSRWQQGNVFSCSVMHEALHNHYTQKSLSLSPG |
| HingeFc hIgG1.agly (KnobS) (SEQ ID NO: 202) | DKTHTCPPCPAPELLGGPSVFLFPPKPKDTLMISRTPEVTCVVVDV<br>SHEDPEVKFNWYVDGVEVHNAKTKPREEQYQSTYRVVSVLTVLHQD<br>WLNGKEYKCKVSNKALPAPIEKTISKAKGQPREPQVYTLPPCRDEL<br>TKNQVSLWCLVKGFYPSDIAVEWESNGQPENNYKTTPPVLDSDGSF<br>FLYSKLTVDKSRWQQGNVFSCSVMHEALHNHYTQKSLSLSPG |
| Fc hIgG1.agly(KnobS) (SEQ ID NO: 203) | KTHTCPPCPAPELLGGPSVFLFPPKPKDTLMISRTPEVTCVVVDVS<br>HEDPEVKFNWYVDGVEVHNAKTKPREEQYQSTYRVVSVLTVLHQDW<br>LNGKEYKCKVSNKALPAPIEKTISKAKGQPREPQVYTLPPCRDELT<br>KNQVSLWCLVKGFYPSDIAVEWESNGQPENNYKTTPPVLDSDGSFF<br>LYSKLTVDKSRWQQGNVFSCSVMHEALHNHYTQKSLSLSPG |
| HingeFc hIgG1.agly (HoleS) (SEQ ID NO: 195) | KTHTCPPCPAPELLGGPSVFLFPPKPKDTLMISRTPEVTCVVVDVS<br>HEDPEVKFNWYVDGVEVHNAKTKPREEQYQSTYRVVSVLTVLHQDW<br>LNGKEYKCKVSNKALPAPIEKTISKAKGQPREPQVCTLPPSRDELT<br>KNQVSLSCAVKGFYPSDIAVEWESNGQPENNYKTTPPVLDSDGSFF<br>LVSKLTVDKSRWQQGNVFSCSVMHEALHNHYTQKSLSLSPG |

TABLE 5-continued

Constant Region and Hinge Sequences

| Domain | Sequence |
|---|---|
| Hinge region | |
| IgG1 hinge A (SEQ ID NO: 53) | EPKSCDKTHTCPPCPAPELLGGP |
| IgG1 hinge B (SEQ ID NO: 54) | EPKSCDKTHTCPP |
| IgG1 hinge C (SEQ ID NO: 55) | EPKSC |
| IgG4 hinge D (SEQ ID NO: 56) | ESKYGPPCPPCPAPEFLGGP |
| IgG4 hinge E (SEQ ID NO: 57) | ESKYGPPCP |
| IgG4 hinge F | ES |
| IgG1 hinge G (SEQ ID NO: 58) | EPKS |
| IgG1 hinge H (SEQ ID NO: 59) | EPKSCD |
| IgG1 hinge I (SEQ ID NO: 60) | EPKSCDK |
| IgG1 hinge J (SEQ ID NO: 61) | EPKSCDKT |
| IgG1 hinge K (SEQ ID NO: 62) | EPKSCDKTH |
| IgG1 hinge L (SEQ ID NO: 63) | EPKSCDKTHT |
| IgG1 hinge M (SEQ ID NO: 64) | EPKSCDKTHTC |
| IgG1 hinge N (SEQ ID NO: 65) | EPKSCDKTHTCP |
| IgG1 hinge O (SEQ ID NO: 66) | EPKSCDKTHTCPPC |
| IgG1 hinge P (SEQ ID NO: 67) | EPKSCDKTHTCPPCP |
| IgG1 hinge Q (SEQ ID NO: 68) | EPKSCDKTHTCPPCPA |
| IgG1 hinge R (SEQ ID NO: 69) | EPKSCDKTHTCPPCPAP |
| IgG1 hinge S (SEQ ID NO: 70) | EPKSCDKTHTCPPCPAPE |
| IgG1 hinge T (SEQ ID NO: 71) | EPKSCDKTHTCPPCPAPEL |
| IgG1 hinge U (SEQ ID NO: 72) | EPKSCDKTHTCPPCPAPELL |
| IgG1 hinge V (SEQ ID NO: 73) | EPKSCDKTHTCPPCPAPELLG |
| IgG1 hinge W (SEQ ID NO: 74) | EPKSCDKTHTCPPCPAPELLGG |
| IgG4 hinge X | ESK |
| IgG4 hinge Y (SEQ ID NO: 75) | ESKY |

TABLE 5-continued

Constant Region and Hinge Sequences

| Domain | Sequence |
|---|---|
| IgG4 hinge Z (SEQ ID NO: 76) | ESKYG |
| IgG4 hinge ZA (SEQ ID NO: 77) | ESKYGP |
| IgG4 hinge ZB (SEQ ID NO: 78) | ESKYGPP |
| IgG4 hinge ZC (SEQ ID NO: 79) | ESKYGPPC |
| IgG4 hinge ZD (SEQ ID NO: 80) | ESKYGPPCPP |
| IgG4 hinge ZE (SEQ ID NO: 81) | ESKYGPPCPPC |
| IgG4 hinge ZF (SEQ ID NO: 82) | ESKYGPPCPPCP |
| IgG4 hinge ZG (SEQ ID NO: 83) | ESKYGPPCPPCPA |
| IgG4 hinge ZH (SEQ ID NO: 84) | ESKYGPPCPPCPAP |
| IgG4 hinge ZI (SEQ ID NO: 85) | ESKYGPPCPPCPAPE |
| IgG4 hinge ZJ (SEQ ID NO: 86) | ESKYGPPCPPCPAPEF |
| IgG4 hinge ZK (SEQ ID NO: 87) | ESKYGPPCPPCPAPEFL |
| IgG4 hinge ZL (SEQ ID NO: 88) | ESKYGPPCPPCPAPEFLG |
| IgG4 hinge ZM (SEQ ID NO: 89) | ESKYGPPCPPCPAPEFLGG |
| IgG4 hinge ZN (SEQ ID NO: 90) | ESKYGPPCPPCPAPEFLGGP |
| CL domain | |
| Human kappa CL (SEQ ID NO: 91) | RTVAAPSVFIFPPSDEQLKSGTASVVCLLNNFYPREAKVQWKVDNA LQSGNSQESVTEQDSKDSTYSLSSTLTLSKADYEKHKVYACEVTHQ GLSSPVTKSFNRGEC |
| Human kappa CL (ΔC214) (SEQ ID NO: 92) | RTVAAPSVFIFPPSDEQLKSGTASVVCLLNNFYPREAKVQWKVDNA LQSGNSQESVTEQDSKDSTYSLSSTLTLSKADYEKHKVYACEVTHQ GLSSPVTKSFNRGE |
| Linker | |
| LinkerS | S |
| LinkerSG2 | SGG |
| LinkgerSG4 (SEQ ID NO: 204) | SGGGG |
| LinkerSG4SG4 (SEQ ID NO: 205) | SGGGGSGGGG |
| LinkerSG4SG4SG4 (SEQ ID NO: 206) | SGGGGSGGGGSGGGG |
| LinkerG3SG5 (SEQ ID NO: 207) | GGGSGGGGG |

TABLE 5-continued

Constant Region and Hinge Sequences

| Domain | Sequence |
|---|---|
| LinkerG4SG4SG4S (SEQ ID NO: 208) | GGGGSGGGGSGGGGS |
| LinkerTG | TG |

Other exemplary constant regions, e.g., hinge regions, that can be combined with the antibody variable regions described herein include but are not limited to the hinge regions described in Peters S J, et al. J Biol Chem. 2012 Jul. 13; 287(29):24525-33; and Heads J T, et al. Protein Sci. 2012 September; 21(9):1315-22; incorporated herein by reference in their entirety.

In some embodiments, an anti-TfR1 antibody comprises a first polypeptide comprising TOC1796 (SEQ ID NO:192) and a second polypeptide comprising TOC1775 (SEQ ID NO:94).

In some embodiments, an anti-TfR1 antibody comprises a first polypeptide comprising TOC1797 (SEQ ID NO:193), a second polypeptide comprising TOC1801 (SEQ ID NO:195), and a third polypeptide comprising TOC1775 (SEQ ID NO:94).

In some embodiments, an anti-TfR1 antibody comprises a first polypeptide comprising TOC1798 (SEQ ID NO:180) and a second polypeptide comprising TOC1775 (SEQ ID NO:94).

In some embodiments, an anti-TfR1 antibody comprises a first polypeptide comprising TOC1799 (SEQ ID NO:194), a second polypeptide comprising TOC1801 (SEQ ID NO:195), and a third polypeptide comprising TOC1775 (SEQ ID NO:94).

In some embodiments, an anti-TfR1 antibody comprises a first polypeptide comprising TOC1785 (SEQ ID NO:174) and a second polypeptide comprising TOC1715 (SEQ ID NO:196).

In some embodiments, an anti-TfR1 antibody comprises a first polypeptide comprising TOC1786 (SEQ ID NO:175) and a second polypeptide comprising TOC1715 (SEQ ID NO:196).

In some embodiments, an anti-TfR1 antibody comprises a first polypeptide comprising TOC1787 (SEQ ID NO:176) and a second polypeptide comprising TOC1715 (SEQ ID NO:196).

In some embodiments, an anti-TfR1 antibody comprises a first polypeptide comprising TOC1710 (SEQ ID NO:177) and a second polypeptide comprising TOC1715 (SEQ ID NO:196).

In some embodiments, an anti-TfR1 antibody comprises a first polypeptide comprising TOC1711 (SEQ ID NO:178) and a second polypeptide comprising TOC1715 (SEQ ID NO:196).

In some embodiments, an anti-TfR1 antibody comprises a first polypeptide comprising TOC1712 (SEQ ID NO:179) and a second polypeptide comprising TOC1715 (SEQ ID NO:196).

In some embodiments, an anti-TfR1 antibody comprises a first polypeptide comprising TOC1713 (SEQ ID NO:180) and a second polypeptide comprising TOC1715 (SEQ ID NO:196).

In some embodiments, an anti-TfR1 antibody comprises a first polypeptide comprising TOC1714 (SEQ ID NO:181) and a second polypeptide comprising TOC1715 (SEQ ID NO:196).

In some embodiments, an anti-TfR1 antibody comprises a first polypeptide comprising TOC1788 (SEQ ID NO:182) and a second polypeptide comprising TOC1721 (SEQ ID NO:197).

In some embodiments, an anti-TfR1 antibody comprises a first polypeptide comprising TOC1789 (SEQ ID NO:183) and a second polypeptide comprising TOC1721 (SEQ ID NO:197).

In some embodiments, an anti-TfR1 antibody comprises a first polypeptide comprising TOC1790 (SEQ ID NO:184) and a second polypeptide comprising TOC1721 (SEQ ID NO:197).

In some embodiments, an anti-TfR1 antibody comprises a first polypeptide comprising TOC1791 (SEQ ID NO:185) and a second polypeptide comprising TOC1721 (SEQ ID NO:197).

In some embodiments, an anti-TfR1 antibody comprises a first polypeptide comprising TOC1792 (SEQ ID NO:186) and a second polypeptide comprising TOC1721 (SEQ ID NO:197).

In some embodiments, an anti-TfR1 antibody comprises a first polypeptide comprising TOC1793 (SEQ ID NO:187) and a second polypeptide comprising TOC1721 (SEQ ID NO:197).

In some embodiments, an anti-TfR1 antibody comprises a first polypeptide comprising TOC1794 (SEQ ID NO:188) and a second polypeptide comprising TOC1721 (SEQ ID NO:197).

In some embodiments, an anti-TfR1 antibody comprises a first polypeptide comprising TOC1795 (SEQ ID NO:189) and a second polypeptide comprising TOC1721 (SEQ ID NO:197).

In some embodiments, an anti-TfR1 antibody comprises a polypeptide comprising TOC1728 (SEQ ID NO:190).

In some embodiments, an anti-TfR1 antibody comprises a polypeptide comprising TOC1729 (SEQ ID NO:191).

Also provided herein are antibodies that compete with one or more of the antibodies described herein for binding to human TfR1. In some embodiments, an antibody of the disclosure binds the same epitope as one of the anti-TfR1 antibodies described herein. In some embodiments, an antibody binds an epitope overlapping with an epitope bound by one of the anti-TfR1 antibodies described herein. In some embodiments, an antibody that competes with one or more of the antibodies described herein for binding to TfR1 is identified using an epitope binning method as described herein.

In some embodiments, an antibody competes for binding to TfR1 with an anti-TfR1 antibody described herein. In some embodiments, an antibody competes for binding to human TfR1 with an anti-TfR1 antibody described herein. In some embodiments, an antibody competes for binding to TfR1 (e.g., human TfR1) with a reference antibody, wherein the reference antibody comprises: (a) a heavy chain variable region comprising a heavy chain variable region CDR1 comprising GIDFSSSGYMC (SEQ ID NO:101), a heavy chain variable region CDR2 comprising CIYTYSSN-TYYAASVKG (SEQ ID NO:103), and a heavy chain variable region CDR3 comprising GTYGYTGYTYTMGYFSL (SEQ ID NO:106), and (b) a light chain variable region CDR1 comprising QASQNINSYLA (SEQ ID NO:107), a light chain variable region CDR2 comprising RASSLES (SEQ ID NO:108), and a light chain variable region CDR3 comprising QSYYYSGSSNYNA (SEQ ID NO:110). In some embodiments, an antibody competes for binding to TfR1 (e.g., human TfR1) with a reference antibody, wherein the reference antibody comprises a heavy chain variable region comprising SEQ ID NO:16 and a light chain variable region comprising SEQ ID NO:35.

In some embodiments, an antibody competes for binding to TfR1 (e.g., human TfR1) with a reference antibody, wherein the reference antibody comprises: (a) a heavy chain variable region comprising a heavy chain variable region CDR1 comprising GFSFSNSYWIC (SEQ ID NO:116), a heavy chain variable region CDR2 comprising CINTDAD-STNYASWARG (SEQ ID NO:117), and a heavy chain variable region CDR3 comprising QNNVFDPGYNL (SEQ ID NO:119); and (b) a light chain variable region comprising a light chain variable region CDR1 comprising RASQNIG-SNLA (SEQ ID NO:120), a light chain variable region CDR2 comprising DASKLES (SEQ ID NO:122), and a light chain variable region CDR3 comprising QCTVRG-GAYGNA (SEQ ID NO:124). In some embodiments, an antibody competes for binding to TfR1 (e.g., human TfR1) with a reference antibody, wherein the reference antibody comprises a heavy chain variable region comprising SEQ ID NO:33 and a light chain variable region comprising SEQ ID NO:41.

In some embodiments, an anti-TfR1 antibody described herein comprises an antibody in which at least one or more of the constant regions has been modified or deleted. In some embodiments, an antibody may comprise one or more modifications to one or more of the heavy chain constant regions (CH1, hinge, CH2 or CH3), and/or to the light chain constant region (CL). In some embodiments, the heavy chain constant region of the modified antibody comprises at least one human constant region. In some embodiments, the heavy chain constant region of the modified antibody comprises more than one human constant region. In some embodiments, modifications to the constant region comprise additions, deletions, or substitutions of one or more amino acids in one or more regions. In some embodiments, one or more regions are partially or entirely deleted from the constant regions or hinge region of a modified antibody. In some embodiments, the entire CH2 domain has been removed from an antibody. In some embodiments, a deleted constant region is replaced by a short amino acid spacer that provides some of the molecular flexibility typically imparted by the absent constant region. In some embodiments, a modified antibody comprises a CH3 domain directly fused to the hinge region of the antibody. In some embodiments, a modified antibody comprises a peptide spacer inserted between the hinge region and modified CH2 and/or CH3 domains.

In some embodiments, an anti-TfR1 antibody comprises a heavy chain having at least 80%, at least 85%, at least 90%, or at least 95% sequence identity to SEQ ID NO:93. In some embodiments, an anti-TfR1 antibody comprises a light chain having at least 80%, at least 85%, at least 90%, or at least 95% sequence identity to SEQ ID NO:94. In some embodiments, an anti-TfR1 antibody comprises a heavy chain having at least 80%, at least 85%, at least 90%, or at least 95% sequence identity to SEQ ID NO:93 and a light chain having at least 80%, at least 85%, at least 90%, or at least 95% sequence identity to SEQ ID NO:94. In some embodiments, an anti-TfR1 antibody comprises a heavy chain having at least 90% sequence identity to SEQ ID NO:93. In some embodiments, an anti-TfR1 antibody comprises a light chain having at least 90% sequence identity to SEQ ID NO:94. In some embodiments, an anti-TfR1 antibody comprises a heavy chain having at least 90% sequence identity to SEQ ID NO:93 and a light chain having at least 90% sequence identity to SEQ ID NO:94. In some embodiments, an anti-TfR1 antibody comprises a heavy chain comprising the amino acid sequence set forth in SEQ ID NO:93. In some embodiments, an anti-TfR1 antibody comprises a light chain comprising the amino acid sequence set forth in SEQ ID NO:94. In some embodiments, an anti-TfR1 antibody comprises a heavy chain comprising the amino acid sequence set forth in SEQ ID NO:93 and a light chain comprising the amino acid sequence set forth in SEQ ID NO:94. In some embodiments, an anti-TfR1 antibody comprises a heavy chain of SEQ ID NO:93 and/or a light chain of SEQ ID NO:94. In some embodiments, an anti-TfR1 antibody comprises a heavy chain of SEQ ID NO:93. In some embodiments, an anti-TfR1 antibody is an antibody that comprises a light chain of SEQ ID NO:94. In some embodiments, an anti-TfR1 antibody comprises a heavy chain of SEQ ID NO:93 and a light chain of SEQ ID NO:94.

In some embodiments, an anti-TfR1 antibody comprises a heavy chain having an amino acid sequence that has one, two, or three, or more modifications (e.g., substitutions, deletions, or insertions) to SEQ ID NO:93. In some embodiments, an anti-TfR1 antibody comprises a light chain having an amino acid sequence that has one, two, or three, or more modifications (e.g., substitutions, deletions, or insertions) to SEQ ID NO:94. In some embodiments, an anti-TfR1 antibody comprises a heavy chain having an amino acid sequence that has one, two, or three, or more modifications (e.g., substitutions, deletions, or insertions) to SEQ ID NO:93 and a light chain having an amino acid sequence that has one, two, or three, or more modifications (e.g., substitutions, deletions, or insertions) to SEQ ID NO:94.

In some embodiments, an anti-TfR1 antibody comprises a heavy chain having at least 80%, at least 85%, at least 90%, or at least 95% sequence identity to SEQ ID NO:95. In some embodiments, an anti-TfR1 antibody comprises a light chain having at least 80%, at least 85%, at least 90%, or at least 95% sequence identity to SEQ ID NO:96. In some embodiments, an anti-TfR1 antibody comprises a heavy chain having at least 80%, at least 85%, at least 90%, or at least 95% sequence identity to SEQ ID NO:95 and a light chain having at least 80%, at least 85%, at least 90%, or at least 95% sequence identity to SEQ ID NO:96. In some embodiments, an anti-TfR1 antibody comprises a heavy chain having at least 90% sequence identity to SEQ ID NO:95. In some embodiments, an anti-TfR1 antibody comprises a light chain having at least 90% sequence identity to SEQ ID NO:96. In some embodiments, an anti-TfR1 antibody comprises a heavy chain having at least 90% sequence identity to SEQ ID NO:95 and a light chain having at least 90% sequence identity to SEQ ID NO:96. In some embodiments, an anti-TfR1 antibody comprises a heavy chain comprising the amino acid sequence set forth in SEQ ID NO:95. In some embodiments, an anti-TfR1 antibody comprises a light chain comprising the amino acid sequence set forth in SEQ ID NO:96. In some embodiments, an anti-TfR1 antibody comprises a heavy chain comprising the amino acid sequence set forth in SEQ ID NO:95 and a light chain comprising the amino acid sequence set forth in SEQ ID NO:96. In some embodiments, an anti-TfR1 antibody comprises a heavy chain of SEQ ID NO:95 and/or a light chain of SEQ ID NO:96. In some embodiments, an anti-TfR1 antibody comprises a heavy chain of SEQ ID NO:95. In some embodiments, an anti-TfR1 antibody is an antibody that comprises a light chain of SEQ ID NO:96. In some embodiments, an anti-TfR1 antibody comprises a heavy chain of SEQ ID NO:95 and a light chain of SEQ ID NO:96.

In some embodiments, an anti-TfR1 antibody comprises a heavy chain having an amino acid sequence that has one, two, or three, or more modifications (e.g., substitutions, deletions, or insertions) to SEQ ID NO:95. In some embodiments, an anti-TfR1 antibody comprises a light chain having an amino acid sequence that has one, two, or three, or more modifications (e.g., substitutions, deletions, or insertions) to SEQ ID NO:96. In some embodiments, an anti-TfR1 antibody comprises a heavy chain having an amino acid sequence that has one, two, or three, or more modifications (e.g., substitutions, deletions, or insertions) to SEQ ID NO:95 and a light chain having an amino acid sequence that has one, two, or three, or more modifications (e.g., substitutions, deletions, or insertions) to SEQ ID NO:96.

In some embodiments, an anti-TfR1 antibody comprises a heavy chain having at least 80%, at least 85%, at least 90%, or at least 95% sequence identity to SEQ ID NO:97. In some embodiments, an anti-TfR1 antibody comprises a light chain having at least 80%, at least 85%, at least 90%, or at least 95% sequence identity to SEQ ID NO:96. In some embodiments, an anti-TfR1 antibody comprises a heavy chain having at least 80%, at least 85%, at least 90%, or at least 95% sequence identity to SEQ ID NO:97 and a light chain having at least 80%, at least 85%, at least 90%, or at least 95% sequence identity to SEQ ID NO:96. In some embodiments, an anti-TfR1 antibody comprises a heavy chain having at least 90% sequence identity to SEQ ID NO:97. In some embodiments, an anti-TfR1 antibody comprises a light chain having at least 90% sequence identity to SEQ ID NO:96. In some embodiments, an anti-TfR1 antibody comprises a heavy chain having at least 90% sequence identity to SEQ ID NO:97 and a light chain having at least 90% sequence identity to SEQ ID NO:96. In some embodiments, an anti-TfR1 antibody comprises a heavy chain comprising the amino acid sequence set forth in SEQ ID NO:97. In some embodiments, an anti-TfR1 antibody comprises a light chain comprising the amino acid sequence set forth in SEQ ID NO:96. In some embodiments, an anti-TfR1 antibody comprises a heavy chain comprising the amino acid sequence set forth in SEQ ID NO:97 and a light chain comprising the amino acid sequence set forth in SEQ ID NO:96. In some embodiments, an anti-TfR1 antibody comprises a heavy chain of SEQ ID NO:97 and/or a light chain of SEQ ID NO:96. In some embodiments, an anti-TfR1 antibody comprises a heavy chain of SEQ ID NO:97. In some embodiments, an anti-TfR1 antibody is an antibody that comprises a light chain of SEQ ID NO:96. In some embodiments, an anti-TfR1 antibody comprises a heavy chain of SEQ ID NO:97 and a light chain of SEQ ID NO:96.

In some embodiments, an anti-TfR1 antibody comprises a heavy chain having an amino acid sequence that has one, two, or three, or more modifications (e.g., substitutions, deletions, or insertions) to SEQ ID NO:97. In some embodiments, an anti-TfR1 antibody comprises a light chain having an amino acid sequence that has one, two, or three, or more modifications (e.g., substitutions, deletions, or insertions) to SEQ ID NO:96. In some embodiments, an anti-TfR1 antibody comprises a heavy chain having an amino acid sequence that has one, two, or three, or more modifications (e.g., substitutions, deletions, or insertions) to SEQ ID NO:97 and a light chain having an amino acid sequence that has one, two, or three, or more modifications (e.g., substitutions, deletions, or insertions) to SEQ ID NO:96.

In some embodiments, an anti-TfR1 antibody comprises a heavy chain having at least 80%, at least 85%, at least 90%, or at least 95% sequence identity to SEQ ID NO:98. In some embodiments, an anti-TfR1 antibody comprises a light chain having at least 80%, at least 85%, at least 90%, or at least 95% sequence identity to SEQ ID NO:96. In some embodiments, an anti-TfR1 antibody comprises a heavy chain having at least 80%, at least 85%, at least 90%, or at least 95% sequence identity to SEQ ID NO:98 and a light chain having at least 80%, at least 85%, at least 90%, or at least 95% sequence identity to SEQ ID NO:96. In some embodiments, an anti-TfR1 antibody comprises a heavy chain having at least 90% sequence identity to SEQ ID NO:98. In some embodiments, an anti-TfR1 antibody comprises a light chain having at least 90% sequence identity to SEQ ID NO:96. In some embodiments, an anti-TfR1 antibody comprises a heavy chain having at least 90% sequence identity to SEQ ID NO:98 and a light chain having at least 90% sequence identity to SEQ ID NO:96. In some embodiments, an anti-TfR1 antibody comprises a heavy chain comprising the amino acid sequence set forth in SEQ ID NO:98. In some embodiments, an anti-TfR1 antibody comprises a light chain comprising the amino acid sequence set forth in SEQ ID NO:96. In some embodiments, an anti-TfR1 antibody comprises a heavy chain comprising the amino acid sequence set forth in SEQ ID NO:98 and a light chain comprising the amino acid sequence set forth in SEQ ID NO:96. In some embodiments, an anti-TfR1 antibody comprises a heavy chain of SEQ ID NO:98 and/or a light chain of SEQ ID NO:96. In some embodiments, an anti-TfR1 antibody comprises a heavy chain of SEQ ID NO:98. In some embodiments, an anti-TfR1 antibody is an antibody that comprises a light chain of SEQ ID NO:96. In some embodiments, an anti-TfR1 antibody comprises a heavy chain of SEQ ID NO:98 and a light chain of SEQ ID NO:96.

In some embodiments, an anti-TfR1 antibody comprises a heavy chain having an amino acid sequence that has one, two, or three, or more modifications (e.g., substitutions, deletions, or insertions) to SEQ ID NO:98. In some embodiments, an anti-TfR1 antibody comprises a light chain having an amino acid sequence that has one, two, or three, or more modifications (e.g., substitutions, deletions, or insertions) to SEQ ID NO:96. In some embodiments, an anti-TfR1 antibody comprises a heavy chain having an amino acid sequence that has one, two, or three, or more modifications (e.g., substitutions, deletions, or insertions) to SEQ ID NO:98 and a light chain having an amino acid sequence that has one, two, or three, or more modifications (e.g., substitutions, deletions, or insertions) to SEQ ID NO:96.

In some embodiments, an anti-TfR1 antibody comprises a heavy chain having at least 80%, at least 85%, at least 90%, or at least 95% sequence identity to SEQ ID NO:99. In some embodiments, an anti-TfR1 antibody comprises a light chain having at least 80%, at least 85%, at least 90%, or at least 95% sequence identity to SEQ ID NO:100. In some embodiments, an anti-TfR1 antibody comprises a heavy chain having at least 80%, at least 85%, at least 90%, or at least 95% sequence identity to SEQ ID NO:99 and a light chain having at least 80%, at least 85%, at least 90%, or at least 95% sequence identity to SEQ ID NO:100. In some embodiments, an anti-TfR1 antibody comprises a heavy chain having at least 90% sequence identity to SEQ ID NO:99. In some embodiments, an anti-TfR1 antibody comprises a light chain having at least 90% sequence identity to SEQ ID NO:100. In some embodiments, an anti-TfR1 antibody comprises a heavy chain having at least 90% sequence identity to SEQ ID NO:99 and a light chain having at least 90% sequence identity to SEQ ID NO:100. In some embodiments, an anti-TfR1 antibody comprises a heavy chain comprising the amino acid sequence set forth in SEQ ID NO:99. In some embodiments, an anti-TfR1 antibody comprises a light chain comprising the amino acid sequence set forth in SEQ ID NO:100. In some embodiments, an anti-TfR1 antibody comprises a heavy chain comprising the amino acid sequence set forth in SEQ ID NO:99 and a light chain comprising the amino acid sequence set forth in SEQ ID NO:100. In some embodiments, an anti-TfR1 antibody comprises a heavy chain of SEQ ID NO:99 and/or a light chain of SEQ ID NO:100. In some embodiments, an anti-TfR1 antibody comprises a heavy chain of SEQ ID NO:99. In some embodiments, an anti-TfR1 antibody is an antibody that comprises a light chain of SEQ ID NO:100. In some embodiments, an anti-TfR1 antibody comprises a heavy chain of SEQ ID NO:99 and a light chain of SEQ ID NO:100.

The present disclosure further embraces additional variants and equivalents that are substantially homologous to the recombinant, monoclonal, chimeric, humanized, and human antibodies, or antibody fragments thereof, described herein. In some embodiments, it is desirable to improve the binding affinity of the antibody. In some embodiments, it is desirable to modulate biological properties of the antibody, including but not limited to, specificity, thermostability, expression level, effector function(s), glycosylation, immunogenicity, and/or solubility. Those skilled in the art will appreciate that amino acid changes may alter post-translational processes of an antibody, such as changing the number or position of glycosylation sites or altering membrane anchoring characteristics.

Effector function of antibodies can be modulated by amino acid mutations and/or domain substitutions (e.g., including but not limited to those described in Dumet et al. MABS 2019; 11(8):1341-50). Additional characteristics such as pharmacokinetics (e.g., Dall'acqua et al J of Immunology 2002; 169 (9) 5171-80), glycosylation, immunogenicity, solubility, and stability can be engineered by modification of Fc by mutations or substitutions. In addition, novel antigen specificity can be engineered into constant domains to create new paratopes (e.g., Wozniak-Knopp et al. PEDS 2010; 23(4):289-97). The affinity or avidity of a Fab may be modulated by changing the linkages between domains of antibodies such as removing the Fab from the top portion of the antibody and linking the Fab to the Fc C-terminus by a linker of any length from zero to 40 amino acids and fusing into the N-terminus of either the VH or VL domain of the Fab creating an "upside-down" antibody with potentially modulated affinity or avidity for binding to antigen, and modulated effector function (e.g., Weber et al. Cell Reports 2018; 22:149-62).

Variations may be a substitution, deletion, or insertion of one or more nucleotides encoding the antibody or polypeptide that results in a change in the amino acid sequence as compared with the native antibody or polypeptide sequence. In some embodiments, amino acid substitutions are the result of replacing one amino acid with another amino acid having similar structural and/or chemical properties, such as the replacement of a leucine with a serine, e.g., conservative amino acid replacements. Insertions or deletions may optionally be in the range of about 1 to 5 amino acids. In some embodiments, the substitution, deletion, or insertion includes less than 25 amino acid substitutions, less than 20 amino acid substitutions, less than 15 amino acid substitutions, less than 10 amino acid substitutions, less than 5 amino acid substitutions, less than 4 amino acid substitutions, less than 3 amino acid substitutions, or less than 2 amino acid substitutions relative to the parent molecule. In some embodiments, variations in the amino acid sequence that are biologically useful and/or relevant may be determined by systematically making insertions, deletions, or substitutions in the sequence and testing the resulting variant proteins for activity as compared to the parent protein.

In some embodiments, variants may include addition of amino acid residues at the amino- and/or carboxyl-terminal end of the antibody or polypeptide. The length of additional amino acids residues may range from one residue to a hundred or more residues. In some embodiments, a variant comprises an N-terminal methionyl residue. In some embodiments, the variant comprises an additional polypeptide/protein (e.g., Fc region) to create a fusion protein. In some embodiments, a variant is engineered to be detectable and may comprise a detectable label and/or protein (e.g., a fluorescent tag or an enzyme).

In some embodiments, a cysteine residue not involved in maintaining the proper conformation of an antibody is substituted or deleted to modulate the antibody's characteristics, for example, to improve oxidative stability and/or prevent aberrant disulfide crosslinking. Conversely, in some embodiments, one or more cysteine residues are added to create disulfide bond(s) to improve stability.

In some embodiments, an antibody of the present disclosure comprises variant hinge regions incapable of forming disulfide linkages between identical heavy chains (e.g., reduce homodimer formation). In some embodiments, the antibodies comprise heavy chains with changes in amino acids that result in altered electrostatic interactions. In some embodiments, the antibodies comprise heavy chains with changes in amino acids that result in altered hydrophobic/hydrophilic interactions.

In some embodiments, an antibody of the present disclosure is "deimmunized". The deimmunization of antibodies generally consists of introducing specific amino acid mutations (e.g., substitutions, deletions, additions) that result in removal of predicted T-cell epitopes without significantly reducing the binding affinity or other desired characteristics of the antibody.

The variant antibodies or polypeptides described herein may be generated using methods known in the art, including but not limited to, site-directed mutagenesis, alanine scanning mutagenesis, and PCR mutagenesis.

In some embodiments an anti-TfR1 antibody described herein is chemically modified. In some embodiments, the anti-TfR1 antibody has been chemically modified by glycosylation, acetylation, pegylation, phosphorylation, amidation, derivatization by known protecting/blocking groups, proteolytic cleavage, and/or linkage to a cellular ligand or other protein. Any of numerous chemical modifications may be carried out by known techniques.

Generally speaking, antigen-antibody interactions are non-covalent and reversible, formed by a combination of hydrogen bonds, hydrophobic interactions, electrostatic and van der Waals forces. When describing the strength of an antigen-antibody complex, the terms affinity and/or avidity are often used. The binding of an antibody to its antigen is a reversible process, and the affinity of the binding is typically reported as an equilibrium dissociation constant ($K_D$). $K_D$ is the ratio of an antibody dissociation rate (koff) (how quickly it dissociates from its antigen) to the antibody association rate (kon) (how quickly it binds to its antigen). In some embodiments, $K_D$ values are determined by measuring the kon and koff rates of a specific antibody/antigen interaction and then using a ratio of these values to calculate the $K_D$ value. In some embodiments, $K_D$ values are used to evaluate and rank the strength of individual antibody/antigen interactions. The lower the $K_D$ of an antibody, the higher the affinity of the antibody for its target. In some embodiments, affinity is measured using SPR technology in a Biacore system. Avidity gives a measure of the overall strength of an antibody-antigen complex. It is dependent on three major parameters: (i) affinity of the antibody for the target, (ii) valency of both the antibody and antigen, and (iii) structural arrangement of the parts that interact.

Binding Characteristics of Anti-TfR1 Antibodies

In some embodiments, an anti-TfR1 antibody binds TfR1 within a $K_D$ range (monovalent affinity) of between about 100 nM to about 0.1 nM. In some embodiments, an anti-TfR1 antibody binds Tfr1 with a $K_D$ (monovalent affinity) of about 1 μM or less, about 100 nM or less, about 40 nM or less, about 20 nM or less, about 10 nM or less, about 1 nM or less, about 0.1 nM or less, 50 pM or less, 10 pM or less, or 1 pM or less. In some embodiments, an anti-TfR1 antibody binds Tfr1 with a $K_D$ (monovalent affinity) of about 20 nM or less. In some embodiments, an anti-TfR1 antibody binds Tfr1 with a $K_D$ (monovalent affinity) of about 10 nM or less. In some embodiments, an anti-TfR1 antibody binds Tfr1 with a $K_D$ (monovalent affinity) of about 1 nM or less. In some embodiments, an anti-TfR1 antibody binds Tfr1 with a $K_D$ (monovalent affinity) of about 0.5 nM or less. In some embodiments, an anti-TfR1 antibody binds Tfr1 with a $K_D$ (monovalent affinity) of about 0.1 nM or less. In some embodiments, an anti-TfR1 antibody binds Tfr1 with a $K_D$ (monovalent affinity) of about 50 pM or less. In some embodiments an anti-TfR1 antibody binds Tfr1 with a $K_D$ (monovalent affinity) of about 25 pM or less. In some embodiments, an anti-TfR1 antibody binds Tfr1 with a $K_D$ (monovalent affinity) of about 10 pM or less. In some embodiments, an anti-TfR1 antibody binds Tfr1 with a $K_D$ (monovalent affinity) of about 1 pM or less. In some embodiments, the dissociation constant of the antibody to TfR1 is the dissociation constant determined using a TfR1 protein or a fragment thereof immobilized on a Biacore chip with the binding agent flowed over the chip. In some embodiments, the dissociation constant of the binding agent (e.g., an antibody) for TfR1 is the dissociation constant determined using the binding agent captured on a Biacore chip with soluble TfR1 flowed over the chip.

In some embodiments, an anti-TfR1 antibody binds TfR1 with a $K_D$ (monovalent affinity) of about 5 nM or less. In some embodiments, an anti-TfR1 antibody binds Tfr1 with a $K_D$ (monovalent affinity) of about 3 nM or less. In some embodiments, an anti-TfR1 antibody binds Tfr1 with a $K_D$ (monovalent affinity) of about 2 nM or less. In some embodiments, an anti-TfR1 antibody binds Tfr1 with a $K_D$ (monovalent affinity) of about 0.01 nM to about 2.5 nM. In some embodiments, an anti-TfR1 antibody binds Tfr1 with a $K_D$ (monovalent affinity) of about 0.1 nM to about 5 nM. In some embodiments, an anti-TfR1 antibody binds Tfr1 with a $K_D$ (monovalent affinity) of about 1 nM to about 5 nM.

In some embodiments, an anti-TfR1 antibody binds TfR1 with a half maximal effective concentration ($EC_{50}$) range of about 1 μM to about 1 nM (monovalent affinity). In some embodiments, an anti-TfR1 antibody binds Tfr1 with an $EC_{50}$ (monovalent affinity) of about 1 μM or less, about 100 nM or less, about 40 nM or less, about 20 nM or less, about 10 nM or less, about 1 nM or less, or about 0.1 nM or less. In some embodiments, an anti-TfR1 antibody binds TfR1 with an $EC_{50}$ (monovalent affinity) of about 1 μM or less, about 100 nM or less, about 40 nM or less, about 20 nM or less, about 10 nM or less, about 1 nM or less, or about 0.1 nM or less. In some embodiments, an anti-TfR1 antibody binds cyno TfR1 and/or human TfR1 with an $EC_{50}$ (monovalent affinity) of about 40 nM or less, about 20 nM or less, about 10 nM or less, about 1 nM or less or about 0.1 nM or less. In some embodiments, an anti-TfR1 antibody binds TfR1 with an $EC_{50}$ (monovalent affinity) of 0.1 nM to 3 nM, 0.1 nM to 2 nM, 0.1 nM to 1 nM, 0.5 nM to 3 nM, 0.5 nM to 2 nM, or 0.5 nM to 1 nM.

In some embodiments, an $EC_{50}$ value is determined by binding of the anti-TfR1 antibody to cells expressing TfR1 using Fluorescence Activated Cell Sorting (FACS). In some embodiments, an $EC_{50}$ value is determined by assays on plates coated with huTfR1 ectodomain including but not limited to Enzyme Linked Immunosorbent Assay (ELISA) and Meso Scale Discovery (MSD).

Methods of Making Anti-TfR1 Antibodies

The anti-TfR1 antibodies described herein can be produced by any suitable method known in the art. Such methods range from direct protein synthesis methods to constructing a DNA sequence encoding polypeptide sequences and expressing those sequences in a suitable host. In some embodiments, a DNA sequence is constructed using recombinant technology by isolating or synthesizing a DNA sequence encoding a wild-type protein of interest. Optionally, the sequence can be mutagenized by site-specific mutagenesis to provide functional variants thereof. In some embodiments, a DNA sequence encoding a polypeptide of interest is constructed by chemical synthesis using an oligonucleotide synthesizer. Oligonucleotides can be designed based on the amino acid sequence of the desired polypeptide and selecting those codons that are favored in the host cell in which the recombinant polypeptide of interest will be produced. Standard methods can be applied to synthesize a polynucleotide sequence encoding an isolated polypeptide of interest. For example, a complete amino acid sequence can be used to construct a back-translated gene. Further, a DNA oligomer containing a nucleotide sequence coding for the particular isolated polypeptide can be synthesized. For example, several small oligonucleotides coding for portions of the desired polypeptide can be synthesized and then ligated. The individual oligonucleotides typically contain 5' or 3' overhangs for complementary assembly.

Once assembled (by synthesis, site-directed mutagenesis, or another method), a polynucleotide sequence encoding a particular polypeptide of interest can be inserted into an expression vector and operatively linked to an expression control sequence appropriate for expression of the protein in a desired host. Proper assembly can be confirmed by nucleotide sequencing, restriction enzyme mapping, and/or expression of a biologically active polypeptide in a suitable host. As is well-known in the art, in order to obtain high expression levels of a transfected gene in a host, the gene must be operatively linked to transcriptional and translational expression control sequences that are functional in the chosen expression host.

In some embodiments, a recombinant expression vector is used to amplify and express DNA encoding an antibody against human TfR1. For example, a recombinant expression vector can be a replicable DNA construct that includes synthetic or cDNA-derived DNA fragments encoding a polypeptide chain of an anti-TfR1 antibody operatively linked to suitable transcriptional and/or translational regulatory elements derived from mammalian, microbial, viral or insect genes. A transcriptional unit generally comprises an assembly of (1) a genetic element or elements having a regulatory role in gene expression, for example, transcriptional promoters or enhancers, (2) a structural or coding sequence that is transcribed into mRNA and translated into protein, and (3) appropriate transcription and translation initiation and termination sequences. Regulatory elements can include an operator sequence to control transcription. The ability to replicate in a host, usually conferred by an origin of replication, and a selection gene to facilitate recognition of transformants can also be included. DNA regions are "operatively linked" when they are functionally related to each other. For example, DNA for a signal peptide (secretory leader) is operatively linked to DNA for a polypeptide if it is expressed as a precursor that participates in the secretion of the polypeptide; a promoter is operatively linked to a coding sequence if it controls the transcription of the sequence; or a ribosome binding site is operatively linked to a coding sequence if it is positioned so as to permit translation. In some embodiments, structural elements intended for use in yeast expression systems include a leader sequence enabling extracellular secretion of translated protein by a host cell. In some embodiments, in situations where recombinant protein is expressed without a leader or transport sequence, a polypeptide may include an N-terminal methionine residue. This residue can optionally be subsequently cleaved from the expressed recombinant protein to provide a final product.

The choice of an expression control sequence and an expression vector generally depends upon the choice of host. A wide variety of expression host/vector combinations can be employed. Useful expression vectors for eukaryotic hosts include, for example, vectors comprising expression control sequences from SV40, bovine papilloma virus, adenovirus, and cytomegalovirus. Useful expression vectors for bacterial hosts include known bacterial plasmids, such as plasmids from *E. coli*, including pCR1, pBR322, pMB9 and their derivatives, and wider host range plasmids, such as M13 and other filamentous single-stranded DNA phages.

In some embodiments, an anti-TfR1 antibody of the present disclosure is expressed from one or more vectors. In some embodiments, a heavy chain polypeptide is expressed by one vector and a light chain polypeptide is expressed by a second vector. In some embodiments, a heavy chain polypeptide and a light chain polypeptide are expressed by one vector. Thus, the present disclosure provides vectors encoding an anti-TfR1 antibody described herein. In one embodiment, the vector encodes a heavy chain polypeptide of an anti-TfR1 antibody described herein. In one embodiment, the vector encodes a light chain polypeptide of an anti-TfR1 antibody described herein. In one embodiment, the vector encodes a heavy chain polypeptide and a light chain polypeptide of an anti-TfR1 antibody described herein.

Suitable host cells for expression of an anti-TfR1 antibody or a TfR1 protein or fragment thereof to use as an antigen or immunogen include prokaryotes, yeast cells, insect cells, or higher eukaryotic cells under the control of appropriate promoters. Prokaryotes include gram-negative or gram-positive organisms, for example *E. coli* or *Bacillus*. Higher eukaryotic cells include established cell lines of mammalian origin as described herein. Cell-free translation systems may also be employed. Appropriate cloning and expression vectors for use with bacterial, fungal, yeast, and mammalian cellular hosts, as well as methods of protein production, including antibody production are well-known in the art.

Various mammalian culture systems may be used to express recombinant polypeptides. Expression of recombinant proteins in mammalian cells may be desirable because these proteins are generally correctly folded, appropriately modified, and biologically functional. Examples of suitable mammalian host cell lines include, but are not limited to, COS-7 (monkey kidney-derived), L-929 (murine fibroblast-derived), C127 (murine mammary tumor-derived), 3T3 (murine fibroblast-derived), CHO (Chinese hamster ovary-derived), HeLa (human cervical cancer-derived), BHK (hamster kidney fibroblast-derived), HEK-293 (human embryonic kidney-derived) cell lines and variants thereof. Mammalian expression vectors can comprise non-transcribed elements such as an origin of replication, a suitable promoter and enhancer linked to the gene to be expressed, and other 5' or 3' flanking non-transcribed sequences, and 5' or 3' non-translated sequences, such as necessary ribosome binding sites, a polyadenylation site, splice donor and acceptor sites, and transcriptional termination sequences.

Expression of recombinant proteins in insect cell culture systems (e.g., baculovirus) also offers a robust method for producing correctly folded and biologically functional proteins. Baculovirus systems for production of heterologous proteins in insect cells are well-known to those of skill in the art.

Thus, the present disclosure provides cells comprising the anti-TfR1 antibody described herein. The present disclosure also provides cells comprising one or more polynucleotides encoding an anti-TfR1 antibody described herein or one or more vectors encoding anti-TfR1 antibody described herein. In one embodiment, the cell comprises a polynucleotide encoding an anti-TfR1 antibody described herein. In one embodiment, the cell comprises a first polynucleotide encoding a heavy chain of an anti-TfR1 antibody described herein and a second polynucleotide encoding a light chain of an anti-TfR1 antibody described herein. In one embodiment, the cell comprises a polynucleotide encoding a heavy chain and a light chain of an anti-TfR1 antibody described herein. In one embodiment, the cell comprises a vector encoding a an anti-TfR1 antibody described herein. In one embodiment, the cell comprises a first vector encoding a heavy chain of an anti-TfR1 antibody described herein and a second vector encoding a light chain of an anti-TfR1 antibody described herein. In one embodiment, the cell comprises a vector encoding a heavy chain and a light chain of an anti-TfR1 antibody described herein. In some embodiments, the cells produce the anti-TfR1 antibodies described herein. In some embodiments, the cells produce an antibody. In some embodiments, the cells produce an antibody that binds human TfR1. In some embodiments, the cells produce an antibody that binds cyno TfR1. In some embodiments, the cells produce an antibody that binds human TfR1 and cyno TfR1. In some embodiments, the cells produce an antibody designated ANTIBODY-A. In some embodiments, the cells produce a humanized version of ANTIBODY-A. In some embodiments, the cells produce an antibody designated ANTIBODY-B. In some embodiments, the cells produce a humanized version of ANTIBODY-B. In some embodiments, the cell is a prokaryotic cell (e.g., *E. coli*). In some embodiments, the cell is a eukaryotic cell. In some embodiments, the cell is a mammalian cell. In some embodiments, the cell is a hybridoma cell.

Proteins produced by a host cell can be purified according to any suitable method. Standard methods include chromatography (e.g., ion exchange, affinity, and sizing column chromatography), centrifugation, differential solubility, or by any other standard technique for protein purification. Affinity tags such as hexa-histidine (SEQ ID NO:209), maltose binding domain, influenza coat sequence, and glutathione-S-transferase can be attached to the protein to allow easy purification by passage over an appropriate affinity column. Affinity chromatography used for purifying immunoglobulins include, but are not limited to, Protein A, Protein G, and Protein L chromatography. Isolated proteins can be physically characterized using techniques known to those of skill in the art, including but not limited to, proteolysis, size exclusion chromatography (SEC), mass spectrometry (MS), nuclear magnetic resonance (NMR), isoelectric focusing (IEF), high performance liquid chromatography (HPLC), and x-ray crystallography. The purity of isolated proteins can be determined using techniques known to those of skill in the art, including but not limited to, SDS-PAGE, SEC, capillary gel electrophoresis, IEF, and capillary isoelectric focusing (cIEF).

In some embodiments, supernatants from expression systems that secrete recombinant protein into culture media are first concentrated using a commercially available protein concentration filter, for example, an Amicon® or Millipore Pellicon® ultrafiltration unit. Following the concentration step, the concentrate can be applied to a suitable purification matrix. In some embodiments, an anion exchange resin is employed, for example, a matrix or substrate having pendant diethylaminoethyl (DEAE) groups. The matrices can be acrylamide, agarose, dextran, cellulose, or other types commonly employed in protein purification. In some embodiments, a cation exchange step is employed. Suitable cation exchangers include various insoluble matrices comprising sulfopropyl or carboxymethyl groups. In some embodiments, a hydroxyapatite media is employed, including but not limited to, ceramic hydroxyapatite (CHT). In some embodiments, one or more reverse-phase HPLC steps employing hydrophobic RP-HPLC media, e.g., silica gel having pendant methyl or other aliphatic groups, are employed to further purify a recombinant protein. In some embodiments, hydrophobic interaction chromatography (HIC) is used to separate recombinant proteins based on their hydrophobicity. HIC is a useful separation technique for purifying proteins while maintaining biological activity due to the use of conditions and matrices that operate under less denaturing conditions than some other techniques. Some or all of the foregoing purification steps, in various combinations, can be employed to provide a homogeneous recombinant protein.

In some embodiments, the antibody of the this disclosure is an Fab that can be generated by first making a full monoclonal Ab followed by digesting the monoclonal antibody by chemical or enzymatic cleavage (e.g., pepsin, papain, or ficin digestion) to yield a F(ab')$_2$ fragment, followed by reduction of those fragments to yield Fab fragments. Such techniques are known in the art. See, e.g., Victor C-G et al., Biosensors and Bioelectronics, 2016 (85):32-45. Alternatively, the antibody of this disclosure is made by recombinant synthesis of F(ab')$_2$ antibody fragments, followed by chemical reduction of these fragments to yield Fab units.

Polynucleotides

In some embodiments, the disclosure encompasses polynucleotides comprising polynucleotides that encode a polypeptide (e.g., an anti-TfR1 antibody) described herein. The term "polynucleotides that encode a polypeptide" encompasses a polynucleotide that includes only coding sequences for the polypeptide as well as a polynucleotide that includes additional coding and/or non-coding sequences. The polynucleotides of the disclosure can be in the form of RNA or in the form of DNA. DNA includes cDNA, genomic DNA, and synthetic DNA; and can be double-stranded or single-stranded, and if single stranded can be the coding strand or non-coding (anti-sense) strand. In some embodiments, the polynucleotide comprises a polynucleotide (e.g., a nucleotide sequence) encoding a heavy chain of an anti-TfR1 antibody described herein. In some embodiments, the polynucleotide comprises a polynucleotide (e.g., a nucleotide sequence) encoding a light chain of an anti-TfR1 antibody described herein. In some embodiments, the polynucleotide comprises a polynucleotide (e.g., a nucleotide sequence) encoding a heavy chain of an anti-TfR1 antibody described herein and a polynucleotide (e.g., a nucleotide sequence) encoding a light chain of an anti-TfR1 antibody.

In some embodiments, the polynucleotide comprises a polynucleotide (e.g., a nucleotide sequence) encoding a polypeptide comprising an amino acid sequence selected from the group consisting of any one of SEQ ID NOs:4-164. In some embodiments, the polynucleotide comprises a polynucleotide (e.g., a nucleotide sequence) encoding a polypeptide comprising an amino acid sequence of any one of SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:93, SEQ ID NO:94, SEQ ID NO:95, SEQ ID NO:96, SEQ ID NO:97, SEQ ID NO:98, SEQ ID NO:99 and SEQ ID NO:100.

In some embodiments, the polynucleotide comprises a polynucleotide (e.g., a nucleotide sequence) encoding a polypeptide comprising more than one amino acid sequence selected from the group consisting of any one of SEQ ID NOs:4-164. In some embodiments, the polynucleotide comprises a polynucleotide encoding (i) a polypeptide comprising an amino acid sequence of SEQ ID NO:93 and (ii) a polypeptide comprising an amino acid sequence of SEQ ID NO:94. In some embodiments, the polynucleotide comprises a polynucleotide encoding (i) a polypeptide comprising an amino acid sequence of SEQ ID NO:95 and (ii) a polypeptide comprising an amino acid sequence of SEQ ID NO:96. In some embodiments, the polynucleotide comprises a polynucleotide encoding (i) a polypeptide comprising an amino acid sequence of SEQ ID NO:97 and (ii) a polypeptide comprising an amino acid sequence of SEQ ID NO:96. In some embodiments, the polynucleotide comprises a polynucleotide encoding (i) a polypeptide comprising an amino acid sequence of SEQ ID NO:98 and (ii) a polypeptide comprising an amino acid sequence of SEQ ID NO:96. In some embodiments, the polynucleotide comprises a polynucleotide encoding (i) a polypeptide comprising an amino acid sequence of SEQ ID NO:99 and (ii) a polypeptide comprising an amino acid sequence of SEQ ID NO:100.

In some embodiments, the polynucleotide comprises a polynucleotide encoding (i) a polypeptide comprising an amino acid sequence of SEQ ID NO:4 and (ii) a polypeptide comprising an amino acid sequence of SEQ ID NO:34. In some embodiments, the polynucleotide comprises a polynucleotide encoding (i) a polypeptide comprising an amino acid sequence of SEQ ID NO:12 and (ii) a polypeptide comprising an amino acid sequence of SEQ ID NO:35. In some embodiments, the polynucleotide comprises a polynucleotide encoding (i) a polypeptide comprising an amino acid sequence of SEQ ID NO:15 and (ii) a polypeptide comprising an amino acid sequence of SEQ ID NO:35. In some embodiments, the polynucleotide comprises a polynucleotide encoding (i) a polypeptide comprising an amino acid sequence of SEQ ID NO:16 and (ii) a polypeptide comprising an amino acid sequence of SEQ ID NO:35. In some embodiments, the polynucleotide comprises a polynucleotide encoding (i) a polypeptide comprising an amino acid sequence of SEQ ID NO:17 and (ii) a polypeptide comprising an amino acid sequence of SEQ ID NO:35. In some embodiments, the polynucleotide comprises a polynucleotide encoding (i) a polypeptide comprising an amino acid sequence of SEQ ID NO:18 and (ii) a polypeptide comprising an amino acid sequence of SEQ ID NO:35.

In some embodiments, the polynucleotide comprises a polynucleotide encoding (i) a polypeptide comprising an amino acid sequence of SEQ ID NO:19 and (ii) a polypeptide comprising an amino acid sequence of SEQ ID NO:38. In some embodiments, the polynucleotide comprises a polynucleotide encoding (i) a polypeptide comprising an amino acid sequence of SEQ ID NO:30 and (ii) a polypeptide comprising an amino acid sequence of SEQ ID NO:41. In some embodiments, the polynucleotide comprises a polynucleotide encoding (i) a polypeptide comprising an amino acid sequence of SEQ ID NO:31 and (ii) a polypeptide comprising an amino acid sequence of SEQ ID NO:41. In some embodiments, the polynucleotide comprises a polynucleotide encoding (i) a polypeptide comprising an amino acid sequence of SEQ ID NO:32 and (ii) a polypeptide comprising an amino acid sequence of SEQ ID NO:41. In some embodiments, the polynucleotide comprises a polynucleotide encoding (i) a polypeptide comprising an amino acid sequence of SEQ ID NO:33 and (ii) a polypeptide comprising an amino acid sequence of SEQ ID NO:42. In some embodiments, the polynucleotide comprises a polynucleotide encoding (i) a polypeptide comprising an amino acid sequence of SEQ ID NO:33 and (ii) a polypeptide comprising an amino acid sequence of SEQ ID NO:43. In some embodiments, the polynucleotide comprises a polynucleotide encoding (i) a polypeptide comprising an amino acid sequence of SEQ ID NO:33 and (ii) a polypeptide comprising an amino acid sequence of SEQ ID NO:44.

The present disclosure also provides variants of the polynucleotides described herein, wherein the variant encodes, for example, fragments, analogs, and/or derivatives of a polypeptide. In some embodiments, the present disclosure provides a polynucleotide comprising a polynucleotide having a nucleotide sequence at least about 80% identical, at least about 85% identical, at least about 90% identical, at least about 95% identical, and in some embodiments, at least about 96%, 97%, 98% or 99% identical to a polynucleotide encoding a polypeptide described herein.

In some embodiments, a polynucleotide comprises a polynucleotide having a nucleotide sequence at least about 80% identical, at least about 85% identical, at least about 90% identical, at least about 95% identical, and in some embodiments, at least about 96%, 97%, 98%, or 99% identical to a polynucleotide encoding an amino acid sequence selected from the group consisting of SEQ ID NOs:4-164. Also provided is a polynucleotide that comprises a polynucleotide that hybridizes to a polynucleotide encoding an amino acid sequence selected from the group consisting of SEQ ID NOs:4-164. In some embodiments, the hybridization is under conditions of high stringency as is known to those skilled in the art.

As used herein, the phrase "a polynucleotide having a nucleotide sequence at least, for example, 95% identical to a reference nucleotide sequence" is intended to mean that the nucleotide sequence of the polynucleotide is identical to the reference sequence except that the polynucleotide sequence can include up to five point mutations per each 100 nucleotides of the reference nucleotide sequence. In other words, to obtain a polynucleotide having a nucleotide sequence at least 95% identical to a reference nucleotide sequence, up to 5% of the nucleotides in the reference sequence can be deleted or substituted with another nucleotide, or a number of nucleotides up to 5% of the total nucleotides in the reference sequence can be inserted into the reference sequence. These mutations of the reference sequence can occur at the 5' or 3' terminal positions of the reference nucleotide sequence or anywhere between those terminal positions, interspersed either individually among nucleotides in the reference sequence or in one or more contiguous groups within the reference sequence.

The polynucleotide variants can contain alterations in the coding regions, non-coding regions, or both. In some embodiments, a polynucleotide variant contains alterations that produce silent substitutions, additions, or deletions, but does not alter the properties or activities of the encoded polypeptide. In some embodiments, a polynucleotide variant comprises silent substitutions that results in no change to the amino acid sequence of the polypeptide (due to the degeneracy of the genetic code). In some embodiments, a polynucleotide variant comprises one or more mutated codons comprising one or more (e.g., 1, 2, or 3) substitutions to the codon that change the amino acid encoded by that codon. Methods for introducing one or more substitutions into a codon are known in the art, such as, e.g., PCR mutagenesis and site-directed mutagenesis. Polynucleotide variants can be produced for a variety of reasons, for example, to optimize codon expression for a particular host (e.g., change codons in the human mRNA to those preferred by a bacterial host such as *E. coli*). In some embodiments, a polynucleotide variant comprises at least one silent mutation in a non-coding or a coding region of the sequence.

In some embodiments, a polynucleotide variant is produced to modulate or alter expression (or expression levels) of the encoded polypeptide. In some embodiments, a polynucleotide variant is produced to increase expression of the encoded polypeptide. In some embodiments, a polynucleotide variant is produced to decrease expression of the encoded polypeptide. In some embodiments, a polynucleotide variant has increased expression of the encoded polypeptide as compared to a parental polynucleotide sequence. In some embodiments, a polynucleotide variant has decreased expression of the encoded polypeptide as compared to a parental polynucleotide sequence.

In some embodiments, a polynucleotide comprises the coding sequence for a polypeptide (e.g., an antibody) fused in the same reading frame to a polynucleotide that aids in expression and secretion of a polypeptide from a host cell (e.g., a leader sequence that functions as a secretory sequence for controlling transport of a polypeptide). The polypeptide can have the leader sequence cleaved by the host cell to form a "mature" form of the polypeptide.

In some embodiments, a polynucleotide comprises the coding sequence for a polypeptide (e.g., an antibody) fused in the same reading frame to a marker or tag sequence. For example, in some embodiments, a marker sequence is a hexa-histidine (SEQ ID NO:209) tag (HIS-tag) that allows for efficient purification of the polypeptide fused to the marker. In some embodiments, a marker sequence is a hemagglutinin (HA) tag derived from the influenza hemagglutinin protein when a mammalian host (e.g., COS-7 cells) is used. In some embodiments, the marker sequence is a FLAG™ tag. In some embodiments, a marker is used in conjunction with other markers or tags.

In some embodiments, the polynucleotides are isolated. In some embodiments, the polynucleotides are substantially pure.

Vectors and Cells

Vectors and cells comprising each and every one of the polynucleotides described herein are also provided. In some embodiments, an expression vector comprises a polynucleotide molecule encoding an anti-TfR1 antibody described herein. In some embodiments, an expression vector comprises a polynucleotide molecule encoding a polypeptide that is part of a an anti-TfR1 antibody described herein. In some embodiments, an expression vector comprises a polynucleotide molecule encoding a heavy chain polypeptide of an anti-TfR1 antibody described herein. In some embodiments, an expression vector comprises a polynucleotide molecule encoding a light chain polypeptide of an anti-TfR1 antibody described herein. In some embodiments, an expression vector comprises a polynucleotide molecule encoding a heavy chain polypeptide and a light chain polypeptide of anti-TfR1 antibody described herein. In some embodiments, a host cell comprises an expression vector comprising the polynucleotide molecule encoding an anti-TfR1 antibody described herein. In some embodiments, a host cell comprises an expression vector comprising the polynucleotide molecule encoding a polypeptide that is part of an anti-TfR1 antibody described herein. In some embodiments, a host cell comprises a polynucleotide molecule encoding an anti-TfR1 antibody described herein. In some embodiments, a host cell comprises an expression vector comprising a polynucleotide molecule encoding a heavy chain polypeptide of an anti-TfR1 antibody described herein. In some embodiments, a host cell comprises an expression vector comprises a polynucleotide molecule encoding a light chain polypeptide of an anti-TfR1 antibody described herein. In some embodiments, a host cell comprises an expression vector comprises a first polynucleotide encoding a heavy chain polypeptide and a second polynucleotide light chain polypeptide of an anti-TfR1 antibody described herein. In some embodiments, a host cell comprises: (ii) a first expression vector comprising a polynucleotide molecule encoding a heavy chain polypeptide of an anti-TfR1 antibody described herein, and (ii) a second expression vector comprising a polynucleotide molecule encoding a light chain polypeptide of the anti-TfR1 antibody.

Analysis of Physical/Chemical Properties of Anti-TfR1 Antibodies

Anti-TfR1 antibodies of the present disclosure may be analyzed for their physical/chemical properties and/or biological activities by various methods known in the art. In some embodiments, an anti-TfR1 antibody is tested for its ability to bind TfR1 (e.g., human TfR1 and/or cyno TfR1). Binding assays include, but are not limited to, SPR (e.g., Biacore), ELISA, and FACS. In some embodiments, an anti-TfR1 antibody is tested for its ability to inhibit, reduce, or block binding of transferrin to its TfR1 receptor. In some embodiments, an anti-TfR1 antibody is tested for its ability to inhibit, reduce, or block TfR1 activity. In some embodiments, an anti-TfR1 antibody is tested for its ability to internalize with TFR1 and induce increased internalization of TfR1. In addition, antibodies may be evaluated for solubility, stability, thermostability, viscosity, expression levels, expression quality, and/or purification efficiency.

In some embodiments, monoclonal antibodies generated against TfR1 are grouped based upon the epitope each individual antibody recognizes, a process known as "epitope binning". Generally, antibodies are tested in a pairwise combinatorial manner and antibodies that compete with each other are grouped together into bins. For example, in a premix binning assay, a first antibody is immobilized on a surface and a premixed solution of the second antibody and antigen is flowed over the immobilized first antibody. In parallel, the target protein is immobilized on a surface and the two antibodies are flowed over the immobilized antigen and compete to bind to the target. From this technique, antibodies that block one another can be identified. A competitive blocking profile is created for each antibody relative to the others. The results determine which bin each antibody is placed in. High-throughput methods of epitope binning are known in the art and allow for screening and characterization of large numbers of antibodies. Antibodies that bind similar epitopes often share a similar function. Conversely, antibodies that bind different epitopes may have different functional activities.

In some embodiments, an epitope bin comprises at least one antibody from the group consisting of: ANTIBODY-A and ANTIBODY-B.

Epitope mapping is a method of identifying the binding site, region, or epitope on a target protein where an antibody (or other binding agent) binds. A variety of methods are known in the art for mapping epitopes on target proteins. These methods include mutagenesis, including but not limited to, shotgun mutagenesis, site-directed mutagenesis, and alanine scanning; domain or fragment scanning; peptide scanning (e.g., Pepscan technology); display methods (e.g., phage display, microbial display, and ribosome/mRNA display); methods involving proteolysis and mass spectroscopy; and structural determination (e.g., X-ray crystallography and NMR). Detailed exemplary methods for mapping an epitope to which an antibody binds are provided in Morris (1996) "Epitope Mapping Protocols," in Methods in Molecular Biology vol. 66 (Humana Press, Totowa, N.J.).

In some embodiments, an anti-TfR1 antibody described herein is characterized by assays including, but not limited to, N-terminal sequencing, amino acid analysis, HPLC, mass spectrometry, ion exchange chromatography, and papain digestion.

In some embodiments, assays are provided for identifying an anti-TfR1 antibody that affects TfR1 activity. In some embodiments, SPR, ELISA, or FACS assays are used to assess the ability of an anti-TfR1 antibody to block binding of TfR1 to Tf. In some embodiments, cytotoxicity assays are used to assess the ability of an anti-TfR1 antibody to affect natural killer (NK) cell activity. In some embodiments, proliferation assays are used to assess the ability of an anti-TfR1 antibody to affect T-cell activity.

In some embodiments, an anti-TfR1 antibody described herein is an antagonist of human TfR1. In some instances, the terms "inhibiting", "inducing", "reducing", "increasing", "enhancing" are relative to levels/activity in the absence of treatment with a conjugate comprising the anti-TfR1 antibody. In some instances, the terms ""inhibiting", "inducing", "reducing", "increasing", "enhancing" are relative to levels/activity prior to treatment with a conjugate comprising the anti-TfR1 antibody.

Anti-TfR1 Antibody Conjugates, Fusions, and Complexes

The present disclosure also provides conjugates, fusions proteins, and complexes comprising an anti-TfR1 antibody described herein. In some embodiments, the anti-TfR1 antibody of the present disclosure can be conjugated to a second molecule. In some embodiments, an anti-TfR1 antibody is conjugated to a cytotoxic agent or moiety. In some embodiments, an anti-TfR1 antibody is conjugated to a cytotoxic agent to form an ADC (antibody-drug conjugate).

Conjugates comprising an anti-TfR1 antibody described herein may be made using any suitable method known in the art. In some embodiments, the components of the conjugate are linked by covalent interactions. In some embodiments, conjugates are made using a variety of bifunctional protein-coupling agents such as N-succinimidyl-3-(2-pyridyidithiol) propionate (SPDP), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis(p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene).

In some embodiments, an anti-TfR1 antibody described herein is conjugated to a detectable substance or molecule that allows the agent to be used for diagnosis and/or detection. A detectable substance can include, but is not limited to, enzymes, such as horseradish peroxidase, alkaline phosphatase, beta-galactosidase, and acetylcholinesterase; prosthetic groups, such as biotin and flavine(s); fluorescent materials, such as, umbelliferone, fluorescein, fluorescein isothiocyanate (FITC), rhodamine, tetramethylrhodamine isothiocyanate (TRITC), dichlorotriazinylamine fluorescein, dansyl chloride, cyanine (Cy3), and phycoerythrin; bioluminescent materials, such as luciferase; radioactive materials, such as $^{212}$Bi, $^{14}$C, $^{57}$Co, $^{51}$Cr, $^{67}$Cu, $^{18}$F, $^{68}$Ga, $^{67}$Ga, $^{153}$Gd, $^{159}$Gd, $^{68}$Ge, $^{3}$H, $^{166}$Ho, $^{131}$I, $^{125}$I, $^{123}$I, $^{121}$I, $^{115}$In, $^{113}$In, $^{112}$In, $^{111}$In, $^{140}$La, $^{177}$Lu, $^{54}$Mn, $^{99}$Mo, $^{32}$P, $^{103}$Pd, $^{149}$Pm, $^{142}$Pr, $^{186}$Re, $^{188}$Re, $^{105}$Rh, $^{97}$Ru, $^{35}$S, $^{47}$Se, $^{75}$Se, $^{153}$Sm, $^{113}$Sn, $^{117}$Sn, $^{85}$Sr, $^{99m}$Tc, $^{201}$Ti, $^{133}$Xe, $^{90}$Y, $^{69}$Yb, $^{175}$Yb, $^{65}$Zn; positron emitting metals; and magnetic metal ions.

An anti-TfR1 antibody described herein can also be conjugated to a second antibody to form an antibody heteroconjugate.

A an anti-TfR1 antibody described herein may be attached to a solid support. Such solid supports include, but are not limited to, glass, cellulose, polyacrylamide, nylon, polystyrene, polyvinyl chloride, or polypropylene. In some embodiments, an immobilized anti-TfR1 antibody is used in an immunoassay. In some embodiments, an immobilized anti-TfR1 antibody is used in purification of the target antigen (e.g., human TfR1 or cyno TfR1).

In some embodiments, the anti-TfR1 antibody of the present disclosure can be conjugated to a molecule or drug, such as a nucleic acid, e.g., an antisense oligonucleotide, a short interfering RNA (siRNA), an RNA such as messenger RNA (mRNA), microRNA (miRNA), guide RNA (gRNA), a phosphoroamidate morpholino oligomer or an aptamer, etc. In some embodiments, the anti-TfR1 antibody is conjugated to a particle, e.g., lipid particle or nanoparticle, which can contain a therapeutic agent such as one described herein. In some embodiments, the anti-TfR1 antibody is conjugated to a viral particle, e.g., a viral particle comprising a therapeutic nucleic acid and/or protein, e.g., a viral particle for gene therapy. The anti-TfR1 antibody may be linked to the drug by a linker. Methods of preparing antibody-nucleic acid conjugates, such as the conjugates contemplated in this disclosure are well-known in the art. See, e.g., US Patent Application Publication No. US20190240346, and U.S. Pat. Nos. 10,881,743 and 10,550,188, and International Patent Application Publication No. WO1991004753, the disclosures of which are incorporated by reference herein in their entirety.

In some embodiments, fusion proteins comprising the anti-TfR1 antibody described herein can be made using any suitable method known in the art. Such a fusion protein can include a fusion of an anti-TfR1 antibody of the disclosure (including bispecific, multispecific, or multivalent anti-TfR1 antibodies) described herein with a therapeutic polypeptide or protein. In one instance, avidin can be added to the C-terminus of the heavy chain to produce a fusion protein as described in Candelaria P V et al. Front Immunol. 2021; 12:607692. The fusion protein may be further conjugated or complexed to a second molecule or drug, such as a biotinylated drug, as described in Daniels T R, et al. Biochim Biophys Acta. 2012; 1820(3):291-317.

In some embodiments, complexes comprising an anti-TfR1 Ab described herein can be made using any suitable method known in the art. In some embodiments, the components of the complex are linked by non-covalent interactions. Such compounds comprise an anti-TfR1 antibody complexed with another agent, e.g., therapeutic agent, or complexed with a lipid or nanoparticle which has a therapeutic polypeptide or protein.

Tissue Targeting and Use of Anti-TfR1 Antibodies

In some embodiments, the antibodies of the present disclosure can be used to target muscle tissue, e.g., skeletal or voluntary muscles, cardiac muscles, smooth muscles, etc. In some embodiments, described herein is a method of treating muscle atrophy or myotonic dystrophy in a subject, which comprises administering to the subject a therapeutically effective amount of conjugates/fusions/complexes comprising the anti-TfR1 antibodies described herein. In some instances, the muscle atrophy is associated and/or induced by cachexia (e.g., cancer cachexia), denervation, myopathy, motor neuron diseases, diabetes, chronic obstructive pulmonary disease, liver disease, congestive heart failure, chronic renal failure, chronic infection, sepsis, fasting, sarcopenia, glucocorticoid-induced atrophy, disuse, or space flight. In some cases, the myotonic dystrophy is DM1. Examples of muscle diseases that can be treated with conjugates comprising the anti-TfR1 antibodies of the disclosure include, but are not limited to, a muscular disease, a muscular atrophy disease, an arteriosclerotic disease, a cardiac-related disease, and a lysosomal storage disease.

Examples of the muscular disease include muscular dystrophy (e.g., Duchenne muscular dystrophy (DMD), Becker muscular dystrophy (Becker MD), Emery-Dreifuss muscular dystrophy, facioscapulohumeral muscular dystrophy, oculopharyngeal muscular dystrophy, distal muscular dystrophy, limb-girdle muscular dystrophy, Fukuyama type congenital muscular dystrophy, myotonic dystrophy), periodic paralysis, diaphragmatic paralysis, diaphragmatic atony, distal myopathy, myotonia syndrome, mitochondrial disease, and muscle wasting disease.

Examples of the muscular atrophy disease include sarcopenia (age-related muscle atrophy), disuse muscle atrophy, cachexia, amyotrophic lateral sclerosis (ALS), and spinal muscular atrophy.

Examples of the diseases with which muscle wasting is associated include DMD, Becker MD, Limb-Girdle MD, Myotonic MD and Facioscapulohumeral muscular dystrophy (FSHD)), myositis, myopathies (including inherited myopathy and acquired myopathy), motoneuron diseases (such as Lou Gehrig's Disease or ALS), and neurodegenerative diseases (such as Parkinson's disease, Huntington's disease and Alzheimer's disease).

Examples of the arteriosclerotic disease include a peripheral arterial occlusive disease.

Examples of the cardiac-related disease include angina pectoris (including effort angina, variant angina), acute coronary syndrome (including unstable angina, acute myocardial infarction, post-myocardial infarction heart failure), heart failure (including HFrEF, HFpEF, acute heart failure, chronic heart failure, decompensated heart failure), cardiomyopathy (including dilated cardiomyopathy, hypertrophic cardiomyopathy, restrictive cardiomyopathy), cor pulmonale, asymptomatic myocardial ischemia, arrhythmia (including conduction disturbances, sinus node dysfunction, ectopic supraventricular rhythm, atrioventricular block, atrial fibrillation, atrial flutter, re-entry supraventricular tachycardia (SVT, PSVT), Wolff-Parkinson-White (WPW) syndrome, legs and bundle block (bundle branch block and fascicular block), ventricular extrasystoles, ventricular tachycardia, ventricular fibrillation, and sudden cardiac death), valvular abnormalities (including aortic insufficiency, aortic valve stenosis, mitral valve prolapse (MVP), mitral regurgitation, mitral valve stenosis, pulmonary valve insufficiency, pulmonary arterial stenosis, tricuspid regurgitation, tricuspid valve stenosis), endocarditis, cardiac tumors, decreased cardiac function after cardiopulmonary bypass surgery, maintenance of cardiac function and prevention of heart accident during non-drug therapies for severe heart failure (e.g., intra-aortic balloon pumping, ventricular assist device, Batista surgery, cell transplantation, gene therapy, heart transplant). For a list of diseases that may be treated with conjugates comprising the anti-TfR1 antibodies of the disclosure, see e.g., US Patent Application Publication No. US20190240346, and U.S. Pat. No. 10,881,743 and 10,550,188, and International Patent Application Publication No. WO1991004753, the disclosures of which are incorporated by reference herein in their entirety.

Apart from muscle, the antibodies of the present disclosure can be used to target other tissues in which TfR1 is expressed. Examples of such tissues include, but are not limited to hepatocytes, immune cells, tumors, and brain tissue. The transferrin receptor is implicated in many kinds of diseases including anemia, neurodegenerative diseases, and cancers. TfR is known to be expressed in hepatic tissues and is implicated in hepatic iron overload in alcoholic liver disease (ALD) (Suzuki Y, et al., Alcohol Clin Exp Res. 2002 August; 26(8 Suppl):26S-31S). It is also expressed on the endothelial cells of the blood brain barrier (Johnsen K B, et al. Progress in Neurobiology. 181: 101665). Further, TfR1 is also known to be abnormally expressed in various cancers (Shen Y, et al. Am J Cancer Res. 2018; 8(6):916-931). TfR expression is also increased upon activation of immune cells (Harel E, et al. PLoS ONE 2011; 6(9): e24202). TfRs are expressed on proliferating cells and are required for their growth, and can be detected after mitogenic stimulation of normal peripheral blood T and B cells (Neckers, L M et al., J Immunol Nov. 1, 1984, 133 (5) 2437-2441).

Pharmaceutical Compositions

The present disclosure provides compositions comprising an anti-TfR1 antibody described herein. The present disclosure also provides pharmaceutical compositions comprising an anti-TfR1 antibody described herein and a pharmaceutically acceptable vehicle.

Formulations are prepared for storage and/or use by combining an anti-TfR1 antibody of the present disclosure with a pharmaceutically acceptable vehicle (e.g., a carrier or excipient). Those of skill in the art generally consider pharmaceutically acceptable carriers, excipients, and/or stabilizers to be inactive ingredients of a formulation or pharmaceutical composition.

Suitable pharmaceutically acceptable vehicles include, but are not limited to, nontoxic buffers such as phosphate, citrate, and other organic acids; salts such as sodium chloride; antioxidants including ascorbic acid and methionine; preservatives such as octadecyldimethylbenzyl ammonium chloride, hexamethonium chloride, benzalkonium chloride, benzethonium chloride, phenol, butyl or benzyl alcohol, alkyl parabens, such as methyl or propyl paraben, catechol, resorcinol, cyclohexanol, 3-pentanol, and m-cresol; low molecular weight polypeptides (e.g., less than about 10 amino acid residues); proteins such as serum albumin, gelatin, or immunoglobulins; hydrophilic polymers such as polyvinylpyrrolidone; amino acids such as glycine, glutamine, asparagine, histidine, arginine, or lysine; carbohydrates such as monosaccharides, disaccharides, glucose, mannose, or dextrins; chelating agents such as EDTA; sugars such as sucrose, mannitol, trehalose or sorbitol; salt-forming counter-ions such as sodium; metal complexes such as Zn-protein complexes; and non-ionic surfactants such as TWEEN or polyethylene glycol (PEG). (*Remington: The Science and Practice of Pharmacy*, 22$^{nd}$ Edition, 2012, Pharmaceutical Press, London). In some embodiments, the formulation is in the form of an aqueous solution. In some embodiments, the formulation is lyophilized or in an alternative dried form.

The therapeutic formulation can be in unit dosage form. Such formulations include tablets, pills, capsules, powders, granules, solutions or suspensions in water or non-aqueous media, or suppositories. In solid compositions such as tablets the principal active ingredient is mixed with a pharmaceutical carrier. Conventional tableting ingredients include corn starch, lactose, sucrose, sorbitol, talc, stearic acid, magnesium stearate, dicalcium phosphate or gums, and diluents (e.g., water). These can be used to form a solid preformulation composition containing a homogeneous mixture of a compound of the present disclosure, or a non-toxic pharmaceutically acceptable salt thereof. The solid preformulation composition is then subdivided into unit dosage forms of a type described above. The tablets, pills, etc. of the formulation or composition can be coated or otherwise compounded to provide a dosage form affording the advantage of prolonged action. For example, the tablet or pill can comprise an inner composition covered by an outer component. Furthermore, the two components can be separated by an enteric layer that serves to resist disintegration and permits the inner component to pass intact through the stomach or to be delayed in release. A variety of materials can be used for such enteric layers or coatings, such materials include a number of polymeric acids and mixtures of polymeric acids with such materials as shellac, cetyl alcohol, and cellulose acetate.

The binding agents of the present disclosure may be formulated in any suitable form for delivery to a target cell/tissue. In some embodiments, an anti-TfR1 antibody can be formulated as a liposome, microparticle, microcapsule, albumin microsphere, microemulsion, nano-particle, nano-capsule, or macroemulsion. In some embodiments, the pharmaceutical formulation includes an anti-TfR1 antibody of the present disclosure complexed with liposomes. Methods to produce liposomes are known to those of skill in the art. For example, some liposomes can be generated by reverse phase evaporation with a lipid composition comprising phosphatidylcholine, cholesterol, and PEG-derivatized phosphatidylethanolamine (PEG-PE).

In some embodiments, an anti-TfR1 antibody is formulated as a sustained-release preparation. Suitable examples of sustained-release preparations include semi-permeable matrices of solid hydrophobic polymers containing an agent, where the matrices are in the form of shaped articles (e.g., films or microcapsules). Sustained-release matrices include but are not limited to polyesters, hydrogels such as poly(2-hydroxyethyl-methacrylate) or poly(vinyl alcohol), polylactides, copolymers of L-glutamic acid and 7 ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), sucrose acetate isobutyrate, and poly-D-(–)-3-hydroxybutyric acid.

The pharmaceutical compositions or formulations of the present disclosure can be administered in any number of ways for either local or systemic treatment. In some embodiments, administration is topical by epidermal or transdermal patches, ointments, lotions, creams, gels, drops, suppositories, sprays, liquids and powders. In some embodiments, administration is pulmonary by inhalation or insufflation of powders or aerosols, including by nebulizer, intratracheal, and intranasal. In some embodiments, administration is oral. In some embodiments, administration is parenteral including intravenous, intraarterial, intratumoral, subcutaneous, intraperitoneal, intramuscular (e.g., injection or infusion), or intracranial (e.g., intrathecal or intraventricular). In some embodiments, administration is by intravenous injection or intravenous infusion. In some embodiments, administration is by intramuscular injection.

Various delivery systems are known and can be used to administer an anti-TfR1 antibody described herein. In some embodiments, an anti-TfR1 antibody or a composition described herein is delivered in a controlled release or sustained release system. In some embodiments, a pump is used to achieve controlled or sustained release. In some embodiments, polymeric materials are used to achieve controlled or sustained release of the anti-TfR1 antibody herein. Examples of polymers used in sustained release formulations include, but are not limited to, poly 2-hydroxy ethyl methacrylate, polymethyl methacrylate, polyacrylic acid, polyethylene-co-vinyl acetate, polymethacrylic acid, polyglycolides (PLG), polyanhydrides, poly N-vinyl pyrrolidone, polyvinyl alcohol (PVA), polyacrylamide, polyethylene glycol (PEG), polylactides (PLA), polylactide-co-glycolides (PLGA), and polyorthoesters. Any polymer used in a sustained release formulation should be inert, free of leachable impurities, stable on storage, sterile, and biodegradable.

Additional delivery systems can be used to administer an anti-TfR1 antibody described herein including, but not limited to, injectable drug delivery devices and osmotic pumps. Injectable drug delivery devices include, for example, handheld devices (e.g., autoinjectors) or wearable devices. Different types of osmotic pump systems may include single compartment systems, dual compartment systems, and multiple compartment systems.

EMBODIMENTS

Embodiment 1. An antibody that binds to human transferrin receptor, comprising a heavy chain variable region (VH) comprising VH complementarity determining region (CDR)1, VH CDR2, and VH CDR3, wherein:

the VH CDR1 comprises the amino acid sequence GIDFSSSGYMX (SEQ ID NO:149), wherein X is any amino acid;

the VH CDR2 comprises the amino acid sequence XIYTYSSNTYYAXXXKG (SEQ ID NO:151), wherein X is any amino acid; and the VH CDR3 comprises the amino acid sequence GTYGYTGYTYTMGYFSL (SEQ ID NO:106); and wherein the antibody comprises a light chain variable region (VL) comprising VL CDR1, VL CDR2, and VL CDR3, wherein:

the VL CDR1 comprises the amino acid sequence QASQNINSYLA (SEQ ID NO:107);

the VL CDR2 comprises the amino acid sequence RASXLXS (SEQ ID NO:153), wherein X is any amino acid; and the VL CDR3 comprises the amino acid sequence QSYYYSGSSNYNA (SEQ ID NO:110).

Embodiment 2. The antibody of Embodiment 1, wherein:
the VH CDR1 comprises the amino acid sequence GIDFSSSGYMX$_1$ (SEQ ID NO:150), wherein X$_1$ is C, A, or H;
the VH CDR2 comprises the amino acid sequence X$_2$IYTYSSNTYYAX$_3$X$_4$X$_5$KG (SEQ ID NO:152), wherein X$_2$ is C or A, wherein X$_3$ is S or A, wherein X$_4$ is W or S, and wherein X$_5$ is A or V;
the VH CDR3 comprises the amino acid sequence GTYGYTGYTYTMGYFSL (SEQ ID NO:106);
the VL CDR1 comprises the amino acid sequence QASQNINSYLA (SEQ ID NO:107);
the VL CDR2 comprises the amino acid sequence RASX$_6$LX$_7$S (SEQ ID NO:154), wherein X$_6$ is T or S, and wherein X$_7$ is A or E; and
the VL CDR3 comprises the amino acid sequence QSYYYSGSSNYNA (SEQ ID NO:110).

Embodiment 3. The antibody of Embodiment 1, wherein the VH-CDR1, the VH-CDR2, and the VH-CDR3 each correspond to the VH CDRs set forth in FIG. 1A for a single VH clone, and wherein the VL-CDR1, the VL-CDR2, and the VL-CDR3 each correspond to the VL CDRs set forth in FIG. 1C for a single VL clone.

Embodiment 4. The antibody of Embodiment 1, wherein the VH-CDR1, the VH-CDR2, the VH-CDR3, the VL-CDR1, the VL-CDR2, and the VL-CDR3 each correspond to the VH and VL CDRs set forth in Table 1A for a single clone.

Embodiment 5. The antibody of Embodiment 1, wherein:
(a) the VH CDR1 comprises the amino acid sequence GIDFSSSGYMC (SEQ ID NO:101); the VH CDR2 comprises the amino acid sequence CIYTYSSNTYYASWAKG (SEQ ID NO:104); the VH CDR3 comprises the amino acid sequence GTYGYTGYTYTMGYFSL (SEQ ID NO:106); the VL CDR1 comprises the amino acid sequence QASQNINSYLA (SEQ ID NO:107); the VL CDR2 comprises the amino acid sequence RASTLAS (SEQ ID NO:109); and the VL CDR3 comprises the amino acid sequence QSYYYSGSSNYNA (SEQ ID NO:110);
(b) the VH CDR1 comprises the amino acid sequence GIDFSSSGYMH (SEQ ID NO:102); the VH CDR2 comprises the amino acid sequence AIYTYSSN-TYYASWAKG (SEQ ID NO:105); the VH CDR3 comprises the amino acid sequence GTYGYTGYTYTMGYFSL (SEQ ID NO:106); the VL CDR1 comprises the amino acid sequence QASQNINSYLA (SEQ ID NO:107); the VL CDR2 comprises the amino acid sequence RASSLES (SEQ ID NO:108); and the VL CDR3 comprises the amino acid sequence QSYYYSGSSNYNA (SEQ ID NO:110);
(c) the VH CDR1 comprises the amino acid sequence GIDFSSSGYMC (SEQ ID NO:101); the VH CDR2 comprises the amino acid sequence CIYTYSSN-TYYAASVKG (SEQ ID NO:103); the VH CDR3 comprises the amino acid sequence GTYGYTGYTYTMGYFSL (SEQ ID NO:106); the VL CDR1 comprises the amino acid sequence QASQNINSYLA (SEQ ID NO:107); the VL CDR2 comprises the amino acid sequence RASSLES (SEQ ID NO:108); and the VL CDR3 comprises the amino acid sequence QSYYYSGSSNYNA (SEQ ID NO:110); or
(d) the VH CDR1 comprises the amino acid sequence GIDFSSSGYMC (SEQ ID NO:101); the VH CDR2 comprises the amino acid sequence CIYTYSSN-TYYASWAKG (SEQ ID NO:104); the VH CDR3 comprises the amino acid sequence GTYGYTGYTYTMGYFSL (SEQ ID NO:106); the VL CDR1 comprises the amino acid sequence QASQNINSYLA (SEQ ID NO:107); the VL CDR2 comprises the amino acid sequence RASSLES (SEQ ID NO:108); and the VL CDR3 comprises the amino acid sequence QSYYYSGSSNYNA (SEQ ID NO:110).

Embodiment 6. The antibody of any one of the preceding Embodiments, wherein:
(i) the VH is at least 80%, 85%, 90%, 95%, 99%, or 100% identical to any one of SEQ ID NOs:12, or 15-18; and
(ii) the VL is at least 80%, 85%, 90%, 95%, 99%, or 100% identical to any one of SEQ ID NOs:35-37.

Embodiment 7. The antibody of Embodiment 1, wherein the VH comprises the amino acid sequence of any one of SEQ ID NOs:4, 12, or 15-18 and the VL comprises the amino acid sequence of SEQ ID NOs:34-37.

Embodiment 8. The antibody of Embodiment 1, wherein:
(a) the VH comprises the amino acid sequence of SEQ ID NO:4 and the VL comprises the amino acid sequence of SEQ ID NO:34;
(b) the VH comprises the amino acid sequence of SEQ ID NO:12 and the VL comprises the amino acid sequence of SEQ ID NO:35;
(c) the VH comprises the amino acid sequence of SEQ ID NO:15 and the VL comprises the amino acid sequence of SEQ ID NO:35;
(d) the VH comprises the amino acid sequence of SEQ ID NO:16 and the VL comprises the amino acid sequence of SEQ ID NO:35;
(e) the VH comprises the amino acid sequence of SEQ ID NO:17 and the VL comprises the amino acid sequence of SEQ ID NO:35; or
(f) the VH comprises the amino acid sequence of SEQ ID NO:18 and the VL comprises the amino acid sequence of SEQ ID NO:35.

Embodiment 9. An antibody that binds to human transferrin receptor and competes for binding to human transferrin receptor with an antibody comprising:
(a) a VH comprising the amino acid sequence of SEQ ID NO:4 and a VL comprising the amino acid sequence of SEQ ID NO:34;
(b) a VH comprising the amino acid sequence of SEQ ID NO:12 and a VL comprising the amino acid sequence of SEQ ID NO:35;
(c) a VH comprising the amino acid sequence of SEQ ID NO:15 and a VL comprising the amino acid sequence of SEQ ID NO:35;
(d) a VH comprising the amino acid sequence of SEQ ID NO:16 and a VL comprising the amino acid sequence of SEQ ID NO:35;
(e) a VH comprising the amino acid sequence of SEQ ID NO:17 and a VL comprising the amino acid sequence of SEQ ID NO:35; or
(f) a VH comprising the amino acid sequence of SEQ ID NO:18 and a VL comprising the amino acid sequence of SEQ ID NO:35.

Embodiment 10. An antibody that binds to human transferrin receptor, comprising a heavy chain variable region (VH) comprising VH complementarity determining region (CDR)1, VH CDR2, and VH CDR3, wherein:
the VH CDR1 comprises the amino acid sequence GFSFSNSYWIX (SEQ ID NO:155), wherein X is any amino acid;
the VH CDR2 comprises the amino acid sequence XINTDADSTNYAXXXXG (SEQ ID NO:157), wherein X is any amino acid; and
the VH CDR3 comprises the amino acid sequence QNNVFDPGYNL (SEQ ID NO:119); and
wherein the antibody comprises a light chain variable region (VL) comprising VL CDR1, VL CDR2, and VL CDR3, wherein:
the VL CDR1 comprises the amino acid sequence XASQNIGSNLA (SEQ ID NO:159);
the VL CDR2 comprises the amino acid sequence DASKLXS (SEQ ID NO:161), wherein X is any amino acid; and
the VL CDR3 comprises the amino acid sequence QXTVRGGAYGXA (SEQ ID NO:163), wherein X is any amino acid.

Embodiment 11. The antibody of Embodiment 10, wherein:
the VH CDR1 comprises the amino acid sequence GFSFSNSYWIX$_1$ (SEQ ID NO:156), wherein X$_1$ is C, A, or H;
the VH CDR2 comprises the amino acid sequence X$_2$INTDADSTNYAX$_3$X$_4$X$_5$X$_6$G (SEQ ID NO:158), wherein X$_2$ is C or A, wherein X$_3$ is S or D, wherein X$_4$ is W or S, wherein X$_5$ is A or V, and wherein X$_6$ is R or K;
the VH CDR3 comprises the amino acid sequence QNNVFDPGYNL (SEQ ID NO:119);
the VL CDR1 comprises the amino acid sequence X$_7$ASQNIGSNLA (SEQ ID NO:160), wherein X$_7$ is Q or R;
the VL CDR2 comprises the amino acid sequence DASKLX$_8$S (SEQ ID NO:162), wherein X$_8$ is A or E; and the VL CDR3 comprises the amino acid sequence QX$_9$TVRGGAYGX$_{10}$A (SEQ ID NO:164), wherein X$_9$ is C, Q, A, S, T, or V, and wherein X$_{10}$ is N or L.

Embodiment 12. The antibody of Embodiment 10, wherein the VH-CDR1, the VH-CDR2, and the VH-CDR3 each correspond to the VH CDRs set forth in FIG. 1B for a single VH clone, and wherein the VL-CDR1, the VL-CDR2, and the VL-CDR3 each correspond to the VL CDRs set forth in FIG. 1D for a single VL clone.

Embodiment 13. The antibody of Embodiment 10, wherein the VH-CDR1, the VH-CDR2, the VH-CDR3, the VL-CDR1, the VL-CDR2, and the VL-CDR3 each correspond to the VH and VL CDRs set forth in Table 2A for a single clone.

Embodiment 14. The antibody of Embodiment 10, wherein:
- (a) the VH CDR1 comprises the amino acid sequence GFSFSNSYWIC (SEQ ID NO:116); the VH CDR2 comprises the amino acid sequence CINTDADSTNYASWARG (SEQ ID NO:117); the VH CDR3 comprises the amino acid sequence QNNVFDPGYNL (SEQ ID NO:119); the VL CDR1 comprises the amino acid sequence QASQNIGSNLA (SEQ ID NO:121); the VL CDR2 comprises the amino acid sequence DASKLAS (SEQ ID NO:123); and the VL CDR3 comprises the amino acid sequence QCTVRGGAYGNA (SEQ ID NO:124);
- (b) the VH CDR1 comprises the amino acid sequence GFSFSNSYWIC (SEQ ID NO:116); the VH CDR2 comprises the amino acid sequence CINTDADSTNYADSVKG (SEQ ID NO:118); the VH CDR3 comprises the amino acid sequence QNNVFDPGYNL (SEQ ID NO:119); the VL CDR1 comprises the amino acid sequence RASQNIGSNLA (SEQ ID NO:120); the VL CDR2 comprises the amino acid sequence DASKLES (SEQ ID NO:122); and the VL CDR3 comprises the amino acid sequence QCTVRGGAYGNA (SEQ ID NO:124);
- (c) the VH CDR1 comprises the amino acid sequence GFSFSNSYWIC (SEQ ID NO:116); the VH CDR2 comprises the amino acid sequence CINTDADSTNYASWARG (SEQ ID NO:117); the VH CDR3 comprises the amino acid sequence QNNVFDPGYNL (SEQ ID NO:119); the VL CDR1 comprises the amino acid sequence RASQNIGSNLA (SEQ ID NO:120); the VL CDR2 comprises the amino acid sequence DASKLES (SEQ ID NO:122); and the VL CDR3 comprises the amino acid sequence QCTVRGGAYGNA (SEQ ID NO:124);
- (d) the VH CDR1 comprises the amino acid sequence GFSFSNSYWIC (SEQ ID NO:116); the VH CDR2 comprises the amino acid sequence CINTDADSTNYASWARG (SEQ ID NO:117); the VH CDR3 comprises the amino acid sequence QNNVFDPGYNL (SEQ ID NO:119); the VL CDR1 comprises the amino acid sequence RASQNIGSNLA (SEQ ID NO:120); the VL CDR2 comprises the amino acid sequence DASKLES (SEQ ID NO:122); and the VL CDR3 comprises the amino acid sequence QSTVRGGAYGNA (SEQ ID NO:125);
- (e) the VH CDR1 comprises the amino acid sequence GFSFSNSYWIC (SEQ ID NO:116); the VH CDR2 comprises the amino acid sequence CINTDADSTNYASWARG (SEQ ID NO:117); the VH CDR3 comprises the amino acid sequence QNNVFDPGYNL (SEQ ID NO:119); the VL CDR1 comprises the amino acid sequence RASQNIGSNLA (SEQ ID NO:120); the VL CDR2 comprises the amino acid sequence DASKLES (SEQ ID NO:122); and the VL CDR3 comprises the amino acid sequence QTTVRGGAYGNA (SEQ ID NO:126); or
- (f) the VH CDR1 comprises the amino acid sequence GFSFSNSYWIC (SEQ ID NO:116); the VH CDR2 comprises the amino acid sequence CINTDADSTNYASWARG (SEQ ID NO:117); the VH CDR3 comprises the amino acid sequence QNNVFDPGYNL (SEQ ID NO:119); the VL CDR1 comprises the amino acid sequence RASQNIGSNLA (SEQ ID NO:120); the VL CDR2 comprises the amino acid sequence DASKLES (SEQ ID NO:122); and the VL CDR3 comprises the amino acid sequence QVTVRGGAYGNA (SEQ ID NO:127).

Embodiment 15. The antibody of any one of Embodiments 10-14, wherein:
- (i) the VH is at least 80%, 85%, 90%, 95%, 99%, or 100% identical to any one of SEQ ID NOs:30-33; and
- (ii) the VL is at least 80%, 85%, 90%, 95%, 99%, or 100% identical to any one of SEQ ID NOs:41-44.

Embodiment 16. The antibody of Embodiment 10, wherein the VH comprises the amino acid sequence of any one of SEQ ID NOs:30-33 and the VL comprises the amino acid sequence of any one of SEQ ID NOs: 41-44.

Embodiment 17. The antibody of Embodiment 10, wherein:
- (a) the VH comprises the amino acid sequence of SEQ ID NO:19 and the VL comprises the amino acid sequence of SEQ ID NO:38;
- (b) the VH comprises the amino acid sequence of SEQ ID NO:30 and the VL comprises the amino acid sequence of SEQ ID NO:41;
- (c) the VH comprises the amino acid sequence of SEQ ID NO:31 and the VL comprises the amino acid sequence of SEQ ID NO:41;
- (d) the VH comprises the amino acid sequence of SEQ ID NO:32 and the VL comprises the amino acid sequence of SEQ ID NO:41;
- (e) the VH comprises the amino acid sequence of SEQ ID NO:33 and the VL comprises the amino acid sequence of SEQ ID NO:41;
- (f) the VH comprises the amino acid sequence of SEQ ID NO:33 and the VL comprises the amino acid sequence of SEQ ID NO:42;
- (g) the VH comprises the amino acid sequence of SEQ ID NO:33 and the VL comprises the amino acid sequence of SEQ ID NO:43; or
- (h) the VH comprises the amino acid sequence of SEQ ID NO:33 and the VL comprises the amino acid sequence of SEQ ID NO:44.

Embodiment 18. An antibody that binds to human transferrin receptor and competes for binding to human transferrin receptor with an antibody comprising:
- (a) a VH comprising the amino acid sequence of SEQ ID NO:19 and a VL comprising the amino acid sequence of SEQ ID NO:38;
- (b) a VH comprising the amino acid sequence of SEQ ID NO:30 and a VL comprising the amino acid sequence of SEQ ID NO:41;
- (c) a VH comprising the amino acid sequence of SEQ ID NO:31 and a VL comprising the amino acid sequence of SEQ ID NO:41;
- (d) a VH comprising the amino acid sequence of SEQ ID NO:32 and a VL comprising the amino acid sequence of SEQ ID NO:41;

(e) a VH comprising the amino acid sequence of SEQ ID NO:33 and a VL comprising the amino acid sequence of SEQ ID NO:41;

(f) a VH comprising the amino acid sequence of SEQ ID NO:33 and a VL comprising the amino acid sequence of SEQ ID NO:42;

(g) a VH comprising the amino acid sequence of SEQ ID NO:33 and a VL comprising the amino acid sequence of SEQ ID NO:43; or (h) a VH comprising the amino acid sequence of SEQ ID NO:33 and a VL comprising the amino acid sequence of SEQ ID NO:44.

Embodiment 19. The antibody of any one of Embodiments 1 to 18, which is an Fab fragment or an Fab' fragment.

Embodiment 20. The antibody of any one of Embodiments 1 to 18, which is a bispecific antibody, single chain antibody, an Fab fragment, an F(ab')$_2$ fragment, an Fab' fragment, an Fsc fragment, an Fv fragment, an scFv, an sc(Fv)$_2$, or a diabody.

Embodiment 21. The antibody of any one of Embodiments 1 to 19, comprising a constant heavy chain (CH) domain and a constant light chain (CL) domain.

Embodiment 22. The antibody of Embodiment 21, wherein the CH domain comprises a CH1 domain comprising the amino acid sequence set forth in any one of SEQ ID NOs:45-52.

Embodiment 23. The antibody of Embodiment 22, wherein the CH1 domain comprises the amino acid sequence set forth in any one of SEQ ID NOs:45, 47, and 49.

Embodiment 24. The antibody of Embodiment 23, wherein the CH1 domain is fused to a hinge comprising the amino acid sequence set forth in any one of SEQ ID NOs:53-55 and 57.

Embodiment 25. The antibody of Embodiment 22, wherein the CH1 domain comprises the amino acid sequence set forth in SEQ ID NO:51.

Embodiment 26. The antibody of Embodiment 25, wherein the CH1 domain is fused to a hinge comprising the amino acid sequence ES or the amino acid sequence set forth in SEQ ID NO:56.

Embodiment 27. The antibody of Embodiment 23 or 25, wherein the CH1 domain is fused to a hinge comprising the amino acid sequence ES, ESK, or the amino acid sequence set forth in any one of SEQ ID NOs: 53-90.

Embodiment 28. The antibody of any one of Embodiments 21 to 27, wherein the CL domain comprises the amino acid sequence set forth in SEQ ID NO:91 or 92.

Embodiment 29. The antibody of Embodiment 21, wherein the antibody comprises:

(i) a heavy chain comprising the amino acid sequence set forth in SEQ ID NO:93, and a light chain comprising the amino acid sequence set forth in SEQ ID NO:94;

(ii) a heavy chain comprising the amino acid sequence set forth in SEQ ID NO:95, and a light chain comprising the amino acid sequence set forth in SEQ ID NO:96;

(iii) a heavy chain comprising the amino acid sequence set forth in SEQ ID NO:97, and a light chain comprising the amino acid sequence set forth in SEQ ID NO:96;

(iv) a heavy chain comprising the amino acid sequence set forth in SEQ ID NO:98, and a light chain comprising the amino acid sequence set forth in SEQ ID NO:96; or (v) a heavy chain comprising the amino acid sequence set forth in SEQ ID NO:99, and a light chain comprising the amino acid sequence set forth in SEQ ID NO:100.

Embodiment 30. A nucleic acid or nucleic acids encoding the antibody of any one of Embodiments 1 to 29.

Embodiment 31. An expression vector or expression vectors comprising the nucleic acid or nucleic acids of Embodiment 30 operably linked to a promoter.

Embodiment 32. An isolated cell comprising the nucleic acid or nucleic acids of Embodiment 30 or the expression vector or expression vectors of Embodiment 31.

Embodiment 33. An isolated cell comprising a first expression vector comprising a first nucleic acid encoding a first polypeptide comprising the VH of the antibody of any one of Embodiments 1 to 20 operably linked to a promoter, and a second expression vector comprising a second nucleic acid encoding a second polypeptide comprising the VL of the antibody of any one of Embodiments 1 to 20 operably linked to a promoter.

Embodiment 34. A method of making the antibody of any one of Embodiments 1 to 29, comprising culturing the cell of Embodiment 32 or 33 and isolating the antibody.

Embodiment 35. A pharmaceutical composition comprising the antibody of any one of Embodiments 1 to 29 and a pharmaceutically acceptable carrier.

Embodiment 36. A conjugate comprising the antibody of any one of Embodiments 1 to 29 and an agent.

Embodiment 37. The conjugate of Embodiment 36, wherein the agent is a nucleic acid.

Embodiment 38. The conjugate of Embodiment 37, wherein the nucleic acid is an mRNA, a siRNA, an antisense oligonucleotide, microRNA (miRNA), guide RNA (gRNA), or a phosphoroamidate morpholino oligomer (PMO).

Embodiment 39. The conjugate of Embodiment 37, wherein the nucleic acid is an antisense oligonucleotide.

Embodiment 40. The conjugate of any one of Embodiments 36 to 39, wherein the agent is linked to the antibody via a linker.

Embodiment 41. A method of delivering an agent in vivo, the method comprising administering to a human subject the conjugate of any one of Embodiments 36 to 40.

Embodiment 42. The method of Embodiment 41, wherein (a) the human subject has a muscular disease, a muscular atrophy disease, an arteriosclerotic disease, a cardiac-related disease, or a lysosomal storage disease, and the method delivers the agent to muscle tissue;

(b) the human subject has a brain disease and the method delivers the agent to brain tissue;

(c) the human subject has a hepatic disease and the method delivers the agent to hepatocytes;

(d) the human subject has cancer and the method delivers the agent to tumor cells; or (e) the human subject has an immune condition and the method delivers the agent to immune cells.

The following examples are provided to better illustrate the claimed invention and are not to be interpreted as limiting the scope of the invention. To the extent that specific materials are mentioned, it is merely for purposes of illustration and is not intended to limit the invention. One skilled in the art can develop equivalent means or reactants without the exercise of inventive capacity and without departing from the scope of the invention.

EXAMPLES

Example 1: Production of Rabbit Anti-Transferrin Receptor 1 (TfR1) Monoclonal Antibodies Rabbit monoclonal anti-TfR1 antibodies were generated by the following process. A White New Zealand rabbit was immunized twice with cyno transferrin receptor as the immunogen and then boosted with human transferrin receptor. Serum reactivity against human and cyno transferrin receptor was confirmed with binding to human and cyno transferrin receptor expressing Ba/F3 cell lines. Whole Blood was harvested two weeks after the last immunization, and peripheral blood mononuclear cells (PBMCs) were isolated using Ficoll-Paque.

For monoclonal antibody generation, cyno transferrin receptor was immobilized onto a plate, incubated with the PBMCs and used to capture B-cells with the correct specificity. The adherent B-cells were incubated for one week with cell culture conditions that promote differentiation and proliferation of antibody secreting cells. Supernatants from individual wells were evaluated for human and cyno transferrin receptor reactivity using fluorescence activated cell sorting (FACS) and enzyme-linked immunosorbent assay (ELISA). The ELISA assay measured binding to transferrin receptor that was complexed with holo transferrin. The format used for the ELISA involved coating human or cyno transferrin receptor onto a 96-well plate, and then adding holo transferrin to each well. After a 1.5 hour incubation time, diluted supernatants were added to the plate for 1 hour. Antibody bound to the plate was detected with an anti-rabbit IgG HRP reagent. The FACS assay used human and cyno transferrin receptor expressing Baf/3 cell lines. B-cells from wells positive for both human and cyno transferrin receptor were harvested for VH and VL antibody sequence retrieval.

RNA was isolated from the B-cells and used for cDNA synthesis. The heavy and light (Vkappa) chains were PCR-amplified and cloned into pCR4 vector by TOPO/TA cloning. Cloned products were transformed into *E. coli*, and resistant colonies were sequenced using Sanger sequencing.

Example 2: Selection of Chimeric Antibodies RabANTIBODY-A and RabANTIBODY-B

Consensus VH and VL sequences were identified and used to express the rabbit antibodies generated above with a human IgG1 framework. Chimeric rabbit antibody candidates were expressed transiently in Chinese Hamster Ovary S (CHO-S) cells and purified. Binding to human and cyno TfR1 were confirmed using FACs binding to Ba/F3 cells over expressing human or cyno TfR1 and then affinities were determined using SPR analysis to recombinant extracellular domains of human or cyno TfR1.

Two antibodies (RabANTIBODY-A and RabANTIBODY-B) were chosen for humanization based on following characteristics:
1) single digit nM monovalent affinity to human TfR1;
2) cross reactivity to cyno TfR1;
3) less than 10× affinity difference between cyno and human TfR1;
4) no cross reactivity to TfR2; and
5) no epitope overlap with transferrin binding region of TfR1.

The amino acid sequences of the complementarity determining regions (CDRs) and the mature heavy chain variable regions and light chain variable regions of RabANTIBODY-A and RabANTIBODY-B are shown below. The CDRs described below and herein include the union of all positions in the Kabat CDR definitions (Kabat, E. A., Wu, T. T., Perry, H. M., Gottesman, K. S. & Foeller, C. (1991) and the Chothia CDR definitions (Chothia, C. & Lesk, A. M. J. Mol. Biol (1987) 196, 901-917) (Chothia, C. et al. Nature (1989) 342, 877-883) (Al-Lazikani, B., Lesk, A. M. & Chothia, C. J. Mol. Biol (1997) 273, 927-948). This "union" definition of the CDRs also known as the "Wolfguy" definition by Bujotzek et al. (Bujotzek A., (2015) Proteins April; 83(4):681-95) is shown herein in Table 6 and as the underlined positions in the sequence alignment in FIGS. 1A-1D. The Chothia definition of the CDRs is shown herein in Table 7 and as the underlined positions in the sequence alignment in FIGS. 2A-2D.

TABLE 6

Rab ANTIBODY-A CDRs (Union definition)

| Domain | RabANTIBODY-A | RabANTIBODY-B |
|---|---|---|
| VHCDR1 | GIDFSSSGYMC (SEQ ID NO: 101) | GFSFSNSYWIC (SEQ ID NO: 116) |
| VHCDR2 | CIYTYSSNTYYASWAKG (SEQ ID NO: 104) | CINTDADSTNYASWARG (SEQ ID NO: 117) |
| VHCDR3 | GTYGYTGYTYTMGYFSL (SEQ ID NO: 106) | QNNVFDPGYNL (SEQ ID NO: 119) |
| VLCDR1 | QASQNINSYLA (SEQ ID NO: 107) | QASQNIGSNLA (SEQ ID NO: 121) |
| VLCDR3 | RASTLAS (SEQ ID NO: 109) | DASKLAS (SEQ ID NO: 123) |
| VLCDR3 | QSYYYSGSSNYNA (SEQ ID NO: 110) | QCTVRGGAYGNA (SEQ ID NO: 124) |

TABLE 7

Rab ANTIBODY-B CDRs (Chothia definition)

| Domain | RabANTIBODY-A | RabANTIBODY-B |
|---|---|---|
| VHCDR1 | GIDFSSSG (SEQ ID NO: 111) | GFSFSNSY (SEQ ID NO: 128) |
| VHCDR2 | TYSS (SEQ ID NO: 112) | TDAD (SEQ ID NO: 129) |
| VHCDR3 | TYGYTGYTYTMGYFS (SEQ ID NO: 113) | NNVFDPGYN (SEQ ID NO: 130) |
| VLCDR1 | SQNINSY (SEQ ID NO: 114) | SQNIGSN (SEQ ID NO: 131) |
| VLCDR3 | RAS | DAS |
| VLCDR3 | YYYSGSSNYN (SEQ ID NO: 115) | TVRGGAYGN (SEQ ID NO: 132) |

RabANTIBODY-A Heavy Chain Variable Region (VH):
(SEQ ID NO: 4)
QSLEESGGGLVQPGASLTLTCKAS<u>GIDFSSSGYMC</u>WVRQAPGKGLEWIG<u>C</u>

<u>IYTYSSNTYYASWAKG</u>RFTISKTSSTTVTLQMTSLTAADTATYFCAR<u>GTY</u>

<u>GYTGYTYTMGYFSL</u>WGPGTLVTVSS

RabANTIBODY-A Light Chain Variable Region (VL):
(SEQ ID NO: 34)
ELDMTQTPASVEAAVGGTVTIKC<u>QASQNINSYLA</u>WYQQKPGQPPKLLIY<u>R</u>

<u>ASTLAS</u>GVPSRFKGSGSGTEFTLTISDLECADAATYYC<u>QSYYYSGSSNYN</u>

<u>A</u>FGGGTELEIL

-continued

RabANTIBODY-B VH:
(SEQ ID NO: 19)
QSLEESGGGLVQPEGSLTLTCKAS<u>GFSFSNSYWIC</u>WVRQAPGKGLEWIG<u>C</u>

<u>INTDADSTNYASWAR</u>GRFTISKTSSTTVTLQMTSLTAADTASYFCAR<u>QNN</u>

<u>VFDPGYNL</u>WGPGTLVTVSS

RabANTIBODY-B VL:
(SEQ ID NO: 38)
ELVLTQTPASVSEAVGGTVTIKC<u>QASQNIGSNLA</u>WYQQKPGQPPKLLIY<u>D</u>

<u>ASKLAS</u>GVPSRFSGSGSGTEFTLTISDLECADAATYYC<u>QCTVRGGAYGNA</u>

FGGGTEVVVK

Example 3: Humanization of Anti-TfR1 Antibodies

The RabANTIBODY-A and RabANTIBODY-B antibodies were humanized using methods described in U.S. Pat. No. 8,961,976, incorporated by reference herein in its entirety. Briefly, the methods involve grafting of mature non-human CDRs into selected human frameworks, followed by introduction of "back-mutations" of human framework residues to their amino acid sequence in the mature non-human sequence to safeguard stability and binding affinity. Further attempts to minimize risk of immunogenicity were used by (i) using the human sequence for some sections of the CDRs that may not affect affinity, and (ii) selecting "forward mutations" of some non-human CDR residues to their amino acid sequence in human antibodies, where it is predicted that the resulting more-human sequence would not significantly sacrifice binding affinity. Such methods are described in U.S. Pat. No. 8,349,324, incorporated by reference herein in its entirety.

Step 1: Selection of Human Acceptor Frameworks:

The selection method included:

(a) scoring all human germline candidates by a method combining multiple methods of sequence comparison, with more weight given to matches at certain positions that are structurally important, (b) evaluating each mismatched position with the aid of homology model 3D structures, and (c) giving some preference for humVH3 over humVH1 due to the greater typical stability of humVH3 and its potential SpA binding, and some preference for humVK1 over humVK3 for its longer track record of past use in rabbit antibody humanizations.

For ANTIBODY-A, the human germlines humIGHV3-72*1+humIGHJ1*1 and humIGKV1-5*1+humIGKJ4*1 were chosen as the human acceptor frameworks. For ANTIBODY-B, the human germlines humIGHV3-30*1+humIGHJ4*1 and humIGKV1-5*1+humIGKJ4*1 were chosen as the human acceptor frameworks.

Step 2: Design the Most-Human Designs H0 and L0:

The most-human designs were dubbed "H0" and "L0"; they are a CDR graft sequence, potentially plus some human CDR residues due, as described above, to use of some sections of human CDR sequence and/or use of "forward mutations". The CDRs have been defined to include the union of all positions in the Kabat CDR definitions (Kabat, E. A., Wu, T. T., Perry, H. M., Gottesman, K. S. & Foeller, C. (1991). Sequences of Proteins of Immunological Interest, 5th edit. National Institutes of Health, Bethesda, MD) and the Chothia CDR definitions (Chothia, C. & Lesk, A. M. J. Mol. Biol (1987) 196, 901-917) (Chothia, C. et al. Nature (1989) 342, 877-883) (Al-Lazikani, B., Lesk, A. M. & Chothia, C. J. Mol. Biol (1997) 273, 927-948). This "union" definition of the CDRs is also known as the "Wolfguy" definition by Bujotzek et al. (Bujotzek A et al., Proteins April; 83(4):681-95) This "union" definition of the CDRs is shown herein as the underlined positions in the sequence alignment in FIGS. 1A-1D. AHo position numbering is used throughout this humanization section. See, e.g., Honegger A & Plueckthun A, JMB 2001 309:657-670. For each of ANTIBODY-A and ANTIBODY-B, design H0 included AHo #C42A C57A (removing the extra disulfide bond from the mature rabbit CDRs). For ANTIBODY-A, design L0 included a human CDR-L2 except for rabbit R58. For ANTIBODY-B, design L0 included Q108 in CDR-L3 rather than the mature rabbit's unpaired cysteine 108C, L137 in CDR-L3, R24 in CDR-L1, and E71 in CDR-L2.

Step 3: Study Predicted Structure to Compose a List of Proposed Mutations:

For each rabbit/human mismatch, and for many of their structural neighbors, rational design (and in some cases computational energy calculations), was used to predict how mutation to the mature rabbit amino acid, or in some cases other de novo amino acids, might improve or risk stability, might be needed to preserve binding affinity, or might raise immunogenicity risk.

For ANTIBODY-A VH, mutations used include the set {E1-(deletion) V2Q Q3S}, Q141P, A24K, the set {A42C A57C}, the set {ASV 72-74 SWA} in the "CDR-H2 Kabat extension", and the set {RDDSKNSL 82-89 KT-SSTTV} ("RDDSKNSL" disclosed as SEQ ID NO:210, and "KT-SSTTV" disclosed as SEQ ID NO:211) or the set {R82K D84-L89V} in the so-called "CDR-H4" framework loop which is shorter in the mature rabbit sequence.

For ANTIBODY-B VH, mutations used include the set {Q1-(deletion) V2Q Q3S}, Q141P, the set {A42C A57C}, A56G which could affect the 42C 57C disulfide bond, the set {DSVK 72-75 SWAR} ("DSVK" disclosed as SEQ ID NO:212, and "SWAR" disclosed as SEQ ID NO:213) in the "CDR-H2 Kabat extension", the set {A24K N87T} and/or D83T and/or N84-(deletion) and/or the set {N87T A24K} and/or L89V in the so-called "CDR-H4" framework loop which is shorter in the mature rabbit sequence.

For ANTIBODY-A VK, mutations used include C98P, the set DIQ 1-3 ELD, and the set S69T E71A.

For ANTIBODY-B VK, mutations used include C98P, Q108C to reintroduce the unpaired cysteine of the mature rabbit sequence, the set {DIQM 1-4 ELVL} ("DIQM" disclosed as SEQ ID NO:214, and "ELVL" disclosed as SEQ ID NO:215), Q108A to try an amino acid as small as 108C but with no potential for incorrect disulfide bonding, and L137N.

Step 4: Group the Mutations into a Few Designs

To triage predicted risks, the mutations of interest were grouped into a few VH designs and a few VK designs. Immunogenicity risks were predicted by comparisons to human germline and by the CD4 episcore method. See, e.g., Dhanda et. al., Frontiers in Immunology, 2018, 9, 1369). For each of ANTIBODY-A and ANTIBODY-B, the number of designs were doubled to try the rabbit extra disulfide VH 42C 57C (in the "C" designs) as well as the human VH A42 A57.

For ANTIBODY-A, ten VH designs (H0, H1, H2, H3, H4, H1C, H2C, H3C, and H4C) and three VL designs (L0, L1, and L2) were made.

For ANTIBODY-B, for reasons similar but not identical to those for ANTIBODY-A, ten VH designs and three VL designs were made.

The humanized variants with Union CDRs are shown in FIGS. 1A-1D. The humanized variants with Chothia CDRs are shown in FIGS. 2A-2D. Various combinations of humanized heavy and light chain plasmids were transiently expressed in CHO-S cells. Titers in the supernatant were estimated using Octet anti-Human Fab-CH1 2nd Generation (FAB2G) Biosensors.

FACS binding assay was performed with Ba/F3 cells overexpressing either human TfR1 or cyno TfR1. Cells were dispensed at 50,000 cells/well/50 µl FACS buffer in a U-bottom 96 well plate and placed on ice. Serially diluted Fab supernatant or purified Fabs were then added to the cells followed by incubation on ice. Cells were washed twice in FACS Buffer and secondary antibody was added to the wells at 1:400 dilution followed by 30 min incubation on ice. Cells were washed twice in FACS Buffer and fixed in 2% PFA prepared in PBS. Finally, flow cytometric analysis was performed by measuring PE fluorescence.

Tables 8 and 9 show expression titers measured by Octet and $EC_{50}$ of humanized versions of ANTIBODY-A and ANTIBODY-B, respectively, from the supernatants of transient transfections. Octet titers were estimated using anti-Human Fab-CH1 2nd Generation (FAB2G) Biosensors. FACS binding assay was performed using serially diluted supernatant. $EC_{50}$ values were determined from the best-fit curves using GraphPad Prism. ~=approximate $EC_{50}$ extrapolated by Prism. >=$EC_{50}$ greater than the value extrapolated by GraphPad Prism. NA=$EC_{50}$ not achieved from the concentration range tested. Fabs that demonstrated strong affinity to both human TfR1 and cyno TfR1 were purified and the FACS binding assay was repeated with purified material.

TABLE 8

Expression Titers/$EC_{50}$ of humanized versions of ANTIBODY-A

| Antibody Name | Octet Titer (mg/L) | $EC_{50}$ (nM) Human | $EC_{50}$ (nM) Cyno |
|---|---|---|---|
| TfR1 ANTIBODY-A HC-H0 hIgG1 Fab'(1C)/LC-L0 hKappa | 116.9 | 18 | >85 |
| TfR1 ANTIBODY-A HC-H0 hIgG1 Fab'(1C)/LC-L1 hKappa | 80.3 | ~19 | >107 |
| TfR1 ANTIBODY-A HC-H0 hIgG1 Fab'(1C)/LC-L2 hKappa | 97.6 | >70 | NA |
| TfR1 ANTIBODY-A HC-H1 hIgG1 Fab'(1C)/LC-L0 hKappa | 110.8 | 25 | >176 |
| TfR1 ANTIBODY-A HC-H1 hIgG1 Fab'(1C)/LC-L1 hKappa | 75.3 | ~30 | >162 |
| TfR1 ANTIBODY-A HC-H1 hIgG1 Fab'(1C)/LC-L2 hKappa | 84.9 | >74 | NA |
| TfR1 ANTIBODY-A HC-H2 hIgG1 Fab'(1C)/LC-L0 hKappa | 88.8 | 2.8 | >26 |
| TfR1 ANTIBODY-A HC-H2 hIgG1 Fab'(1C)/LC-L1 hKappa | 87.9 | 4.4 | >36 |
| TfR1 ANTIBODY-A HC-H2 hIgG1 Fab'(1C)/LC-L2 hKappa | 94.5 | 6.5 | >52 |
| TfR1 ANTIBODY-A HC-H3 hIgG1 Fab'(1C)/LC-L0 hKappa | 107.8 | 2.6 | ~19 |
| TfR1 ANTIBODY-A HC-H3 hIgG1 Fab'(1C)/LC-L1 hKappa | 90.3 | 3.3 | >26 |
| TfR1 ANTIBODY-A HC-H3 hIgG1 Fab'(1C)/LC-L2 hKappa | 102.7 | 7.6 | >38 |
| TfR1 ANTIBODY-A HC-H4 hIgG1 Fab'(1C)/LC-L0 hKappa | 110.8 | 4.1 | >29 |
| TfR1 ANTIBODY-A HC-H4 hIgG1 Fab'(1C)/LC-L1 hKappa | 60.3 | 3.3 | >21 |
| TfR1 ANTIBODY-A HC-H4 hIgG1 Fab'(1C)/LC-L2 hKappa | 88.3 | 7.2 | >64 |
| TfR1 ANTIBODY-A HC-H0C hIgG1 Fab'(1C)/LC-L0 hKappa | 126.2 | 1.9 | 11.5 |
| TfR1 ANTIBODY-A HC-H0C hIgG1 Fab'(1C)/LC-L1 hKappa | 99.4 | 3.2 | ~22 |
| TfR1 ANTIBODY-A HC-H0C hIgG1 Fab'(1C)/LC-L2 hKappa | 112.1 | 3.6 | ~32 |
| TfR1 ANTIBODY-A HC-H1C hIgG1 Fab'(1C)/LC-L0 hKappa | 112.2 | 2.5 | 15.5 |
| TfR1 ANTIBODY-A HC-H1C hIgG1 Fab'(1C)/LC-L1 hKappa | 90.7 | 3.6 | ~26 |
| TfR1 ANTIBODY-A HC-H1C hIgG1 Fab'(1C)/LC-L2 hKappa | 103.2 | 3.6 | ~39 |
| TfR1 ANTIBODY-A HC-H2C hIgG1 Fab'(1C)/LC-L0 hKappa | 117.2 | 1.7 | 2.8 |
| TfR1 ANTIBODY-A HC-H2C hIgG1 Fab'(1C)/LC-L1 hKappa | 93.9 | 2.6 | 3.3 |
| TfR1 ANTIBODY-A HC-H2C hIgG1 Fab'(1C)/LC-L2 hKappa | 105.2 | 2.8 | 7.4 |
| TfR1 ANTIBODY-A HC-H3C hIgG1 Fab'(1C)/LC-L0 hKappa | 120.7 | 2.5 | 2.7 |
| TfR1 ANTIBODY-A HC-H3C hIgG1 Fab'(1C)/LC-L1 hKappa | 100.2 | 2.1 | 4.5 |
| TfR1 ANTIBODY-A HC-H3C hIgG1 Fab'(1C)/LC-L2 hKappa | 108.3 | 1.6 | 10.4 |
| TfR1 ANTIBODY-A HC-H4C hIgG1 Fab'(1C)/LC-L0 hKappa | 114.2 | 1.4 | 1.8 |
| TfR1 ANTIBODY-A HC-H4C hIgG1 Fab'(1C)/LC-L1 hKappa | 97.9 | 2.2 | 1.8 |
| TfR1 ANTIBODY-A HC-H4C hIgG1 Fab'(1C)/LC-L2 hKappa | 106.5 | 1.6 | 3.3 |

TABLE 9

Expression Titers/$EC_{50}$ of humanized versions of ANTIBODY-B

| Antibody Name | Octet Titer (mg/L) | $EC_{50}$ (nM) Human | $EC_{50}$ (nM) Cyno |
|---|---|---|---|
| TfR1 ANTIBODY-B HC-H0 hIgG1 Fab'(1C)/LC-L0 hKappa | 142.9 | — | — |
| TfR1 ANTIBODY-B HC-H0 hIgG1 Fab'(1C)/LC-L1 hKappa | 128.2 | — | — |
| TfR1 ANTIBODY-B HC-H0 hIgG1 Fab'(1C)/LC-L2 hKappa | 148.4 | 167.6 | 44.5 |
| TfR1 ANTIBODY-B HC-H1 hIgG1 Fab'(1C)/LC-L0 hKappa | 119.4 | — | — |
| TfR1 ANTIBODY-B HC-H1 hIgG1 Fab'(1C)/LC-L1 hKappa | 126.6 | — | — |
| TfR1 ANTIBODY-B HC-H1 hIgG1 Fab'(1C)/LC-L2 hKappa | 122.4 | 9.6 | 4.9 |
| TfR1 ANTIBODY-B HC-H2 hIgG1 Fab'(1C)/LC-L0 hKappa | 141.3 | — | — |
| TfR1 ANTIBODY-B HC-H2 hIgG1 Fab'(1C)/LC-L1 hKappa | 92.0 | — | — |
| TfR1 ANTIBODY-B HC-H2 hIgG1 Fab'(1C)/LC-L2 hKappa | 130.0 | 10.2 | 7.7 |
| TfR1 ANTIBODY-B HC-H3 hIgG1 Fab'(1C)/LC-L0 hKappa | 167.8 | — | — |

TABLE 9-continued

Expression Titers/EC$_{50}$ of humanized versions of ANTIBODY-B

| Antibody Name | Octet Titer (mg/L) | EC$_{50}$ (nM) Human | EC$_{50}$ (nM) Cyno |
|---|---|---|---|
| TfR1 ANTIBODY-B HC-H3 hIgG1 Fab'(1C)/LC-L1 hKappa | 105.3 | — | — |
| TfR1 ANTIBODY-B HC-H3 hIgG1 Fab'(1C)/LC-L2 hKappa | 163.8 | 15.7 | 5.7 |
| TfR1 ANTIBODY-B HC-H4 hIgG1 Fab'(1C)/LC-L0 hKappa | 141.8 | — | — |
| TfR1 ANTIBODY-B HC-H4 hIgG1 Fab'(1C)/LC-L1 hKappa | 79.6 | — | — |
| TfR1 ANTIBODY-B HC-H4 hIgG1 Fab'(1C)/LC-L2 hKappa | 141.3 | 2.3 | 4.6 |
| TfR1 ANTIBODY-B HC-H0C hIgG1 Fab'(1C)/LC-L0 hKappa | 160.3 | — | — |
| TfR1 ANTIBODY-B HC-H0C hIgG1 Fab'(1C)/LC-L1 hKappa | 102.2 | — | — |
| TfR1 ANTIBODY-B HC-H0C hIgG1 Fab'(1C)/LC-L2 hKappa | 163.7 | 9.3 | 5.5 |
| TfR1 ANTIBODY-B HC-H1C hIgG1 Fab'(1C)/LC-L0 hKappa | 167.5 | — | — |
| TfR1 ANTIBODY-B HC-H1C hIgG1 Fab'(1C)/LC-L1 hKappa | 104.9 | — | — |
| TfR1 ANTIBODY-B HC-H1C hIgG1 Fab'(1C)/LC-L2 hKappa | 149.3 | 3.8 | 2.8 |
| TfR1 ANTIBODY-B HC-H2C hIgG1 Fab'(1C)/LC-L0 hKappa | 169.7 | — | — |
| TfR1 ANTIBODY-B HC-H2C hIgG1 Fab'(1C)/LC-L1 hKappa | 108.5 | — | — |
| TfR1 ANTIBODY-B HC-H2C hIgG1 Fab'(1C)/LC-L2 hKappa | 161.8 | 3.3 | 2.2 |
| TfR1 ANTIBODY-B HC-H3C hIgG1 Fab'(1C)/LC-L0 hKappa | 176.2 | — | — |
| TfR1 ANTIBODY-B HC-H3C hIgG1 Fab'(1C)/LC-L1 hKappa | 119.3 | — | — |
| TfR1 ANTIBODY-B HC-H3C hIgG1 Fab'(1C)/LC-L2 hKappa | 178.9 | 6.8 | 2.6 |
| TfR1 ANTIBODY-B HC-H4C hIgG1 Fab'(1C)/LC-L0 hKappa | 173.1 | — | — |
| TfR1 ANTIBODY-B HC-H4C hIgG1 Fab'(1C)/LC-L1 hKappa | 106.1 | — | — |
| TfR1 ANTIBODY-B HC-H4C hIgG1 Fab'(1C)/LC-L2 hKappa | 172.9 | 4.7 | 2.9 |

Tables 10 and 11 show the EC$_{50}$ of selected humanized versions of ANTIBODY-A and ANTIBODY-B, respectively, from purified material. FACS binding assay was performed using serially diluted purified material. EC$_{50}$ values were determined from the best-fit curves using GraphPad Prism.

TABLE 10

EC$_{50}$ of selected humanized versions of ANTIBODY-A

| Antibody Name | EC$_{50}$ (nM) Human | EC$_{50}$ (nM) Cyno |
|---|---|---|
| TfR1 ANTIBODY-A HC-H2C hIgG1 Fab'(1C)/LC-L0 hKappa | 1.7 | 1.5 |
| TfR1 ANTIBODY-A HC-H2C hIgG1 Fab'(1C)/LC-L1 hKappa | 1.3 | 3.3 |
| TfR1 ANTIBODY-A HC-H3C hIgG1 Fab'(1C)/LC-L0 hKappa | 1.6 | 5.0 |
| TfR1 ANTIBODY-A HC-H3C hIgG1 Fab'(1C)/LC-L1 hKappa | 1.5 | 5.5 |
| TfR1 ANTIBODY-A HC-H4C hIgG1 Fab'(1C)/LC-L0 hKappa | 1.4 | 2.0 |
| TfR1 ANTIBODY-A HC-H4C hIgG1 Fab'(1C)/LC-L1 hKappa | 1.8 | 2.4 |

TABLE 11

EC$_{50}$ of selected humanized versions of ANTIBODY-B

| Antibody Name | EC$_{50}$ (nM) Human | EC$_{50}$ (nM) Cyno |
|---|---|---|
| TfR1 ANTIBODY-B HC-H4 hIgG1 Fab'(1C)/LC-L2 hKappa | 9.8 | 3.4 |
| TfR1 ANTIBODY-B HC-H1C hIgG1 Fab'(1C)/LC-L2 hKappa | 8.2 | 2.3 |
| TfR1 ANTIBODY-B HC-H2C hIgG1 Fab'(1C)/LC-L2 hKappa | 6.5 | 2.6 |
| TfR1 ANTIBODY-B HC-H3C hIgG1 Fab'(1C)/LC-L2 hKappa | 5.5 | 1.9 |
| TfR1 ANTIBODY-B HC-H4C hIgG1 Fab'(1C)/LC-L2 hKappa | 4.8 | 2.0 |

The full heavy chain and light chain sequences of exemplary constructs described above are shown below in Table 12.

TABLE 12

Heavy and Light Chain sequences for exemplary constructs

| Antibody | Domain | Sequence |
|---|---|---|
| (i) TfR1 ANTIBODY-A HC-H2C hIgG1 Fab'(IC)/ LC-L0 hKappa | Heavy chain (SEQ ID NO: 93) (constant region in bold; hinge in bold underline) | QSLVESGGGLVQPGGSLRLSCAASGIDFSSSGYMCWVRQAPGKGL EWVGCIYTYSSNTYYAASVKGRFTISKTSSTTVYLQMNSLKTEDT AVYYCARGTYGYTGYTYTMGYFSLWGQGTLVTVSSASTKGPSVFP LAPSSKSTSGGTAALGCLVKDYFPEPVTVSWNSGALTSGVHTFPA VLQSSGLYSLSSVVTVPSSSLGTQTYICNVNHKPSNTKVDKKV<u>EP KSCDKTHTCPP</u> |
| | Light chain (SEQ ID NO: 94) (constant region in bold) | DIQMTQSPSTLSASVGDRVTITCQASQNINSYLAWYQQKPGKAPK LLIYRASSLESGVPSRFSGSGSGTEFTLTISSLQPDDFATYYCQS YYYSGSSNYNAFGGGTKVEIKRTVAAPSVFIFPPSDEQLKSGTAS VVCLLNNFYPREAKVQWKVDNALQSGNSQESVTEQDSKDSTYSLS STLTLSKADYEKHKVYACEVTHQGLSSPVTKSFNRGEC |
| (ii) TfR1 ANTIBODY-A | Heavy chain (SEQ ID NO: 95) | QSLVESGGGLVQPGGSLRLSCAASGIDFSSSGYMCWVRQAPGKGL EWVGCIYTYSSNTYYAASVKGRFTISKTSSTTVYLQMNSLKTEDT |

TABLE 12-continued

Heavy and Light Chain sequences for exemplary constructs

| Antibody | Domain | Sequence |
|---|---|---|
| HC-H2C hIgG4Fab/ LC-L0 hKappa (ΔC214) | (constant region in bold; hinge in bold underline) | AVYYCARGTYGYTGYTYTMGYFSLWGQGTLVTVSSASTKGPSVFP LAPCSRSTSESTAALGCLVKDYFPEPVTVSWNSGALTSGVHTFPA VLQSSGLYSLSSVVTVPSSSLGTKTVTCNVDHKPSNTKVDKRV<u>ES</u> |
| | Light chain (SEQ ID NO: 96) (constant region in bold) | DIQMTQSPSTLSASVGDRVTITCQASQNINSYLAWYQQKPGKAPK LLIYRASSLESGVPSRFSGSGSGTEFTLTISSLQPDDFAIYYCQS YYYSGSSNYNAFGGGTKVEIKRTVAAPSVFIFPPSDEQLKSGTAS VVCLLNNFYPREAKVQWKVDNALQSGNSQESVTEQDSKDSTYSLS STLTLSKADYEKHKVYACEVTHQGLSSPVTKSFNRGE |
| (iii) TfR ANTIBODY-A HC-H2C hIgG1G4 Fab'(1C) (PPCP)/LC-L0 hKappa (ΔC214) | Heavy chain (SEQ ID NO: 97) (constant region in bold; hinge in bold underline) | QSLVESGGGLVQPGGSLRLSCAASGIDFSSSGYMCWVRQAPGKGL EWVGCIYTYSSNTYYAASVKGRFTISKTSSTTVYLQMNSLKTEDT AVYYCARGTYGYTGYTYTMGYFSLWGQGTLVTVSSASTKGPSVFP LAPSSKSTSGGTAALGGLVKDYFPEPVTVSWNSGALTSGVHTFPA VLQSSGLYSLSSVVTVPSSSLGTQTYICNVNHKPSNTKVDKRV<u>ES</u> <u>KYGPPCP</u> |
| | Light chain (SEQ ID NO: 96) (constant region in bold) | DIQMTQSPSTLSASVGDRVTITCQASQNINSYLAWYQQKPGKAPK LLIYRASSLESGVPSRFSGSGSGTEFTLTISSLQPDDFATYYCQS YYYSGSSNYNAFGGGTKVEIKRTVAAPSVFIFPPSDEQLKSGTAS VVCLLNNFYPREAKVQWKVDNALQSGNSQESVTEQDSKDSTYSLS STLTLSKADYEKHKVYACEVTHQGLSSPVTKSFNRGE |
| (iv) TfR1 ANTIBODY-A HC-H2C hIgG1Fab/ LC-L0 hKappa (ΔC214) | Heavy chain (SEQ ID NO: 98) (constant region in bold; hinge in bold underline) | QSLVESGGGLVQPGGSLRLSCAASGIDFSSSGYMCWVRQAPGKGL EWVGCIYTYSSNTYYAASVKGRFTISKTSSTTVYLQMNSLKTEDT AVYYCARGTYGYTGYTYTMGYFSLWGQGTLVTVSSASTKGPSVFP LAPSSKSTSGGTAALGCLVKDYFPEPVTVSWNSGALTSGVHTFPA VLQSSGLYSLSSVVTVPSSSLGTQTYICNVNHKPSNTKVDKKV<u>EP</u> <u>KSC</u> |
| | Light chain (SEQ ID NO: 96) (constant region in bold) | DIQMTQSPSTLSASVGDRVTITCQASQNINSYLAWYQQKPGKAPK LLIYRASSLESGVPSRFSGSGSGTEFTLTISSLQPDDFATYYCQS YYYSGSSNYNAFGGGTKVEIKRTVAAPSVFIFPPSDEQLKSGTAS VVCLLNNFVPREAKVQWKVDNALQSGNSQESVTEQDSKDSTYSLS STLTLSKADYEKHKVYACEVTHQGLSSPVTKSFNRGE |
| (v) TfR1 ANTIBODY-B HC-H4C hIgG1 Fab'(1C)/ LC-L2 hKappa | Heavy chain (SEQ ID NO: 99) (constant region in bold; hinge in bold underline) | QSLVESGGGVVQPGRSLRLSCKASGFSFSNSYWICWVRQAPGKGL EWVGCINTDADSTNYASWARGRFTISKTSSTTVYLQMNSLRAEDT AVYYCARQNNVFDPGYNLWGPGTLVTVSSASTKGPSVFPLAPSSK STSGGTAALGCLVKDYFPEPVTVSWNSGALTSGVHTFPAVLQSSG LYSLSSVVTVPSSSLGTQTYICNVNHKPSNTKVDKKV<u>EPKSCDKT</u> <u>HTCPP</u> |
| | Light chain (SEQ ID NO: 100) (constant region in bold) | ELVLTQSPSTLSASVGDRVTITCRASQNIGSNLAWYQQKPGKAPK LLIYDASKLESGVPSRFSGSGSGTEFTLTISSLQPDDFATYYCQC TVRGGAYGNAFGGGTKVETKRTVAAPSVFIFPPSDEQLKSGTASV VCLLNNFYPREAKVQWKVDNALQSGNSQESVTEQDSKDSTYSLSS TLTLSKADYEKHKVYACEVTHQGLSSPVTKSFNRGEC |

Example 4: Follow-on Anti-TfR1 Antibody Designs to Remove Extra Disulfide and Unpaired Cysteine and Selection Process In the initial designs, the extra rabbit VH disulfide bond was removed by mutating C35 C50 (AHo #C42 C57) from C,C to A,A. Further, the unpaired cysteine C90 (AHo #C108) ANTIBODY-B VL was removed by mutating it to Q or A. These attempts were found to weaken binding affinity in the constructs tested and a follow-on round of designs was therefore made. In the context of ANTIBODY-A H3/L0, and also in the context of ANTIBODY-B H1/L2, the second disulfide's C,C was mutated to S,V or S,R or S,Y or H,A, each borrowed from various similar human germline sequences and then confirmed as plausible by molecular modeling, energetics calculations, and/or publicly available structures. In the context of ANTIBODY-B H1C/L2, and also in the context of ANTIBODY-B H4C/L2, the unpaired cysteine was mutated to S or T or V. The follow-on designs to remove extra disulfide and unpaired cysteine are shown in FIGS. 1A-1D.

Table 13 shows expression titers measured by Octet and $EC_{50}$ of the mutants of humanized versions of anti-TfR1 antibodies ANTIBODY-A and ANTIBODY-B from the supernatant of transient transfection. Octet titers were estimated using anti-Human Fab-CH1 2nd Generation (FAB2G) Biosensors. FACS binding assay was performed using serially diluted supernatant. $EC_{50}$ values were determined from the best-fit curves using GraphPad Prism.

TABLE 13

Expression Titers/EC$_{50}$ of humanized versions of
ANTIBODY-A and ANTIBODY-B disulfide mutants

| Antibody Name | Octet titer (mg/L) | EC$_{50}$ (nM) Human | EC$_{50}$ (nM) Cyno |
|---|---|---|---|
| TfRANTIBODY-A HC-H3(SV) hIgG1Fab'(1C)/LC-L0 hKappa | 158 | >150 | No binding |
| TfRANTIBODY-A HC-H3(SR) hIgG1Fab'(1C)/LC-L0 hKappa | 105.5 | >290 | No binding |
| TfRANTIBODY-A HC-H3(SY) hIgG1Fab'(1C)/LC-L0 hKappa | 141.3 | >125 | No binding |
| TfRANTIBODY-A HC-H3(HA) hIgG1Fab'(1C)/LC-L0 hKappa | 145.2 | 16.8 | ~30 |
| TfRANTIBODY-A HC-H3C hIgG1Fab'(1C)/LC-L0 hKappa | 165 | 1.1 | 1.5 |
| TfRANTIBODY-B HC-H1(SV) hIgG1Fab'(1C)/LC-L2 hKappa | 307.9 | 98.6 | 30 |
| TfRANTIBODY-B HC-H1(SR) hIgG1Fab'(1C)/LC-L2 hKappa | 349.6 | No binding | No binding |
| TfRANTIBODY-B HC-H1(SY) hIgG1Fab'(1C)/LC-L2 hKappa | 256.2 | 113.4 | >55 |
| TfRANTIBODY-B HC-H1(HA) hIgG1Fab'(1C/LC-L2 hKappa | 325.2 | 18.2 | 7.1 |
| TfRANTIBODY-B HC-H1C hIgG1Fab'(1C)/LC-L2 hKappa | 291.2 | 10.1 | 2.8 |

Table 14 shows Octet titers and EC$_{50}$ from supernatants of transient transfection of mutants of humanized versions of ANTIBODY-A and ANTIBODY-B where the extra rabbit disulfide pair was removed. Octet titers were estimated using anti-Human Fab-CH1 2nd Generation (FAB2G) Biosensors. FACS binding assay was performed using serially diluted supernatant. EC$_{50}$ values were determined from the best-fit curves using GraphPad Prism.

TABLE 14

Expression Titers/EC$_{50}$ of humanized versions of ANTIBODY-B mutants

| Antibody Name | Octet titer (mg/L) | EC$_{50}$ (nM) Human | EC$_{50}$ (nM) Cyno |
|---|---|---|---|
| TfRANTIBODY-B HC-H1C/LC-L2 (C90V) hIgG1Fab'(1C) | 149.2 | 10.7 | 2.9 |
| TfRANTIBODY-B HC-H3C/LC-L2 (C90V) hIgG1Fab'(1C) | 167.5 | 7.7 | 3.2 |
| TfRANTIBODY-B HC-H4C/LC-L2 (C90V) hIgG1Fab'(1C) | 167.6 | 4.9 | 2.2 |
| TfRANTIBODY-B HC-H1C/LC-L2 (C90S) hIgG1Fab'(1C) | 133.6 | 14.9 | 4.4 |
| TfRANTIBODY-B HC-H3C/LC-L2 (C90S) hIgG1Fab'(1C) | 155.8 | 16.8 | 6.2 |
| TfRANTIBODY-B HC-H4C/LC-L2 (C90S) hIgG1Fab'(1C) | 139.7 | 11.3 | 3.3 |
| TfRANTIBODY-B HC-H1C/LC-L2 (C90T) hIgG1Fab'(1C) | 168.8 | 12.6 | 5.4 |
| TfRANTIBODY-B HC-H3C/LC-L2 (C90T) hIgG1Fab'(1C) | 160.6 | 15.9 | 6.3 |
| TfRANTIBODY-B HC-H4C/LC-L2 (C90T) hIgG1Fab'(1C) | 154.9 | 7.7 | 2.9 |
| TfRANTIBODY-B HC-H1C/LC-L2 hIgG1Fab'(1C) | 187.3 | 5.9 | 2.3 |
| TfRANTIBODY-B HC-H3C/LC-L2 hIgG1Fab'(1C) | 278.3 | 7.0 | 4.0 |
| TfRANTIBODY-B HC-H4C/LC-L2 hIgG1Fab'(1C) | 192 | 5.4 | 1.9 |

Table 15 shows the EC$_{50}$ of selected mutants of ANTIBODY-B from purified material. In these mutants, the unpaired cysteine was mutated on the light chain. FACS binding assay was performed using serially diluted purified Fabs. EC$_{50}$ values were determined from the best-fit curves using GraphPad Prism.

TABLE 15

EC$_{50}$ of selected humanized mutants of ANTIBODY-B

| Antibody Name | EC$_{50}$ (nM) Human | EC$_{50}$ (nM) Cyno |
|---|---|---|
| TfRANTIBODY B HC-H1C/LC-L2 (C90S) hIgG1Fab'(1C) | 6.1 | 3.2 |
| TfRANTIBODY B HC-H4C/LC-L2 (C90S) hIgG1Fab'(1C) | 7.3 | 1.5 |
| TfRANTIBODY B HC-H1C/LC-L2 (C90T) hIgG1Fab'(1C) | 13.6 | 3.2 |
| TfRANTIBODY B HC-H4C/LC-L2 (C90T) hIgG1Fab'(1C) | 5.1 | 3.4 |

Example 5: Affinity and Kinetics for Binding Human and Cynomolgus TfR1

Kinetics and affinity values from evaluation of anti-TfR1 Fab fragments, in chimeric rabbit and humanized forms, binding to recombinant human and cyno transferrin receptor extracellular domains was evaluated using SPR.

SPR results were obtained using a Biacore 8K+ (Cytiva) with a CM5 sensor chip (Series S, Cytiva) prepared for capture of histidine-tagged ligands according to the manufacturer's protocol (His Capture Kit; Cytiva). Running buffer was 10 mM HEPES, 150 mM NaCl, 3 mM EDTA, 0.05% bovine serum albumin, 0.005% surfactant P20, pH 7.4, flowed at 30 ul/min. For kinetics and affinity determination, recombinant human or cyno monkey TfR1 ECD-His was captured at 15-20 sensor response units (RU) and Fab fragments were serially injected at 0.78, 3.1, 12.5, 50, and 200 nM for 4 min each (in single-cycle kinetics mode) followed by 15 min of buffer flow to monitor dissociation. For Tf competition binding analysis, human or cyno TfR1 ECD-His was captured at 25-40 RU followed by an injection of either buffer or 1 mM holo human transferrin (Sigma T0665) for 4 min, serial 3 min injections of Fabs at 50 and 500 nM with or without 1 mM holo human transferrin, respectively, and dissociation was monitored for 10 min. The capture surface was regenerated after each cycle with 2×1 min injections of 10 mM glycine, pH 1.5. SPR responses, reference subtracted against the signal from sensor surfaces with no TfR1 and against cycles injecting buffer instead of Fab. Kinetics and affinity parameters were determined by fitting the data to a 1:1 binding model using the Biacore Insight Evaluation Software (Cytiva).

TfR1 ECD protein was captured on the SPR sensor surface. Association rates ($k_a$), dissociation rates ($k_d$), and corresponding equilibrium dissociation constants ($K_D$) were determined from fitting SPR binding responses from serial injections of Fab (at 0.78-200 nM) to a 1:1 binding model. Table 16 shows the affinity and kinetics parameters for each Fab tested.

TABLE 16

Affinity and kinetics parameters for anti-TfR1 antibodies tested

| Anti-TfR1 Fab | Human TfR1 ECD | | | Cyno TfR1 ECD | | |
|---|---|---|---|---|---|---|
| | $k_a$ (/M/s) | $k_d$ (1/s) | $K_D$ (nM) | $k_a$ (/M/s) | $k_d$ (1/s) | $K_D$ (nM) |
| Rabbit ANTIBODY-A chi Fab | 1.92E+05 | 1.01E−03 | 5.2 | 3.17E+05 | 9.25E−03 | 29 |
| ANTIBODY-A HC-H2C hIgG1 Fab'(1C)/LC-L0 hKappa | 8.62E+05 | 1.03E−03 | 1.2 | 1.60E+06 | 6.74E−03 | 4.2 |
| ANTIBODY-A HC-H2C hIgG1 Fab'(1C)/LC-L1 hKappa | 7.73E+05 | 9.47E−04 | 1.2 | 6.56E+06 | 1.95E−02 | 3.0 |
| ANTIBODY-A HC-H2C hIgG1 Fab'(1C)/LC-L2 hKappa | 9.52E+05 | 2.13E−03 | 2.2 | 1.76E+06 | 1.37E−02 | 7.8 |
| ANTIBODY-A HC-H3C hIgG1 Fab'(1C)/LC-L0 hKappa | 8.35E+05 | 1.20E−03 | 1.4 | 4.10E+06 | 1.03E−02 | 2.5 |
| ANTIBODY-A HC-H3C hIgG1 Fab'(1C)/LC-L1 hKappa | 1.02E+06 | 1.26E−03 | 1.2 | 2.58E+06 | 1.06E−02 | 4.1 |
| ANTIBODY-A HC-H3C hIgG1 Fab'(1C)/LC-L2 hKappa | 8.86E+05 | 2.15E−03 | 2.4 | 2.16E+06 | 1.78E−02 | 8.3 |
| ANTIBODY-A HC-H4C hIgG1 Fab'(1C)/LC-L0 hKappa | 8.87E+05 | 8.78E−04 | 0.99 | 1.75E+06 | 5.83E−03 | 3.3 |
| ANTIBODY-A HC-H4C hIgG1 Fab'(1C)/LC-L1 hKappa | 9.83E+05 | 8.94E−04 | 0.91 | 4.40E+06 | 1.14E−02 | 2.6 |
| ANTIBODY-A HC-H4C hIgG1 Fab'(1C)/LC-L2 hKappa | 9.31E+05 | 1.48E−03 | 1.6 | 2.16E+06 | 1.34E−02 | 6.2 |
| Rabbit ANTIBODY-B chi Fab | 9.92E+04 | 5.73E−04 | 5.8 | 2.83E+05 | 4.36E−04 | 1.5 |
| ANTIBODY-B HC-H1 hIgG1 Fab'(1C)/LC-L2 hKappa | 9.47E+04 | 4.53E−03 | 47.8 | 8.83E+04 | 1.05E−03 | 12 |
| ANTIBODY-B HC-H2 hIgG1 Fab'(1C)/LC-L2 hKappa | 8.32E+04 | 3.28E−03 | 39.4 | 1.29E+05 | 1.13E−03 | 8.7 |
| ANTIBODY-B HC-H3 hIgG1 Fab'(1C)/LC-L2 hKappa | 9.15E+04 | 5.95E−03 | 65.0 | 1.43E+05 | 1.72E−03 | 12 |
| ANTIBODY-B HC-H4 hIgG1 Fab'(1C)/LC-L2 hKappa | 1.34E+05 | 1.55E−03 | 11.6 | 2.28E+05 | 5.08E−04 | 2.2 |
| ANTIBODY-B HC-H0C hIgG1 Fab'(1C)/LC-L2 hKappa | 2.44E+05 | 3.43E−03 | 14.1 | 2.10E+05 | 1.36E−03 | 6.5 |
| ANTIBODY-B HC-H1C hIgG1 Fab'(1C)/LC-L2 hKappa | 1.71E+05 | 1.15E−03 | 6.7 | 3.15E+05 | 4.25E−04 | 1.3 |
| ANTIBODY-B HC-H2C hIgG1 Fab'(1C)/LC-L2 hKappa | 1.70E+05 | 9.99E−04 | 5.8 | 4.45E+05 | 4.72E−04 | 1.1 |
| ANTIBODY-B HC-H3C hIgG1 Fab'(1C)/LC-L2 hKappa | 2.00E+05 | 1.47E−03 | 7.4 | 3.48E+05 | 6.08E−04 | 1.7 |
| ANTIBODY-B HC-H4C hIgG1 Fab'(1C)/LC-L2 hKappa | 2.23E+05 | 7.67E−04 | 3.4 | 3.98E+05 | 2.79E−04 | 0.7 |

Example 6: Transferrin Competition in Binding Human and Cynomolgus TfR1

The effect of holo human transferrin in binding of anti-TfR1 Fab fragments to human and cyno TfR1 by SPR was assessed. Binding kinetics ($k_a$, $k_d$), affinity ($K_D$), and response level ($R_{max}$) parameters were determined (Table 17) for chimeric rabbit Fab fragments (used at 50 and 500 nM) binding surface-captured human and cyno TfR1 in the absence and presence of a saturating concentration (1 mM) of holo human transferrin.

TABLE 17

Effect of holo human transferrin on binding on anti-TfR1 Fab fragments

| | Human TfR1 ECD | | | | Cyno TfR1 ECD | | | |
|---|---|---|---|---|---|---|---|---|
| | $k_a$ (/M/s) | $k_d$ (1/s) | $K_D$ (nM) | $R_{max}$ (RU) | $k_a$ (/M/s) | $k_d$ (1/s) | $K_D$ (nM) | $R_{max}$ (RU) |
| Rabbit ANTIBODY-A chi Fab | 1.7E+05 | 1.2E−03 | 7.0 | 22 | 2.3E+05 | 1.0E−02 | 43 | 18 |
| Rabbit ANTIBODY-A chi Fab + 1 mM holo-huTf | 1.7E+05 | 1.2E−03 | 6.8 | 22 | 2.3E+05 | 1.0E−02 | 43 | 18 |
| Rabbit ANTIBODY-B chi Fab | 1.4E+05 | 1.8E−03 | 12 | 7.3 | 2.5E+05 | 9.5E−04 | 3.8 | 11 |
| Rabbit ANTIBODY-B chi Fab + 1 mM holo-huTf | 1.8E+05 | 1.5E−03 | 8.2 | 7.7 | 2.7E+05 | 9.4E−04 | 3.5 | 10 |

These assays show that the presence of holo-huTf in the competition assay did not significantly change the binding of Rabbit ANTIBODY-A chi Fab or Rabbit ANTIBODY-B chi Fab to either the human TfR1 extracellular domain (ECD) or cyno TfR1 ECD. This suggests that neither of the antibodies compete with transferrin.

Example 7: Anti-TfR1 Antibodies do not Bind to TfR2

The cross-reactivity of anti-TfR1 antibodies with TfR2 was evaluated during FACS. Briefly, FACS binding assay was performed with BaF3 cells overexpressing human TfR2. Cells were dispensed at 50,000 cells/well/50 µl FACS buffer in a U-bottom 96 well plate and placed on ice. 250 nM bivalent huIgG1 antibodies were then added to the cells followed by incubation on ice. Cells were washed twice in FACS Buffer and secondary antibody was added to the wells at 1:400 dilution followed by 30 min incubation on ice. Cells were washed twice in FACS Buffer and fixed in 2% PFA prepared in PBS. Finally, flow cytometric analysis was performed by measuring PE fluorescence.

Cells incubated with chimeric ANTIBODY-A mAb or chimeric ANTIBODY B mAb did not show any shift in PE signal compared to cells incubated with secondary antibody alone showing lack of binding to TfR2 receptor on the surface of the cells (data not shown).

Example 8: Exemplary Anti-TfR1 Antibodies

The following exemplary anti-TfR1 antibodies were constructed and shown to bind to target (TfR1) with high affinity:
  (1) (i) heavy chain of SEQ ID NO:93+light chain of SEQ ID NO:94;
  (2) (ii) heavy chain of SEQ ID NO:95+light chain of SEQ ID NO:96;
  (3) (iii) heavy chain of SEQ ID NO:97+light chain of SEQ ID NO:96;
  (4) (iv) heavy chain of SEQ ID NO:98+light chain of SEQ ID NO:96; and Any of these antibodies can be linked to an agent (such as a nucleic acid (e.g., an antisense oligonucleotide, a short interfering RNA (siRNA), messenger RNA (mRNA), microRNA (miRNA), guide RNA (gRNA), a phosphoroamidate morpholino oligomer, or an aptamer) to create a conjugate. In some embodiments, the anti-TfR1 antibody is conjugated to a particle, e.g., lipid particle or nanoparticle, which can contain a therapeutic agent such as one described herein.

Example 9: ANTIBODY-A Cryo-EM Structure

To explore the molecular basis for antigen recognition, the cryo-EM structure of a humanized ANTIBODY-A Fab (containing the heavy chain sequence set forth in SEQ ID NO:95 and the light chain sequence set forth in SEQ ID NO:96) in complex with the human (hu) transferrin receptor (TfR) and hu transferrin (Tf) at 3.4 Å resolution was determined. An atomic model of the complex was obtained by fitting a homology model of ANTIBODY-A and available crystal structures of TfR and Tf into the cryo-EM density map (FIG. 3). The final model revealed that ANTIBODY-A binds to a conformational epitope located at the apical domain of TfR. There are 22 residues from TfR and 18 residues from the ANTIBODY-A Fab that are within 5 Å of the binding partner. The discontinuous epitope is formed by residues K231, D245, L246, Y247, T248, P249, E350, G351, D352, C353, P354, S355, D356, K358, T359, D360, S361, R364, M365, V366, T367, E369 of hu TfR and contains a combination of hydrophobic, hydrophilic, and charged residues. The antigen-binding site of ANTIBODY-A is formed by four CDRs (H1, H2, H3, L3) and is composed of S29, S30, S31, Y33, Y52, Y54, S55, N57, Y59, Y100, Y102, T103, G104, Y105, T106, and Y107 of the heavy chain, and Y93 and G95 of the light chain (Table 18).

TABLE 18

ANTIBODY-A paratope residues that contact TfR

| CDR | Contact residue (<5Å) | CDR sequence |
|---|---|---|
| CDR H1 | S29, S30 S31, Y33 | GIDFSSSGYMC (SEQ ID NO: 101) |
| CDR H2 | Y52, Y54, S55, N57, Y59 | CIYTYSSNTYYAASVKG (SEQ ID NO: 103) |
| CDR H3 | Y100, Y102, T103, G104, Y105, T106, Y107 | GTYGYTGYTYTMGYFSL (SEQ ID NO: 106) |
| CDR L1 | | QASQNINSYLA (SEQ ID NO: 107) |
| CDR L2 | | RASSLES (SEQ ID NO: 108) |
| CDR L3 | Y93, G95 | QSYYYSGSSNYNA (SEQ ID NO: 110) |

Contact residues within 5.0 Å of TfR are in bold underline.

Contact residues within 5.0 Å of TfR are in bold underline.

ANTIBODY-A recognizes TfR in humans and cynomolgus monkeys, but it does not cross-react with mouse TfR. These structural studies provide detailed insights into the binding properties of ANTIBODY-A. The binding epitope in the apical domain of TfR is mostly conserved between human and cynomolgus monkey, but differs significantly from mouse, consistent with the lack of binding of ANTIBODY-A from this species (FIG. 4).

Example 10: ANTIBODY-B Cryo-EM Structure

To explore the molecular basis for antigen recognition, the cryo-EM structure of a humanized ANTIBODY-B Fab (containing the heavy chain sequence set forth in SEQ ID NO:99 and the light chain sequence set forth in SEQ ID NO:100) in complex with the hu TfR and hu Tf at 3.96 Å resolution was determined. An atomic model of the complex was obtained by fitting a homology model of ANTIBODY-B and available crystal structures of TfR and Tf into the cryo-EM density map (FIG. 5). The final model revealed that ANTIBODY-B binds to a conformational epitope located at the protease-like domain of TfR. There are 15 residues from TfR and 18 residues from the ANTIBODY-B Fab that are within 5 Å of the binding partner. The discontinuous epitope is formed by residues D139, T141, K145, G490, T491, V517, T518, Y573, K574, I577, E578, R579, I580, P581, and E582 of hu TfR and contains a combination of hydrophobic, hydrophilic, and charged residues. The antigen-binding site of ANTIBODY-B is formed by five CDRs (H1, H2, H3, L1, and L3) and is composed of N30, W33, N52, D54, A55, D56, S57, T58, N59, N100, and V101 of the heavy chain, and N28, I29, G30, V92, R93, G94, and G95 of the light chain (Table 19).

TABLE 19

ANTIBODY-B paratope residues that contact TfR

| CDR | Contact residue (<5Å) | CDR sequence |
|---|---|---|
| CDR H1 | N30, W33 | GFSFSNSYWIC (SEQ ID NO: 116) |
| CDR H2 | N52, D54, A55, D56, S57, T58, N59 | CINTDADSTNYASWARG (SEQ ID NO: 117) |
| CDR H3 | N100, V101 | QNNVFDPGYNL (SEQ ID NO: 119) |
| CDR L1 | N28, I29, G30 | RASQNIGSNLA (SEQ ID NO: 120) |
| CDR L2 | | DASKLES (SEQ ID NO: 122) |
| CDR L3 | V92, R93, G94, G95 | QCTVRGGAYGNA (SEQ ID NO: 124) |

Contact residues within 5.0 Å of TfR are in bold underline.

Contact residues within 5.0 Å of TfR are in bold underline.

Figure 6:
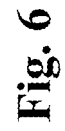
FIG. 6 is a partial alignment of transferrin receptor protease-like domain sequences with ANTIBODY-B epitope. The residues within 5 Å of ANTIBODY-B, as observed in the cryo-EM structure of ANTIBODY-B bound to the cyno transferrin receptor ectodomain, are highlighted in grey. Epitope residues that differ from human transferrin receptor are in bold. Strictly conserved residues are denoted by asterisk, strongly conserved residues by colon, and moderately conserved residues by period. Sources of sequences: Human (*Homo sapiens*, Uniprot P02786.2); Cynomolgus (*Macaca fascicularis*, Uniprot G8F602); Mouse (*Mus musculus*, GenBank NP_035768.1).

ANTIBODY-B recognizes TfR in humans and cynomolgus monkeys, but it does not cross-react with mouse TfR. These structural studies provide detailed insights into the binding properties of ANTIBODY-B. The binding epitope in the protease-like domain of TfR is mostly conserved between human and cynomolgus monkey, but differs significantly from mouse, consistent with the lack of binding of ANTIBODY-B from this species (FIG. 6).

Example 11: Format Variants of a Humanized Version of ANTIBODY-A 22 different format variants of a humanized version of ANTIBODY-A were prepared. Table 20 describes each of the antibody variants by an index number (which is used to identify the antibody used in experiments), the names of the individual proteins (Fc chains and/or non-Fc chains) that make up the antibody, an identification of the figure (selected from FIGS. 7A-7E) that depicts the general structure of the antibody, and a description of the antibody. The amino acid sequences for each of the individual proteins (Fc chains and/or non-Fc chains) that make up each antibody are provided in Table 21.

TABLE 20

Protein Descriptions of Humanized ANTIBODY-A Format Variants

Figure 7A:
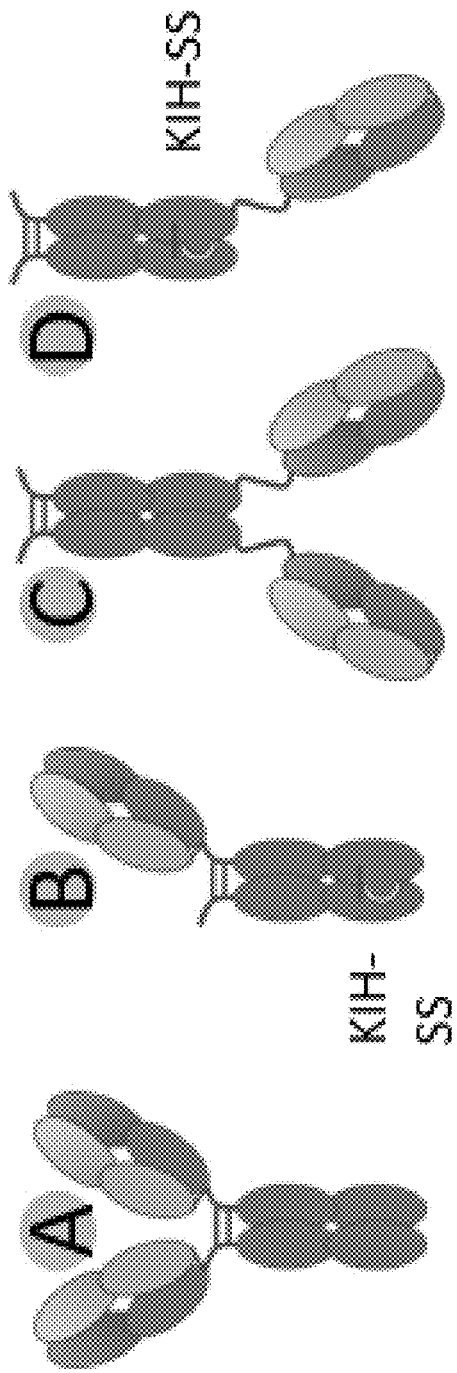
FIG. 7A depicts the structures of the antibodies corresponding to protein index 1 ("A"), protein index 2 ("B"), protein index 3 ("C"), and protein index 4 ("D").

| Protein Index | Fc Chain #1 | Fc Chain #2 | Non-Fc Chain | "Code"/FIG. Depiction | Description |
|---|---|---|---|---|---|
| 1 | TOC1796 | | TOC1775 | A in FIG. 7A | huANTIBODY-A bivalent RSU hIgG1.agly |
| 2 | TOC1797 | TOC1801 | TOC1775 | B in FIG. 7A | huANTIBODY-A monovalent RSU hIgG1.agly (KIH-SS) |

TABLE 20-continued

Protein Descriptions of Humanized ANTIBODY-A Format Variants

Figure 7B:
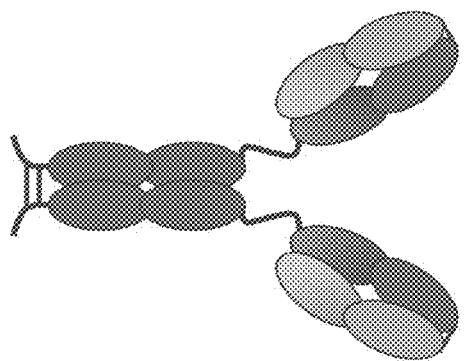
FIG. 7B depicts the structure of the antibodies corresponding to protein index 5, 6, 7, 8, 9, 10, 11, and 12.
Figure 7C:
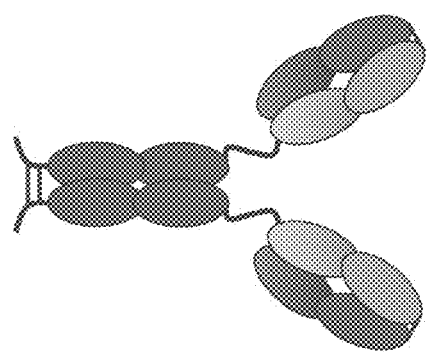
FIG. 7C depicts the structure of the antibodies corresponding to protein index 13, 14, 15, 16, 17, 18, 19, and 20.
Figure 7D:
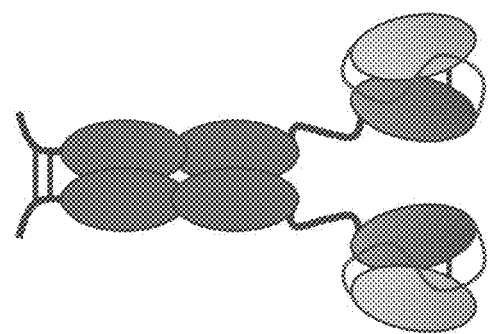
FIG. 7D depicts the structure of the antibody corresponding to protein index 21.
Figure 7E:
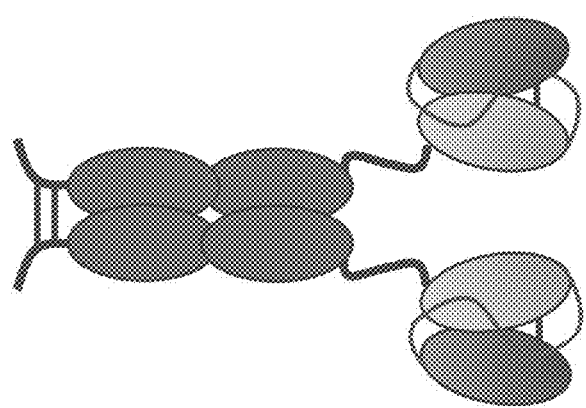
FIG. 7E depicts the structure of the antibody corresponding to protein index 22.

| Protein Index | Fc Chain #1 | Fc Chain #2 | Non-Fc Chain | "Code"/FIG. Depiction | Description |
|---|---|---|---|---|---|
| 3 | TOC1798 | | TOC1775 | C in FIG. 7A | Fc hIgG1.agly ANTIBODY-A Fab bivalent USD |
| 4 | TOC1799 | TOC1801 | TOC1775 | D in FIG. 7A | Fc hIgG1.agly ANTIBODY-A Fab monovalent USD (KIH-SS) |
| 5 | TOC1785 | | TOC1715 | VH fusion set/FIG. 7B | Fc hIgG1.agly-DelPG-ANTIBODY-A Fab VH fusion |
| 6 | TOC1786 | | TOC1715 | VH fusion set | Fc hIgG1.agly-DelG-ANTIBODY-A Fab VH fusion |
| 7 | TOC1787 | | TOC1715 | VH fusion set/FIG. 7B | Fc hIgG1.agly-ANTIBODY-A Fab VH fusion |
| 8 | TOC1710 | | TOC1715 | VH fusion set/FIG. 7B | Fc hIgG1.agly-S-ANTIBODY-A Fab VH fusion |
| 9 | TOC1711 | | TOC1715 | VH fusion set/FIG. 7B | Fc hIgG1.agly-SG2-ANTIBODY-A Fab VH fusion |
| 10 | TOC1712 | | TOC1715 | VH fusion set/FIG. 7B | Fc hIgG1.agly-SG4-ANTIBODY-A Fab VH fusion |
| 11 | TOC1713 | | TOC1715 | VH fusion set/FIG. 7B | Fc hIgG1.agly-SG4SG4-ANTIBODY-A Fab VH fusion |
| 12 | TOC1714 | | TOC1715 | VH fusion set/FIG. 7B | Fc hIgG1.agly-SG4SG4SG4-ANTIBODY-A Fab VH fusion |
| 13 | TOC1788 | | TOC1721 | VL fusion set/FIG. 7C | Fc hIgG1.agly-DelPG-ANTIBODY-A Fab VL fusion |
| 14 | TOC1789 | | TOC1721 | VL fusion set/FIG. 7C | Fc hIgG1.agly-DelG-ANTIBODY-A Fab VL fusion |
| 15 | TOC1790 | | TOC1721 | VL fusion set/FIG. 7C | Fc hIgG1.agly-ANTIBODY-A Fab VL fusion |
| 16 | TOC1791 | | TOC1721 | VL fusion set/FIG. 7C | Fc hIgG1.agly-S-ANTIBODY-A Fab VL fusion |
| 17 | TOC1792 | | TOC1721 | VL fusion set/FIG. 7C | Fc hIgG1.agly-SG2-ANTIBODY-A Fab VL fusion |
| 18 | TOC1793 | | TOC1721 | VL fusion set/FIG. 7C | Fc hIgG1.agly-SG4-ANTIBODY-A Fab VL fusion |
| 19 | TOC1794 | | TOC1721 | VL fusion set/FIG. 7C | Fc hIgG1.agly-SG4SG4-ANTIBODY-A Fab VL fusion |
| 20 | TOC1795 | | TOC1721 | VL fusion set/FIG. 7C | Fc hIgG1.agly-SG4SG4SG4-ANTIBODY-A Fab VL fusion |
| 21 | TOC1728 | | | J/FIG. 7D | Fc hIgG1.agly-SG4SG4-ANTIBODY-A VH-VL scFv |
| 22 | TOC1729 | | | K/FIG. 7E | Fc hIgG1.agly-SG4SG4-ANTIBODY-A VL-VH scFv |

TABLE 21

Protein Sequences for Antibody Components

| Protein ID | Protein Description | Protein Sequence |
|---|---|---|
| TOC1785 | hIgG1.agly-DelPG-ANTIBODY-A VH-CH1 (SEQ ID NO: 174) | KTHTCPPCPAPELLGGPSVFLFPPKPKDTLMISRTPEVT CVVVDVSHEDPEVKFNWYVDGVEVHNAKTKPREEQYQST YRVVSVLTVLHQDWLNGKEYKCKVSNKALPAPIEKTISK AKGQPREPQVYTLPPSRDELTKNQVSLTCLVKGFYPSDI AVEWESNGQPENNYKTTPPVLDSDGSFFLYSKLTVDKSR WQQGNVFSCSVMHEALHNHYTQKSLSLSQSLVESGGGLV QPGGSLRLSCAASGIDFSSSGYMCWVRQAPGKGLEWVGC IYTYSSNTYYAASVKGRFTISKTSSTTVYLQMNSLKTED TAVYYCARGTYGYTGYTYTMGYFSLWGQGTLVTVSSAST KGPSVFPLAPSSKSTSGGTAALGCLVKDYFPEPVTVSWN SGALTSGVHTFPAVLQSSGLYSLSSWTVPSSSLGTQTYI CNVNHKPSNTKVDKKVEPKSC |
| TOC1786 | hIgG1.agly-DelG-ANTIBODY-A VH-CH1 (SEQ ID NO: 175) | KTHTCPPCPAPELLGGPSVFLFPPKPKDTLMISRTPEVT CVVVDVSHEDPEVKFNWYVDGVEVHNAKTKPREEQYQST YRVVSVLTVLHQDWLNGKEYKCKVSNKALPAPIEKTISK AKGQPREPQVYTLPPSRDELTKNQVSLTCLVKGFYPSDI AVEWESNGQPENNYKTTPPVLDSDGSFFLYSKLTVDKSR WQQGNVFSCSVMHEALHNHYTQKSLSLSPQSLVESGGGL VQPGGSLRLSCAASGIDFSSSGYMCWVRQAPGKGLEWVG CIYTYSSNTYYAASVKGRFTISKTSSTTVYLQMNSLKTE DTAVYYCARGTYGYTGYTYTMGYFSLWGQGTLVTVSSAS |

TABLE 21-continued

Protein Sequences for Antibody Components

| Protein ID | Protein Description | Protein Sequence |
|---|---|---|
| | | TKGPSVFPLAPSSKSTSGGTAALGCLVKDYFPEPVTVSW NSGALTSGVHTFPAVLQSSGLYSLSSVVTVPSSSLGTQT YICNVNHKPSNTKVDKKVEPKSC |
| TOC1787 | hIgG1.agly-ANTIBODY-A VH-CH1 (SEQ ID NO: 176) | KTHTCPPCPAPELLGGPSVFLFPPKPKDTLMISRTPEVT CVVVDVSHEDPEVKFNWYVDGVEVHNAKTKPREEQYQST YRVVSVLTVLHQDWLNGKEYKCKVSNKALPAPIEKTISK AKGQPREPQVYTLPPSRDELTKNQVSLTCLVKGFYPSDI AVEWESNGQPENNYKTTPPVLDSDGSFFLYSKLTVDKSR WQQGNVFSCSVMHEALHNHYTQKSLSLSPGQSLVESGGG LVQPGGSLRLSCAASGIDFSSSGYMCWVRQAPGKGLEWV GCIYTYSSNTYYAASVKGRFTISKTSSTTVYLQMNSLKT EDTAVYYCARGTYGYTGYTYTMGYFSLWGQGTLVTVSSA STKGPSVFPLAPSSKSTSGGTAALGCLVKDYFPEPVTVS WNSGALTSGVHTFPAVLQSSGLYSLSSVVTVPSSSLGTQ TYICNVNHKPSNTKVDKKVEPKSC |
| TOC1710 | hIgG1.agly-S-ANTIBODY-A VH-CH1 (SEQ ID NO: 177) | KTHTCPPCPAPELLGGPSVFLFPPKPKDTLMISRTPEVT CVVVDVSHEDPEVKFNWYVDGVEVHNAKTKPREEQYQST YRVVSVLTVLHQDWLNGKEYKCKVSNKALPAPIEKTISK AKGQPREPQVYTLPPSRDELTKNQVSLTCLVKGFYPSDI AVEWESNGQPENNYKTTPPVLDSDGSFFLYSKLTVDKSR WQQGNVFSCSVMHEALHNHYTQKSLSLSPGSQSLVESGG GLVQPGGSLRLSCAASGIDFSSSGYMCWVRQAPGKGLEW VGCIYTYSSNTYYAASVKGRFTISKTSSTTVYLQMNSLK TEDTAVYYCARGTYGYTGYTYTMGYFSLWGQGTLVTVSS ASTKGPSVFPLAPSSKSTSGGTAALGCLVKDYFPEPVTV SWNSGALTSGVHTFPAVLQSSGLYSLSSVVTVPSSSLGT QTYICNVNHKPSNTKVDKKVEPKSC |
| TOC1711 | hIgG1.agly-SG2-ANTIBODY-A VH-CH1 (SEQ ID NO: 178) | KTHTCPPCPAPELLGGPSVFLFPPKPKDTLMISRTPEVT CVVVDVSHEDPEVKFNWYVDGVEVHNAKTKPREEQYQST YRVVSVLTVLHQDWLNGKEYKCKVSNKALPAPIEKTISK AKGQPREPQVYTLPPSRDELTKNQVSLTCLVKGFYPSDI AVEWESNGQPENNYKTTPPVLDSDGSFFLYSKLTVDKSR WQQGNVFSCSVMHEALHNHYTQKSLSLSPGSGGQSLVES GGGLVQPGGSLRLSCAASGIDFSSSGYMCWVRQAPGKGL EWVGCIYTYSSNTYYAASVKGRFTISKTSSTTVYLQMNS LKTEDTAVYYCARGTYGYTGYTYTMGYFSLWGQGTLVTV SSASTKGPSVFPLAPSSKSTSGGTAALGCLVKDYFPEPV TVSWNSGALTSGVHTFPAVLQSSGLYSLSSWTVPSSSLG TQTYICNVNHKPSNTKVDKKVEPKSC |
| TOC1712 | hIgG1.agly-SG4-ANTIBODY-A VH-CH1 (SEQ ID NO: 179) | KTHTCPPCPAPELLGGPSVFLFPPKPKDTLMISRTPEVT CVVVDVSHEDPEVKFNWYVDGVEVHNAKTKPREEQYQST YRVVSVLTVLHQDWLNGKEYKCKVSNKALPAPIEKTISK AKGQPREPQVYTLPPSRDELTKNQVSLTCLVKGFYPSDI AVEWESNGQPENNYKTTPPVLDSDGSFFLYSKLTVDKSR WQQGNVFSCSVMHEALHNHYTQKSLSLSPGSGGGGQSLV ESGGGLVQPGGSLRLSCAASGIDFSSSGYMCWVRQAPGK GLEWVGCIYTYSSNTYYAASVKGRFTISKTSSTTVYLQM NSLKTEDTAVYYCARGTYGYTGYTYTMGYFSLWGQGTLV TVSSASTKGPSVFPLAPSSKSTSGGTAALGCLVKDYFPE PVTVSWNSGALTSGVHTFPAVLQSSGLYSLSSWTVPSSS LGTQTYICNVNHKPSNTKVDKKVEPKSC |
| TOC1713 | hIgG1.agly-SG4SG4-ANTIBODY-A VH-CH1 (SEQ ID NO: 180) | KTHTCPPCPAPELLGGPSVFLFPPKPKDTLMISRTPEVT CVVVDVSHEDPEVKFNWYVDGVEVHNAKTKPREEQYQST YRVVSVLTVLHQDWLNGKEYKCKVSNKALPAPIEKTISK AKGQPREPQVYTLPPSRDELTKNQVSLTCLVKGFYPSDI AVEWESNGQPENNYKTTPPVLDSDGSFFLYSKLTVDKSR WQQGNVFSCSVMHEALHNHYTQKSLSLSPGSGGGGSGGG GQSLVESGGGLVQPGGSLRLSCAASGIDFSSSGYMCWVR QAPGKGLEWVGCIYTYSSNTYYAASVKGRFTISKTSSTT VYLQMNSLKTEDTAVYYCARGTYGYTGYTYTMGYFSLWG QGTLVTVSSASTKGPSVFPLAPSSKSTSGGTAALGCLVK DYFPEPVTVSWNSGALTSGVHTFPAVLQSSGLYSLSSVV TVPSSSLGTQTYICNVNHKPSNTKVDKKVEPKSC |
| TOC1714 | hIgG1.agly-SG4SG4SG4-ANTIBODY-A VH-CH1 (SEQ ID NO: 181) | KTHTCPPCPAPELLGGPSVFLFPPKPKDTLMISRTPEVT CVVVDVSHEDPEVKFNWYVDGVEVHNAKTKPREEQYQST YRVVSVLTVLHQDWLNGKEYKCKVSNKALPAPIEKTISK AKGQPREPQVYTLPPSRDELTKNQVSLTCLVKGFYPSDI AVEWESNGQPENNYKTTPPVLDSDGSFFLYSKLTVDKSR WQQGNVFSCSVMHEALHNHYTQKSLSLSPGSGGGGSGGG |

TABLE 21-continued

Protein Sequences for Antibody Components

| Protein ID | Protein Description | Protein Sequence |
|---|---|---|
| | | GSGGGGQSLVESGGGLVQPGGSLRLSCAASGIDFSSSGY MCWVRQAPGKGLEWVGCIYTYSSNTYYAASVKGRFTISK TSSTTVYLQMNSLKTEDTAVYYCARGTYGYTGYTYTMGY FSLWGQGTLVTVSSASTKGPSVFPLAPSSKSTSGGTAAL GCLVKDYFPEPVTVSWNSGALTSGVHTFPAVLQSSGLYS LSSVVTVPSSSLGTQTYICNVNHKPSNTKVDKKVEPKSC |
| TOC1788 | hIgG1.agly-DelPG-ANTIBODY-A VL-Ck (SEQ ID NO: 182) | KTHTCPPCPAPELLGGPSVFLFPPKPKDTLMISRTPEVT CVVVDVSHEDPEVKFNWYVDGVEVHNAKTKPREEQYQST YRVVSVLTVLHQDWLNGKEYKCKVSNKALPAPIEKTISK AKGQPREPQVYTLPPSRDELTKNQVSLTCLVKGFYPSDI AVEWESNGQPENNYKTTPPVLDSDGSFFLYSKLTVDKSR WQQGNVFSCSVMHEALHNHYTQKSLSLSDIQMTQSPSTL SASVGDRVTITCQASQNINSYLAWYQQKPGKAPKLLIYR ASSLESGVPSRFSGSGSGTEFTLTISSLQPDDFATYYCQ SYYYSGSSNYNAFGGGTKVEIKRTVAAPSVFIFPPSDEQ LKSGTASVVCLLNNFYPREAKVQWKVDNALQSGNSQESV TEQDSKDSTYSLSSTLTLSKADYEKHKVYACEVTHQGLS SPVTKSFNRGEC |
| TOC1789 | hIgG1.agly-DelG-ANTIBODY-A VL-Ck (SEQ ID NO: 183) | KTHTCPPCPAPELLGGPSVFLFPPKPKDTLMISRTPEVT CVVVDVSHEDPEVKFNWYVDGVEVHNAKTKPREEQYQST YRVVSVLTVLHQDWLNGKEYKCKVSNKALPAPIEKTISK AKGQPREPQVYTLPPSRDELTKNQVSLTCLVKGFYPSDI AVEWESNGQPENNYKTTPPVLDSDGSFFLYSKLTVDKSR WQQGNVFSCSVMHEALHNHYTQKSLSLSPDIQMTQSPST LSASVGDRVTITCQASQNINSYLAWYQQKPGKAPKLLIY RASSLESGVPSRFSGSGSGTEFTLTISSLQPDDFATYYC QSYYYSGSSNYNAFGGGTKVEIKRTVAAPSVFIFPPSDE QLKSGTASVVCLLNNFYPREAKVQWKVDNALQSGNSQES VTEQDSKDSTYSLSSTLTLSKADYEKHKVYACEVTHQGL SSPVTKSFNRGEC |
| TOC1790 | hIgG1.agly-ANTIBODY-A VL-Ck (SEQ ID NO: 184) | KTHTCPPCPAPELLGGPSVFLFPPKPKDTLMISRTPEVT CVVVDVSHEDPEVKFNWYVDGVEVHNAKTKPREEQYQST YRVVSVLTVLHQDWLNGKEYKCKVSNKALPAPIEKTISK AKGQPREPQVYTLPPSRDELTKNQVSLTCLVKGFYPSDI AVEWESNGQPENNYKTTPPVLDSDGSFFLYSKLTVDKSR WQQGNVFSCSVMHEALHNHYTQKSLSLSPGDIQMTQSPS TLSASVGDRVTITCQASQNINSYLAWYQQKPGKAPKLLI YRASSLESGVPSRFSGSGSGTEFTLTISSLQPDDFATYY CQSYYYSGSSNYNAFGGGTKVEIKRTVAAPSVFIFPPSD EQLKSGTASVVCLLNNFYPREAKVQWKVDNALQSGNSQE SVTEQDSKDSTYSLSSTLTLSKADYEKHKVYACEVTHQG LSSPVTKSFNRGEC |
| TOC1791 | hIgG1.agly-S-ANTIBODY-A VL-Ck (SEQ ID NO: 185) | KTHTCPPCPAPELLGGPSVFLFPPKPKDTLMISRTPEVT CVVVDVSHEDPEVKFNWYVDGVEVHNAKTKPREEQYQST YRVVSVLTVLHQDWLNGKEYKCKVSNKALPAPIEKTISK AKGQPREPQVYTLPPSRDELTKNQVSLTCLVKGFYPSDI AVEWESNGQPENNYKTTPPVLDSDGSFFLYSKLTVDKSR WQQGNVFSCSVMHEALHNHYTQKSLSLSPGSDIQMTQSP STLSASVGDRVTITCQASQNINSYLAWYQQKPGKAPKLL IYRASSLESGVPSRFSGSGSGTEFTLTISSLQPDDFATY YCQSYYYSGSSNYNAFGGGTKVEIKRTVAAPSVFIFPPS DEQLKSGTASVVCLLNNFYPREAKVQWKVDNALQSGNSQ ESVTEQDSKDSTYSLSSTLTLSKADYEKHKVYACEVTHQ GLSSPVTKSFNRGEC |
| TOC1792 | hIgG1.agly-SG2-ANTIBODY-A VL-Ck (SEQ ID NO: 186) | KTHTCPPCPAPELLGGPSVFLFPPKPKDTLMISRTPEVT CVVVDVSHEDPEVKFNWYVDGVEVHNAKTKPREEQYQST YRVVSVLTVLHQDWLNGKEYKCKVSNKALPAPIEKTISK AKGQPREPQVYTLPPSRDELTKNQVSLTCLVKGFYPSDI AVEWESNGQPENNYKTTPPVLDSDGSFFLYSKLTVDKSR WQQGNVFSCSVMHEALHNHYTQKSLSLSPGSGGDIQMTQ SPSTLSASVGDRVTITCQASQNINSYLAWYQQKPGKAPK LLIYRASSLESGVPSRFSGSGSGTEFTLTISSLQPDDFA TYYCQSYYYSGSSNYNAFGGGTKVEIKRTVAAPSVFIFP PSDEQLKSGTASVVCLLNNFYPREAKVQWKVDNALQSGN SQESVTEQDSKDSTYSLSSTLTLSKADYEKHKVYACEVT HQGLSSPVTKSFNRGEC |
| TOC1793 | hIgG1.agly-SG4-ANTIBODY- | KTHTCPPCPAPELLGGPSVFLFPPKPKDTLMISRTPEVT CVVVDVSHEDPEVKFNWYVDGVEVHNAKTKPREEQYQST YRVVSVLTVLHQDWLNGKEYKCKVSNKALPAPIEKTISK |

TABLE 21-continued

Protein Sequences for Antibody Components

| Protein ID | Protein Description | Protein Sequence |
|---|---|---|
| | A VL-Ck (SEQ ID NO: 187) | AKGQPREPQVYTLPPSRDELTKNQVSLTCLVKGFYPSDI AVEWESNGQPENNYKTTPPVLDSDGSFFLYSKLTVDKSR WQQGNVFSCSVMHEALHNHYTQKSLSLSPGSGGGGDIQM TQSPSTLSASVGDRVTITCQASQNINSYLAWYQQKPGKA PKLLIYRASSLESGVPSRFSGSGSGTEFTLTISSLQPDD FATYYCQSYYYSGSSNYNAFGGGTKVEIKRTVAAPSVFI FPPSDEQLKSGTASVVCLLNNFYPREAKVQWKVDNALQS GNSQESVTEQDSKDSTYSLSSTLTLSKADYEKHKVYACE VTHQGLSSPVTKSFNRGEC |
| TOC1794 | hIgG1.agly-SG4SG4-ANTIBODY-A VL-Ck (SEQ ID NO: 188) | KTHTCPPCPAPELLGGPSVFLFPPKPKDTLMISRTPEVT CVVVDVSHEDPEVKFNWYVDGVEVHNAKTKPREEQYQST YRVVSVLTVLHQDWLNGKEYKCKVSNKALPAPIEKTISK AKGQPREPQVYTLPPSRDELTKNQVSLTCLVKGFYPSDI AVEWESNGQPENNYKTTPPVLDSDGSFFLYSKLTVDKSR WQQGNVFSCSVMHEALHNHYTQKSLSLSPGSGGGGSGGG GDIQMTQSPSTLSASVGDRVTITCQASQNINSYLAWYQQ KPGKAPKLLIYRASSLESGVPSRFSGSGSGTEFTLTISS LQPDDFATYYCQSYYYSGSSNYNAFGGGTKVEIKRTVAA PSVFIFPPSDEQLKSGTASVVCLLNNFYPREAKVQWKVD NALQSGNSQESVTEQDSKDSTYSLSSTLTLSKADYEKHK VYACEVTHQGLSSPVTKSFNRGEC |
| TOC1795 | hIgG1.agly-SG4SG4SG4-ANTIBODY-A VL-Ck (SEQ ID NO: 189) | KTHTCPPCPAPELLGGPSVFLFPPKPKDTLMISRTPEVT CVVVDVSHEDPEVKFNWYVDGVEVHNAKTKPREEQYQST YRVVSVLTVLHQDWLNGKEYKCKVSNKALPAPIEKTISK AKGQPREPQVYTLPPSRDELTKNQVSLTCLVKGFYPSDI AVEWESNGQPENNYKTTPPVLDSDGSFFLYSKLTVDKSR WQQGNVFSCSVMHEALHNHYTQKSLSLSPGSGGGGSGGG GSGGGGDIQMTQSPSTLSASVGDRVTITCQASQNINSYL AWYQQKPGKAPKLLIYRASSLESGVPSRFSGSGSGTEFT LTISSLQPDDFATYYCQSYYYSGSSNYNAFGGGTKVEIK RTVAAPSVFIFPPSDEQLKSGTASVVCLLNNFYPREAKV QWKVDNALQSGNSQESVTEQDSKDSTYSLSSTLTLSKAD YEKHKVYACEVTHQGLSSPVTKSFNRGEC |
| TOC1728 | hIgG1.agly-SG4SG4-ANTIBODY-A VH-VL scFv (SEQ ID NO: 190) | KTHTCPPCPAPELLGGPSVFLFPPKPKDTLMISRTPEVT CVVVDVSHEDPEVKFNWYVDGVEVHNAKTKPREEQYQST YRVVSVLTVLHQDWLNGKEYKCKVSNKALPAPIEKTISK AKGQPREPQVYTLPPSRDELTKNQVSLTCLVKGFYPSDI AVEWESNGQPENNYKTTPPVLDSDGSFFLYSKLTVDKSR WQQGNVFSCSVMHEALHNHYTQKSLSLSPGSGGGGSGGG GQSLVESGGGLVQPGGSLRLSCAASGIDFSSSGYMCWVR QAPGKGLEWVGCIYTYSSNTYYAASVKGRFTISKTSSTT VYLQMNSLKTEDTAVYYCARGTYGYTGYTYTMGYFSLWG QGTLVTVSSGGGGSGGGGSGGGGSDIQMTQSPSTLSASV GDRVTITCQASQNINSYLAWYQQKPGKAPKLLIYRASSL ESGVPSRFSGSGSGTEFTLTISSLQPDDFATYYCQSYYY SGSSNYNAFGGGTKVEIK |
| TOC1729 | hIgG1.agly-SG4SG4-ANTIBODY-A VL-VH scFv (SEQ ID NO: 191) | KTHTCPPCPAPELLGGPSVFLFPPKPKDTLMISRTPEVT CVVVDVSHEDPEVKFNWYVDGVEVHNAKTKPREEQYQST YRVVSVLTVLHQDWLNGKEYKCKVSNKALPAPIEKTISK AKGQPREPQVYTLPPSRDELTKNQVSLTCLVKGFYPSDI AVEWESNGQPENNYKTTPPVLDSDGSFFLYSKLTVDKSR WQQGNVFSCSVMHEALHNHYTQKSLSLSPGSGGGGSGGG GDIQMTQSPSTLSASVGDRVTITCQASQNINSYLAWYQQ KPGKAPKLLIYRASSLESGVPSRFSGSGSGTEFTLTISS LQPDDFATYYCQSYYYSGSSNYNAFGGGTKVEIKGGGGS GGGGSGGGGSQSLVESGGGLVQPGGSLRLSCAASGIDFS SSGYMCWVRQAPGKGLEWVGCIYTYSSNTYYAASVKGRF TISKTSSTTVYLQMNSLKTEDTAVYYCARGTYGYTGYTY TMGYFSLWGQGTLVTVSS |
| TOC1796 | huANTIBODY-A bivalent RSU hIgG1.agly (SEQ ID NO: 192) | QSLVESGGGLVQPGGSLRLSCAASGIDFSSSGYMCWVRQ APGKGLEWVGCIYTYSSNTYYAASVKGRFTISKTSSTTV YLQMNSLKTEDTAVYYCARGTYGYTGYTYTMGYFSLWGQ GTLVTVSSASTKGPSVFPLAPSSKSTSGGTAALGCLVKD YFPEPVTVSWNSGALTSGVHTFPAVLQSSGLYSLSSVVT VPSSSLGTQTYICNVNHKPSNTKVDKKVEPKSCDKTHTC PPCPAPELLGGPSVFLFPPKPKDTLMISRTPEVTCVVVD VSHEDPEVKFNWYVDGVEVHNAKTKPREEQYQSTYRVVS VLTVLHQDWLNGKEYKCKVSNKALPAPIEKTISKAKGQP |

TABLE 21-continued

Protein Sequences for Antibody Components

| Protein ID | Protein Description | Protein Sequence |
|---|---|---|
| | | REPQVYTLPPSRDELTKNQVSLTCLVKGFYPSDIAVEWE SNGQPENNYKTTPPVLDSDGSFFLYSKLTVDKSRWQQGN VFSCSVMHEALHNHYTQKSLSLSPG |
| TOC1797 | huANTIBODY-A one-armed RSU hIgG1.agly (knob + cys) (SEQ ID NO: 193) | QSLVESGGGLVQPGGSLRLSCAASGIDFSSSGYMCWVRQ APGKGLEWVGCIYTYSSNTYYAASVKGRFTISKTSSTTV YLQMNSLKTEDTAVYYCARGTYGYTGYTYTMGYFSLWGQ GTLVTVSSASTKGPSVFPLAPSSKSTSGGTAALGCLVKD YFPEPVTVSWNSGALTSGVHTFPAVLQSSGLYSLSSVVT VPSSSLGTQTYICNVNHKPSNTKVDKKVEPKSCDKTHTC PPCPAPELLGGPSVFLFPPKPKDTLMISRTPEVTCVVVD VSHEDPEVKFNWYVDGVEVHNAKTKPREEQYQSTYRVVS VLTVLHQDWLNGKEYKCKVSNKALPAPIEKTISKAKGQP REPQVYTLPPCRDELTKNQVSLWCLVKGFYPSDIAVEWE SNGQPENNYKTTPPVLDSDGSFFLYSKLTVDKSRWQQGN VFSCSVMHEALHNHYTQKSLSLSPG |
| TOC1798 | Fc hIgG1.agly ANTIBODY-A Fab bivalent USD (SEQ ID NO: 180) | KTHTCPPCPAPELLGGPSVFLFPPKPKDTLMISRTPEVT CVVVDVSHEDPEVKFNWYVDGVEVHNAKTKPREEQYQST YRVVSVLTVLHQDWLNGKEYKCKVSNKALPAPIEKTISK AKGQPREPQVYTLPPSRDELTKNQVSLTCLVKGFYPSDI AVEWESNGQPENNYKTTPPVLDSDGSFFLYSKLTVDKSR WQQGNVFSCSVMHEALHNHYTQKSLSLSPGSGGGSGGGG GQSLVESGGGLVQPGGSLRLSCAASGIDFSSSGYMCWVR QAPGKGLEWVGCIYTYSSNTYYAASVKGRFTISKTSSTT VYLQMNSLKTEDTAVYYCARGTYGYTGYTYTMGYFSLWG QGTLVTVSSASTKGPSVFPLAPSSKSTSGGTAALGCLVK DYFPEPVTVSWNSGALTSGVHTFPAVLQSSGLYSLSSVV TVPSSSLGTQTYICNVNHKPSNTKVDKKVEPKSC |
| TOC1799 | Fc hIgG1.agly ANTIBODY-A Fab one-armed USD (knob + cys) (SEQ ID NO: 194) | KTHTCPPCPAPELLGGPSVFLFPPKPKDTLMISRTPEVT CVVVDVSHEDPEVKFNWYVDGVEVHNAKTKPREEQYQST YRVVSVLTVLHQDWLNGKEYKCKVSNKALPAPIEKTISK AKGQPREPQVYTLPPCRDELTKNQVSLWCLVKGFYPSDI AVEWESNGQPENNYKTTPPVLDSDGSFFLYSKLTVDKSR WQQGNVFSCSVMHEALHNHYTQKSLSLSPGGGGSGGGGG QSLVESGGGLVQPGGSLRLSCAASGIDFSSSGYMCWVRQ APGKGLEWVGCIYTYSSNTYYAASVKGRFTISKTSSTTV YLQMNSLKTEDTAVYYCARGTYGYTGYTYTMGYFSLWGQ GTLVTVSSASTKGPSVFPLAPSSKSTSGGTAALGCLVKD YFPEPVTVSWNSGALTSGVHTFPAVLQSSGLYSLSSVVT VPSSSLGTQTYICNVNHKPSNTKVDKKVEPKSC |
| TOC1801 | Fc hIgG1.ag (N297Q) (hole + cys) (SEQ ID NO: 195) | KTHTCPPCPAPELLGGPSVFLFPPKPKDTLMISRTPEVT CVVVDVSHEDPEVKFNWYVDGVEVHNAKTKPREEQYQST YRVVSVLTVLHQDWLNGKEYKCKVSNKALPAPIEKTISK AKGQPREPQVCTLPPSRDELTKNQVSLSCAVKGFYPSDI AVEWESNGQPENNYKTTPPVLDSDGSFFLVSKLTVDKSR WQQGNVFSCSVMHEALHNHYTQKSLSLSPG |
| TOC1715 | ANTIBODY-A LC hKappa Cterm HA (SEQ ID NO: 196) | DIQMTQSPSTLSASVGDRVTITCQASQNINSYLAWYQQK PGKAPKLLIYRASSLESGVPSRFSGSGSGTEFTLTISSL QPDDFATYYCQSYYYSGSSNYNAFGGGTKVEIKRTVAAP SVFIFPPSDEQLKSGTASVVCLLNNFYPREAKVQWKVDN ALQSGNSQESVTEQDSKDSTYSLSSTLTLSKADYEKHKV YACEVTHQGLSSPVTKSFNRGECTGYPYDVPDYA |
| TOC1721 | ANTIBODY-A VH CH1 HA fusion (SEQ ID NO: 197) | QSLVESGGGLVQPGGSLRLSCAASGIDFSSSGYMCWVRQ APGKGLEWVGCIYTYSSNTYYAASVKGRFTISKTSSTTV YLQMNSLKTEDTAVYYCARGTYGYTGYTYTMGYFSLWGQ GTLVTVSSASTKGPSVFPLAPSSKSTSGGTAALGCLVKD YFPEPVTVSWNSGALTSGVHTFPAVLQSSGLYSLSSVVT VPSSSLGTQTYICNVNHKPSNTKVDKKVEPKSCTGYPYD VPDYA |
| TOC1775 | ANTIBODY-A LC hKappa (SEQ ID NO: 94) | DIQMTQSPSTLSASVGDRVTITCQASQNINSYLAWYQQK PGKAPKLLIYRASSLESGVPSRFSGSGSGTEFTLTISSL QPDDFATYYCQSYYYSGSSNYNAFGGGTKVEIKRTVAAP SVFIFPPSDEQLKSGTASVVCLLNNFYPREAKVQWKVDN ALQSGNSQESVTEQDSKDSTYSLSSTLTLSKADYEKHKV YACEVTHQGLSSPVTKSFNRGEC |

CHO cells deficient for hamster TfR were transduced using lentiviral plasmids to express either full-length human or cynomolgus monkey TfR. Flow cytometry was performed by incubation of CHO cells with either cynomolgus or human TfR, 50,000 cells per well, 100 microliters, 1 hour on ice with titration of test article (antibody identified by protein index 1, 2, 3, or 4), followed by two washes, incubation with secondary anti-human Fc PE labeled conjugate (Jackson Immunoresearch), two washes, and fixation with 1% paraformaldehyde before analysis on a flow cytometer.

Figure 8A:
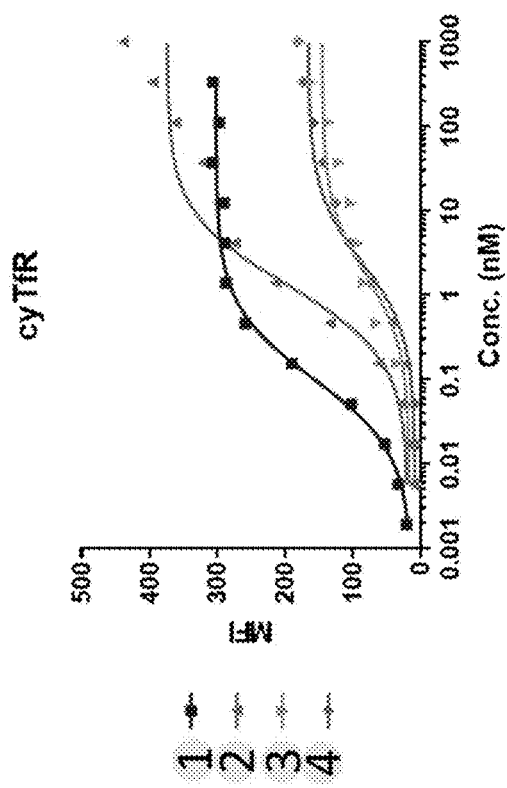
FIG. 8A is a graph depicting antibodies identified by protein index 1, 2, 3, and 4 binding to cynomolgus transferrin receptor (cyTfR).
Figure 8B:
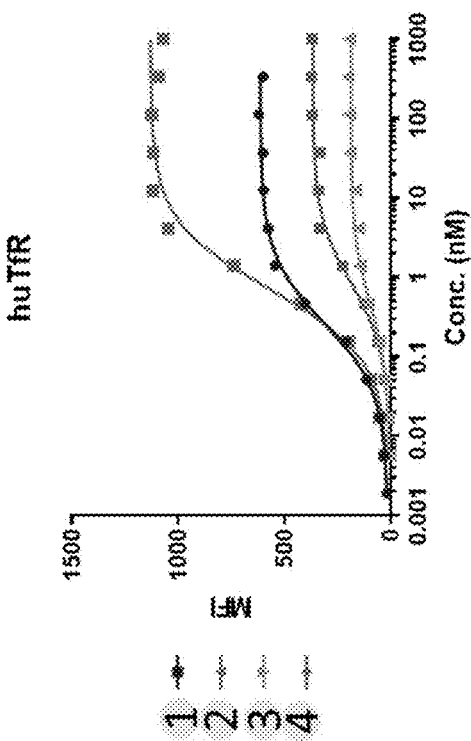
FIG. 8B is a graph depicting antibodies identified by protein index 1, 2, 3, and 4 binding to human transferrin receptor (huTfR).

All four antibody formats tested (antibodies identified by protein index 1, 2, 3, and 4) bound well to both cynomolgus and human TfR with nearly identical binding to the two species (FIGS. 8A-8B and Table 22). Bivalent constructs exhibited slightly higher binding to cells due to the avidity of their binding.

TABLE 22

Binding of Humanized ANTIBODY-A Format Variants to Cynomolgus and Human TfR

| Protein Index | Description | EC50 (nM) cyTfR | EC50 (nM) huTfR |
| --- | --- | --- | --- |
| 1 | huANTIBODY-A bivalent RSU hIgG1.agly | 0.1 | 0.3 |
| 2 | huANTIBODY-A monovalent RSU hIgG1.agly (KIH-SS) | 1.3 | 0.7 |
| 3 | Fc hIgG1.agly ANTIBODY-A Fab bivalent USD | 1.7 | 0.5 |
| 4 | Fc hIgG1.agly ANTIBODY-A Fab monovalent USD (KIH-SS) | 2.5 | 0.8 |

Transferrin displacement by a humanized version of ANTIBODY-A was assessed in different formats. CHO cells deficient in hamster TfR and over-expressing human TfR were incubated with AlexaFluor647-conjugated transferrin at 3 nM and a titration of test article (antibody identified by protein index 1, 2, 3, or 4) at indicated concentrations for 1 hour on ice, washed three times, fixed with 1% paraformaldehyde, and analyzed by flow cytometry for displacement of fluorescent transferrin.

Figure 9A:
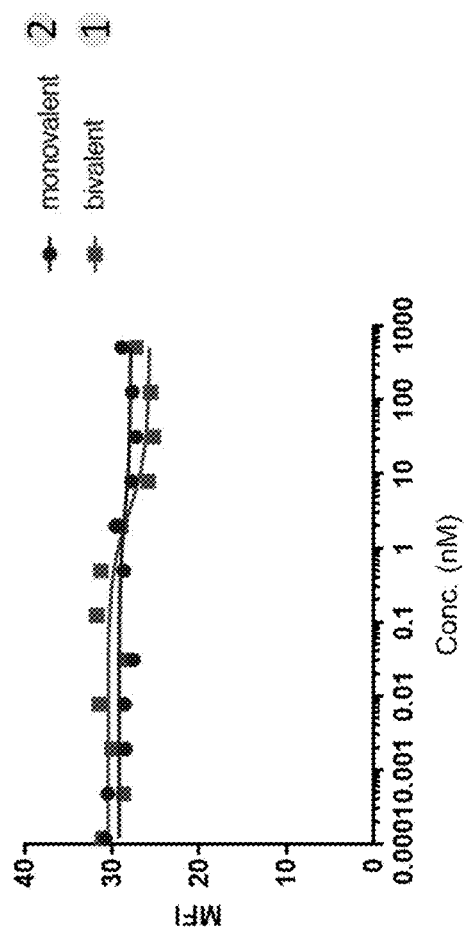
FIG. 9A is a graph depicting transferrin displacement by antibodies identified by protein index 1 and 2 binding to human transferrin receptor.

Right-side up ("RSU") constructs (protein index 1 and 2) both showed minimal Tf displacement (FIG. 9A). Bivalent RSU (protein index 1) showed about 10% Tf displacement at concentrations >2 nM.

Figure 9B:
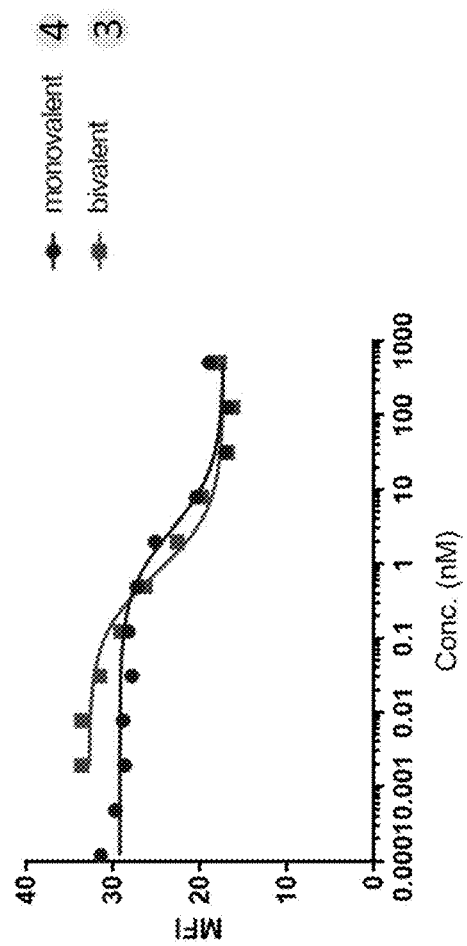
FIG. 9B is a graph depicting transferrin displacement by antibodies identified by protein index 3 and 4 binding to human transferrin receptor.

Upside-down ("USD") constructs (protein index 3 and 4) both showed about 40% Tf displacement (FIG. 9B). This was presumably caused by a steric clash between the Fc of these constructs and transferrin.

Binding of anti-TfR humanized ANTIBODY-A monovalent Fc fusions (protein index 2 and 4) to TfR in the presence or absence of human holo-transferrin were studied by surface plasmon resonance on a Biacore 8K+instrument at 25 Celsius using anti-His tag capture on a CM5 chip to capture the ectodomain (ECD) of human or cynomolgus monkey TfR with an N-terminal His×6 tag. Binding was performed in hepes buffered saline with 3 mM EDTA, 0.05% BSA, 0.005% P20 at pH 7.4. For testing of competition with transferrin, the surface captured TfR ECD was pre-saturated with 1 micromolar holo-human transferrin before injecting test article (protein index 2 or 4). Monovalent antibody was titrated in a 4-fold dilution series from 0.2 to 200 nM. Multi-cycle kinetics were fit to 1:1 binding model to generate binding parameters. The binding of anti-TfR humanized ANTIBODY-A monovalent Fc fusions to TfR was not affected by transferrin (Table 23).

TABLE 23

Binding of Humanized ANTIBODY-A Monovalent Fc Fusions to TfR in the Presence or Absence of Transferrin

| | Tf (1 uM) | Human TfR ECD binding | | | | Cyno TfR ECD binding | | | |
| --- | --- | --- | --- | --- | --- | --- | --- | --- | --- |
| | | $k_a$ (/M · s) | $k_d$ (/s) | $K_D$ (nM) | $R_{max}$ (%) | $k_a$ (/M · s) | $k_d$ (/s) | $K_D$ (nM) | $R_{max}$ (%) |
| Protein Index 2 (huANTIBODY-A monovalent RSU hIgG1.agly (KIH-SS)) | − | 6.3E+05 | 1.1E−03 | 1.7 | 74 | 1.4E+06 | 6.8E−03 | 5.0 | 80 |
| | + | 7.0E+05 | 8.9E−04 | 1.3 | 73 | 1.5E+06 | 7.6E−03 | 5.2 | 76 |
| Protein Index 4 (Fc hIgG1.agly ANTIBODY-A Fab monovalent USD (KIH-SS)) | − | 4.1E+05 | 9.8E−04 | 2.4 | 75 | 8.2E+05 | 4.9E−03 | 6.0 | 80 |
| | + | 3.0E+05 | 7.6E−04 | 2.5 | 76 | 6.0E+05 | 5.8E−03 | 9.6 | 78 |

Binding of human holo-transferrin to cyno TfR ECD in the presence or absence of monovalent versions of humanized ANTIBODY-A (protein index 2 and 4) was studied by surface plasmon resonance on a Biacore 8K+instrument at 25 Celsius using anti-His tag capture on a CM5 chip to capture the ectodomain (ECD) of human or cynomolgus monkey TfR with an N-terminal His×6 tag. Binding was performed in hepes buffered saline with 3 mM EDTA, 0.05% BSA, 0.005% P20 at pH 7.4. For testing of competition with TfR, the surface captured TfR ECD was pre-saturated with 200 nM of humanized ANTIBODY-A (protein index 2 or 4) before injecting human holo-transferrin in a 4-fold dilution series from 0.2 to 200 nM. Multi-cycle kinetics were fit to 1:1 binding model to generate binding parameters. In the upside-down format (USD, Fc-Fab), monovalent anti-TfR humanized ANTIBODY-A weakened transferrin binding to TfR (Table 24). In the right-side up format (RSU, Fab-Fc) monovalent anti-TfR humanized ANTIBODY-A had no impact on transferrin binding to TfR (Table 24).

TABLE 24

Effect of Monovalent Humanized ANTIBODY-A
Fc Fusions on Transferrin Binding to TfR

| | | cyTfR ECD | |
|---|---|---|---|
| Test Article | Pre-Saturated Competitor | Apparent KD (nM) | Rmax (%) |
| Holo huTf | None | 3.1 | 38 |
| Holo huTf | 200 nM Protein Index 2 (ANTIBODY-A hIgG1.agly monovalent RSU) | 3.9 | 34 |
| Holo huTf | 200 nM Protein Index 4 (hIgG1.agly - ANTIBODY-A monovalent USD) | 9.8 | 31 |

Figure 10:
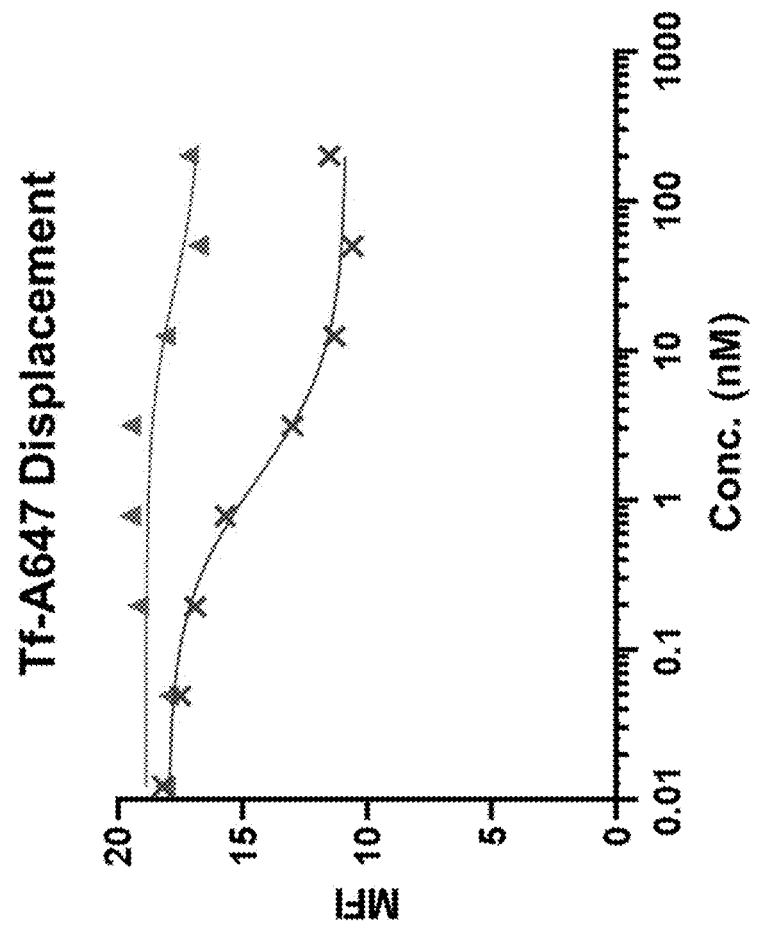
FIG. 10 is a graph depicting transferrin displacement by antibodies identified by protein index 3 ("x") and protein index 14 (triangle) binding to human transferrin receptor.

CHO cells deficient in hamster TfR and over-expressing human TfR were incubated with AlexaFluor647-conjugated transferrin at 3 nM and a titration of test article (antibody-protein index 3 or 14) at indicated concentrations for 1 hour on ice, washed three times, fixed with 1% paraformaldehyde, and analyzed by flow cytometry for displacement of fluorescent transferrin. Humanized ANTIBODY-A in USD format, with the Fab linked to the C-terminus of the Fc through the Fab VH N-terminus, induces an approximate 40% displacement of transferrin (Tf-AF647) from cell surface huTfR (FIG. 10; protein index 3 identified by "x"). This was minimized by linking the Fab to the Fc through the N-terminus of its VL domain and shortening the linker between Fc and Fab (FIG. 10; protein index 14 identified by triangle).

CHO cells deficient for hamster TfR and over-expressing full length human TfR were used to test binding of anti-TfR antibodies in a flow cytometry experiment. Flow cytometry was performed by incubation of CHO cells expressing human TfR, approximately 50,000 cells per well, 100 microliters, 1 hour on ice with titration of test article (protein index 5, 6, 7, 8, 9, 10, 11, 12, 13, 14, 16, 17, 18, 19, or 20), followed by two washes, incubation with secondary anti-human IgG PE conjugate (Jackson Immunoresearch), two washes, and fixation with 1% paraformaldehyde before analysis on a flow cytometer.

Humanized ANTIBODY-A Fab fused to the C-terminus of Fc via either its VH N-terminus (protein index 5, 6, 7, 8, 9, 10, 11, and 12) or its VL N-terminus (protein index 13, 14, 16, 17, 18, 19, and 20) yielded similar binding results (Table 25). Furthermore, the linker between the Fc and Fab can vary from 15 amino acids (3×SG4) down to "negative 2" (in which the last two residues of the CH3 domain (Pro-Gly) are removed). Note that the maximal mean fluorescence intensity changes when the Fc is fused to the VL domain of the Fab and the linker is short, which is likely due to a steric hindrance of secondary antibody on the test article.

TABLE 25

Humanized ANTIBODY-A Can Be Fused to Fc Via its
VH or VL N-Termini and with Longer or Shorter
Linkers With no Apparent Loss of Binding

| Protein Index | EC50 (nM) | Max MFI (Fit) |
|---|---|---|
| 5 | 0.29 | 1191 |
| 6 | 0.35 | 1189 |
| 7 | 0.27 | 1183 |
| 8 | 0.21 | 1232 |
| 9 | 0.26 | 1244 |
| 10 | 0.20 | 1290 |
| 11 | 0.22 | 1300 |
| 12 | 0.15 | 1359 |
| 13 | 0.20 | 553 |
| 14 | 0.31 | 498 |
| 16 | 0.20 | 567 |
| 17 | 0.32 | 497 |
| 18 | 0.26 | 527 |
| 19 | 0.33 | 659 |
| 20 | 0.32 | 1167 |

CHO cells deficient for hamster TfR and over-expressing full length human TfR were used to test binding of anti-TfR antibodies in a flow cytometry experiment. Flow cytometry was performed by incubation of CHO cells expressing human TfR, approximately 50,000 cells per well, 100 microliters, 1 hour on ice with titration of test article (protein index 3, 21, or 22), followed by two washes, incubation with secondary anti-human IgG PE conjugate (Jackson Immunoresearch), two washes, and fixation with 1% paraformaldehyde before analysis on a flow cytometer.

When the VH and VL domains of humanized ANTIBODY-A were converted into an scFv format and fused to the C-terminus of a human IgG Fc, they retained binding to human TfR (Table 26). The apparent difference in MFI is likely due to greater epitopes available for the secondary detection antibody in the non-scFv format.

TABLE 26

Humanized ANTIBODY-A Re-formatted
as an scFv Retains Binding to TfR

| Protein Index | Description | EC50 (nM) | Max MFI (Fit) |
|---|---|---|---|
| 3 | Fc hIgG1.agly ANTIBODY-A Fab bivalent USD | 0.28 | 1325 |
| 21 | Fc hIgG1.agly-SG4SG4-ANTIBODY-A VH-VL scFv | 0.21 | 415 |
| 22 | Fc hIgG1.agly-SG4SG4-ANTIBODY-A VL-VH scFv | 0.18 | 395 |

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

SEQUENCE LISTING

```
Sequence total quantity: 215
SEQ ID NO: 1            moltype = AA  length = 760
FEATURE                 Location/Qualifiers
source                  1..760
                        mol_type = protein
                        organism = Homo sapiens
SEQUENCE: 1
MMDQARSAFS NLFGGEPLSY TRFSLARQVD GDNSHVEMKL AVDEEENADN NTKANVTKPK   60
RCSGSICYGT IAVIVFFLIG FMIGYLGYCK GVEPKTECER LAGTESPVRE EPGEDFPAAR  120
RLYWDDLKRK LSEKLDSTDF TGTIKLLNEN SYVPREAGSQ KDENLALYVE NQFREFKLSK  180
VWRDQHFVKI QVKDSAQNSV IIVDKNGRLV YLVENPGGYV AYSKAATVTG KLVHANFGTK  240
KDFEDLYTPV NGSIVIVRAG KITFAEKVAN AESLNAIGVL IYMDQTKFPI VNAELSFFGH  300
AHLGTGDPYT PGFPSFNHTQ FPPSRSSGLP NIPVQTISRA AAEKLFGNME GDCPSDWKTD  360
STCRMVTSES KNVKLTVSNV LKEIKILNIF GVIKGFVEPD HYVVVGAQRD AWGPGAAKSG  420
VGTALLLKLA QMFSDMVLKD GFQPSRSIIF ASWSAGDFGS VGATEWLEGY LSSLHLKAFT  480
YINLDKAVLG TSNFKVSASP LLYTLIEKTM QNVKHPVTGQ FLYQDSNWAS KVEKLTLDNA  540
APPFLAYSGI PAVSFCFCED TDYPYLGTTM DTYKELIERI PELNKVARAA AEVAGQFVIK  600
LTHDVELNLD YERYNSQLLS FVRDLNQYRA DIKEMGLSLQ WLYSARGDFF RATSRLTTDF  660
GNAEKTDRFV MKKLNDRVMR VEYHFLSPYV SPKESPFRHV FWGSGSHTLP ALLENLKLRK  720
QNNGAFNETL FRNQLALATW TIQGAANALS GDVWDIDNEF                        760

SEQ ID NO: 2            moltype = AA  length = 760
FEATURE                 Location/Qualifiers
source                  1..760
                        mol_type = protein
                        organism = Macaca fascicularis
SEQUENCE: 2
MMDQARSAFS NLFGGEPLSY TRFSLARQVD GDNSHVEMKL AVDDEENADN NTKANGTKPK   60
RCGGNICYGT IAVIIFFLIG FMIGYLGYCK GVEPKTECER LAGTESPARE EPEEDFPAAP  120
RLYWDDLKRK LSEKLDTTDF TSTIKLLNEN LYVPREAGSQ KDENLALYIE NQFREFKLSK  180
VWRDQHFVKI QVKDSAQNSV IIVDKNGGLV YLVENPGGYV AYSKAATVTG KLVHANFGTK  240
KDFEDLDSPV NGSIVIVRAG KITFAEKVAN AESLNAIGVL IYMDQTKFPI VKADLSFFGH  300
AHLGTGDPYT PGFPSFNHTQ FPPSQSSGLP NIPVQTISRA AAEKLFGNME GDCPSDWKTD  360
STCKMVTSEN KSVKLTVSNV LKETKILNIF GVIKGFVEPD HYVVVGAQRD AWGPGAAKSS  420
VGTALLLKLA QMFSDMVLKD GFQPSRSIIF ASWSAGDFGS VGATEWLEGY LSSLHLKAFT  480
YINLDKAVLG TSNFKVSASP LLYTLIEKTM QDVKHPVTGR SLYQDSNWAS KVEKLTLDNA  540
APPFLAYSGI PAVSFCFCED TDYPYLGTTM DTYKELVERI PELNKVARAA AEVAGQFVIK  600
LTHDTELNLD YERYNSQLLL FLRDLNQYRA DVKEMGLSLQ WLYSARGDFF RATSRLTTDF  660
RNAEKRDKFV MKKLNDRVMR VEYYFLSPYV SPKESPFRHV FWGSGSHTLS ALLESLKLRR  720
QNNSAFNETL FRNQLALATW TIQGAANALS GDVWDIDNEF                        760

SEQ ID NO: 3            moltype = AA  length = 763
FEATURE                 Location/Qualifiers
source                  1..763
                        mol_type = protein
                        organism = Mus musculus
SEQUENCE: 3
MMDQARSAFS NLFGGEPLSY TRFSLARQVD GDNSHVEMKL AADEEENADN NMKASVRKPK   60
RFNGRLCFAA IALVIFFLIG FMSGYLGYCK RVEQKEECVK LAETEETDKS ETMETEDVPT  120
SSRLYWADLK TLLSEKLNSI EFADTIKQLS QNTYTPREAG SQKDESLAYY IENQFHEFKF  180
SKVWRDEHYV KIQVKSSIGQ NMVTIVQSNG NLDPVESPEG YVAFSKPTEV SGKLVHANFG  240
TKKDFEELSY SVNGSLVIVR AGEITFAEKV ANAQSFNAIG VLIIYMDKNKF PVVEADLALF  300
GHAHLGTGDP YTPGFPSFNH TQFPPSQSSG LPNIPVQTIS RAAAEKLFGK MEGSCPARWN  360
IDSSCKLELS QNQNVKLIVK NVLKERRILN IFGVIKGYEE PDRYVVVGAQ RDALGAGVAA  420
KSSVGTGLLL KLAQVFSDMI SKDGFRPSRS IIFASWTAGD FGAVGATEWL EGYLSSLHLK  480
AFTYINLDKV VLGTSNFKVS ASPLLYTLMG KIMQDVKHPV DGKSLYRDSN WISKVEKLSF  540
DNAAYPFLAY SGIPAVSFCF CEDADYPYLG TRLDTYEALT QKVPQLNQMV RTAAEVAGQL  600
IIKLTHDVEL NLDYEMYNSK LLSFMKDLNQ FKTDIRDMGL SLQWLYSARG DYFRATSRLT  660
TDFHNAEKTN RFVMREINDR IMKVEYHFLS PYVSPRESPF RHIFWGSGSH TLSALVENLK  720
LRQKNITAFN ETLFRNQLAL ATWTIQGVAN ALSGDIWNID NEF                    763

SEQ ID NO: 4            moltype = AA  length = 125
FEATURE                 Location/Qualifiers
source                  1..125
                        mol_type = protein
                        organism = synthetic construct
SEQUENCE: 4
QSLEESGGGL VQPGASLTLT CKASGIDFSS SGYMCWVRQA PGKGLEWIGC IYTYSSNTYY   60
ASWAKGRFTI SKTSSTTVTL QMTSLTAADT ATYFCARGTY GYTGYTYTMG YFSLWGPGTL  120
VTVSS                                                              125

SEQ ID NO: 5            moltype = AA  length = 127
FEATURE                 Location/Qualifiers
source                  1..127
                        mol_type = protein
                        organism = synthetic construct
SEQUENCE: 5
EVQLVESGGG LVQPGGSLRL SCAASGIDFS SSGYMAWVRQ APGKGLEWVG AIYTYSSNTY   60
```

```
YAASVKGRFT ISRDDSKNSL YLQMNSLKTE DTAVYYCARG TYGYTGYTYT MGYFSLWGQG    120
TLVTVSS                                                             127

SEQ ID NO: 6            moltype = AA  length = 126
FEATURE                 Location/Qualifiers
source                  1..126
                        mol_type = protein
                        organism = synthetic construct
SEQUENCE: 6
QSLVESGGGL VQPGGSLRLS CAASGIDFSS SGYMAWVRQA PGKGLEWVGA IYTYSSNTYY    60
AASVKGRFTI SRDDSKNSLY LQMNSLKTED TAVYYCARGT YGYTGYTYTM GYFSLWGQGT    120
LVTVSS                                                               126

SEQ ID NO: 7            moltype = AA  length = 125
FEATURE                 Location/Qualifiers
source                  1..125
                        mol_type = protein
                        organism = synthetic construct
SEQUENCE: 7
QSLVESGGGL VQPGGSLRLS CAASGIDFSS SGYMAWVRQA PGKGLEWVGA IYTYSSNTYY    60
AASVKGRFTI SKTSSTTVYL QMNSLKTEDT AVYYCARGTY GYTGYTYTMG YFSLWGQGTL    120
VTVSS                                                                125

SEQ ID NO: 8            moltype = AA  length = 125
FEATURE                 Location/Qualifiers
source                  1..125
                        mol_type = protein
                        organism = synthetic construct
SEQUENCE: 8
QSLVESGGGL VQPGGSLRLS CKASGIDFSS SGYMAWVRQA PGKGLEWVGA IYTYSSNTYY    60
ASWAKGRFTI SKDSKNSVYL QMNSLKTEDT AVYYCARGTY GYTGYTYTMG YFSLWGPGTL    120
VTVSS                                                                125

SEQ ID NO: 9            moltype = AA  length = 125
FEATURE                 Location/Qualifiers
source                  1..125
                        mol_type = protein
                        organism = synthetic construct
SEQUENCE: 9
QSLVESGGGL VQPGGSLRLS CKASGIDFSS SGYMSWVRQA PGKGLEWVGV IYTYSSNTYY    60
ASWAKGRFTI SKDSKNSVYL QMNSLKTEDT AVYYCARGTY GYTGYTYTMG YFSLWGPGTL    120
VTVSS                                                                125

SEQ ID NO: 10           moltype = AA  length = 125
FEATURE                 Location/Qualifiers
source                  1..125
                        mol_type = protein
                        organism = synthetic construct
SEQUENCE: 10
QSLVESGGGL VQPGGSLRLS CKASGIDFSS SGYMSWVRQA PGKGLEWVGR IYTYSSNTYY    60
ASWAKGRFTI SKDSKNSVYL QMNSLKTEDT AVYYCARGTY GYTGYTYTMG YFSLWGPGTL    120
VTVSS                                                                125

SEQ ID NO: 11           moltype = AA  length = 125
FEATURE                 Location/Qualifiers
source                  1..125
                        mol_type = protein
                        organism = synthetic construct
SEQUENCE: 11
QSLVESGGGL VQPGGSLRLS CKASGIDFSS SGYMSWVRQA PGKGLEWVGY IYTYSSNTYY    60
ASWAKGRFTI SKDSKNSVYL QMNSLKTEDT AVYYCARGTY GYTGYTYTMG YFSLWGPGTL    120
VTVSS                                                                125

SEQ ID NO: 12           moltype = AA  length = 125
FEATURE                 Location/Qualifiers
source                  1..125
                        mol_type = protein
                        organism = synthetic construct
SEQUENCE: 12
QSLVESGGGL VQPGGSLRLS CKASGIDFSS SGYMHWVRQA PGKGLEWVGA IYTYSSNTYY    60
ASWAKGRFTI SKDSKNSVYL QMNSLKTEDT AVYYCARGTY GYTGYTYTMG YFSLWGPGTL    120
VTVSS                                                                125

SEQ ID NO: 13           moltype = AA  length = 125
FEATURE                 Location/Qualifiers
source                  1..125
                        mol_type = protein
                        organism = synthetic construct
```

```
SEQUENCE: 13
QSLVESGGGL VQPGGSLRLS CKASGIDFSS SGYMAWVRQA PGKGLEWVGA IYTYSSNTYY      60
ASWAKGRFTI SKTSSTTVYL QMNSLKTEDT AVYYCARGTY GYTGYTYTMG YFSLWGPGTL     120
VTVSS                                                                125

SEQ ID NO: 14           moltype = AA   length = 127
    FEATURE                 Location/Qualifiers
    source                  1..127
                            mol_type = protein
                            organism = synthetic construct
SEQUENCE: 14
EVQLVESGGG LVQPGGSLRL SCAASGIDFS SSGYMCWVRQ APGKGLEWVG CIYTYSSNTY      60
YAASVKGRFT ISRDDSKNSL YLQMNSLKTE DTAVYYCARG TYGYTGYTYT MGYFSLWGQG     120
TLVTVSS                                                              127

SEQ ID NO: 15           moltype = AA   length = 126
    FEATURE                 Location/Qualifiers
    source                  1..126
                            mol_type = protein
                            organism = synthetic construct
SEQUENCE: 15
QSLVESGGGL VQPGGSLRLS CAASGIDFSS SGYMCWVRQA PGKGLEWVGC IYTYSSNTYY      60
AASVKGRFTI SRDDSKNSLY LQMNSLKTED TAVYYCARGT YGYTGYTYTM GYFSLWGQGT     120
LVTVSS                                                               126

SEQ ID NO: 16           moltype = AA   length = 125
    FEATURE                 Location/Qualifiers
    source                  1..125
                            mol_type = protein
                            organism = synthetic construct
SEQUENCE: 16
QSLVESGGGL VQPGGSLRLS CAASGIDFSS SGYMCWVRQA PGKGLEWVGC IYTYSSNTYY      60
AASVKGRFTI SKTSSTTVYL QMNSLKTEDT AVYYCARGTY GYTGYTYTMG YFSLWGQGTL     120
VTVSS                                                                125

SEQ ID NO: 17           moltype = AA   length = 125
    FEATURE                 Location/Qualifiers
    source                  1..125
                            mol_type = protein
                            organism = synthetic construct
SEQUENCE: 17
QSLVESGGGL VQPGGSLRLS CKASGIDFSS SGYMCWVRQA PGKGLEWVGC IYTYSSNTYY      60
ASWAKGRFTI SKDSKNSVYL QMNSLKTEDT AVYYCARGTY GYTGYTYTMG YFSLWGPGTL     120
VTVSS                                                                125

SEQ ID NO: 18           moltype = AA   length = 125
    FEATURE                 Location/Qualifiers
    source                  1..125
                            mol_type = protein
                            organism = synthetic construct
SEQUENCE: 18
QSLVESGGGL VQPGGSLRLS CKASGIDFSS SGYMCWVRQA PGKGLEWVGC IYTYSSNTYY      60
ASWAKGRFTI SKTSSTTVYL QMNSLKTEDT AVYYCARGTY GYTGYTYTMG YFSLWGPGTL     120
VTVSS                                                                125

SEQ ID NO: 19           moltype = AA   length = 119
    FEATURE                 Location/Qualifiers
    source                  1..119
                            mol_type = protein
                            organism = synthetic construct
SEQUENCE: 19
QSLEESGGGL VQPEGSLTLT CKASGFSFSN SYWICWVRQA PGKGLEWIGC INTDADSTNY      60
ASWARGRFTI SKTSSTTVTL QMTSLTAADT ASYFCARQNN VFDPGYNLWG PGTLVTVSS      119

SEQ ID NO: 20           moltype = AA   length = 121
    FEATURE                 Location/Qualifiers
    source                  1..121
                            mol_type = protein
                            organism = synthetic construct
SEQUENCE: 20
QVQLVESGGG VVQPGRSLRL SCAASGFSFS NSYWIAWVRQ APGKGLEWVA AINTDADSTN      60
YADSVKGRFT ISRDNSKNTL YLQMNSLRAE DTAVYYCARQ NNVFDPGYNL WGQGTLVTVS     120
S                                                                    121

SEQ ID NO: 21           moltype = AA   length = 120
    FEATURE                 Location/Qualifiers
    source                  1..120
                            mol_type = protein
                            organism = synthetic construct
```

```
SEQUENCE: 21
QSLVESGGGV VQPGRSLRLS CAASGFSFSN SYWIAWVRQA PGKGLEWVAA INTDADSTNY    60
ADSVKGRFTI SKDNSKNTVY LQMNSLRAED TAVYYCARQN NVFDPGYNLW GQGTLVTVSS   120

SEQ ID NO: 22              moltype = AA   length = 120
FEATURE                    Location/Qualifiers
source                     1..120
                           mol_type = protein
                           organism = synthetic construct
SEQUENCE: 22
QSLVESGGGV VQPGRSLRLS CAASGFSFSN SYWISWVRQA PGKGLEWVAV INTDADSTNY    60
ADSVKGRFTI SKDNSKNTVY LQMNSLRAED TAVYYCARQN NVFDPGYNLW GQGTLVTVSS   120

SEQ ID NO: 23              moltype = AA   length = 120
FEATURE                    Location/Qualifiers
source                     1..120
                           mol_type = protein
                           organism = synthetic construct
SEQUENCE: 23
QSLVESGGGV VQPGRSLRLS CAASGFSFSN SYWISWVRQA PGKGLEWVAR INTDADSTNY    60
ADSVKGRFTI SKDNSKNTVY LQMNSLRAED TAVYYCARQN NVFDPGYNLW GQGTLVTVSS   120

SEQ ID NO: 24              moltype = AA   length = 120
FEATURE                    Location/Qualifiers
source                     1..120
                           mol_type = protein
                           organism = synthetic construct
SEQUENCE: 24
QSLVESGGGV VQPGRSLRLS CAASGFSFSN SYWISWVRQA PGKGLEWVAY INTDADSTNY    60
ADSVKGRFTI SKDNSKNTVY LQMNSLRAED TAVYYCARQN NVFDPGYNLW GQGTLVTVSS   120

SEQ ID NO: 25              moltype = AA   length = 120
FEATURE                    Location/Qualifiers
source                     1..120
                           mol_type = protein
                           organism = synthetic construct
SEQUENCE: 25
QSLVESGGGV VQPGRSLRLS CAASGFSFSN SYWIHWVRQA PGKGLEWVAA INTDADSTNY    60
ADSVKGRFTI SKDNSKNTVY LQMNSLRAED TAVYYCARQN NVFDPGYNLW GQGTLVTVSS   120

SEQ ID NO: 26              moltype = AA   length = 119
FEATURE                    Location/Qualifiers
source                     1..119
                           mol_type = protein
                           organism = synthetic construct
SEQUENCE: 26
QSLVESGGGV VQPGRSLRLS CKASGFSFSN SYWIAWVRQA PGKGLEWVAA INTDADSTNY    60
ADSVKGRFTI SKDSSTTVYL QMNSLRAEDT AVYYCARQNN VFDPGYNLWG QGTLVTVSS    119

SEQ ID NO: 27              moltype = AA   length = 120
FEATURE                    Location/Qualifiers
source                     1..120
                           mol_type = protein
                           organism = synthetic construct
SEQUENCE: 27
QSLVESGGGV VQPGRSLRLS CAASGFSFSN SYWIAWVRQA PGKGLEWVAA INTDADSTNY    60
ASWARGRFTI SKDNSKNTLY LQMNSLRAED TAVYYCARQN NVFDPGYNLW GQGTLVTVSS   120

SEQ ID NO: 28              moltype = AA   length = 119
FEATURE                    Location/Qualifiers
source                     1..119
                           mol_type = protein
                           organism = synthetic construct
SEQUENCE: 28
QSLVESGGGV VQPGRSLRLS CKASGFSFSN SYWIAWVRQA PGKGLEWVAA INTDADSTNY    60
ASWARGRFTI SKTSSTTVYL QMNSLRAEDT AVYYCARQNN VFDPGYNLWG PGTLVTVSS    119

SEQ ID NO: 29              moltype = AA   length = 121
FEATURE                    Location/Qualifiers
source                     1..121
                           mol_type = protein
                           organism = synthetic construct
SEQUENCE: 29
QVQLVESGGG VVQPGRSLRL SCAASGFSFS NSYWICWVRQ APGKGLEWVG CINTDADSTN    60
YADSVKGRFT ISRDNSKNTL YLQMNSLRAE DTAVYYCARQ NNVFDPGYNL WGQGTLVTVS   120
S                                                                  121

SEQ ID NO: 30              moltype = AA   length = 120
FEATURE                    Location/Qualifiers
```

```
source                         1..120
                               mol_type = protein
                               organism = synthetic construct
SEQUENCE: 30
QSLVESGGGV VQPGRSLRLS CAASGFSFSN SYWICWVRQA PGKGLEWVGC INTDADSTNY    60
ADSVKGRFTI SKDNSKNTVY LQMNSLRAED TAVYYCARQN NVFDPGYNLW GQGTLVTVSS   120

SEQ ID NO: 31                  moltype = AA   length = 119
FEATURE                        Location/Qualifiers
source                         1..119
                               mol_type = protein
                               organism = synthetic construct
SEQUENCE: 31
QSLVESGGGV VQPGRSLRLS CKASGFSFSN SYWICWVRQA PGKGLEWVGC INTDADSTNY    60
ADSVKGRFTI SKDSSTTVYL QMNSLRAEDT AVYYCARQNN VFDPGYNLWG QGTLVTVSS    119

SEQ ID NO: 32                  moltype = AA   length = 120
FEATURE                        Location/Qualifiers
source                         1..120
                               mol_type = protein
                               organism = synthetic construct
SEQUENCE: 32
QSLVESGGGV VQPGRSLRLS CAASGFSFSN SYWICWVRQA PGKGLEWVGC INTDADSTNY    60
ASWARGRFTI SKDNSKNTLY LQMNSLRAED TAVYYCARQN NVFDPGYNLW GQGTLVTVSS   120

SEQ ID NO: 33                  moltype = AA   length = 119
FEATURE                        Location/Qualifiers
source                         1..119
                               mol_type = protein
                               organism = synthetic construct
SEQUENCE: 33
QSLVESGGGV VQPGRSLRLS CKASGFSFSN SYWICWVRQA PGKGLEWVGC INTDADSTNY    60
ASWARGRFTI SKTSSTTVYL QMNSLRAEDT AVYYCARQNN VFDPGYNLWG PGTLVTVSS    119

SEQ ID NO: 34                  moltype = AA   length = 111
FEATURE                        Location/Qualifiers
source                         1..111
                               mol_type = protein
                               organism = synthetic construct
SEQUENCE: 34
ELDMTQTPAS VEAAVGGTVT IKCQASQNIN SYLAWYQQKP GQPPKLLIYR ASTLASGVPS    60
RFKGSGSGTE FTLTISDLEC ADAATYYCQS YYYSGSSNYN AFGGGTELEI L            111

SEQ ID NO: 35                  moltype = AA   length = 111
FEATURE                        Location/Qualifiers
source                         1..111
                               mol_type = protein
                               organism = synthetic construct
SEQUENCE: 35
DIQMTQSPST LSASVGDRVT ITCQASQNIN SYLAWYQQKP GKAPKLLIYR ASSLESGVPS    60
RFSGSGSGTE FTLTISSLQP DDFATYYCQS YYYSGSSNYN AFGGGTKVEI K            111

SEQ ID NO: 36                  moltype = AA   length = 111
FEATURE                        Location/Qualifiers
source                         1..111
                               mol_type = protein
                               organism = synthetic construct
SEQUENCE: 36
DIQMTQSPST LSASVGDRVT ITCQASQNIN SYLAWYQQKP GKAPKLLIYR ASTLASGVPS    60
RFSGSGSGTE FTLTISSLQP DDFATYYCQS YYYSGSSNYN AFGGGTKVEI K            111

SEQ ID NO: 37                  moltype = AA   length = 111
FEATURE                        Location/Qualifiers
source                         1..111
                               mol_type = protein
                               organism = synthetic construct
SEQUENCE: 37
ELDMTQSPST LSASVGDRVT ITCQASQNIN SYLAWYQQKP GKAPKLLIYR ASTLASGVPS    60
RFSGSGSGTE FTLTISSLQP DDFATYYCQS YYYSGSSNYN AFGGGTKVEI K            111

SEQ ID NO: 38                  moltype = AA   length = 110
FEATURE                        Location/Qualifiers
source                         1..110
                               mol_type = protein
                               organism = synthetic construct
SEQUENCE: 38
ELVLTQTPAS VSEAVGGTVT IKCQASQNIG SNLAWYQQKP GQPPKLLIYD ASKLASGVPS    60
RFSGSGSGTE FTLTISDLEC ADAATYYCQC TVRGGAYGNA FGGGTEVVVK              110
```

SEQ ID NO: 39              moltype = AA   length = 110
FEATURE                    Location/Qualifiers
source                     1..110
                           mol_type = protein
                           organism = synthetic construct
SEQUENCE: 39
DIQMTQSPST LSASVGDRVT ITCRASQNIG SNLAWYQQKP GKAPKLLIYD ASKLESGVPS    60
RFSGSGSGTE FTLTISSLQP DDFATYYCQQ TVRGGAYGLA FGGGTKVEIK              110

SEQ ID NO: 40              moltype = AA   length = 110
FEATURE                    Location/Qualifiers
source                     1..110
                           mol_type = protein
                           organism = synthetic construct
SEQUENCE: 40
ELVLTQSPST LSASVGDRVT ITCRASQNIG SNLAWYQQKP GKAPKLLIYD ASKLESGVPS    60
RFSGSGSGTE FTLTISSLQP DDFATYYCQA TVRGGAYGLA FGGGTKVEIK              110

SEQ ID NO: 41              moltype = AA   length = 110
FEATURE                    Location/Qualifiers
source                     1..110
                           mol_type = protein
                           organism = synthetic construct
SEQUENCE: 41
ELVLTQSPST LSASVGDRVT ITCRASQNIG SNLAWYQQKP GKAPKLLIYD ASKLESGVPS    60
RFSGSGSGTE FTLTISSLQP DDFATYYCQC TVRGGAYGNA FGGGTKVEIK              110

SEQ ID NO: 42              moltype = AA   length = 110
FEATURE                    Location/Qualifiers
source                     1..110
                           mol_type = protein
                           organism = synthetic construct
SEQUENCE: 42
ELVLTQSPST LSASVGDRVT ITCRASQNIG SNLAWYQQKP GKAPKLLIYD ASKLESGVPS    60
RFSGSGSGTE FTLTISSLQP DDFATYYCQS TVRGGAYGNA FGGGTKVEIK              110

SEQ ID NO: 43              moltype = AA   length = 110
FEATURE                    Location/Qualifiers
source                     1..110
                           mol_type = protein
                           organism = synthetic construct
SEQUENCE: 43
ELVLTQSPST LSASVGDRVT ITCRASQNIG SNLAWYQQKP GKAPKLLIYD ASKLESGVPS    60
RFSGSGSGTE FTLTISSLQP DDFATYYCQT TVRGGAYGNA FGGGTKVEIK              110

SEQ ID NO: 44              moltype = AA   length = 110
FEATURE                    Location/Qualifiers
source                     1..110
                           mol_type = protein
                           organism = synthetic construct
SEQUENCE: 44
ELVLTQSPST LSASVGDRVT ITCRASQNIG SNLAWYQQKP GKAPKLLIYD ASKLESGVPS    60
RFSGSGSGTE FTLTISSLQP DDFATYYCQV TVRGGAYGNA FGGGTKVEIK              110

SEQ ID NO: 45              moltype = AA   length = 98
FEATURE                    Location/Qualifiers
source                     1..98
                           mol_type = protein
                           organism = synthetic construct
SEQUENCE: 45
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKV                            98

SEQ ID NO: 46              moltype = AA   length = 111
FEATURE                    Location/Qualifiers
source                     1..111
                           mol_type = protein
                           organism = synthetic construct
SEQUENCE: 46
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP P            111

SEQ ID NO: 47              moltype = AA   length = 98
FEATURE                    Location/Qualifiers
source                     1..98
                           mol_type = protein
                           organism = synthetic construct -continued

```
SEQUENCE: 47
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKRV                            98

SEQ ID NO: 48           moltype = AA  length = 107
FEATURE                 Location/Qualifiers
source                  1..107
                        mol_type = protein
                        organism = synthetic construct
SEQUENCE: 48
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKRVES KYGPPCP                 107

SEQ ID NO: 49           moltype = AA  length = 98
FEATURE                 Location/Qualifiers
source                  1..98
                        mol_type = protein
                        organism = synthetic construct
SEQUENCE: 49
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKV                            98

SEQ ID NO: 50           moltype = AA  length = 103
FEATURE                 Location/Qualifiers
source                  1..103
                        mol_type = protein
                        organism = synthetic construct
SEQUENCE: 50
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSC                     103

SEQ ID NO: 51           moltype = AA  length = 98
FEATURE                 Location/Qualifiers
source                  1..98
                        mol_type = protein
                        organism = synthetic construct
SEQUENCE: 51
ASTKGPSVFP LAPCSRSTSE STAALGCLVK DYFPEPVTVS WNSGALTSGV HTFPAVLQSS    60
GLYSLSSVVT VPSSSLGTKT YTCNVDHKPS NTKVDKRV                            98

SEQ ID NO: 52           moltype = AA  length = 100
FEATURE                 Location/Qualifiers
source                  1..100
                        mol_type = protein
                        organism = synthetic construct
SEQUENCE: 52
ASTKGPSVFP LAPCSRSTSE STAALGCLVK DYFPEPVTVS WNSGALTSGV HTFPAVLQSS    60
GLYSLSSVVT VPSSSLGTKT YTCNVDHKPS NTKVDKRVES                         100

SEQ ID NO: 53           moltype = AA  length = 23
FEATURE                 Location/Qualifiers
source                  1..23
                        mol_type = protein
                        organism = synthetic construct
SEQUENCE: 53
EPKSCDKTHT CPPCPAPELL GGP                                            23

SEQ ID NO: 54           moltype = AA  length = 13
FEATURE                 Location/Qualifiers
source                  1..13
                        mol_type = protein
                        organism = synthetic construct
SEQUENCE: 54
EPKSCDKTHT CPP                                                       13

SEQ ID NO: 55           moltype = AA  length = 5
FEATURE                 Location/Qualifiers
source                  1..5
                        mol_type = protein
                        organism = synthetic construct
SEQUENCE: 55
EPKSC                                                                 5

SEQ ID NO: 56           moltype = AA  length = 20
FEATURE                 Location/Qualifiers
source                  1..20
                        mol_type = protein
                        organism = synthetic construct
```

```
SEQUENCE: 56
ESKYGPPCPP CPAPEFLGGP                                                   20

SEQ ID NO: 57           moltype = AA   length = 9
FEATURE                 Location/Qualifiers
source                  1..9
                        mol_type = protein
                        organism = synthetic construct
SEQUENCE: 57
ESKYGPPCP                                                                9

SEQ ID NO: 58           moltype = AA   length = 4
FEATURE                 Location/Qualifiers
source                  1..4
                        mol_type = protein
                        organism = synthetic construct
SEQUENCE: 58
EPKS                                                                     4

SEQ ID NO: 59           moltype = AA   length = 6
FEATURE                 Location/Qualifiers
source                  1..6
                        mol_type = protein
                        organism = synthetic construct
SEQUENCE: 59
EPKSCD                                                                   6

SEQ ID NO: 60           moltype = AA   length = 7
FEATURE                 Location/Qualifiers
source                  1..7
                        mol_type = protein
                        organism = synthetic construct
SEQUENCE: 60
EPKSCDK                                                                  7

SEQ ID NO: 61           moltype = AA   length = 8
FEATURE                 Location/Qualifiers
source                  1..8
                        mol_type = protein
                        organism = synthetic construct
SEQUENCE: 61
EPKSCDKT                                                                 8

SEQ ID NO: 62           moltype = AA   length = 9
FEATURE                 Location/Qualifiers
source                  1..9
                        mol_type = protein
                        organism = synthetic construct
SEQUENCE: 62
EPKSCDKTH                                                                9

SEQ ID NO: 63           moltype = AA   length = 10
FEATURE                 Location/Qualifiers
source                  1..10
                        mol_type = protein
                        organism = synthetic construct
SEQUENCE: 63
EPKSCDKTHT                                                              10

SEQ ID NO: 64           moltype = AA   length = 11
FEATURE                 Location/Qualifiers
source                  1..11
                        mol_type = protein
                        organism = synthetic construct
SEQUENCE: 64
EPKSCDKTHT C                                                            11

SEQ ID NO: 65           moltype = AA   length = 12
FEATURE                 Location/Qualifiers
source                  1..12
                        mol_type = protein
                        organism = synthetic construct
SEQUENCE: 65
EPKSCDKTHT CP                                                           12
```

```
SEQ ID NO: 66          moltype = AA  length = 14
FEATURE                Location/Qualifiers
source                 1..14
                       mol_type = protein
                       organism = synthetic construct
SEQUENCE: 66
EPKSCDKTHT CPPC                                                       14

SEQ ID NO: 67          moltype = AA  length = 15
FEATURE                Location/Qualifiers
source                 1..15
                       mol_type = protein
                       organism = synthetic construct
SEQUENCE: 67
EPKSCDKTHT CPPCP                                                      15

SEQ ID NO: 68          moltype = AA  length = 16
FEATURE                Location/Qualifiers
source                 1..16
                       mol_type = protein
                       organism = synthetic construct
SEQUENCE: 68
EPKSCDKTHT CPPCPA                                                     16

SEQ ID NO: 69          moltype = AA  length = 17
FEATURE                Location/Qualifiers
source                 1..17
                       mol_type = protein
                       organism = synthetic construct
SEQUENCE: 69
EPKSCDKTHT CPPCPAP                                                    17

SEQ ID NO: 70          moltype = AA  length = 18
FEATURE                Location/Qualifiers
source                 1..18
                       mol_type = protein
                       organism = synthetic construct
SEQUENCE: 70
EPKSCDKTHT CPPCPAPE                                                   18

SEQ ID NO: 71          moltype = AA  length = 19
FEATURE                Location/Qualifiers
source                 1..19
                       mol_type = protein
                       organism = synthetic construct
SEQUENCE: 71
EPKSCDKTHT CPPCPAPEL                                                  19

SEQ ID NO: 72          moltype = AA  length = 20
FEATURE                Location/Qualifiers
source                 1..20
                       mol_type = protein
                       organism = synthetic construct
SEQUENCE: 72
EPKSCDKTHT CPPCPAPELL                                                 20

SEQ ID NO: 73          moltype = AA  length = 21
FEATURE                Location/Qualifiers
source                 1..21
                       mol_type = protein
                       organism = synthetic construct
SEQUENCE: 73
EPKSCDKTHT CPPCPAPELL G                                               21

SEQ ID NO: 74          moltype = AA  length = 22
FEATURE                Location/Qualifiers
source                 1..22
                       mol_type = protein
                       organism = synthetic construct
SEQUENCE: 74
EPKSCDKTHT CPPCPAPELL GG                                              22

SEQ ID NO: 75          moltype = AA  length = 4
FEATURE                Location/Qualifiers
source                 1..4
                       mol_type = protein
                       organism = synthetic construct
```

```
SEQUENCE: 75
ESKY                                                                        4

SEQ ID NO: 76           moltype = AA  length = 5
FEATURE                 Location/Qualifiers
source                  1..5
                        mol_type = protein
                        organism = synthetic construct
SEQUENCE: 76
ESKYG                                                                       5

SEQ ID NO: 77           moltype = AA  length = 6
FEATURE                 Location/Qualifiers
source                  1..6
                        mol_type = protein
                        organism = synthetic construct
SEQUENCE: 77
ESKYGP                                                                      6

SEQ ID NO: 78           moltype = AA  length = 7
FEATURE                 Location/Qualifiers
source                  1..7
                        mol_type = protein
                        organism = synthetic construct
SEQUENCE: 78
ESKYGPP                                                                     7

SEQ ID NO: 79           moltype = AA  length = 8
FEATURE                 Location/Qualifiers
source                  1..8
                        mol_type = protein
                        organism = synthetic construct
SEQUENCE: 79
ESKYGPPC                                                                    8

SEQ ID NO: 80           moltype = AA  length = 10
FEATURE                 Location/Qualifiers
source                  1..10
                        mol_type = protein
                        organism = synthetic construct
SEQUENCE: 80
ESKYGPPCPP                                                                 10

SEQ ID NO: 81           moltype = AA  length = 11
FEATURE                 Location/Qualifiers
source                  1..11
                        mol_type = protein
                        organism = synthetic construct
SEQUENCE: 81
ESKYGPPCPP C                                                               11

SEQ ID NO: 82           moltype = AA  length = 12
FEATURE                 Location/Qualifiers
source                  1..12
                        mol_type = protein
                        organism = synthetic construct
SEQUENCE: 82
ESKYGPPCPP CP                                                              12

SEQ ID NO: 83           moltype = AA  length = 13
FEATURE                 Location/Qualifiers
source                  1..13
                        mol_type = protein
                        organism = synthetic construct
SEQUENCE: 83
ESKYGPPCPP CPA                                                             13

SEQ ID NO: 84           moltype = AA  length = 14
FEATURE                 Location/Qualifiers
source                  1..14
                        mol_type = protein
                        organism = synthetic construct
SEQUENCE: 84
ESKYGPPCPP CPAP                                                            14
```

```
SEQ ID NO: 85            moltype = AA  length = 15
FEATURE                  Location/Qualifiers
source                   1..15
                         mol_type = protein
                         organism = synthetic construct
SEQUENCE: 85
ESKYGPPCPP CPAPE                                                          15

SEQ ID NO: 86            moltype = AA  length = 16
FEATURE                  Location/Qualifiers
source                   1..16
                         mol_type = protein
                         organism = synthetic construct
SEQUENCE: 86
ESKYGPPCPP CPAPEF                                                         16

SEQ ID NO: 87            moltype = AA  length = 17
FEATURE                  Location/Qualifiers
source                   1..17
                         mol_type = protein
                         organism = synthetic construct
SEQUENCE: 87
ESKYGPPCPP CPAPEFL                                                        17

SEQ ID NO: 88            moltype = AA  length = 18
FEATURE                  Location/Qualifiers
source                   1..18
                         mol_type = protein
                         organism = synthetic construct
SEQUENCE: 88
ESKYGPPCPP CPAPEFLG                                                       18

SEQ ID NO: 89            moltype = AA  length = 19
FEATURE                  Location/Qualifiers
source                   1..19
                         mol_type = protein
                         organism = synthetic construct
SEQUENCE: 89
ESKYGPPCPP CPAPEFLGG                                                      19

SEQ ID NO: 90            moltype = AA  length = 20
FEATURE                  Location/Qualifiers
source                   1..20
                         mol_type = protein
                         organism = synthetic construct
SEQUENCE: 90
ESKYGPPCPP CPAPEFLGGP                                                     20

SEQ ID NO: 91            moltype = AA  length = 107
FEATURE                  Location/Qualifiers
source                   1..107
                         mol_type = protein
                         organism = Homo sapiens
SEQUENCE: 91
RTVAAPSVFI FPPSDEQLKS GTASVVCLLN NFYPREAKVQ WKVDNALQSG NSQESVTEQD          60
SKDSTYSLSS TLTLSKADYE KHKVYACEVT HQGLSSPVTK SFNRGEC                       107

SEQ ID NO: 92            moltype = AA  length = 106
FEATURE                  Location/Qualifiers
source                   1..106
                         mol_type = protein
                         organism = Homo sapiens
SEQUENCE: 92
RTVAAPSVFI FPPSDEQLKS GTASVVCLLN NFYPREAKVQ WKVDNALQSG NSQESVTEQD          60
SKDSTYSLSS TLTLSKADYE KHKVYACEVT HQGLSSPVTK SFNRGE                        106

SEQ ID NO: 93            moltype = AA  length = 236
FEATURE                  Location/Qualifiers
source                   1..236
                         mol_type = protein
                         organism = synthetic construct
SEQUENCE: 93
QSLVESGGGL VQPGGSLRLS CAASGIDFSS SGYMCWVRQA PGKGLEWVGC IYTYSSNTYY          60
AASVKGRFTI SKTSSTTVYL QMNSLKTEDT AVYYCARGTY GYTGYTYTMG YFSLWGQGTL          120
VTVSSASTKG PSVFPLAPSS KSTSGGTAAL GCLVKDYFPE PVTVSWNSGA LTSGVHTFPA          180
VLQSSGLYSL SSVVTVPSSS LGTQTYICNV NHKPSNTKVD KKVEPKSCDK THTCPP             236
```

```
SEQ ID NO: 94           moltype = AA  length = 218
FEATURE                 Location/Qualifiers
source                  1..218
                        mol_type = protein
                        organism = synthetic construct
SEQUENCE: 94
DIQMTQSPST LSASVGDRVT ITCQASQNIN SYLAWYQQKP GKAPKLLIYR ASSLESGVPS    60
RFSGSGSGTE FTLTISSLQP DDFATYYCQS YYYSGSSNYN AFGGGTKVEI KRTVAAPSVF   120
IFPPSDEQLK SGTASVVCLL NNFYPREAKV QWKVDNALQS GNSQESVTEQ DSKDSTYSLS   180
STLTLSKADY EKHKVYACEV THQGLSSPVT KSFNRGEC                           218

SEQ ID NO: 95           moltype = AA  length = 225
FEATURE                 Location/Qualifiers
source                  1..225
                        mol_type = protein
                        organism = synthetic construct
SEQUENCE: 95
QSLVESGGGL VQPGGSLRLS CAASGIDFSS SGYMCWVRQA PGKGLEWVGC IYTYSSNTYY    60
AASVKGRFTI SKTSSTTVYL QMNSLKTEDT AVYYCARGTY GYTGYTYTMG YFSLWGQGTL   120
VTVSSASTKG PSVFPLAPCS RSTSESTAAL GCLVKDYFPE PVTVSWNSGA LTSGVHTFPA   180
VLQSSGLYSL SSVVTVPSSS LGTKTYTCNV DHKPSNTKVD KRVES                   225

SEQ ID NO: 96           moltype = AA  length = 217
FEATURE                 Location/Qualifiers
source                  1..217
                        mol_type = protein
                        organism = synthetic construct
SEQUENCE: 96
DIQMTQSPST LSASVGDRVT ITCQASQNIN SYLAWYQQKP GKAPKLLIYR ASSLESGVPS    60
RFSGSGSGTE FTLTISSLQP DDFATYYCQS YYYSGSSNYN AFGGGTKVEI KRTVAAPSVF   120
IFPPSDEQLK SGTASVVCLL NNFYPREAKV QWKVDNALQS GNSQESVTEQ DSKDSTYSLS   180
STLTLSKADY EKHKVYACEV THQGLSSPVT KSFNRGE                            217

SEQ ID NO: 97           moltype = AA  length = 232
FEATURE                 Location/Qualifiers
source                  1..232
                        mol_type = protein
                        organism = synthetic construct
SEQUENCE: 97
QSLVESGGGL VQPGGSLRLS CAASGIDFSS SGYMCWVRQA PGKGLEWVGC IYTYSSNTYY    60
AASVKGRFTI SKTSSTTVYL QMNSLKTEDT AVYYCARGTY GYTGYTYTMG YFSLWGQGTL   120
VTVSSASTKG PSVFPLAPSS KSTSGGTAAL GCLVKDYFPE PVTVSWNSGA LTSGVHTFPA   180
VLQSSGLYSL SSVVTVPSSS LGTQTYICNV NHKPSNTKVD KRVESKYGPP CP           232

SEQ ID NO: 98           moltype = AA  length = 228
FEATURE                 Location/Qualifiers
source                  1..228
                        mol_type = protein
                        organism = synthetic construct
SEQUENCE: 98
QSLVESGGGL VQPGGSLRLS CAASGIDFSS SGYMCWVRQA PGKGLEWVGC IYTYSSNTYY    60
AASVKGRFTI SKTSSTTVYL QMNSLKTEDT AVYYCARGTY GYTGYTYTMG YFSLWGQGTL   120
VTVSSASTKG PSVFPLAPSS KSTSGGTAAL GCLVKDYFPE PVTVSWNSGA LTSGVHTFPA   180
VLQSSGLYSL SSVVTVPSSS LGTQTYICNV NHKPSNTKVD KKVEPKSC                228

SEQ ID NO: 99           moltype = AA  length = 230
FEATURE                 Location/Qualifiers
source                  1..230
                        mol_type = protein
                        organism = synthetic construct
SEQUENCE: 99
QSLVESGGGV VQPGRSLRLS CKASGFSFSN SYWICWVRQA PGKGLEWVGC INTDADSTNY    60
ASWARGRFTI SKTSSTTVYL QMNSLRAEDT AVYYCARQNN VFDPGYNLWG PGTLVTVSSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKKVEPK SCDKTHTCPP              230

SEQ ID NO: 100          moltype = AA  length = 217
FEATURE                 Location/Qualifiers
source                  1..217
                        mol_type = protein
                        organism = synthetic construct
SEQUENCE: 100
ELVLTQSPST LSASVGDRVT ITCRASQNIG SNLAWYQQKP GKAPKLLIYD ASKLESGVPS    60
RFSGSGSGTE FTLTISSLQP DDFATYYCQC TVRGGAYGNA FGGGTKVEIK RTVAAPSVFI   120
FPPSDEQLKS GTASVVCLLN NFYPREAKVQ WKVDNALQSG NSQESVTEQD SKDSTYSLSS   180
TLTLSKADYE KHKVYACEVT HQGLSSPVTK SFNRGEC                            217
```

```
SEQ ID NO: 101        moltype = AA  length = 11
FEATURE               Location/Qualifiers
source                1..11
                      mol_type = protein
                      organism = synthetic construct
SEQUENCE: 101
GIDFSSSGYM C                                                              11

SEQ ID NO: 102        moltype = AA  length = 11
FEATURE               Location/Qualifiers
source                1..11
                      mol_type = protein
                      organism = synthetic construct
SEQUENCE: 102
GIDFSSSGYM H                                                              11

SEQ ID NO: 103        moltype = AA  length = 17
FEATURE               Location/Qualifiers
source                1..17
                      mol_type = protein
                      organism = synthetic construct
SEQUENCE: 103
CIYTYSSNTY YAASVKG                                                        17

SEQ ID NO: 104        moltype = AA  length = 17
FEATURE               Location/Qualifiers
source                1..17
                      mol_type = protein
                      organism = synthetic construct
SEQUENCE: 104
CIYTYSSNTY YASWAKG                                                        17

SEQ ID NO: 105        moltype = AA  length = 17
FEATURE               Location/Qualifiers
source                1..17
                      mol_type = protein
                      organism = synthetic construct
SEQUENCE: 105
AIYTYSSNTY YASWAKG                                                        17

SEQ ID NO: 106        moltype = AA  length = 17
FEATURE               Location/Qualifiers
source                1..17
                      mol_type = protein
                      organism = synthetic construct
SEQUENCE: 106
GTYGYTGYTY TMGYFSL                                                        17

SEQ ID NO: 107        moltype = AA  length = 11
FEATURE               Location/Qualifiers
source                1..11
                      mol_type = protein
                      organism = synthetic construct
SEQUENCE: 107
QASQNINSYL A                                                              11

SEQ ID NO: 108        moltype = AA  length = 7
FEATURE               Location/Qualifiers
source                1..7
                      mol_type = protein
                      organism = synthetic construct
SEQUENCE: 108
RASSLES                                                                   7

SEQ ID NO: 109        moltype = AA  length = 7
FEATURE               Location/Qualifiers
source                1..7
                      mol_type = protein
                      organism = synthetic construct
SEQUENCE: 109
RASTLAS                                                                   7

SEQ ID NO: 110        moltype = AA  length = 13
FEATURE               Location/Qualifiers
source                1..13
                      mol_type = protein
                      organism = synthetic construct
```

```
SEQUENCE: 110
QSYYYSGSSN YNA                                                          13

SEQ ID NO: 111         moltype = AA  length = 8
FEATURE                Location/Qualifiers
source                 1..8
                       mol_type = protein
                       organism = synthetic construct
SEQUENCE: 111
GIDFSSSG                                                                 8

SEQ ID NO: 112         moltype = AA  length = 4
FEATURE                Location/Qualifiers
source                 1..4
                       mol_type = protein
                       organism = synthetic construct
SEQUENCE: 112
TYSS                                                                     4

SEQ ID NO: 113         moltype = AA  length = 15
FEATURE                Location/Qualifiers
source                 1..15
                       mol_type = protein
                       organism = synthetic construct
SEQUENCE: 113
TYGYTGYTYT MGYFS                                                        15

SEQ ID NO: 114         moltype = AA  length = 7
FEATURE                Location/Qualifiers
source                 1..7
                       mol_type = protein
                       organism = synthetic construct
SEQUENCE: 114
SQNINSY                                                                  7

SEQ ID NO: 115         moltype = AA  length = 10
FEATURE                Location/Qualifiers
source                 1..10
                       mol_type = protein
                       organism = synthetic construct
SEQUENCE: 115
YYYSGSSNYN                                                              10

SEQ ID NO: 116         moltype = AA  length = 11
FEATURE                Location/Qualifiers
source                 1..11
                       mol_type = protein
                       organism = synthetic construct
SEQUENCE: 116
GFSFSNSYWI C                                                            11

SEQ ID NO: 117         moltype = AA  length = 17
FEATURE                Location/Qualifiers
source                 1..17
                       mol_type = protein
                       organism = synthetic construct
SEQUENCE: 117
CINTDADSTN YASWARG                                                      17

SEQ ID NO: 118         moltype = AA  length = 17
FEATURE                Location/Qualifiers
source                 1..17
                       mol_type = protein
                       organism = synthetic construct
SEQUENCE: 118
CINTDADSTN YADSVKG                                                      17

SEQ ID NO: 119         moltype = AA  length = 11
FEATURE                Location/Qualifiers
source                 1..11
                       mol_type = protein
                       organism = synthetic construct
SEQUENCE: 119
QNNVFDPGYN L                                                            11
```

| SEQ ID NO: 120 | moltype = AA   length = 11 | |
| --- | --- | --- |
| FEATURE | Location/Qualifiers | |
| source | 1..11 | |
| | mol_type = protein | |
| | organism = synthetic construct | |
| SEQUENCE: 120 | | |
| RASQNIGSNL A | | 11 |

| SEQ ID NO: 121 | moltype = AA   length = 11 | |
| --- | --- | --- |
| FEATURE | Location/Qualifiers | |
| source | 1..11 | |
| | mol_type = protein | |
| | organism = synthetic construct | |
| SEQUENCE: 121 | | |
| QASQNIGSNL A | | 11 |

| SEQ ID NO: 122 | moltype = AA   length = 7 | |
| --- | --- | --- |
| FEATURE | Location/Qualifiers | |
| source | 1..7 | |
| | mol_type = protein | |
| | organism = synthetic construct | |
| SEQUENCE: 122 | | |
| DASKLES | | 7 |

| SEQ ID NO: 123 | moltype = AA   length = 7 | |
| --- | --- | --- |
| FEATURE | Location/Qualifiers | |
| source | 1..7 | |
| | mol_type = protein | |
| | organism = synthetic construct | |
| SEQUENCE: 123 | | |
| DASKLAS | | 7 |

| SEQ ID NO: 124 | moltype = AA   length = 12 | |
| --- | --- | --- |
| FEATURE | Location/Qualifiers | |
| source | 1..12 | |
| | mol_type = protein | |
| | organism = synthetic construct | |
| SEQUENCE: 124 | | |
| QCTVRGGAYG NA | | 12 |

| SEQ ID NO: 125 | moltype = AA   length = 12 | |
| --- | --- | --- |
| FEATURE | Location/Qualifiers | |
| source | 1..12 | |
| | mol_type = protein | |
| | organism = synthetic construct | |
| SEQUENCE: 125 | | |
| QSTVRGGAYG NA | | 12 |

| SEQ ID NO: 126 | moltype = AA   length = 12 | |
| --- | --- | --- |
| FEATURE | Location/Qualifiers | |
| source | 1..12 | |
| | mol_type = protein | |
| | organism = synthetic construct | |
| SEQUENCE: 126 | | |
| QTTVRGGAYG NA | | 12 |

| SEQ ID NO: 127 | moltype = AA   length = 12 | |
| --- | --- | --- |
| FEATURE | Location/Qualifiers | |
| source | 1..12 | |
| | mol_type = protein | |
| | organism = synthetic construct | |
| SEQUENCE: 127 | | |
| QVTVRGGAYG NA | | 12 |

| SEQ ID NO: 128 | moltype = AA   length = 8 | |
| --- | --- | --- |
| FEATURE | Location/Qualifiers | |
| source | 1..8 | |
| | mol_type = protein | |
| | organism = synthetic construct | |
| SEQUENCE: 128 | | |
| GFSFSNSY | | 8 |

| SEQ ID NO: 129 | moltype = AA   length = 4 | |
| --- | --- | --- |
| FEATURE | Location/Qualifiers | |
| source | 1..4 | |
| | mol_type = protein | |
| | organism = synthetic construct | |

| | | |
|---|---|---|
| SEQUENCE: 129 | | |
| TDAD | | 4 |
| | | |
| SEQ ID NO: 130 | moltype = AA   length = 9 | |
| FEATURE | Location/Qualifiers | |
| source | 1..9 | |
| | mol_type = protein | |
| | organism = synthetic construct | |
| SEQUENCE: 130 | | |
| NNVFDPGYN | | 9 |
| | | |
| SEQ ID NO: 131 | moltype = AA   length = 7 | |
| FEATURE | Location/Qualifiers | |
| source | 1..7 | |
| | mol_type = protein | |
| | organism = synthetic construct | |
| SEQUENCE: 131 | | |
| SQNIGSN | | 7 |
| | | |
| SEQ ID NO: 132 | moltype = AA   length = 9 | |
| FEATURE | Location/Qualifiers | |
| source | 1..9 | |
| | mol_type = protein | |
| | organism = synthetic construct | |
| SEQUENCE: 132 | | |
| TVRGGAYGN | | 9 |
| | | |
| SEQ ID NO: 133 | moltype = AA   length = 11 | |
| FEATURE | Location/Qualifiers | |
| source | 1..11 | |
| | mol_type = protein | |
| | organism = synthetic construct | |
| SEQUENCE: 133 | | |
| GIDFSSSGYM A | | 11 |
| | | |
| SEQ ID NO: 134 | moltype = AA   length = 11 | |
| FEATURE | Location/Qualifiers | |
| source | 1..11 | |
| | mol_type = protein | |
| | organism = synthetic construct | |
| SEQUENCE: 134 | | |
| GIDFSSSGYM S | | 11 |
| | | |
| SEQ ID NO: 135 | moltype = AA   length = 17 | |
| FEATURE | Location/Qualifiers | |
| source | 1..17 | |
| | mol_type = protein | |
| | organism = synthetic construct | |
| SEQUENCE: 135 | | |
| AIYTYSSNTY YAASVKG | | 17 |
| | | |
| SEQ ID NO: 136 | moltype = AA   length = 17 | |
| FEATURE | Location/Qualifiers | |
| source | 1..17 | |
| | mol_type = protein | |
| | organism = synthetic construct | |
| SEQUENCE: 136 | | |
| VIYTYSSNTY YASWAKG | | 17 |
| | | |
| SEQ ID NO: 137 | moltype = AA   length = 17 | |
| FEATURE | Location/Qualifiers | |
| source | 1..17 | |
| | mol_type = protein | |
| | organism = synthetic construct | |
| SEQUENCE: 137 | | |
| RIYTYSSNTY YASWAKG | | 17 |
| | | |
| SEQ ID NO: 138 | moltype = AA   length = 17 | |
| FEATURE | Location/Qualifiers | |
| source | 1..17 | |
| | mol_type = protein | |
| | organism = synthetic construct | |
| SEQUENCE: 138 | | |
| YIYTYSSNTY YASWAKG | | 17 |

-continued

```
SEQ ID NO: 139           moltype = AA  length = 11
FEATURE                  Location/Qualifiers
source                   1..11
                         mol_type = protein
                         organism = synthetic construct
SEQUENCE: 139
GFSFSNSYWI A                                                                11

SEQ ID NO: 140           moltype = AA  length = 11
FEATURE                  Location/Qualifiers
source                   1..11
                         mol_type = protein
                         organism = synthetic construct
SEQUENCE: 140
GFSFSNSYWI S                                                                11

SEQ ID NO: 141           moltype = AA  length = 11
FEATURE                  Location/Qualifiers
source                   1..11
                         mol_type = protein
                         organism = synthetic construct
SEQUENCE: 141
GFSFSNSYWI H                                                                11

SEQ ID NO: 142           moltype = AA  length = 17
FEATURE                  Location/Qualifiers
source                   1..17
                         mol_type = protein
                         organism = synthetic construct
SEQUENCE: 142
AINTDADSTN YADSVKG                                                          17

SEQ ID NO: 143           moltype = AA  length = 17
FEATURE                  Location/Qualifiers
source                   1..17
                         mol_type = protein
                         organism = synthetic construct
SEQUENCE: 143
VINTDADSTN YADSVKG                                                          17

SEQ ID NO: 144           moltype = AA  length = 17
FEATURE                  Location/Qualifiers
source                   1..17
                         mol_type = protein
                         organism = synthetic construct
SEQUENCE: 144
RINTDADSTN YADSVKG                                                          17

SEQ ID NO: 145           moltype = AA  length = 17
FEATURE                  Location/Qualifiers
source                   1..17
                         mol_type = protein
                         organism = synthetic construct
SEQUENCE: 145
YINTDADSTN YADSVKG                                                          17

SEQ ID NO: 146           moltype = AA  length = 17
FEATURE                  Location/Qualifiers
source                   1..17
                         mol_type = protein
                         organism = synthetic construct
SEQUENCE: 146
AINTDADSTN YASWARG                                                          17

SEQ ID NO: 147           moltype = AA  length = 12
FEATURE                  Location/Qualifiers
source                   1..12
                         mol_type = protein
                         organism = synthetic construct
SEQUENCE: 147
QQTVRGGAYG LA                                                               12

SEQ ID NO: 148           moltype = AA  length = 12
FEATURE                  Location/Qualifiers
source                   1..12
                         mol_type = protein
                         organism = synthetic construct
```

```
SEQUENCE: 148
QATVRGGAYG LA                                                            12

SEQ ID NO: 149          moltype = AA  length = 11
FEATURE                 Location/Qualifiers
source                  1..11
                        mol_type = protein
                        organism = synthetic construct
VARIANT                 11
                        note = Any amino acid
SEQUENCE: 149
GIDFSSSGYM X                                                             11

SEQ ID NO: 150          moltype = AA  length = 11
FEATURE                 Location/Qualifiers
source                  1..11
                        mol_type = protein
                        organism = synthetic construct
VARIANT                 11
                        note = cysteine, alanine or histidine
SEQUENCE: 150
GIDFSSSGYM X                                                             11

SEQ ID NO: 151          moltype = AA  length = 17
FEATURE                 Location/Qualifiers
source                  1..17
                        mol_type = protein
                        organism = synthetic construct
VARIANT                 1
                        note = Any amino acid
VARIANT                 13
                        note = Any amino acid
VARIANT                 14
                        note = Any amino acid
VARIANT                 15
                        note = Any amino acid
SEQUENCE: 151
XIYTYSSNTY YAXXXKG                                                       17

SEQ ID NO: 152          moltype = AA  length = 17
FEATURE                 Location/Qualifiers
source                  1..17
                        mol_type = protein
                        organism = synthetic construct
VARIANT                 1
                        note = cysteine or alanine
VARIANT                 13
                        note = serine or alanine
VARIANT                 14
                        note = tryptophan or serine
VARIANT                 15
                        note = alanine or valine
SEQUENCE: 152
XIYTYSSNTY YAXXXKG                                                       17

SEQ ID NO: 153          moltype = AA  length = 7
FEATURE                 Location/Qualifiers
source                  1..7
                        mol_type = protein
                        organism = synthetic construct
VARIANT                 4
                        note = Any amino acid
VARIANT                 6
                        note = Any amino acid
SEQUENCE: 153
RASXLXS                                                                  7

SEQ ID NO: 154          moltype = AA  length = 7
FEATURE                 Location/Qualifiers
source                  1..7
                        mol_type = protein
                        organism = synthetic construct
VARIANT                 4
                        note = threonine or serine
VARIANT                 6
                        note = alanine or glutamic acid
SEQUENCE: 154
RASXLXS                                                                  7
```

-continued

| | | |
|---|---|---|
| SEQ ID NO: 155<br>FEATURE<br>source<br><br>VARIANT<br><br>SEQUENCE: 155<br>GFSFSNSYWI X | moltype = AA  length = 11<br>Location/Qualifiers<br>1..11<br>mol_type = protein<br>organism = synthetic construct<br>11<br>note = Any amino acid | 11 |
| SEQ ID NO: 156<br>FEATURE<br>source<br><br>VARIANT<br><br>SEQUENCE: 156<br>GFSFSNSYWI X | moltype = AA  length = 11<br>Location/Qualifiers<br>1..11<br>mol_type = protein<br>organism = synthetic construct<br>11<br>note = cysteine, alanine, or histidine | 11 |
| SEQ ID NO: 157<br>FEATURE<br>source<br><br>VARIANT<br><br>VARIANT<br><br>VARIANT<br><br>VARIANT<br><br>VARIANT<br><br>SEQUENCE: 157<br>XINTDADSTN YAXXXXG | moltype = AA  length = 17<br>Location/Qualifiers<br>1..17<br>mol_type = protein<br>organism = synthetic construct<br>1<br>note = Any amino acid<br>13<br>note = Any amino acid<br>14<br>note = Any amino acid<br>15<br>note = Any amino acid<br>16<br>note = Any amino acid | 17 |
| SEQ ID NO: 158<br>FEATURE<br>source<br><br>VARIANT<br><br>VARIANT<br><br>VARIANT<br><br>VARIANT<br><br>VARIANT<br><br>SEQUENCE: 158<br>XINTDADSTN YAXXXXG | moltype = AA  length = 17<br>Location/Qualifiers<br>1..17<br>mol_type = protein<br>organism = synthetic construct<br>1<br>note = cysteine or alanine<br>13<br>note = serine or aspartic acid<br>14<br>note = tryptophan or serine<br>15<br>note = alanine or valine<br>16<br>note = arginine or lysine | 17 |
| SEQ ID NO: 159<br>FEATURE<br>source<br><br>VARIANT<br><br>SEQUENCE: 159<br>XASQNIGSNL A | moltype = AA  length = 11<br>Location/Qualifiers<br>1..11<br>mol_type = protein<br>organism = synthetic construct<br>1<br>note = Any amino acid | 11 |
| SEQ ID NO: 160<br>FEATURE<br>source<br><br>VARIANT<br><br>SEQUENCE: 160<br>XASQNIGSNL A | moltype = AA  length = 11<br>Location/Qualifiers<br>1..11<br>mol_type = protein<br>organism = synthetic construct<br>1<br>note = glutamine or arginine | 11 |
| SEQ ID NO: 161<br>FEATURE<br>source | moltype = AA  length = 7<br>Location/Qualifiers<br>1..7 | |

```
                            mol_type = protein
                            organism = synthetic construct
VARIANT                     6
                            note = Any amino acid
SEQUENCE: 161
DASKLXS                                                                    7

SEQ ID NO: 162              moltype = AA   length = 7
FEATURE                     Location/Qualifiers
source                      1..7
                            mol_type = protein
                            organism = synthetic construct
VARIANT                     6
                            note = alanine or glutamic acid
SEQUENCE: 162
DASKLXS                                                                    7

SEQ ID NO: 163              moltype = AA   length = 12
FEATURE                     Location/Qualifiers
source                      1..12
                            mol_type = protein
                            organism = synthetic construct
VARIANT                     2
                            note = Any amino acid
VARIANT                     11
                            note = Any amino acid
SEQUENCE: 163
QXTVRGGAYG XA                                                             12

SEQ ID NO: 164              moltype = AA   length = 12
FEATURE                     Location/Qualifiers
source                      1..12
                            mol_type = protein
                            organism = synthetic construct
VARIANT                     2
                            note = cysteine, glutamine, alanine, serine, threonine, or
                             valine
VARIANT                     11
                            note = asparagine or leucine
SEQUENCE: 164
QXTVRGGAYG XA                                                             12

SEQ ID NO: 165              moltype = AA   length = 239
FEATURE                     Location/Qualifiers
source                      1..239
                            mol_type = protein
                            organism = Homo sapiens
SEQUENCE: 165
SKVWRDQHFV KIQVKDSAQN SVIIVDKNGR LVYLVENPGG YVAYSKAATV TGKLVHANFG          60
TKKDFEDLYT PVNGSIVIVR AGKITFAEKV ANAESLNAIG VLIYMDQTKF PIVNAELSFF         120
GHAHLGTGDP YTPGFPSFNH TQFPPSRSSG LPNIPVQTIS RAAAEKLFGN MEGDCPSDWK         180
TDSTCRMVTS ESKNVKLTVS NVLKEIKILN IFGVIKGFVE PDHYVVVGAQ RDAWGPGAA         239

SEQ ID NO: 166              moltype = AA   length = 239
FEATURE                     Location/Qualifiers
source                      1..239
                            mol_type = protein
                            organism = Macaca fascicularis
SEQUENCE: 166
SKVWRDQHFV KIQVKDSAQN SVIIVDKNGG LVYLVENPGG YVAYSKAATV TGKLVHANFG          60
TKKDFEDLDS PVNGSIVIVR AGKITFAEKV ANAESLNAIG VLIYMDQTKF PIVKADLSFF         120
GHAHLGTGDP YTPGFPSFNH TQFPPSQSSG LPNIPVQTIS RAAAEKLFGN MEGDCPSDWK         180
TDSTCKMVTS ENKSVKLTVS NVLKETKILN IFGVIKGFVE PDHYVVVGAQ RDAWGPGAA         239

SEQ ID NO: 167              moltype = AA   length = 240
FEATURE                     Location/Qualifiers
source                      1..240
                            mol_type = protein
                            organism = Mus musculus
SEQUENCE: 167
SKVWRDEHYV KIQVKSSIGQ NMVTIVQSNG NLDPVESPEG YVAFSKPTEV SGKLVHANFG          60
TKKDFEELSY SVNGSLVIVR AGEITFAEKV ANAQSFNAIG VLIYMDKNKF PVVEADLALF         120
GHAHLGTGDP YTPGFPSFNH TQFPPSQSSG LPNIPVQTIS RAAAEKLFGK MEGSCPARWN         180
IDSSCKLELS QNQNVKLIVK NVLKERRILN IFGVIKGYEE PDRYVVVGAQ RDALGAGVAA         240
```

```
SEQ ID NO: 168          moltype = AA   length = 60
FEATURE                 Location/Qualifiers
source                  1..60
                        mol_type = protein
                        organism = Homo sapiens
SEQUENCE: 168
ARRLYWDDLK RKLSEKLDST DFTGTIKLLN ENSYVPREAG SQKDENLALY VENQFREFKL  60

SEQ ID NO: 169          moltype = AA   length = 60
FEATURE                 Location/Qualifiers
source                  1..60
                        mol_type = protein
                        organism = Macaca fascicularis
SEQUENCE: 169
APRLYWDDLK RKLSEKLDTT DFTSTIKLLN ENLYVPREAG SQKDENLALY IENQFREFKL  60

SEQ ID NO: 170          moltype = AA   length = 60
FEATURE                 Location/Qualifiers
source                  1..60
                        mol_type = protein
                        organism = Mus musculus
SEQUENCE: 170
SSRLYWADLK TLLSEKLNSI EFADTIKQLS QNTYTPREAG SQKDESLAYY IENQFHEFKF  60

SEQ ID NO: 171          moltype = AA   length = 120
FEATURE                 Location/Qualifiers
source                  1..120
                        mol_type = protein
                        organism = Homo sapiens
SEQUENCE: 171
APTYINLDKA VLGTSNFKVS ASPLLYTLIE KTMQNVKHPV TGQFLYQDSN WASKVEKLTL  60
DNAAFPFLAY SGIPAVSFCF CEDTDYPYLG TTMDTYKELI ERIPELNKVA RAAAEVAGQF 120

SEQ ID NO: 172          moltype = AA   length = 120
FEATURE                 Location/Qualifiers
source                  1..120
                        mol_type = protein
                        organism = Macaca fascicularis
SEQUENCE: 172
APTYINLDKA VLGTSNFKVS ASPLLYTLIE KTMQDVKHPV TGRSLYQDSN WASKVEKLTL  60
DNAAFPFLAY SGIPAVSFCF CEDTDYPYLG TTMDTYKELV ERIPELNKVA RAAAEVAGQF 120

SEQ ID NO: 173          moltype = AA   length = 120
FEATURE                 Location/Qualifiers
source                  1..120
                        mol_type = protein
                        organism = Mus musculus
SEQUENCE: 173
APTYINLDKV VLGTSNFKVS ASPLLYTLMG KIMQDVKHPV DGKSLYRDSN WISKVEKLSF  60
DNAAYPFLAY SGIPAVSFCF CEDADYPYLG TRLDTYEALT QKVPQLNQMV RTAAEVAGQL 120

SEQ ID NO: 174          moltype = AA   length = 451
FEATURE                 Location/Qualifiers
source                  1..451
                        mol_type = protein
                        organism = synthetic construct
SEQUENCE: 174
KTHTCPPCPA PELLGGPSVF LFPPKPKDTL MISRTPEVTC VVVDVSHEDP EVKFNWYVDG  60
VEVHNAKTKP REEQYQSTYR VVSVLTVLHQ DWLNGKEYKC KVSNKALPAP IEKTISKAKG 120
QPREPQVYTL PPSRDELTKN QVSLTCLVKG FYPSDIAVEW ESNGQPENNY KTTPPVLDSD 180
GSFFLYSKLT VDKSRWQQGN VFSCSVMHEA LHNHYTQKSL SLSQSLVESG GGLVQPGGSL 240
RLSCAASGID FSSSGYMCWV RQAPGKGLEW VGCIYTYSSN TYYAASVKGR FTISKTSSTT 300
VYLQMNSLKT EDTAVYYCAR GTYGYTGYTY TMGYFSLWGQ GTLVTVSSAS TKGPSVFPLA 360
PSSKSTSGGT AALGCLVKDY FPEPVTVSWN SGALTSGVHT FPAVLQSSGL YSLSSVVTVP 420
SSSLGTQTYI CNVNHKPSNT KVDKKVEPKS C                                451

SEQ ID NO: 175          moltype = AA   length = 452
FEATURE                 Location/Qualifiers
source                  1..452
                        mol_type = protein
                        organism = synthetic construct
SEQUENCE: 175
KTHTCPPCPA PELLGGPSVF LFPPKPKDTL MISRTPEVTC VVVDVSHEDP EVKFNWYVDG  60
VEVHNAKTKP REEQYQSTYR VVSVLTVLHQ DWLNGKEYKC KVSNKALPAP IEKTISKAKG 120
QPREPQVYTL PPSRDELTKN QVSLTCLVKG FYPSDIAVEW ESNGQPENNY KTTPPVLDSD 180
GSFFLYSKLT VDKSRWQQGN VFSCSVMHEA LHNHYTQKSL SLSQSLVES GGGLVQPGGS 240
LRLSCAASGI DFSSSGYMCW VRQAPGKGLE WVGCIYTYSS NTYYAASVKG RFTISKTSST 300
TVYLQMNSLK TEDTAVYYCA RGTYGYTGYT YTMGYFSLWG QGTLVTVSSA STKGPSVFPL 360
```

```
APSSKSTSGG TAALGCLVKD YFPEPVTVSW NSGALTSGVH TFPAVLQSSG LYSLSSVVTV    420
PSSSLGTQTY ICNVNHKPSN TKVDKKVEPK SC                                 452

SEQ ID NO: 176          moltype = AA   length = 453
FEATURE                 Location/Qualifiers
source                  1..453
                        mol_type = protein
                        organism = synthetic construct
SEQUENCE: 176
KTHTCPPCPA PELLGGPSVF LFPPKPKDTL MISRTPEVTC VVVDVSHEDP EVKFNWYVDG    60
VEVHNAKTKP REEQYQSTYR VVSVLTVLHQ DWLNGKEYKC KVSNKALPAP IEKTISKAKG    120
QPREPQVYTL PPSRDELTKN QVSLTCLVKG FYPSDIAVEW ESNGQPENNY KTTPPVLDSD    180
GSFFLYSKLT VDKSRWQQGN VFSCSVMHEA LHNHYTQKSL SLSPGQSLVE SGGGLVQPGG    240
SLRLSCAASG IDFSSSGYMC WVRQAPGKGL EWVGCIYTYS SNTYYAASVK GRFTISKTSS    300
TTVYLQMNSL KTEDTAVYYC ARGTYGYTGY TYTMGYFSLW GQGTLVTVSS ASTKGPSVFP    360
LAPSSKSTSG GTAALGCLVK DYFPEPVTVS WNSGALTSGV HTFPAVLQSS GLYSLSSVVT    420
VPSSSLGTQT YICNVNHKPS NTKVDKKVEP KSC                                453

SEQ ID NO: 177          moltype = AA   length = 454
FEATURE                 Location/Qualifiers
source                  1..454
                        mol_type = protein
                        organism = synthetic construct
SEQUENCE: 177
KTHTCPPCPA PELLGGPSVF LFPPKPKDTL MISRTPEVTC VVVDVSHEDP EVKFNWYVDG    60
VEVHNAKTKP REEQYQSTYR VVSVLTVLHQ DWLNGKEYKC KVSNKALPAP IEKTISKAKG    120
QPREPQVYTL PPSRDELTKN QVSLTCLVKG FYPSDIAVEW ESNGQPENNY KTTPPVLDSD    180
GSFFLYSKLT VDKSRWQQGN VFSCSVMHEA LHNHYTQKSL SLSPGSQSLV ESGGGLVQPG    240
GSLRLSCAAS GIDFSSSGYM CWVRQAPGKG LEWVGCIYTY SSNTYYAASV KGRFTISKTS    300
STTVYLQMNS LKTEDTAVYY CARGTYGYTG YTYTMGYFSL WGQGTLVTVS SASTKGPSVF    360
PLAPSSKSTS GGTAALGCLV KDYFPEPVTV SWNSGALTSG VHTFPAVLQS SGLYSLSSVV    420
TVPSSSLGTQ TYICNVNHKP SNTKVDKKVE PKSC                               454

SEQ ID NO: 178          moltype = AA   length = 456
FEATURE                 Location/Qualifiers
source                  1..456
                        mol_type = protein
                        organism = synthetic construct
SEQUENCE: 178
KTHTCPPCPA PELLGGPSVF LFPPKPKDTL MISRTPEVTC VVVDVSHEDP EVKFNWYVDG    60
VEVHNAKTKP REEQYQSTYR VVSVLTVLHQ DWLNGKEYKC KVSNKALPAP IEKTISKAKG    120
QPREPQVYTL PPSRDELTKN QVSLTCLVKG FYPSDIAVEW ESNGQPENNY KTTPPVLDSD    180
GSFFLYSKLT VDKSRWQQGN VFSCSVMHEA LHNHYTQKSL SLSPGSGGQS LVESGGGLVQ    240
PGGSLRLSCA ASGIDFSSSG YMCWVRQAPG KGLEWVGCIY TYSSNTYYAA SVKGRFTISK    300
TSSTTVYLQM NSLKTEDTAV YYCARGTYGY TGYTYTMGYF SLWGQGTLVT VSSASTKGPS    360
VFPLAPSSKS TSGGTAALGC LVKDYFPEPV TVSWNSGALT SGVHTFPAVL QSSGLYSLSS    420
VVTVPSSSLG TQTYICNVNH KPSNTKVDKK VEPKSC                             456

SEQ ID NO: 179          moltype = AA   length = 458
FEATURE                 Location/Qualifiers
source                  1..458
                        mol_type = protein
                        organism = synthetic construct
SEQUENCE: 179
KTHTCPPCPA PELLGGPSVF LFPPKPKDTL MISRTPEVTC VVVDVSHEDP EVKFNWYVDG    60
VEVHNAKTKP REEQYQSTYR VVSVLTVLHQ DWLNGKEYKC KVSNKALPAP IEKTISKAKG    120
QPREPQVYTL PPSRDELTKN QVSLTCLVKG FYPSDIAVEW ESNGQPENNY KTTPPVLDSD    180
GSFFLYSKLT VDKSRWQQGN VFSCSVMHEA LHNHYTQKSL SLSPGSGGGG QSLVESGGGL    240
VQPGGSLRLS CAASGIDFSS SGYMCWVRQA PGKGLEWVGC IYTYSSNTYY AASVKGRFTI    300
SKTSSTTVYL QMNSLKTEDT AVYYCARGTY GYTGYTYTMG YFSLWGQGTL VTVSSASTKG    360
PSVFPLAPSS KSTSGGTAAL GCLVKDYFPE PVTVSWNSGA LTSGVHTFPA VLQSSGLYSL    420
SSVVTVPSSS LGTQTYICNV NHKPSNTKVD KKVEPKSC                           458

SEQ ID NO: 180          moltype = AA   length = 463
FEATURE                 Location/Qualifiers
source                  1..463
                        mol_type = protein
                        organism = synthetic construct
SEQUENCE: 180
KTHTCPPCPA PELLGGPSVF LFPPKPKDTL MISRTPEVTC VVVDVSHEDP EVKFNWYVDG    60
VEVHNAKTKP REEQYQSTYR VVSVLTVLHQ DWLNGKEYKC KVSNKALPAP IEKTISKAKG    120
QPREPQVYTL PPSRDELTKN QVSLTCLVKG FYPSDIAVEW ESNGQPENNY KTTPPVLDSD    180
GSFFLYSKLT VDKSRWQQGN VFSCSVMHEA LHNHYTQKSL SLSPGSGGGG SGGGGQSLVE    240
SGGGLVQPGG SLRLSCAASG IDFSSSGYMC WVRQAPGKGL EWVGCIYTYS SNTYYAASVK    300
GRFTISKTSS TTVYLQMNSL KTEDTAVYYC ARGTYGYTGY TYTMGYFSLW GQGTLVTVSS    360
ASTKGPSVFP LAPSSKSTSG GTAALGCLVK DYFPEPVTVS WNSGALTSGV HTFPAVLQSS    420
GLYSLSSVVT VPSSSLGTQT YICNVNHKPS NTKVDKKVEP KSC                     463
```

```
SEQ ID NO: 181         moltype = AA  length = 468
FEATURE                Location/Qualifiers
source                 1..468
                       mol_type = protein
                       organism = synthetic construct
SEQUENCE: 181
KTHTCPPCPA PELLGGPSVF LFPPKPKDTL MISRTPEVTC VVVDVSHEDP EVKFNWYVDG    60
VEVHNAKTKP REEQYQSTYR VVSVLTVLHQ DWLNGKEYKC KVSNKALPAP IEKTISKAKG   120
QPREPQVYTL PPSRDELTKN QVSLTCLVKG FYPSDIAVEW ESNGQPENNY KTTPPVLDSD   180
GSFFLYSKLT VDKSRWQQGN VFSCSVMHEA LHNHYTQKSL SLSPGSGGGG SGGGGSGGGG   240
QSLVESGGGL VQPGGSLRLS CAASGIDFSS SGYMCWVRQA PGKGLEWVGC IYTYSSNTYY   300
AASVKGRFTI SKTSSTTVYL QMNSLKTEDT AVYYCARGTY GYTGTYTMG YFSLWGQGTL    360
VTVSSASTKG PSVFPLAPSS KSTSGGTAAL GCLVKDYFPE PVTVSWNSGA LTSGVHTFPA   420
VLQSSGLYSL SSVVTVPSSS LGTQTYICNV NHKPSNTKVD KKVEPKSC                468

SEQ ID NO: 182         moltype = AA  length = 441
FEATURE                Location/Qualifiers
source                 1..441
                       mol_type = protein
                       organism = synthetic construct
SEQUENCE: 182
KTHTCPPCPA PELLGGPSVF LFPPKPKDTL MISRTPEVTC VVVDVSHEDP EVKFNWYVDG    60
VEVHNAKTKP REEQYQSTYR VVSVLTVLHQ DWLNGKEYKC KVSNKALPAP IEKTISKAKG   120
QPREPQVYTL PPSRDELTKN QVSLTCLVKG FYPSDIAVEW ESNGQPENNY KTTPPVLDSD   180
GSFFLYSKLT VDKSRWQQGN VFSCSVMHEA LHNHYTQKSL SLSDIQMTQS PSTLSASVGD   240
RVTITCQASQ NINSYLAWYQ QKPGKAPKLL IYRASSLESG VPSRFSGSGS GTEFTLTISS   300
LQPDDFATYY CQSYYYSGSS NYNAFGGGTK VEIKRTVAAP SVFIFPPSDE QLKSGTASVV   360
CLLNNFYPRE AKVQWKVDNA LQSGNSQESV TEQDSKDSTY SLSSTLTLSK ADYEKHKVYA   420
CEVTHQGLSS PVTKSFNRGE C                                             441

SEQ ID NO: 183         moltype = AA  length = 442
FEATURE                Location/Qualifiers
source                 1..442
                       mol_type = protein
                       organism = synthetic construct
SEQUENCE: 183
KTHTCPPCPA PELLGGPSVF LFPPKPKDTL MISRTPEVTC VVVDVSHEDP EVKFNWYVDG    60
VEVHNAKTKP REEQYQSTYR VVSVLTVLHQ DWLNGKEYKC KVSNKALPAP IEKTISKAKG   120
QPREPQVYTL PPSRDELTKN QVSLTCLVKG FYPSDIAVEW ESNGQPENNY KTTPPVLDSD   180
GSFFLYSKLT VDKSRWQQGN VFSCSVMHEA LHNHYTQKSL SLSPDIQMTQ SPSTLSASVG   240
DRVTITCQAS QNINSYLAWY QQKPGKAPKL LIYRASSLES GVPSRFSGSG SGTEFTLTIS   300
SLQPDDFATY YCQSYYYSGS SNYNAFGGGT KVEIKRTVAA PSVFIFPPSD EQLKSGTASV   360
VCLLNNFYPR EAKVQWKVDN ALQSGNSQES VTEQDSKDST YSLSSTLTLS KADYEKHKVY   420
ACEVTHQGLS SPVTKSFNRG EC                                            442

SEQ ID NO: 184         moltype = AA  length = 443
FEATURE                Location/Qualifiers
source                 1..443
                       mol_type = protein
                       organism = synthetic construct
SEQUENCE: 184
KTHTCPPCPA PELLGGPSVF LFPPKPKDTL MISRTPEVTC VVVDVSHEDP EVKFNWYVDG    60
VEVHNAKTKP REEQYQSTYR VVSVLTVLHQ DWLNGKEYKC KVSNKALPAP IEKTISKAKG   120
QPREPQVYTL PPSRDELTKN QVSLTCLVKG FYPSDIAVEW ESNGQPENNY KTTPPVLDSD   180
GSFFLYSKLT VDKSRWQQGN VFSCSVMHEA LHNHYTQKSL SLSPGDIQMT QSPSTLSASV   240
GDRVTITCQA SQNINSYLAW YQQKPGKAPK LLIYRASSLE SGVPSRFSGS GSGTEFTLTI   300
SSLQPDDFAT YYCQSYYYSG SSNYNAFGGG TKVEIKRTVA APSVFIFPPS DEQLKSGTAS   360
VVCLLNNFYP REAKVQWKVD NALQSGNSQE SVTEQDSKDS TYSLSSTLTL SKADYEKHKV   420
YACEVTHQGL SSPVTKSFNR GEC                                           443

SEQ ID NO: 185         moltype = AA  length = 444
FEATURE                Location/Qualifiers
source                 1..444
                       mol_type = protein
                       organism = synthetic construct
SEQUENCE: 185
KTHTCPPCPA PELLGGPSVF LFPPKPKDTL MISRTPEVTC VVVDVSHEDP EVKFNWYVDG    60
VEVHNAKTKP REEQYQSTYR VVSVLTVLHQ DWLNGKEYKC KVSNKALPAP IEKTISKAKG   120
QPREPQVYTL PPSRDELTKN QVSLTCLVKG FYPSDIAVEW ESNGQPENNY KTTPPVLDSD   180
GSFFLYSKLT VDKSRWQQGN VFSCSVMHEA LHNHYTQKSL SLSPGSDIQM TQSPSTLSAS   240
VGDRVTITCQ ASQNINSYLA WYQQKPGKAP KLLIYRASSL ESGVPSRFSG SGSGTEFTLT   300
ISSLQPDDFA TYYCQSYYYS GSSNYNAFGG GTKVEIKRTV AAPSVFIFPP SDEQLKSGTA   360
SVVCLLNNFY PREAKVQWKV DNALQSGNSQ ESVTEQDSKD STYSLSSTLT LSKADYEKHK   420
VYACEVTHQG LSSPVTKSFN RGEC                                          444
```

```
SEQ ID NO: 186          moltype = AA  length = 446
FEATURE                 Location/Qualifiers
source                  1..446
                        mol_type = protein
                        organism = synthetic construct
SEQUENCE: 186
KTHTCPPCPA PELLGGPSVF LFPPKPKDTL MISRTPEVTC VVVDVSHEDP EVKFNWYVDG   60
VEVHNAKTKP REEQYQSTYR VVSVLTVLHQ DWLNGKEYKC KVSNKALPAP IEKTISKAKG  120
QPREPQVYTL PPSRDELTKN QVSLTCLVKG FYPSDIAVEW ESNGQPENNY KTTPPVLDSD  180
GSFFLYSKLT VDKSRWQQGN VFSCSVMHEA LHNHYTQKSL SLSPGSGGDI QMTQSPSTLS  240
ASVGDRVTIT CQASQNINSY LAWYQQKPGK APKLLIYRAS SLESGVPSRF SGSGSGTEFT  300
LTISSLQPDD FATYYCQSYY YSGSSNYNAF GGGTKVEIKR TVAAPSVFIF PPSDEQLKSG  360
TASVVCLLNN FYPREAKVQW KVDNALQSGN SQESVTEQDS KDSTYSLSST LTLSKADYEK  420
HKVYACEVTH QGLSSPVTKS FNRGEC                                       446

SEQ ID NO: 187          moltype = AA  length = 448
FEATURE                 Location/Qualifiers
source                  1..448
                        mol_type = protein
                        organism = synthetic construct
SEQUENCE: 187
KTHTCPPCPA PELLGGPSVF LFPPKPKDTL MISRTPEVTC VVVDVSHEDP EVKFNWYVDG   60
VEVHNAKTKP REEQYQSTYR VVSVLTVLHQ DWLNGKEYKC KVSNKALPAP IEKTISKAKG  120
QPREPQVYTL PPSRDELTKN QVSLTCLVKG FYPSDIAVEW ESNGQPENNY KTTPPVLDSD  180
GSFFLYSKLT VDKSRWQQGN VFSCSVMHEA LHNHYTQKSL SLSPGSGGGG DIQMTQSPST  240
LSASVGDRVT ITCQASQNIN SYLAWYQQKP GKAPKLLIYR ASSLESGVPS RFSGSGSGTE  300
FTLTISSLQP DDFATYYCQS YYYSGSSNYN AFGGGTKVEI KRTVAAPSVF IFPPSDEQLK  360
SGTASVVCLL NNFYPREAKV QWKVDNALQS GNSQESVTEQ DSKDSTYSLS STLTLSKADY  420
EKHKVYACEV THQGLSSPVT KSFNRGEC                                     448

SEQ ID NO: 188          moltype = AA  length = 453
FEATURE                 Location/Qualifiers
source                  1..453
                        mol_type = protein
                        organism = synthetic construct
SEQUENCE: 188
KTHTCPPCPA PELLGGPSVF LFPPKPKDTL MISRTPEVTC VVVDVSHEDP EVKFNWYVDG   60
VEVHNAKTKP REEQYQSTYR VVSVLTVLHQ DWLNGKEYKC KVSNKALPAP IEKTISKAKG  120
QPREPQVYTL PPSRDELTKN QVSLTCLVKG FYPSDIAVEW ESNGQPENNY KTTPPVLDSD  180
GSFFLYSKLT VDKSRWQQGN VFSCSVMHEA LHNHYTQKSL SLSPGSGGGG SGGGGDIQMT  240
QSPSTLSASV GDRVTITCQA SQNINSYLAW YQQKPGKAPK LLIYRASSLE SGVPSRFSGS  300
GSGTEFTLTI SSLQPDDFAT YYCQSYYYSG SSNYNAFGGG TKVEIKRTVA APSVFIFPPS  360
DEQLKSGTAS VVCLLNNFYP REAKVQWKVD NALQSGNSQE SVTEQDSKDS TYSLSSTLTL  420
SKADYEKHKV YACEVTHQGL SSPVTKSFNR GEC                                453

SEQ ID NO: 189          moltype = AA  length = 458
FEATURE                 Location/Qualifiers
source                  1..458
                        mol_type = protein
                        organism = synthetic construct
SEQUENCE: 189
KTHTCPPCPA PELLGGPSVF LFPPKPKDTL MISRTPEVTC VVVDVSHEDP EVKFNWYVDG   60
VEVHNAKTKP REEQYQSTYR VVSVLTVLHQ DWLNGKEYKC KVSNKALPAP IEKTISKAKG  120
QPREPQVYTL PPSRDELTKN QVSLTCLVKG FYPSDIAVEW ESNGQPENNY KTTPPVLDSD  180
GSFFLYSKLT VDKSRWQQGN VFSCSVMHEA LHNHYTQKSL SLSPGSGGGG SGGGGSGGGG  240
DIQMTQSPST LSASVGDRVT ITCQASQNIN SYLAWYQQKP GKAPKLLIYR ASSLESGVPS  300
RFSGSGSGTE FTLTISSLQP DDFATYYCQS YYYSGSSNYN AFGGGTKVEI KRTVAAPSVF  360
IFPPSDEQLK SGTASVVCLL NNFYPREAKV QWKVDNALQS GNSQESVTEQ DSKDSTYSLS  420
STLTLSKADY EKHKVYACEV THQGLSSPVT KSFNRGEC                           458

SEQ ID NO: 190          moltype = AA  length = 486
FEATURE                 Location/Qualifiers
source                  1..486
                        mol_type = protein
                        organism = synthetic construct
SEQUENCE: 190
KTHTCPPCPA PELLGGPSVF LFPPKPKDTL MISRTPEVTC VVVDVSHEDP EVKFNWYVDG   60
VEVHNAKTKP REEQYQSTYR VVSVLTVLHQ DWLNGKEYKC KVSNKALPAP IEKTISKAKG  120
QPREPQVYTL PPSRDELTKN QVSLTCLVKG FYPSDIAVEW ESNGQPENNY KTTPPVLDSD  180
GSFFLYSKLT VDKSRWQQGN VFSCSVMHEA LHNHYTQKSL SLSPGSGGGG SGGGGQSLVE  240
SGGGLVQPGG SLRLSCAASG IDFSSSGYMC WVRQAPGKGL EWVGCIYTYS SNTYYAASVK  300
GRFTISKTSS TTVYLQMNSL KTEDTAVYYC ARGTYGYTGY TYTMGYFSLW GQGTLVTVSS  360
GGGGSGGGGS GGGGSDIQMT QSPSTLSASV GDRVTITCQA SQNINSYLAW YQQKPGKAPK  420
LLIYRASSLE SGVPSRFSGS GSGTEFTLTI SSLQPDDFAT YYCQSYYYSG SSNYNAFGGG  480
TKVEIK                                                             486
```

```
SEQ ID NO: 191            moltype = AA  length = 486
FEATURE                   Location/Qualifiers
source                    1..486
                          mol_type = protein
                          organism = synthetic construct
SEQUENCE: 191
KTHTCPPCPA PELLGGPSVF LFPPKPKDTL MISRTPEVTC VVVDVSHEDP EVKFNWYVDG    60
VEVHNAKTKP REEQYQSTYR VVSVLTVLHQ DWLNGKEYKC KVSNKALPAP IEKTISKAKG   120
QPREPQVYTL PPSRDELTKN QVSLTCLVKG FYPSDIAVEW ESNGQPENNY KTTPPVLDSD   180
GSFFLYSKLT VDKSRWQQGN VFSCSVMHEA LHNHYTQKSL SLSPGSGGGG SGGGGDIQMT   240
QSPSTLSASV GDRVTITCQA SQNINSYLAW YQQKPGKAPK LLIYRASSLE SGVPSRFSGS   300
GSGTEFTLTI SSLQPDDFAT YYCQSYYYSG SSNYNAFGGG TKVEIKGGGS SGGGGSGGGG   360
SQSLVESGGG LVQPGGSLRL SCAASGIDFS SSGYMCWVRQ APGKGLEWVG CIYTYSSNTY   420
YAASVKGRFT ISKTSSTTVY LQMNSLKTED TAVYYCARGT YGYTGYTYTM GYFSLWGQGT   480
LVTVSS                                                              486

SEQ ID NO: 192            moltype = AA  length = 454
FEATURE                   Location/Qualifiers
source                    1..454
                          mol_type = protein
                          organism = synthetic construct
SEQUENCE: 192
QSLVESGGGL VQPGGSLRLS CAASGIDFSS SGYMCWVRQA PGKGLEWVGC IYTYSSNTYY    60
AASVKGRFTI SKTSSTTVYL QMNSLKTEDT AVYYCARGTY GYTGYTYTMG YFSLWGQGTL   120
VTVSSASTKG PSVFPLAPSS KSTSGGTAAL GCLVKDYFPE PVTVSWNSGA LTSGVHTFPA   180
VLQSSGLYSL SSVVTVPSSS LGTQTYICNV NHKPSNTKVD KKVEPKSCDK THTCPPCPAP   240
ELLGGPSVFL FPPKPKDTLM ISRTPEVTCV VVDVSHEDPE VKFNWYVDGV EVHNAKTKPR   300
EEQYQSTYRV VSVLTVLHQD WLNGKEYKCK VSNKALPAPI EKTISKAKGQ PREPQVYTLP   360
PSRDELTKNQ VSLTCLVKGF YPSDIAVEWE SNGQPENNYK TTPPVLDSDG SFFLYSKLTV   420
DKSRWQQGNV FSCSVMHEAL HNHYTQKSLS LSPG                               454

SEQ ID NO: 193            moltype = AA  length = 454
FEATURE                   Location/Qualifiers
source                    1..454
                          mol_type = protein
                          organism = synthetic construct
SEQUENCE: 193
QSLVESGGGL VQPGGSLRLS CAASGIDFSS SGYMCWVRQA PGKGLEWVGC IYTYSSNTYY    60
AASVKGRFTI SKTSSTTVYL QMNSLKTEDT AVYYCARGTY GYTGYTYTMG YFSLWGQGTL   120
VTVSSASTKG PSVFPLAPSS KSTSGGTAAL GCLVKDYFPE PVTVSWNSGA LTSGVHTFPA   180
VLQSSGLYSL SSVVTVPSSS LGTQTYICNV NHKPSNTKVD KKVEPKSCDK THTCPPCPAP   240
ELLGGPSVFL FPPKPKDTLM ISRTPEVTCV VVDVSHEDPE VKFNWYVDGV EVHNAKTKPR   300
EEQYQSTYRV VSVLTVLHQD WLNGKEYKCK VSNKALPAPI EKTISKAKGQ PREPQVYTLP   360
PCRDELTKNQ VSLWCLVKGF YPSDIAVEWE SNGQPENNYK TTPPVLDSDG SFFLYSKLTV   420
DKSRWQQGNV FSCSVMHEAL HNHYTQKSLS LSPG                               454

SEQ ID NO: 194            moltype = AA  length = 462
FEATURE                   Location/Qualifiers
source                    1..462
                          mol_type = protein
                          organism = synthetic construct
SEQUENCE: 194
KTHTCPPCPA PELLGGPSVF LFPPKPKDTL MISRTPEVTC VVVDVSHEDP EVKFNWYVDG    60
VEVHNAKTKP REEQYQSTYR VVSVLTVLHQ DWLNGKEYKC KVSNKALPAP IEKTISKAKG   120
QPREPQVYTL PPCRDELTKN QVSLWCLVKG FYPSDIAVEW ESNGQPENNY KTTPPVLDSD   180
GSFFLYSKLT VDKSRWQQGN VFSCSVMHEA LHNHYTQKSL SLSPGGGGGS GGGGQSLVES   240
GGGLVQPGGS LRLSCAASGI DFSSSGYMCW VRQAPGKGLE WVGCIYTYSS NTYYAASVKG   300
RFTISKTSST TVYLQMNSLK TEDTAVYYCA RGTYGYTGYT YTMGYFSLWG QGTLVTVSSA   360
STKGPSVFPL APSSKSTSGG TAALGCLVKD YFPEPVTVSW NSGALTSGVH TFPAVLQSSG   420
LYSLSSVVTV PSSSLGTQTY ICNVNHKPSN TKVDKKVEPK SC                      462

SEQ ID NO: 195            moltype = AA  length = 225
FEATURE                   Location/Qualifiers
source                    1..225
                          mol_type = protein
                          organism = synthetic construct
SEQUENCE: 195
KTHTCPPCPA PELLGGPSVF LFPPKPKDTL MISRTPEVTC VVVDVSHEDP EVKFNWYVDG    60
VEVHNAKTKP REEQYQSTYR VVSVLTVLHQ DWLNGKEYKC KVSNKALPAP IEKTISKAKG   120
QPREPQVCTL PPSRDELTKN QVSLSCAVKG FYPSDIAVEW ESNGQPENNY KTTPPVLDSD   180
GSFFLVSKLT VDKSRWQQGN VFSCSVMHEA LHNHYTQKSL SLSPG                   225

SEQ ID NO: 196            moltype = AA  length = 229
FEATURE                   Location/Qualifiers
source                    1..229
                          mol_type = protein
                          organism = synthetic construct
```

```
SEQUENCE: 196
DIQMTQSPST LSASVGDRVT ITCQASQNIN SYLAWYQQKP GKAPKLLIYR ASSLESGVPS     60
RFSGSGSGTE FTLTISSLQP DDFATYYCQS YYYSGSSNYN AFGGGTKVEI KRTVAAPSVF    120
IFPPSDEQLK SGTASVVCLL NNFYPREAKV QWKVDNALQS GNSQESVTEQ DSKDSTYSLS    180
STLTLSKADY EKHKVYACEV THQGLSSPVT KSFNRGECTG YPYDVPDYA                229

SEQ ID NO: 197          moltype = AA   length = 239
FEATURE                 Location/Qualifiers
source                  1..239
                        mol_type = protein
                        organism = synthetic construct
SEQUENCE: 197
QSLVESGGGL VQPGGSLRLS CAASGIDFSS SGYMCWVRQA PGKGLEWVGC IYTYSSNTYY     60
AASVKGRFTI SKTSSTTVYL QMNSLKTEDT AVYYCARGTY GYTGYTYTMG YFSLWGQGTL    120
VTVSSASTKG PSVFPLAPSS KSTSGGTAAL GCLVKDYFPE PVTVSWNSGA LTSGVHTFPA    180
VLQSSGLYSL SSVVTVPSSS LGTQTYICNV NHKPSNTKVD KKVEPKSCTG YPYDVPDYA     239

SEQ ID NO: 198          moltype = AA   length = 223
FEATURE                 Location/Qualifiers
source                  1..223
                        mol_type = protein
                        organism = synthetic construct
SEQUENCE: 198
KTHTCPPCPA PELLGGPSVF LFPPKPKDTL MISRTPEVTC VVVDVSHEDP EVKFNWYVDG     60
VEVHNAKTKP REEQYQSTYR VVSVLTVLHQ DWLNGKEYKC KVSNKALPAP IEKTISKAKG    120
QPREPQVYTL PPSRDELTKN QVSLTCLVKG FYPSDIAVEW ESNGQPENNY KTTPPVLDSD    180
GSFFLYSKLT VDKSRWQQGN VFSCSVMHEA LHNHYTQKSL SLS                      223

SEQ ID NO: 199          moltype = AA   length = 224
FEATURE                 Location/Qualifiers
source                  1..224
                        mol_type = protein
                        organism = synthetic construct
SEQUENCE: 199
KTHTCPPCPA PELLGGPSVF LFPPKPKDTL MISRTPEVTC VVVDVSHEDP EVKFNWYVDG     60
VEVHNAKTKP REEQYQSTYR VVSVLTVLHQ DWLNGKEYKC KVSNKALPAP IEKTISKAKG    120
QPREPQVYTL PPSRDELTKN QVSLTCLVKG FYPSDIAVEW ESNGQPENNY KTTPPVLDSD    180
GSFFLYSKLT VDKSRWQQGN VFSCSVMHEA LHNHYTQKSL SLSP                     224

SEQ ID NO: 200          moltype = AA   length = 225
FEATURE                 Location/Qualifiers
source                  1..225
                        mol_type = protein
                        organism = synthetic construct
SEQUENCE: 200
KTHTCPPCPA PELLGGPSVF LFPPKPKDTL MISRTPEVTC VVVDVSHEDP EVKFNWYVDG     60
VEVHNAKTKP REEQYQSTYR VVSVLTVLHQ DWLNGKEYKC KVSNKALPAP IEKTISKAKG    120
QPREPQVYTL PPSRDELTKN QVSLTCLVKG FYPSDIAVEW ESNGQPENNY KTTPPVLDSD    180
GSFFLYSKLT VDKSRWQQGN VFSCSVMHEA LHNHYTQKSL SLSPG                    225

SEQ ID NO: 201          moltype = AA   length = 226
FEATURE                 Location/Qualifiers
source                  1..226
                        mol_type = protein
                        organism = synthetic construct
SEQUENCE: 201
DKTHTCPPCP APELLGGPSV FLFPPKPKDT LMISRTPEVT CVVVDVSHED PEVKFNWYVD     60
GVEVHNAKTK PREEQYQSTY RVVSVLTVLH QDWLNGKEYK CKVSNKALPA PIEKTISKAK    120
GQPREPQVYT LPPSRDELTK NQVSLTCLVK GFYPSDIAVE WESNGQPENN YKTTPPVLDS    180
DGSFFLYSKL TVDKSRWQQG NVFSCSVMHE ALHNHYTQKS LSLSPG                   226

SEQ ID NO: 202          moltype = AA   length = 226
FEATURE                 Location/Qualifiers
source                  1..226
                        mol_type = protein
                        organism = synthetic construct
SEQUENCE: 202
DKTHTCPPCP APELLGGPSV FLFPPKPKDT LMISRTPEVT CVVVDVSHED PEVKFNWYVD     60
GVEVHNAKTK PREEQYQSTY RVVSVLTVLH QDWLNGKEYK CKVSNKALPA PIEKTISKAK    120
GQPREPQVYT LPPCRDELTK NQVSLWCLVK GFYPSDIAVE WESNGQPENN YKTTPPVLDS    180
DGSFFLYSKL TVDKSRWQQG NVFSCSVMHE ALHNHYTQKS LSLSPG                   226

SEQ ID NO: 203          moltype = AA   length = 225
FEATURE                 Location/Qualifiers
source                  1..225
                        mol_type = protein
                        organism = synthetic construct
```

```
SEQUENCE: 203
KTHTCPPCPA PELLGGPSVF LFPPKPKDTL MISRTPEVTC VVVDVSHEDP EVKFNWYVDG    60
VEVHNAKTKP REEQYQSTYR VVSVLTVLHQ DWLNGKEYKC KVSNKALPAP IEKTISKAKG   120
QPREPQVYTL PPCRDELTKN QVSLWCLVKG FYPSDIAVEW ESNGQPENNY KTTPPVLDSD   180
GSFFLYSKLT VDKSRWQQGN VFSCSVMHEA LHNHYTQKSL SLSPG                   225

SEQ ID NO: 204            moltype = AA  length = 5
FEATURE                   Location/Qualifiers
source                    1..5
                          mol_type = protein
                          organism = synthetic construct
SEQUENCE: 204
SGGGG                                                                 5

SEQ ID NO: 205            moltype = AA  length = 10
FEATURE                   Location/Qualifiers
source                    1..10
                          mol_type = protein
                          organism = synthetic construct
SEQUENCE: 205
SGGGGSGGGG                                                           10

SEQ ID NO: 206            moltype = AA  length = 15
FEATURE                   Location/Qualifiers
source                    1..15
                          mol_type = protein
                          organism = synthetic construct
SEQUENCE: 206
SGGGGSGGGG SGGGG                                                     15

SEQ ID NO: 207            moltype = AA  length = 9
FEATURE                   Location/Qualifiers
source                    1..9
                          mol_type = protein
                          organism = synthetic construct
SEQUENCE: 207
GGGSGGGGG                                                             9

SEQ ID NO: 208            moltype = AA  length = 15
FEATURE                   Location/Qualifiers
source                    1..15
                          mol_type = protein
                          organism = synthetic construct
SEQUENCE: 208
GGGGSGGGGS GGGGS                                                     15

SEQ ID NO: 209            moltype = AA  length = 6
FEATURE                   Location/Qualifiers
source                    1..6
                          mol_type = protein
                          organism = synthetic construct
SEQUENCE: 209
HHHHHH                                                                6

SEQ ID NO: 210            moltype = AA  length = 8
FEATURE                   Location/Qualifiers
source                    1..8
                          mol_type = protein
                          organism = synthetic construct
SEQUENCE: 210
RDDSKNSL                                                              8

SEQ ID NO: 211            moltype = AA  length = 7
FEATURE                   Location/Qualifiers
source                    1..7
                          mol_type = protein
                          organism = synthetic construct
SEQUENCE: 211
KTSSTTV                                                               7

SEQ ID NO: 212            moltype = AA  length = 4
FEATURE                   Location/Qualifiers
source                    1..4
                          mol_type = protein
                          organism = synthetic construct
SEQUENCE: 212
DSVK                                                                  4
```

```
SEQ ID NO: 213         moltype = AA   length = 4
FEATURE                Location/Qualifiers
source                 1..4
                       mol_type = protein
                       organism = synthetic construct
SEQUENCE: 213
SWAR                                                                 4

SEQ ID NO: 214         moltype = AA   length = 4
FEATURE                Location/Qualifiers
source                 1..4
                       mol_type = protein
                       organism = synthetic construct
SEQUENCE: 214
DIQM                                                                 4

SEQ ID NO: 215         moltype = AA   length = 4
FEATURE                Location/Qualifiers
source                 1..4
                       mol_type = protein
                       organism = synthetic construct
SEQUENCE: 215
ELVL                                                                 4
```

What is claimed is:

1. An antibody that binds to human transferrin receptor, comprising a heavy chain variable region (VH) comprising VH complementarity determining region (CDR)1, VH CDR2, and VH CDR3, wherein the antibody comprises a light chain variable region (VL) comprising VL CDR1, VL CDR2, and VL CDR3, and wherein the VH CDR1 comprises the amino acid sequence GIDFSSSGYMC (SEQ ID NO:101), the VH CDR2 comprises the amino acid sequence CIYTYSSNTYYAASVKG (SEQ ID NO:103), the VH CDR3 comprises the amino acid sequence GTYGYTGYTYTMGYFSL (SEQ ID NO:106), the VL CDR1 comprises the amino acid sequence QASQNINSYLA (SEQ ID NO:107), the VL CDR2 comprises the amino acid sequence RASSLES (SEQ ID NO:108), and the VL CDR3 comprises the amino acid sequence QSYYYSGSSNYNA (SEQ ID NO:110).

2. A pharmaceutical composition comprising the antibody of claim 1 and a pharmaceutically acceptable carrier.

3. A conjugate comprising the antibody of claim 1.

4. The antibody of claim 1, which is an Fab fragment or an Fab' fragment.

5. An antibody that binds to human transferrin receptor, comprising a heavy chain variable region (VH) and a light chain variable region (VL), wherein the VH comprises the amino acid sequence of SEQ ID NO:16 and the VL comprises the amino acid sequence of SEQ ID NO:35.

6. The antibody of claim 5, which is an Fab fragment or an Fab' fragment.

7. A pharmaceutical composition comprising the antibody of claim 5 and a pharmaceutically acceptable carrier.

8. A conjugate comprising the antibody of claim 5.

9. An antibody that binds to human transferrin receptor, comprising a heavy chain comprising the amino acid sequence set forth in SEQ ID NO:95, and a light chain comprising the amino acid sequence set forth in SEQ ID NO:96.

10. A pharmaceutical composition comprising the antibody of claim 9 and a pharmaceutically acceptable carrier.

11. A conjugate comprising the antibody of claim 9.

* * * * *